(12) United States Patent
Kiuchi et al.

(10) Patent No.: US 7,115,635 B2
(45) Date of Patent: Oct. 3, 2006

(54) BENZYLPIPERIDINE COMPOUND

(75) Inventors: Masatoshi Kiuchi, Tokyo (JP); Takanobu Kuroita, Katano (JP); Hideo Tomozane, Tokyo (JP); Shuuzou Takeda, Tokyo (JP); Yoshihito Tanaka, Tokyo (JP); Hidemitsu Higashi, Tokyo (JP); Shigeki Kuwahara, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 138 days.

(21) Appl. No.: 10/476,149

(22) PCT Filed: Apr. 26, 2002

(86) PCT No.: PCT/JP02/04291

§ 371 (c)(1),
(2), (4) Date: Dec. 15, 2003

(87) PCT Pub. No.: WO02/088111

PCT Pub. Date: Nov. 7, 2002

(65) Prior Publication Data

US 2004/0158071 A1  Aug. 12, 2004

(30) Foreign Application Priority Data

Apr. 27, 2001 (JP) .............................. 2001-132853
Sep. 12, 2001 (JP) .............................. 2001-277139

(51) Int. Cl.
A61K 31/445 (2006.01)
C07D 419/12 (2006.01)

(52) U.S. Cl. .............. 514/326; 514/217.04; 514/236.8; 514/253.01; 514/255.05; 514/278; 514/307; 514/316; 514/318; 514/323; 540/597; 544/129; 544/364; 544/405; 546/16; 546/144; 546/187; 546/194; 546/201; 546/209; 546/211

(58) Field of Classification Search ................ 546/209, 546/144, 16, 187, 211, 194, 201; 544/364, 544/129, 405; 540/597; 514/326, 307, 278, 514/316, 318, 323, 253.01, 236.8, 255.05, 514/217.04

See application file for complete search history.

(56) References Cited

U.S. PATENT DOCUMENTS

2004/0102483 A1* 5/2004 Brough et al. .............. 514/326

FOREIGN PATENT DOCUMENTS

| WO | 94/08582 | 4/1994 |
|---|---|---|
| WO | 94/8582 | 4/1994 |
| WO | 97/24325 | 7/1997 |
| WO | 98/02151 | 1/1998 |
| WO | 98/04554 | 2/1998 |
| WO | 98/25617 | 6/1998 |
| WO | 99/25686 | 5/1999 |
| WO | 99/55324 | 11/1999 |
| WO | 99/55330 | 11/1999 |
| WO | 00/31033 | 6/2000 |
| WO | 00/34278 | 6/2000 |
| WO | 00/53600 | 9/2000 |
| WO | 00/58305 | 10/2000 |
| WO | 01/14333 | 3/2001 |
| WO | 02/066460 | 8/2002 |

OTHER PUBLICATIONS

Rollins BJ. Blood. 1997, 90(3): 909-928.*
Hesselgesser et al. J. Biol. Chem. 1996, 273 (25) :15687-15692.*

* cited by examiner

*Primary Examiner*—Celia Chang
(74) *Attorney, Agent, or Firm*—Wenderoth, Lind & Ponack, L.L.P.

(57) ABSTRACT

The object of the present invention is to provide a compound having a treatment effect based on a chemokine inhibitory activity, which is satisfactory as a pharmaceutical product for oral administration.

The present inventors have found that the following benzylpiperidine derivative (the formula (1)) has a chemokine inhibitory activity. Further intensive studies have resulted in successful enhancement of the chemokine inhibitory activity and stability in blood of the present compound, as well as the completion of the present invention.

$$Y^2-W-Y^1-A-Z-X-(CH_2)_n-\underset{H}{\overset{O}{C-N}}-\underset{}{\overset{}{\bigcirc}}-N-CH_2-\underset{R^2}{\overset{R^1}{\bigcirc}}$$ (1)

wherein each symbol is as defined in the specification.

21 Claims, 1 Drawing Sheet

BENZYLPIPERIDINE COMPOUND

This application is a U.S. national stage of International Application No. PCT/JP02/04291 filed Apr. 26, 2002.

TECHNICAL FIELD

The present invention relates to a novel benzylpiperidine compound having affinity for a chemokine receptor, which is useful as a therapeutic and/or prophylactic drug of atherosclerosis, rheumatoid arthritis, osteoarthritis, psoriasis, asthma, allergic rhinitis, allergic conjunctivitis, allergic myelitis, atopic dermatitis, food allergy, ulcerative colitis, multiple sclerosis, chronic obstructive respiratory disease, myocarditis, rejection in organ transplantation, human immunodeficiency syndrome and the like, wherein cells having a chemokine receptor play a key role in the onset, progress and maintenance of the disease state.

BACKGROUND ART

As a chemotactic substance that induces migration and topical infiltration of leukocytes such as neutrophile, monocyte and the like, there exist classic chemotactic factors such as decomposition products of a complement (e.g., C3a and C5a), metabolites of arachidonic acid (e.g., leukotriene $B_4$ and the like), platelet-activating factors, formylated peptides derived from bacteria, and the like. These are secondary products that mainly accompany tissue injury. In contrast, a series of cytokines produced by a new gene expression, which are responsible for induction and activation of specific leukocytes, i.e., chemokines, were proved to exist by interleukin (IL)-8 (CXCL8) purified and genetically cloned by Matsushima et al. in 1987 (e.g., Proc. Natl. Acad. Sci. USA, vol. 84, pp. 9223–9237 (1987), and J. Exp. Med., vol. 167, pp. 1883–1893 (1988).

To date, 45 kinds of chemokines have been identified and classified into four subgroups based on the characteristics of their amino acid sequences (e.g., immunity, vol. 12, pp. 121–127 (2000)). Namely, C chemokine, CC chemokine, CXC chemokine and $CX_3C$ chemokine.

XCL1 belonging to C chemokine has a chemotactic activity for T and NK cells. On the other hand, CC chemokine has a chemotactic activity for monocytes other than neutrophile, lymphocytes, Langerhans cells, dendritic cells, eosinophile, mast cells and basocytes. Furthermore, CXC chemokine mainly acts on neutrophiles, as represented by CXCL8, and $CX_3C$ chemokine mainly acts on the migration of NK cells. These chemokines exert their actions when bound with a G protein-coupled receptor (chemokine receptor), and 18 kinds of chemokine receptors have been identified to date (e.g., Cell Technology, vol. 17, pp. 1072–1029, 1998 and Immunity, vol. 12, pp. 121–127, 2000).

Therefore, a substance that prevents binding between chemokine and receptor thereof inhibits selective migration and activation of leukocytes, and is considered to be useful as a pharmaceutical product for the prophylaxis or treatment of acute and chronic inflammatory diseases including allergic diseases, and futher, human immunodeficiency syndrome and the like.

In view of the above, a compound having affinity for a chemokine receptor is expected to be useful as a pharmaceutical product for the prophylaxis or treatment of immune and inflammatory diseases. The present invention aims to provide a pharmaceutical product having affinity for a chemokine receptor and used for treatment or prophylaxis of immune and inflammatory diseases.

With regard to the therapeutic agent of immune and inflammatory diseases, which has affinity for a chemokine receptor, for example, the following patent applications have been published. International publication WO97/24325 discloses diphenylmethane derivatives, WO98/25617 discloses compounds having affinity for a chemokine receptor, such as arylpiperazine derivatives and the like, WO98/02151, WO98/04554 and WO00/34278 disclose tricyclic heteroaromatic derivatives having affinity for a chemokine receptor, and the like, international publications WO99/55324 and WO99/55330 disclose phenylalanine derivatives having affinity for a chemokine receptor, and the like and international publication WO00/58305 discloses piperazine derivatives having affinity for a chemokine receptor, and the like. In addition, international publications WO00/31033, WO00/53600 and WO01/14333 disclose piperidine derivatives and the like, which have affinity for a chemokine receptor.

However, there has been no report to date on a compound having efficacy in a model of allergic disease and the like by oral administration. A compound having efficacy in such disease models and the like is expected to suppress selective migration and activation of leukocytes and be a pharmaceutical product for the treatment or prophylaxis of acute and chronic inflammatory diseases inclusive of allergic diseases, and further, human immunodeficiency syndrome and the like.

DISCLOSURE OF THE INVENTION

In view of the above-mentioned situation, the present inventors have conducted intensive studies in an attempt to find a non-peptide compound having chemokine receptor antagonism and found that a novel benzylpiperidine compound of the formula (1) wherein W (W is aryl, heteroaryl or thiazoline) has $Y^2$ (basic substituent or amino group that formed amide with various acids etc.), an optical isomer thereof and a pharmaceutically acceptable salt thereof have high affinity for chemokine receptors and inhibit binding between chemokine and receptors thereof. Furthermore, the compound of the formula (1) showed efficacy in a model of allergic disease and the like by oral administration after pharmacokinetical improvements. Accordingly, the compound of the present invention suppresses selective migration and activation of leukocytes and can be a pharmaceutical product for the treatment or prophylaxis of acute and chronic inflammatory diseases inclusive of allergic diseases, and further human immunodeficiency syndrome and the like, which resulted in the completion of the present invention.

Accordingly, the present invention relates to the compounds of the following (1) to (23), salts thereof, and the like.

(1) An optionally N-oxidized benzylpiperidine compound represented by the formula (1):

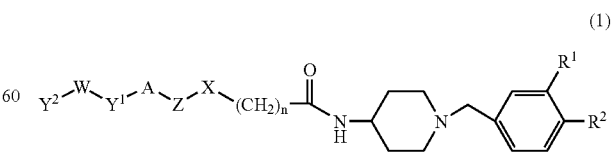

wherein
R$^1$ and R$^2$ are the same or different and each is hydrogen, halogen, cyano, nitro, amino, hydroxy, alkoxy or alkyl, n is an integer of 1 to 5, X is a bond, an oxygen atom, a sulfur atom, SO or $SO_2$, Z is a bond, aryl, heteroaryl or cycloalkyl, $Y^1$ is a bond, an alkylene chain having 1 to 4 carbon atoms, —CO—, -Q-$(CH_2)_m$— or —$(CH_2)_m$-Q- [wherein Q is —NH—, —$NR^3$— (wherein $R^3$ is alkyl), an oxygen atom, a sulfur atom, SO or $SO_2$, m is an integer of 0 to 4], A is aryl or heteroaryl, W is aryl, heteroaryl or thiazoline, $Y^2$ is amino, alkylamino, arylamino, arylalkylamino, acylamino, acylaminoalkyl, alkoxycarbonylamino, carboxymethylamino, aminoalkylamino, —$NR^4CONR^5R^6$ ($R^4$, $R^5$ and $R^6$ may be the same or different and each is hydrogen or alkyl), sulfonylamino, —$CONR^7R^8$ ($R^7$ and $R^8$ may be the same or different and each is hydrogen, alkyl, aryl or arylalkyl, provided that they do not show hydrogen at the same time), aminoalkyl, alkylaminoalkyl, arylaminoalkyl, arylalkylaminoalkyl, cyclic amino, hydrazino, guanidino, amidino, hydroxyamidino, alkoxyamidino, aminomethyleneamino, iminomethylamino, imino or —$SR^{16}$ ($R^{16}$ is alkyl), provided that the above-mentioned aryl, heteroaryl, cycloalkyl, alkylene chain, alkylamino, arylamino, arylalkylamino, acylamino, acylaminoalkyl, alkoxycarbonylamino, carboxymethylamino, aminoalkylamino, sulfonylamino, —$CONR^7R^8$, aminoalkyl, alkylaminoalkyl, arylaminoalkyl, arylalkylaminoalkyl, cyclic amino, hydrazino, guanidino, amidino, aminomethyleneamino, iminomethylamino and imino optionally have substituents, and nitrogen atom in amide, carbamate or sulfonamide contained in the above-mentioned acylamino, acylaminoalkyl, alkoxycarbonylamino and sulfonylamino may be substituted by alkyl, an optical isomer thereof or a pharmaceutically acceptable salt thereof.

(2) The benzylpiperidine compound of the aforementioned (1), wherein, in the formula (1), $Y^2$ is amino, alkylamino, arylamino, arylalkylamino, acylamino, alkoxycarbonylamino, —$NR^4 CONR^5R^6$ ($R^4$, $R^5$ and $R^6$ may be the same or different and each is hydrogen or alkyl), sulfonylamino, aminoalkyl, alkylaminoalkyl, cyclic amino, hydrazino, guanidino, amidino, hydroxyamidino, alkoxyamidino, aminomethyleneamino, iminomethylamino or imino, an optical isomer thereof or a pharmaceutically acceptable salt thereof.

(3) The benzylpiperidine compound of the aforementioned (1), wherein, in the formula (1), $R^1$ and $R^2$ are the same or different and each is hydrogen, halogen, nitro, cyano or alkyl, n is an integer of 1 to 4, Z is a bond or heteroaryl, and $Y^1$ is a bond, an alkylene chain having 1 or 2 carbon atoms, -Q-$(CH_2)_m$— or —$(CH_2)_m$-Q- [wherein Q is —NH—, —$NR^3$— (wherein $R^3$ is alkyl), an oxygen atom, a sulfur atom, SO or $SO_2$, and m is an integer of 0 or 1], an optical isomer thereof or a pharmaceutically acceptable salt thereof.

(4) The benzylpiperidine compound of the aforementioned (1), wherein, in the formula (1), $R^1$ and $R^2$ are the same or different and each is halogen or nitro, n is an integer of 1 to 4, Z is a bond or heteroaryl, $Y^1$ is a bond, and $Y^2$ is amino, alkylamino, arylalkylamino, acylamino, alkoxycarbonylamino, sulfonylamino, cyclic amino, hydrazino, guanidino, amidino, hydroxyamidino, alkoxyamidino, iminomethylamino or imino, an optical isomer thereof or a pharmaceutically acceptable salt thereof.

(5) The benzylpiperidine compound of the aforementioned (1), wherein, in the formula (1), $R^1$ and $R^2$ are the same or different and each is halogen, n is an integer of 1 to 4, X is a bond, an oxygen atom or a sulfur atom, Z and $Y^1$ are each a bond, and $Y^2$ amino, alkylamino, arylalkylamino, acylamino, alkoxycarbonylamino, sulfonylamino, cyclic amino, hydrazino, guanidino, amidino, hydroxyamidino, alkoxyamidino or imino, an optical isomer thereof or a pharmaceutically acceptable salt thereof.

(6) The benzylpiperidine compound of any of the aforementioned (1) to (5), which is selected from [4-(3-aminophenyl)thiazol-2-ylthio]-N-[1-(3,4-dichlorobenzyl)piperidin-4-yl]acetamide, N-[1-(3,4-dichlorobenzyl)-1-oxopiperidin-4-yl]-{4-[3-($N^2$-hydroxyamidino)phenyl]thiazol-2-ylthio}acetamide, N-[1-(3,4-dichlorobenzyl)piperidin-4-yl]-{4-[4-($N^2$-hydroxyamidino)phenyl]thiazol-2-ylthio}acetamide, {4-[3-(L-alanylamino)phenyl]thiazol-2-ylthio}-N-[1-(3,4-dichlorobenzyl)piperidin-4-yl]acetamide, N-[1-(3,4-dichlorobenzyl)piperidin-4-yl]-{4-[3-(4-imidazolecarboxamide)phenyl]thiazol-2-ylthio}acetamide, N-[1-(3,4-dichlorobenzyl)piperidin-4-yl]-{4-[3-(imidazol-2-yl-methylamino)phenyl]thiazol-2-ylthio}acetamide, N-[1-(3,4-dichlorobenzyl)piperidin-4-yl]-{4-[3-(imidazol-4-yl-methylamino)phenyl]thiazol-2-ylthio}acetamide, N-[1-(3,4-dichlorobenzyl)piperidin-4-yl]-4-[4-(2-guanidinothiazol-4-yl)-3-methylphenyloxy]butylamide, [4-(3-aminophenyl)thiazol-2-ylthio]-N-[1-(3,4-dichlorobenzyl)-1-oxopiperidin-4-yl]acetamide, N-[1-(3,4-dichlorobenzyl)piperidin-4-yl]-{4-[3-($N^2$-hydroxyamidino)phenyl]thiazol-2-ylthio}acetamide, N-[1-(3,4-dichlorobenzyl)-1-oxopiperidin-4-yl]-{4-[4-($N^2$-hydroxyamidino)phenyl]thiazol-2-ylthio}acetamide, N-[1-(3,4-dichlorobenzyl)piperidin-4-yl]-{4-[3-(imidazol-4-ylacetamide)phenyl]thiazol-2-ylthio}acetamide, N-[1-(3,4-dichlorobenzyl)piperidin-4-yl]-{4-[3-(2-pyridylmethylamino)phenyl]thiazol-2-ylthio}acetamide, N-[1-(3,4-dichlorobenzyl)piperidin-4-yl]-[5-(2-guanidinothiazol-4-yl)-4-methylthiazol-2-ylthio]acetamide, N-[1-(3,4-dichlorobenzyl)piperidin-4-yl]-{4-[3-(pyridin-3-ylcarboxamide)phenyl]thiazol-2-ylthio}acetamide, and N-[1-(3,4-dichlorobenzyl)piperidin-4-yl]-{4-[3-(pyrrol-2-ylcarboxamide)phenyl]thiazol-2-ylthio}acetamide, or a pharmaceutically acceptable salt thereof.

(7) A pharmaceutical composition comprising a benzylpiperidine compound of any of the aforementioned (1) to (6), an optical isomer thereof or a pharmaceutically acceptable salt thereof, and a pharmaceutically acceptable carrier.

(8) The pharmaceutical composition of the aforementioned (7), which is an agent for the prophylaxis or treatment of rheumatoid arthritis, asthma, allergic rhinitis, allergic conjunctivitis, allergic myelitis, atopic dermatitis or ulcerative colitis.

(9) The benzylpiperidine compound of the aforementioned (1), which is not N-oxidized, wherein, in the formula (1), $Y^2$ is amino, alkylamino, arylamino, arylalkylamino, acylamino, acylaminoalkyl, alkoxycarbonylamino, —$NR^4 CONR^5R^6$ ($R^4$, $R^5$ and $R^6$ may be the same or different and each is hydrogen or alkyl), sulfonylamino, —$CONR^7R^8$ ($R^7$ and $R^8$ may be the same or different and each is hydrogen, alkyl, aryl or arylalkyl, provided that they do not show hydrogen at the same time), aminoalkyl, alkylaminoalkyl, arylaminoalkyl, arylalkylaminoalkyl, cyclic amino, hydrazino, guanidino, amidino, hydroxyamidino, alkoxyamidino, aminomethyleneamino or imino, an optical isomer thereof or a pharmaceutically acceptable salt thereof.

(10) The benzylpiperidine compound of the aforementioned (9), wherein, in the formula (1),
$Y^2$ is amino, alkylamino, arylamino, acylamino, alkoxycarbonylamino, —$NR^4CONR^5R^6$ ($R^4$, $R^5$ and $R^6$ may be the same or different and each is hydrogen or alkyl), sulfonylamino, aminoalkyl, alkylaminoalkyl, cyclic amino, hydrazino, guanidino, amidino, aminomethyleneamino or imino, an optical isomer thereof or a pharmaceutically acceptable salt thereof.

(11) The benzylpiperidine compound of the aforementioned (9), wherein, in the formula (1),
$R^1$ and $R^2$ are the same or different and each is hydrogen, halogen, nitro, cyano or alkyl,
n is an integer of 1 to 4,
Z is a bond or heteroaryl, and
$Y^1$ is a bond, an alkylene chain having 1 or 2 carbon atoms, -Q-$(CH_2)_m$— or —$(CH_2)_m$-Q- [wherein Q is —NH—, —$NR^3$— (wherein $R^3$ is alkyl), an oxygen atom, a sulfur atom, SO or $SO_2$, and m is an integer of from 0 or 1], an optical isomer thereof or a pharmaceutically acceptable salt thereof.

(12) The benzylpiperidine compound of the aforementioned (9), wherein, in the formula (1),
$R^1$ and $R^2$ are the same or different and each is halogen or nitro,
n is an integer of 1 to 4,
Z is a bond or heteroaryl,
$Y^1$ is a bond, and
$Y^2$ is amino, alkylamino, arylalkylamino, acylamino, alkoxycarbonylamino, sulfonylamino, cyclic amino, hydrazino, guanidino, amidino, hydroxyamidino, alkoxyamidino or imino, an optical isomer thereof or a pharmaceutically acceptable salt thereof.

(13) The benzylpiperidine compound of the aforementioned (9), wherein, in the formula (1),
$R^1$ and $R^2$ are the same or different and each is halogen,
n is an integer of 1 to 4,
X is a bond, an oxygen atom or a sulfur atom,
Z and $Y^1$ are each a bond, and
$Y^2$ is amino, alkylamino, acylamino, alkoxycarbonylamino, sulfonylamino, cyclic amino, hydrazino, guanidino, amidino, hydroxyamidino, alkoxyamidino or imino, an optical isomer thereof or a pharmaceutically acceptable salt thereof.

(14) The benzylpiperidine compound of any of the aforementioned (9) to (13), which is selected from N-[1-(3,4-dichlorobenzyl)piperidin-4-yl]-5-[4-(2-guanidinothiazol-4-yl)phenyl]valeramide, N-[1-(3,4-dichlorobenzyl)piperidin-4-yl]-4-[4-(2-guanidinothiazol-4-yl)phenyloxy]butylamide, N-[1-(3,4-dichlorobenzyl)piperidin-4-yl]-4-[4-(2-guanidinothiazol-4-yl)phenylthio]butylamide, [4-(4-aminophenyl)thiazol-2-ylthio]-N-[1-(3,4-dichlorobenzyl)piperidin-4-yl]acetamide, [4-(4-acetylaminophenyl)thiazol-2-ylthio]-N-[1-(3,4-dichlorobenzyl)piperidin-4-yl]acetamide, 4-[4-(2-aminothiazol-4-yl)-3-methylphenyloxy]-N-[1-(3,4-dichlorobenzyl)piperidin-4-yl]butylamide, N-[1-(3,4-dichlorobenzyl)piperidin-4-yl]-4-[4-(2-guanidinothiazol-4-yl)-3-methylphenyloxy]butylamide, [4-(3-aminophenyl)thiazol-2-ylthio]-N-[1-(3,4-dichlorobenzyl)piperidin-4-yl]acetamide, N-[1-(3,4-dichlorobenzyl)piperidin-4-yl]-{4-[3-(4-imidazolecarboxamide)phenyl]thiazol-2-ylthio}acetamide, N-[1-(3,4-dichlorobenzyl)piperidin-4-yl]-{4-[3-(pyrrol-2-ylcarboxamide)phenyl]thiazol-2-ylthio}acetamide, N-[1-(3,4-dichlorobenzyl)piperidin-4-yl]-{4-[3-(pyridin-2-ylcarboxamide)phenyl]thiazol-2-ylthio}acetamide, N-[1-(3,4-dichlorobenzyl)piperidin-4-yl]-{4-[3-(pyridin-3-ylcarboxamide)phenyl]thiazol-2-ylthio}acetamide, {4-[3-(L-prolylamino)phenyl]thiazol-2-ylthio)-N-[1-(3,4-dichlorobenzyl)piperidin-4-yl]acetamide, [4-(2-aminopyridin-5-yl)thiazol-2-ylthio]-N-[1-(3,4-dichlorobenzyl)piperidin-4-yl]acetamide and [4-(2-aminopyridin-4-yl)thiazol-2-ylthio]-N-[1-(3,4-dichlorobenzyl)piperidin-4-yl]acetamide, or a pharmaceutically acceptable salt thereof.

(15) A pharmaceutical composition comprising a benzylpiperidine compound of any of the aforementioned (9) to (14), an optical isomer thereof or a pharmaceutically acceptable salt thereof, and a pharmaceutically acceptable carrier.

(16) The pharmaceutical composition of the aforementioned (15), which is an agent for the prophylaxis or treatment of rheumatoid arthritis, asthma, allergic rhinitis, allergic conjunctivitis, allergic myelitis, atopic dermatitis or ulcerative colitis.

(17) The benzylpiperidine compound of the aforementioned (1), which is not N-oxidized, wherein, in the formula (1),
$Y^2$ is amino, alkylamino, arylamino, acylamino, alkoxycarbonylamino, —$NR^4CONR^5R^6$ ($R^4$, $R^5$ and $R^6$ may be the same or different and each is hydrogen or alkyl), sulfonylamino, aminoalkyl, alkylaminoalkyl, cyclic amino, hydrazino, guanidino, amidino, aminomethyleneamino or imino, an optical isomer thereof or a pharmaceutically acceptable salt thereof.

(18) The benzylpiperidine compound of the aforementioned (17), wherein, in the formula (1),
$R^1$ and $R^2$ are the same or different and each is hydrogen, halogen, nitro, cyano or alkyl,
n is an integer of 1 to 4,
Z is a bond or heteroaryl, and
$Y^1$ is a bond, an alkylene chain having 1 or 2 carbon atoms, -Q-$(CH_2)_m$— or —$(CH_2)_m$-Q- [wherein Q is —NH—, —$NR^3$— (wherein $R^3$ is alkyl), an oxygen atom, a sulfur atom, SO or $SO_2$, and m is an integer of from 0 or 1], an optical isomer thereof or a pharmaceutically acceptable salt thereof.

(19) The benzylpiperidine compound of the aforementioned (17), wherein, in the formula (1),
$R^1$ and $R^2$ are the same or different and each is halogen or nitro,
n is an integer of 1 to 4,
Z is a bond or heteroaryl,
$Y^1$ is a bond, and
$Y^2$ is amino, alkylamino, acylamino, alkoxycarbonylamino, cyclic amino, hydrazino, guanidino, amidino or imino, an optical isomer thereof or a pharmaceutically acceptable salt thereof.

(20) The benzylpiperidine compound of the aforementioned (17), wherein, in the formula (1),
$R^1$ and $R^2$ are the same or different and each is halogen,
n is an integer of 1 to 4,
X is a bond, an oxygen atom or a sulfur atom,
Z and $Y^1$ are each a bond, and
$Y^2$ is amino, alkylamino, acylamino, alkoxycarbonylamino, cyclic amino, hydrazino, guanidino, amidino or imino, an optical isomer thereof or a pharmaceutically acceptable salt thereof.

(21) The benzylpiperidine compound of any of the aforementioned (17) to (20), which is selected from N-[1-(3, 4-dichlorobenzyl)piperidin-4-yl]-5-[4-(2-guanidinothiazol-4-yl)phenyl]valeramide, N-[1-(3,4-dichlorobenzyl)piperidin-4-yl]-4-[4-(2-guanidinothiazol-4-yl)phenyloxy]butylamide, N-[1-(3,4-dichlorobenzyl)piperidin-4-yl]-4-[4-(2-guanidinothiazol-4-yl)phenylthio]butylamide, [4-(4-aminophenyl)thiazol-2-ylthio]-N-[1-(3,4-dichlorobenzyl)piperidin-4-yl]acetamide and [4-(4-acetylaminophenyl)thiazol-2-ylthio]-N-[1-(3,4-dichlorobenzyl)piperidin-4-yl]acetamide, or a pharmaceutically acceptable salt thereof.

(22) A pharmaceutical composition comprising a benzylpiperidine compound of any of the aforementioned (17) to (21), an optical isomer thereof or a pharmaceutically acceptable salt thereof, and a pharmaceutically acceptable carrier.

(23) The pharmaceutical composition of the aforementioned (22), which is an agent for the prophylaxis or treatment of rheumatoid arthritis, asthma, allergic rhinitis, allergic conjunctivitis, allergic myelitis, atopic dermatitis or ulcerative colitis.

DETAILED DESCRIPTION OF THE INVENTION

Figure 1:
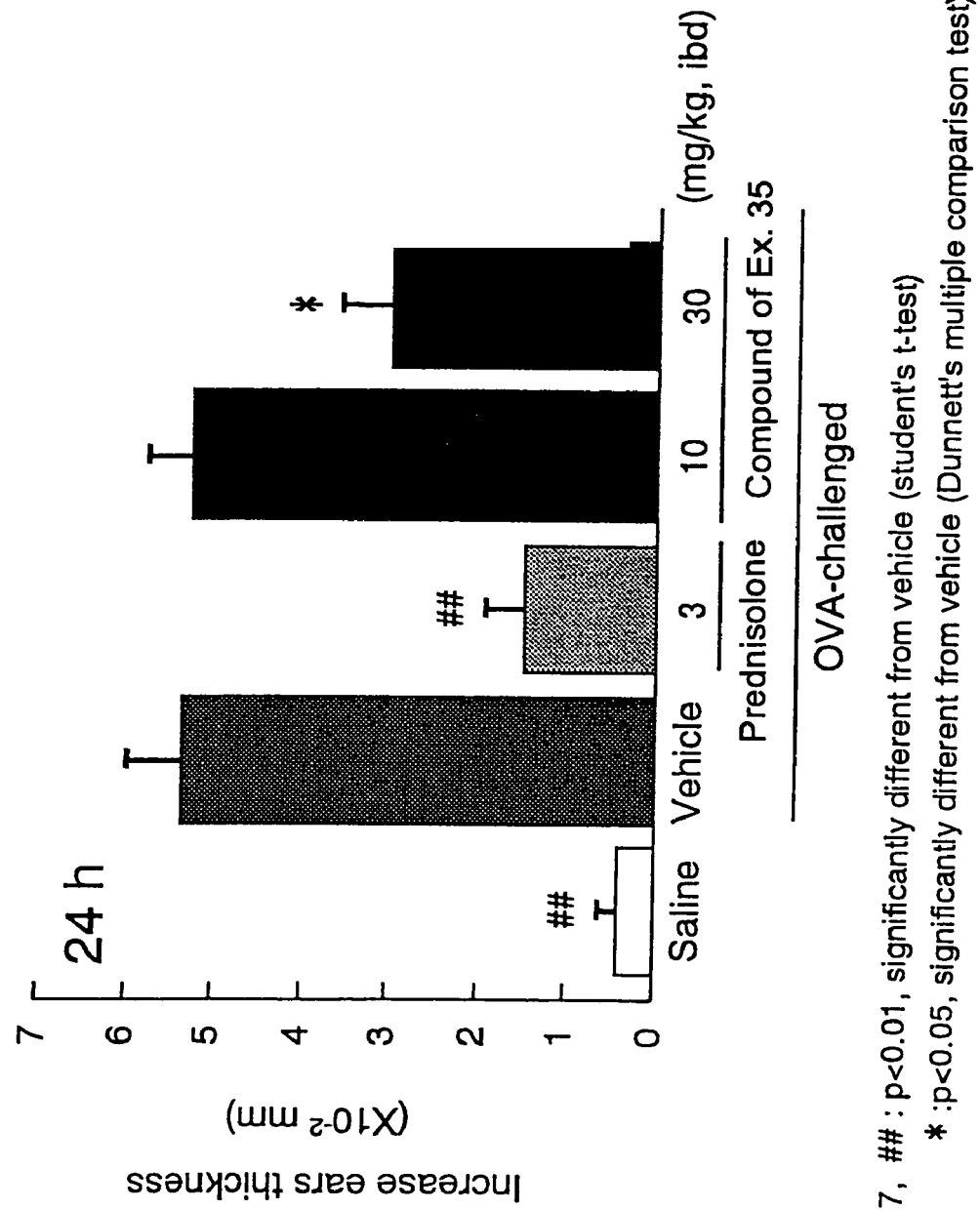
FIG. 1 is a graph showing the effect of the compound of the present invention on a mouse antigen-induced biphasic ear edema model (delayed response).

Some of the terms used in the present specification are defined as follows.

By the "substituent necessary for heteroaryl construction" is meant a substituent necessary for constructing heteroaryl by addition, in most cases, by acid or base catalyst, light, heat and the like, or by a condensation reaction accompanying elimination of water, alcohol, acid, hydrogen halide and the like.

As the specific substituent, any of the combination of bromoacetyl and thiamide for construction of thiazole, any of the combination of hydrazide and carboxylic acid for construction of 1,3,4-oxadiazole, any of the combination of acetyloxime and carboxylic acid ester for construction of 1,2,4-oxadiazole, any of the combination of oxime and carboxylic acid for construction of isoxazole, any of the combination of S-methylthiamide and hydrazide for construction of 1,2,4-triazole, and the like can be mentioned.

The substituent of the "optionally having substituents" means halogen (fluorine, chlorine, bromine, iodine etc.), haloalkyl having 1 to 6 carbon atoms (trifluoromethyl etc.), alkyl having 1 to 6 carbon atoms (methyl, ethyl, propyl, isopropyl, butyl, isobutyl, tert-butyl etc.), alkoxy having 1 to 8 carbon atoms (methoxy, ethoxy, propoxy, isopropoxy, butoxy, isobutoxy, tert-butoxy, pentyloxy, hexyloxy, heptyloxy, octyloxy etc.), aryl having 6 to 10 carbon atoms (phenyl, naphthyl etc.), hydroxy, mercapto, carboxy, nitro, amino or alkylamino having 1 to 8 carbon atoms (methylamino, ethylamino, dimethylamino, propylamino, isopropylamino, butylamino, diisopropylamino etc.).

The number of the above-mentioned substituent is not particularly limited.

By the "optionally N-oxidized" is meant that, in the compound of the formula (1), an "oxidizable nitrogen atom" may be oxidized by a method known to those of ordinary skill in the art of the organic synthesis. The "oxidizable nitrogen atom" is not particularly limited, and, for example, a nitrogen atom in the piperidyl group of the formula (1):

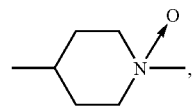

a nitrogen atom in the heteroaryl for Z, A and W in the formula (1), a nitrogen atom contained in the group for $Y^1$ in the formula (1), and a nitrogen atom in the hetero ring and cyclic amino contained in the group for $Y^2$ in the formula (1) and a nitrogen atom in the nitrogen-containing group contained in the group for $Y^2$ in the formula (1) to be definined in the following, and the like can be mentioned.

The definition of each symbol and the like used in the resent specification is as follows.

For $R^1$ or $R^2$, the halogen means fluorine, chlorine, bromine, iodine and the like; the alkoxy means alkoxy having 1 to 8 carbon atoms, such as methoxy, ethoxy, propoxy, isopropoxy, butoxy, isobutoxy, tert-butoxy, pentyloxy, hexyloxy, heptyloxy, octyloxy and the like; and the alkyl means alkyl having 1 to 18 carbon atoms, such as methyl, ethyl, propyl, isopropyl, butyl, isobutyl, tert-butyl, pentyl, hexyl, heptyl, octyl, decyl, hexadecyl, octadecyl and the like.

As the substituents of $R^1$ and $R^2$, chlorine, fluorine and nitro, which are the same or different, can be preferably mentioned.

n is an integer of 1 to 5, preferably an integer of 1 to 4.

The cycloalkyl for Z means cycloalkyl having 3 to 8 carbon atoms, such as cyclopropyl, cyclobutyl, cyclopentyl, cyclohexyl, cycloheptyl, cyclooctyl and the like.

The aryl for Z, A or W means aryl having 6 to 10 carbon atoms, such as phenyl, naphthyl, or indanyl or tetrahydronaphthyl wherein the cycloalkyl and a benzene ring are condensed, and the like.

The heteroaryl means a 5- or 6-membered aromatic heterocycle containing 1 or 2 kinds of 1 to 3 hetero atoms selected from nitrogen atom, sulfur atom and oxygen atom, such as furyl, thienyl, pyrrolyl, thiazolyl, pyrazolyl, oxazolyl, isoxazolyl, imidazolyl, 1,2,4-oxadiazolyl, 1,3,4-oxadiazolyl, 1,2,3-triazolyl, 1,2,4-triazolyl, 1,2,4-thiadiazolyl, 1,3,4-thiadiazolyl, pyridyl, pyrimidinyl and the like. The nitrogen atom that may be contained in the aromatic heterocycle may be N-oxidized.

In addition, the heteroaryl means an aromatic heterocycle wherein the 5- or 6-membered aromatic heterocycle containing 1 or 2 kinds of 1 or 2 hetero atoms selected from nitrogen atom, sulfur atom and oxygen atom is condensed with a benzene ring, such as indolyl, benzo[b]furyl, benzo[b]thienyl, benzimidazolyl, benzoxazolyl, benzisoxazolyl, benzothiazolyl, benzisothiazolyl, quinolyl and the like. The nitrogen atom that may be contained in the aromatic heterocycle condensed with the benzene ring may be N-oxidized.

As the thiazoline for W, for example, thiazoline such as 4-thiazoline and the like can be mentioned, and 4-thiazolin-4-yl is particularly preferable.

The alkylene chain having 1 to 4 carbon atoms for $Y^1$ means methylene, ethylene, trimethylene, tetramethylene and the like, and when substituted by 1 or more alkyl, it shows branched alkylene chain (methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene etc.).

As the alkylene chain for $Y^1$, methylene and ethylene are preferable.

In -Q-$(CH_2)_m$— and —$(CH_2)_m$-Q- for $Y^1$, Q means —NH—, —$NR^3$— (wherein $R^3$ is alkyl), oxygen atom, sulfur atom, SO or $SO_2$.

As the alkyl for $R^3$, alkyl having 1 to 6 carbon atoms can be mentioned, wherein the alkyl means the same as alkyl for $R^1$ and $R^2$.

m is an integer of 0 to 4, which is preferably 0 or 1.

The alkylamino for $Y^2$ means alkylamino having 1 to 6 carbon atoms, such as methylamino, dimethylamino, ethylamino, diethylamino, propylamino, dipropylamino, cyclopropylamino, cyclobutylamino and the like.

The arylamino means arylamino having 6 to 12 carbon atoms, such as phenylamino, diphenylamino and the like.

The arylalkylamino means, for example, arylalkylamino having 7 to 11 carbon atoms, such as benzylamino, phenethylamino and the like. It encompasses heteroarylalkylamino having 2 to 10 carbon atoms, such as pyridylmethylamino, imidazolylmethylamino and the like.

The acylamino means acylamino having 1 to 20 carbon atoms, such as alkylcarbonylamino having 1 to 6 carbon atoms (e.g., acetylamino, trifluoromethylcarbonylamino, propanoylamino, butyroylamino, isobutyroylcarbonylamino and the like), cycloalkylcarbonylamino having 4 to 8 carbon atoms (e.g., cyclopropylcarbonylamino, cyclohexylcarbonylamino and the like), alkenylcarbonylamino having 3 to 8 carbon atoms (e.g., acryloyl, crotonoyl and the like), alkynylcarbonylamino having 3 to 8 carbon atoms (e.g., propyoyl and the like), arylcarbonylamino having 7 to 11 carbon atoms (e.g., benzoylamino and the like), heteroarylcarbonylamino having 2 to 10 carbon atoms (e.g., pyridylcarbonylamino, piperidylcarbonylamino, imidazolylcarbonylamino, pyrrolylcarbonylamino, pyrazolylcarbonylamino, isoxazolylcarbonylamino, thienylcarbonylamino and the like), heteroarylalkylcarbonylamino (e.g., imidazolylacetamino, pyridylacetoamino, pyridylpropionylamino etc.), aminoalkylcarbonylamino having 2 to 7 carbon atoms (e.g., glycylamino, 2-aminopropanoylamino, 3-aminopropanoylamino, 4-aminobutanoylamino and the like) and amino protected groups thereof, nitrogen-containing cycloalkylcarbonylamino having 4 to 8 carbon atoms (e.g., piperidylcarbonylamino, piperazylcarbonylamino, pyrrolidylcarbonylamino, morpholylcarbonylamino and the like) and amino protected groups thereof.

The above-mentioned alkylcarbonylamino, cycloalkylcarbonylamino, arylcarbonylamino, heteroarylcarbonylamino and nitrogen-containing cycloalkylcarbonylamino may have 1 to 4 substituents. In addition, the aminoalkylcarbonylamino and amino protected groups thereof may have 1 or 2 substituents. As the substituents, hydroxy, alkyl group, hydroxyalkyl group such as hydroxymethyl and the like, aryl group, arylalkyl group having 7 to 13 carbon atoms such as benzyl and the like, heteroarylalkyl group such as pyridylmethyl and the like, as well as, side chain of amino acid such as aspartic acid [the carboxyl group may be protected by ester and the like (e.g., tert-butyl ester etc.)], threonine [the hydroxy may be protected by ether and the like (e.g., benzyl ether etc.)], tyrosine [the hydroxy may be protected by ether and the like (e.g., tert-butyl ether etc.)], lysin [the amino group may be protected by acyl and the like (e.g., acetyl etc.)], phenylalanine, tryptophan, valine, norvaline and the like, and side chain of abnormal amino acid such as cyclohexylglycine, homophenylalanine, hydroxyalanine and the like can be mentioned. The term "side chain of amino acid" used in the above means a substituent part possessed by α carbon in amino acid (including L-amino acids, D-amino acids and abnormal amino acids).

As the amino-protecting group for the above-mentioned "aminoalkylcarbonylamino and amino protected groups thereof", "nitrogen-containing cycloalkylcarbonylamino and amino protected groups thereof", general amino-protecting groups can be mentioned, which are free of any particularly limitation, and tert-butoxycarbonyl is particularly preferable.

The acylaminoalkyl means acylaminoalkyl having 2 to 12 carbon atoms, such as the above-mentioned acylamino groups having methyl or ethyl group attached thereto. Examples thereof include pyridylcarbonylaminomethyl, imidazolylcarbonylaminomethyl and the like.

The alkoxycarbonylamino means alkoxycarbonylamino having 2 to 10 carbon atoms, such as methoxycarbonylamino, ethoxycarbonylamino, phenyloxycarbonylamino, benzyloxycarbonylamino and the like.

The carboxymethylamino means $HOOCCH_2NH$—, including that wherein the carboxyl group is protected by an ester (e.g., ethyl ester etc.).

The alkyl for $R^4$, $R^5$ or $R^6$ means alkyl having 1 to 6 carbon atoms, which is similar to alkyl for $R^1$ or $R^2$.

The sulfonylamino means a group having a sulfonamide bond (—$SO_2NH$—), and includes, for example, alkylsulfonylamino having 1 to 6 carbon atoms such as methanesulfonylamino, ethanesulfonylamino and the like, cycloalkylsulfonylamino having 3 to 9 carbon atoms such as cyclopropylsulfonylamino, cyclohexylsulfonylamino and the like, arylsulfonylamino having 6 to 10 carbon atoms such as phenylsulfonylamino and the like, heteroarylsulfonylamino such as pyridylsulfonylamino, imidazolylsulfonylamino, pyrrolylsulfonylamino and the like, aminoalkylsulfonylamino having 1 to 6 carbon atoms such as aminomethylsulfonylamino, 3-aminopropylsulfonylamino, 4-aminobutylsulfonylamino and the like, and amino protected groups thereof, nitrogen-containing cycloalkylsulfonylamino having 3 to 7 carbon atoms such as piperidylsulfonylamino, piperazylsulfonylamino, pyrrolidylsulfonylamino, morpholylsulfonylamino and the like, and amino protected groups thereof.

The above-mentioned alkylsulfonylamino, cycloalkylsulfonylamino, arylsulfonylamino, heteroarylsulfonylamino and nitrogen-containing cycloalkylsulfonylamino may have 1 to 4 substituents. The aminoalkylsulfonylamino and amino protected groups thereof may have 1 or 2 substituents. Examples of the substituent include alkyl group, aryl group, side chain of amino acid such as aspartic acid, lysin, tryptophan and the like, and side chain of abnormal amino acid such as cyclohexylglycine, homophenylalanine and the like.

The amino protected group of the "aminoalkylsulfonylamino and amino protected groups thereof", and the "nitrogen-containing cycloalkylsulfonylamino and amino protected groups thereof" means that the amino group is protected by a conventional amino-protecting group (e.g., tert-butoxycarbonyl etc.) by a method known to those of ordinary skill in the art of the organic synthesis.

The alkyl for $R^7$ or $R^8$ is alkyl having 1 to 6 carbon atoms and means the same as alkyl for $R^1$ or $R^2$. The aryl for $R^7$ or $R^8$ means aryl having 6 to 10 carbon atoms such as phenyl and the like, and encompasses heteroaryl such as pyridyl, imidazolyl and the like. The arylalkyl for $R^7$ or $R^8$ means arylalkyl having 7 to 13 carbon atoms such as benzyl and the like, and encompasses heteroarylalkyl having 2 to 10 carbon atoms such as pyridylmethyl, pyridylethyl, imidazolylmethyl and the like.

The aminoalkyl is, for example, aminoalkyl having 1 to 8 carbon atoms, such as aminomethyl, 1-aminoethyl, 2-aminoethyl, 3-aminopropyl, 4-aminobutyl and the like. The amino may be protected by a conventional amino-protecting group (e.g., tert-butoxycarbonyl etc.).

The arylaminoalkyl means arylaminoalkyl having 7 to 13 carbon atoms, such as phenylaminomethyl and the like, and encompasses heteroarylaminoalkyl having 2 to 10 carbon atoms such as pyridylaminomethyl and the like.

The arylalkylaminoalkyl means arylalkylaminoalkyl having 8 to 14 carbon atoms, such as benzylaminomethyl and the like and encompasses heteroarylalkylaminoalkyl having 3 to 11 carbon atoms, such as pyridylmethylaminomethyl and the like.

The alkylaminoalkyl means alkylaminoalkyl having 2 to 14 carbon atoms, such as methylaminomethyl, dimethylaminomethyl, 2-(methylamino)ethyl, 2-(dimethylamino)ethyl and the like.

The alkoxyamidino means alkoxyamidino having 2 to 10 carbon atoms, such as methoxyamidino, phenoxyamidino and the like.

The aminoalkylamino means a group represented by H$_2$N—(CH$_2$)$_t$—NH— (wherein t is an integer of 2 to 6) wherein the amine terminal may be protected by a conventional amino-protecting group (e.g., tert-butoxycarbonyl etc.), and wherein the alkyl moiety may have, as a substituent, for example, alkyl group having 1 to 6 carbon atoms (e.g., methyl, ethyl, propyl etc.), hydroxyalkyl group having 1 to 6 carbon atoms (e.g., hydroxymethyl etc.), alkoxyalkyl having 2 to 8 carbon atoms (e.g., methoxymethyl, ethoxymethyl, isopropoxymethyl etc.) and the like.

When the alkyl moiety of the aminoalkylamino has, as a substituent, an alkyl group, the alkyl group may form a ring together with the terminal amino group. For example,

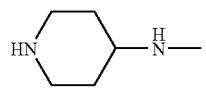

wherein the nitrogen atom in the piperidine ring may be protected by an amino-protecting group such as tert-butoxycarbonyl and the like) and the like can be mentioned.

When the alkyl moiety of the aminoalkylamino has, as a substituent, an alkoxyalkyl group, the alkoxyalkyl group may form a ring together with the terminal amino group. For example,

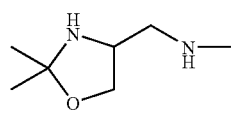

wherein the nitrogen atom in the oxazolidine ring may be protected by an amino-protecting group such as tert-butoxycarbonyl and the like, and the like can be mentioned.

In addition, the terminal amino group may be taken together with the alkyl moiety to form a ring. For example,

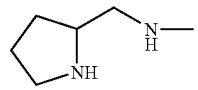

wherein the nitrogen atom in the pyrrolidine ring may be protected by an amino-protecting group such as tert-butoxycarbonyl and the like, and the like can be mentioned.

The nitrogen atoms of the above-mentioned rings may be N-oxidized by a a method known to those of ordinary skill in the art of the organic synthesis As the ring that the aminoalkylamino encompasses, heterocycles has 3 to 7 carbon atoms and 1 to 3 nitrogen atoms can be mentioned, such as pyrrolidine, piperidine and the like, and it may further contain 1 or 2 oxygen atoms. As a heterocycle containing an oxygen atom, for example, oxazolidine and the like can be mentioned. The nitrogen atom in the heterocycle may be N-oxidized and/or may be protected with an amino-protecting group such as tert-butoxycarbonyl and the like.

As the aminoalkylamino having a ring, for example, pyrrolidin-2-ylmethylamino, piperidin-4-ylamino, 2,2-dimethyloxazolidin-4-ylmethylamino and the like can be mentioned, and the nitrogen atom in the ring may be protected with an amino-protecting group such as tert-butoxycarbonyl and the like.

The iminomethylamino is a group represented by HN=CH—NH—, and the group may have substituent(s). As the substituent, for example, hydroxy, methoxy, ethoxy and the like can be entioned, with preference given to HO—N=CH—NH—.

The cyclic amino for Y$^2$ is a cyclic amino containing 1 to 3 nitrogen atoms and 3 to 7 carbon atoms, such as pyrrolizinyl, piperidinyl, piperazinyl, morpholinyl, homopiperidinyl and the like. These cyclic aminos may have the same or different substituents such as amino, acylamino, hydroxy, alkoxy, alkyl, acyl (e.g., acetyl, trifluoroacetyl, propanoyl, butyroyl, isobutyroyl, cycloheptylcarbonyl, benzoyl, phenylacetyl etc.), aryl (e.g., phenyl, naphthyl etc.), arylalkyl (e.g., benzyl, phenethyl, phenylpropyl, naphthylmethyl etc.) and the like, wherein, as the acylamino, the acylamino for Y$^2$ can be mentioned, and as the alkoxy and alkyl, those similar to the alkoxy and alkyl for R$^1$ can be mentioned. The nitrogen atom in the cyclic amino may be protected with a conventional amino-protecting group (e.g., tert-butoxycarbonyl etc.) and/or may be N-oxidized. The cyclic amino may be condensed with a benzene ring, and as a cyclic amino condensed with a benzene ring, for example, 1,2,3,4-tetrahydroisoquinolinyl and the like can be mentioned. The nitrogen atom in the cyclic amino condensed with a benzene ring may be protected with a conventional amino-protecting group (e.g., tert-butoxycarbonyl etc.) and/or may be N-oxidized. When a carbon atom in the cyclic amino has two hydroxy substituents, the hydroxys may be crosslinked with alkylene (e.g., ethylene etc.) to form a spiro ring such as

This spiro ring may further be N-oxidized.

The hydrazino, guanidino, amidino, aminomethyleneamino and imino for Y$^2$ may have alkyl or phenyl on the substitutable nitrogen atom. As this alkyl, those similar to the alkyl for $R^1$ can be mentioned, and when plural alkyls are present, two of them are bonded with each other, and may form a 5 or 6-membered ring together with hydrazino, guanidine or amidino they attached to.

In —$SR^{16}$ denoted by $Y^2$, $R^{16}$ means alkyl having 1 to 8 carbon atoms, and the alkyl means those similar to the alkyl for $R^1$ and $R^2$.

In the formula (1), n is an integer of 1 to 5, with preference given to an integer of 1 to 4.

As the preferable compounds of the formula (1), a compound selected from N-[1-(3,4-dichlorobenzyl)piperidin-4-yl]-5-[4-(2-guanidinothiazol-4-yl)phenyl]valeramide, N-[1-(3,4-dichlorobenzyl)piperidin-4-yl]-4-[4-(2-guanidinothiazol-4-yl)phenyloxy]butylamide, N-[1-(3,4-dichlorobenzyl)piperidin-4-yl]-4-[4-(2-guanidinothiazol-4-yl)phenylthio]butylamide, [4-(4-aminophenyl)thiazol-2-ylthio]-N-[1-(3,4-dichlorobenzyl)piperidin-4-yl]acetamide, [4-(4-acetylaminophenyl)thiazol-2-ylthio]-N-[1-(3,4-dichlorobenzyl)piperidin-4-yl]acetamide, 4-[4-(2-aminothiazol-4-yl)-3-methylphenyloxy]-N-[1-(3,4-dichlorobenzyl)piperidin-4-yl]butylamide, N-[1-(3,4-dichlorobenzyl)piperidin-4-yl]-4-[4-(2-guanidinothiazol-4-yl)-3-methylphenyloxy]butylamide, [4-(3-aminophenyl)thiazol-2-ylthio]-N-[1-(3,4-dichlorobenzyl)piperidin-4-yl]acetamide, N-[1-(3,4-dichlorobenzyl)piperidin-4-yl]-{4-[3-(4-imidazolecarboxamide)phenyl]thiazol-2-ylthio}acetamide, N-[1-(3,4-dichlorobenzyl)piperidin-4-yl]-{4-[3-(pyrrol-2-ylcarboxamide)phenyl]thiazol-2-ylthio)acetamide, N-[1-(3,4-dichlorobenzyl)piperidin-4-yl]-{4-[3-(pyridin-2-ylcarboxamide)phenyl]thiazol-2-ylthio)acetamide, N-[1-(3,4-dichlorobenzyl)piperidin-4-yl]-(4-[3-(pyridin-3-ylcarboxamide)phenyl]thiazol-2-ylthio}acetamide, {4-[3-(L-prolylamino)phenyl]thiazol-2-ylthio}-N-[1-(3,4-dichlorobenzyl)piperidin-4-yl]acetamide, [4-(2-aminopyridin-5-yl)thiazol-2-ylthio]-N-[1-(3,4-dichlorobenzyl)piperidin-4-yl]acetamide, [4-(2-aminopyridin-4-yl)thiazol-2-ylthio]-N-[1-(3,4-dichlorobenzyl)piperidin-4-yl]acetamide, {4-[3-(L-alanylamino)phenyl]thiazol-2-ylthio}-N-[1-(3,4-dichlorobenzyl)piperidin-4-yl]acetamide, N-[1-(3,4-dichlorobenzyl)piperidin-4-yl]-(4-[3-(imidazol-4-yl-methylamino)phenyl]thiazol-2-ylthio}acetamide, N-[1-(3,4-dichlorobenzyl)piperidin-4-yl]-{4-[3-(2-pyridylmethylamino)phenyl]thiazol-2-ylthio}acetamide, N-[1-(3,4-dichlorobenzyl)piperidin-4-yl]-{4-[3-(imidazol-2-yl-methylamino)phenyl]thiazol-2-ylthio}acetamide, N-[1-(3,4-dichlorobenzyl)-1-oxopiperidin-4-yl]-{4-[3-(N²-hydroxyamidino)phenyl]thiazol-2-ylthio}acetamide, N-[1-(3,4-dichlorobenzyl)piperidin-4-yl]-{4-[4-(N²-hydroxyamidino)phenyl]thiazol-2-ylthio}acetamide, N-[1-(3,4-dichlorobenzyl)piperidin-4-yl]-(4-[3-(hydroxyiminomethylamino)phenyl]thiazol-2-ylthio}acetamide, and [4-(3-aminophenylthiazol-2-ylthio)]-N-[1-(3,4-dichlorobenzyl)-1-oxopiperidin-4-yl]acetamide, or a pharmaceutically acceptable salt thereof can be mentioned.

Among the preferable compounds of the formula (1), a particularly preferable compound is a compound selected from [4-(3-aminophenyl)thiazol-2-ylthio]-N-[1-(3,4-dichlorobenzyl)piperidin-4-yl]acetamide, N-[1-(3,4-dichlorobenzyl)-1-oxopiperidin-4-yl]-{4-[3-(N²-hydroxyamidino)phenyl]thiazol-2-ylthio}acetamide, N-[1-(3,4-dichlorobenzyl)piperidin-4-yl]-{4-[4-(N²-hydroxyamidino)phenyl]thiazol-2-ylthio}acetamide, {4-[3-(L-alanylamino)phenyl]thiazol-2-ylthio}-N-[1-(3,4-dichlorobenzyl)piperidin-4-yl]acetamide, N-[1-(3,4-dichlorobenzyl)piperidin-4-yl]-{4-[3-(4-imidazolecarboxamide)phenyl]thiazol-2-ylthio}acetamide, N-[1-(3,4-dichlorobenzyl)piperidin-4-yl]-{4-[3-(imidazol-2-yl-methylamino)phenyl]thiazol-2-ylthio}acetamide, N-[1-(3,4-dichlorobenzyl)piperidin-4-yl]-(4-[3-(imidazol-4-yl-methylamino)phenyl]thiazol-2-ylthio}acetamide, N-[1-(3,4-dichlorobenzyl)piperidin-4-yl]-4-[4-(2-guanidinothiazol-4-yl)-3-methylphenyloxy]butylamide, [4-(3-aminophenyl)thiazol-2-ylthio]-N-[1-(3,4-dichlorobenzyl)-1-oxopiperidin-4-yl]acetamide, N-[1-(3,4-dichlorobenzyl)piperidin-4-yl]-{4-[3-(N²-hydroxyamidino)phenyl[thiazol-2-ylthio}acetamide, N-[1-(3,4-dichlorobenzyl)-1-oxopiperidin-4-yl]-{4-[4-(N²-hydroxyamidino)phenyl]thiazol-2-ylthio}acetamide, N-[1-(3,4-dichlorobenzyl)piperidin-4-yl]-(4-[3-(imidazol-4-ylacetamide)phenyl]thiazol-2-ylthio}acetamide, N-[1-(3,4-dichlorobenzyl)piperidin-4-yl]-{4-[3-(2-pyridylmethylamino)phenyl]thiazol-2-ylthio}acetamide, N-[1-(3,4-dichlorobenzyl)piperidin-4-yl]-[5-(2-guanidinothiazol-4-yl)-4-methylthiazol-2-ylthio]acetamide, N-[1-(3,4-dichlorobenzyl)piperidin-4-yl]-{4-[3-(pyridin-3-ylcarboxamide)phenyl]thiazol-2-ylthio}acetamide and N-[1-(3,4-dichlorobenzyl)piperidin-4-yl]-(4-[3-(pyrrol-2-ylcarboxamide)phenyl]thiazol-2-ylthio}acetamide, and a pharmaceutically acceptable salt thereof can be mentioned.

The compound of the formula (1) and a pharmaceutically acceptable salt thereof may present in the form of a hydrate or a solvate, and these hydrates and solvates are also encompassed in the present invention. When the compound of the formula (1) has asymmetric atoms, at least two kinds of optical isomers are present. These optical isomers and racemate thereof are encompassed in the present invention.

The compound of the present invention, which is represented by the formula (1), can be synthesized by the following methods (1)–(12) and a method analogous thereto.

These methods may be used in combination.

Method (1)

A compound of the formula (2):

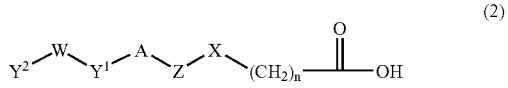

(2)

wherein each symbol is as defined above, or an acid addition salt thereof (hydrochloride, hydrobromide, sulfate, oxalate etc.) is reacted with a compound of the formula (3):

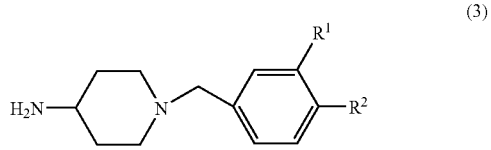

(3)

wherein each symbol is as defined above, or an acid addition salt thereof (hydrochloride, hydrobromide, sulfate, oxalate etc.) in a suitable solvent that does not inhibit the reaction, such as tetrahydrofuran (hereinafter abbreviated as THF), dichloromethane, N,N-dimethylformamide (hereinafter abbreviated as DMF) or an optionally mixed solvent of these etc., in the presence of tertiary amine such as triethylamine, diisopropylethylamine and the like, using a condensing agent (e.g., dicyclohexylcarbodiimide (hereinafter abbreviated as DCC), N-(3-dimethylaminopropyl)-N'-ethylcarbodiimide (hereinafter abbreviated as EDC) or a hydrochloride thereof, 2-ethoxy-1-ethoxycarbonyl-1,2-dihydroxyquinoline (hereinafter abbreviated as EEDQ), carbodiimidazole (hereinafter abbreviated as CDI), diethylphosphorylcyanide, benzotriazol-1-yloxytripyrrolidinophosphonium hexafluorophosphate (hereinafter abbreviated as PyBOP), diphenylphosphorylazide (hereinafter abbreviated as DPPA), isobutyl chloroformate, diethylacetyl chloride, trimethylacetyl chloride and the like) alone or in combination with an additive such as N-hydroxysuccinimide (hereinafter abbreviated as HONSU), hydroxybenzotriazole (hereinafter abbreviated as HOBT), or 3-hydroxy-4-oxo-3,4-dihydro-1,2,3-benzotriazine (hereinafter abbreviated as HOOBT), 4-dimethylaminopyridine (hereinafter abbreviated as DMAP) and the like generally at a temperature of –30° C. to 80° C., preferably –10° C. to 25° C., for 1–24 hr to give a compound of the formula (1):

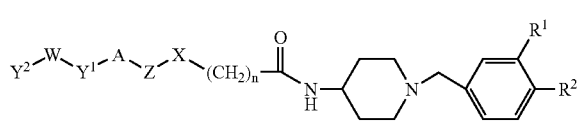
(1)

wherein each symbol is as defined above.

In addition, by a reaction in the same manner using a reactive derivative of a compound of the formula (2) (acid chloride, acylimidazole etc.), a compound of the formula (1) can be obtained.

Generally, this reaction is carried out in a suitable solvent that does not inhibit the reaction (THF, dichloromethane, chloroform, benzene or an optionally mixed solvent of these etc.) in the presence of tertiary amine such as triethylamine and the like or pyridine and the like, under ice-cooling or at room temperature for 1–24 hr.

Method (2)

A compound of the formula (2):

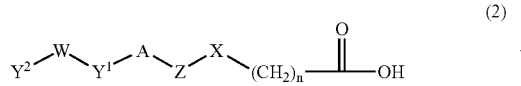
(2)

wherein each symbol is as defined above, or an acid addition salt thereof (hydrochloride, hydrobromide, sulfate, oxalate etc.) is reacted with a compound of the formula (4):

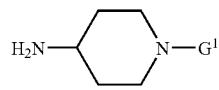
(4)

wherein $G^1$ is a protecting group (e.g., tert-butoxycarbonyl (Boc), benzyloxycarbonyl(Cbz)), or an acid addition salt thereof (hydrochloride, hydrobromide, sulfate, oxalate etc.) in a suitable solvent that does not inhibit the reaction (THF, dichloromethane, DMF or an optionally mixed solvent of these etc.), in the presence of tertiary amine such as triethylamine, diisopropylethylamine and the like, a condensing agent (the same condensing agent as described in Method (1), under ice-cooling or at room temperature for 1–24 hr to give a compound of the formula (5):

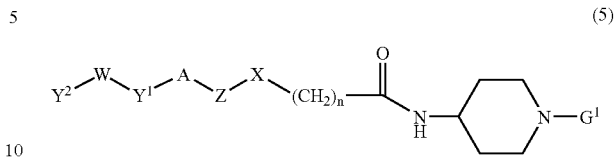
(5)

wherein each symbol is as defined above. When the protecting group is a Boc group, for example, this compound is reacted in an inert solvent such as acetonitrile, THF, 1,4-dioxane, ethyl acetate and the like using hydrogen chloride or an acid such as trifluoroacetic acid (hereinafter abbreviated as TFA) and the like generally at –30° C. to 60° C. for 10 min to 24 hr for deprotection, and when the protecting group is Cbz, for example, it is subjected to a catalytic reduction with hydrogen in an inert solvent such as methanol, ethanol, ethyl acetate and the like in the presence of a catalyst such as palladium carbon and the like, or reacted using an acid such as hydrobromic acid-acetic acid and the like generally at –30° C. to 60° C. for 10 min to 24 hr for deprotection to give a compound of the formula (6):

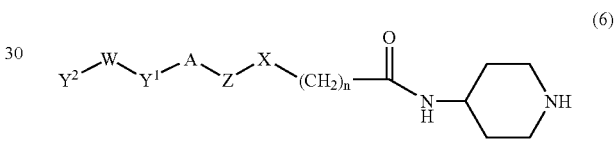
(6)

wherein each symbol is as defined above.

This compound is reacted with a compound of the formula (7):

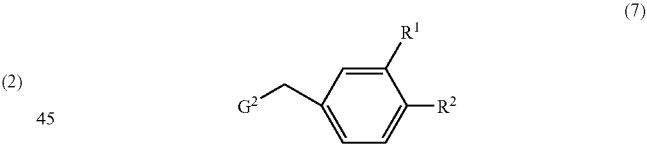
(7)

wherein $G^2$ is a leaving group such as chlorine, bromine, iodine, methanesulfonyloxy, p-toluenesulfonyloxy, trifluoromethanesulfonyloxy and the like, and $R^1$ and $R^2$ are as defined above, in a suitable solvent that does not inhibit the reaction (THF, dichloromethane, DMF or an optionally mixed solvent of these etc.), in the presence of a base such as triethylamine, pyridine, DMAP, potassium carbonate, sodium hydrogen carbonate, sodium hydroxide and the like, under ice-cooling or at room temperature for 1 to 24 hr to give a compound of the formula (1):

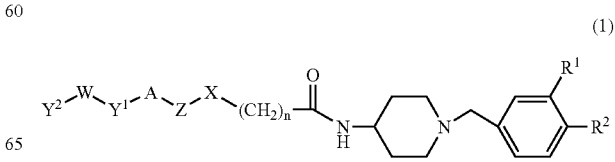
(1)

wherein each symbol is as defined above.

These compounds of the formula (1):

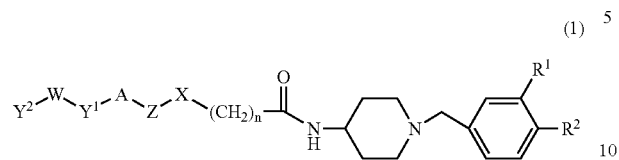

wherein each symbol is as defined above are prepared by a reaction between the compound of the formula (6) and a benzaldehyde compound of the formula (8):

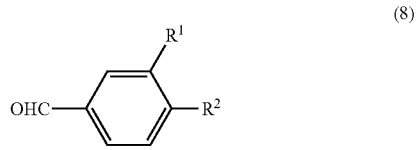

wherein each symbol is as defined above, in the presence of sodium borohydride, sodium cyanoborohydride, sodium triacetoxyborohydride and the like, in a suitable solvent that does not inhibit the reaction (methanol, ethanol, dichloromethane, THF, acetonitrile, 1,4-dioxane etc.) using, where necessary, an acidic catalyst such as acetic acid, p-toluenesulfonic acid, boron trifluoride-diethyl ether complex and the like generally at 0° C. to 100° C. for 10 min to 10 hr.

Method (3)

A compound of the formula (1) wherein X is an oxygen atom or a sulfur atom can be also synthesized by the following method.

A compound of the formula (9):

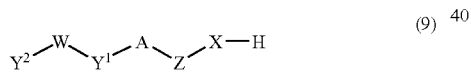

wherein X is an oxygen atom or a sulfur atom, and other symbols are as defined above, or an acid addition salt thereof (hydrochloride, hydrobromide, sulfate, oxalate etc.) is reacted with a compound of the formula (10):

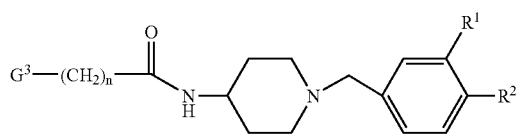

wherein $G^3$ is a leaving group such as chlorine, bromine, iodine, methanesulfonyloxy, p-toluenesulfonyloxy, trifluoromethanesulfonyloxy and the like and $R^1$ and $R^2$ are as defined above, or an acid addition salt thereof (hydrochloride, hydrobromide, sulfate, oxalate etc.) in a suitable solvent that does not inhibit the reaction (dichloromethane, chloroform, dichloroethane, diethyl ether, water or an optionally mixed solvent of these etc., in the presence of a base such as triethylamine, pyridine, DMAP, potassium carbonate, sodium hydrogen carbonate, sodium hydroxide and the like, under ice-cooling or at room temperature for 1 to 24 hr to give a compound of the formula (1):

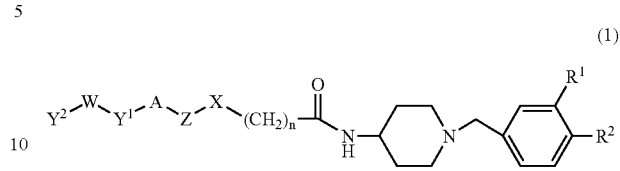

wherein X is an oxygen atom or a sulfur atom, and other symbols are as defined above.

Method (4)

A compound of the formula (1) wherein Z is heteroaryl and X is a bond can be also synthesized by the following method.

That is, a compound of the formula (11):

wherein $L^1$ is a substituent necessary for heteroaryl construction, and other symbols are as defined above, or an acid addition salt thereof (hydrochloride, hydrobromide, sulfate, oxalate etc.) is reacted with a compound of the formula (12):

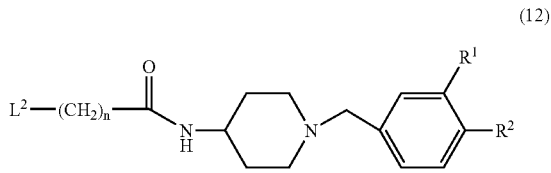

wherein $L^2$ is a substituent necessary for heteroaryl construction, and other symbols are as defined above, or an acid addition salt thereof (hydrochloride, hydrobromide, sulfate, oxalate etc.) to give a compound of the formula (1):

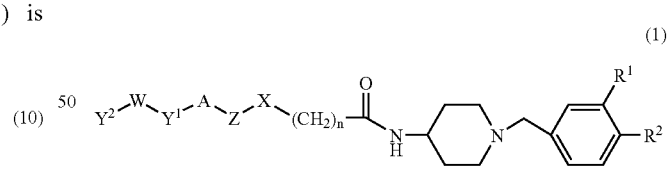

wherein Z is heteroaryl, X is a bond, and other symbols are as defined above.

Method (5)

A compound of the formula (1) wherein A is heteroaryl can be also synthesized by the following method.

That is, a compound of the formula (13):

wherein $L^3$ is a substituent necessary for heteroaryl construction, and other symbols are as defined above, or an acid addition salt thereof (hydrochloride, hydrobromide, sulfate, oxalate etc.) is reacted with a compound of the formula (14):

(14)

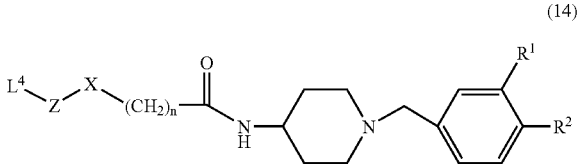

wherein $L^4$ is a substituent necessary for heteroaryl construction, and other symbols are as defined above, or an acid addition salt thereof (hydrochloride, hydrobromide, sulfate, oxalate etc.) to give a compound of the formula (1):

(1)

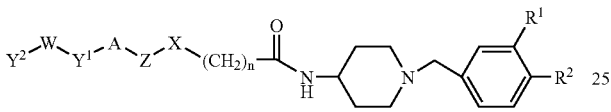

wherein A is heteroaryl and other symbols are as defined above.

Method (6)

A compound of the formula. (1) wherein $Y^1$ is -Q-$(CH_2)_m$— [wherein Q is —NH—, —$NR^3$— (wherein $R^3$ is alkyl), an oxygen atom or a sulfur atom, and m is an integer of 0 to 4] can be also synthesized by the following method.

That is, a compound of the formula (15):

(15)

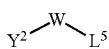

wherein $L^5$ is —$NH_2$, —$NHR^3$ (wherein $R^3$ is alkyl), OH or SH, and other symbols are as defined above, or an acid addition salt thereof (hydrochloride, hydrobromide, sulfate, oxalate etc.) is reacted with a compound of the formula (16):

(16)

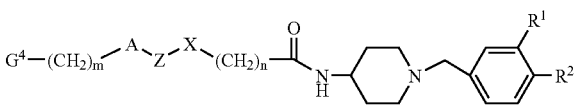

wherein $G^4$ is a leaving group such as chlorine, bromine, iodine, methanesulfonyloxy, p-toluenesulfonyloxy, trifluoromethanesulfonyloxy and the like, and other symbols are as defined above, or an acid addition salt thereof (e.g., hydrochloride, hydrobromide, sulfate, oxalate etc.) in a suitable solvent that does not inhibit the reaction (dichloromethane, chloroform, dichloroethane, diethyl ether, water or an optionally mixed solvent of these etc.) in the presence of a base (triethylamine, pyridine, DMAP, potassium carbonate, sodium hydrogen carbonate, sodium hydroxide etc.) under ice-cooling or at room temperature for 1 to 24 hr to give a compound of the formula (1):

(1)

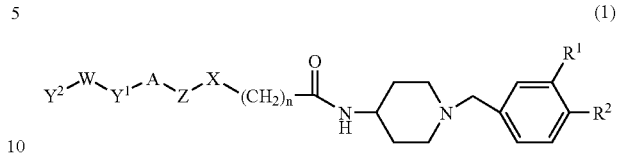

wherein $Y^1$ is -Q-$(CH_2)_m$— [wherein Q is —NH—, —$NR^3$— (wherein $R^3$ is alkyl), an oxygen atom or a sulfur atom, and m is an integer of 0 to 4, and other symbols are as defined above].

Method (7)

A compound of the formula (1) wherein $Y^1$ is —$(CH_2)_m$-Q- [wherein Q is —NH—, —$NR^3$— (wherein $R^3$ is alkyl), an oxygen atom or a sulfur atom, and m is an integer of 0 to 4] can be also synthesized by the following method.

That is, a compound of the formula (17):

(17)

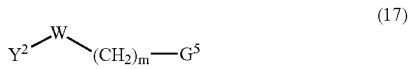

wherein $G^5$ is a leaving group such as chlorine, bromine, iodine, methanesulfonyloxy, p-toluenesulfonyloxy, trifluoromethanesulfonyloxy and the like, and other symbols are as defined above, or an acid addition salt thereof (hydrochloride, hydrobromide, sulfate, oxalate etc.) is reacted with a compound of the formula (18):

(18)

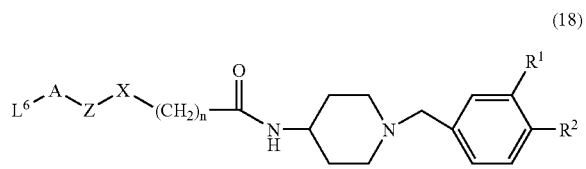

wherein $L^6$ is —$NH_2$, —$NHR^3$ (wherein $R^3$ is alkyl), OH or SH, and other symbols are as defined above, or an acid addition salt thereof (hydrochloride, hydrobromide, sulfate, oxalate etc.) in a suitable solvent that does not inhibit the reaction (dichloromethane, chloroform, dichloroethane, diethyl ether, water or an optionally mixed solvent of these etc.) in the presence of a base such as triethylamine, pyridine, DMAP, potassium carbonate, sodium hydrogen carbonate, sodium hydroxide and the like under ice-cooling or at room temperature for 1 to 24 hr to give a compound of the formula (1):

(1)

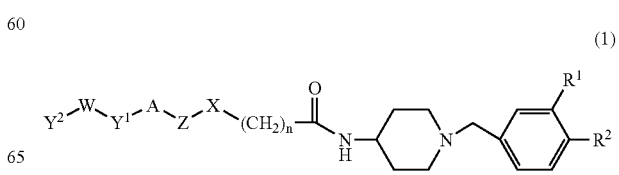

wherein $Y^1$ is —$(CH_2)_m$-Q- [wherein Q is —NH—, —$NR^3$— (wherein $R^3$ is alkyl), an oxygen atom or a sulfur atom, m is an integer of 0 to 4, and other symbols are as defined above].

Method (8)

A compound of the formula (1) wherein W is heteroaryl can be also synthesized by the following method.

That is, a compound of the formula (19):

(19)

$$Y^2{-}L^7$$

wherein $L^7$ is a substituent necessary for heteroaryl construction, and other symbols are as defined above, or an acid addition salt thereof (hydrochloride, hydrobromide, sulfate, oxalate etc.) is reacted with a compound of the formula (20):

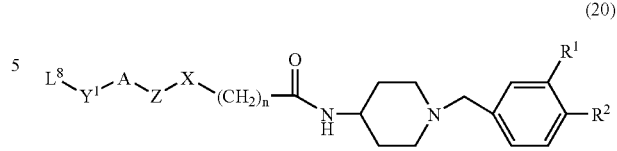

(20)

wherein $L^8$ is a substituent necessary for heteroaryl construction, and other symbols are as defined above, or an acid addition salt thereof (hydrochloride, hydrobromide, sulfate, oxalate etc.) to give a compound of the formula (1):

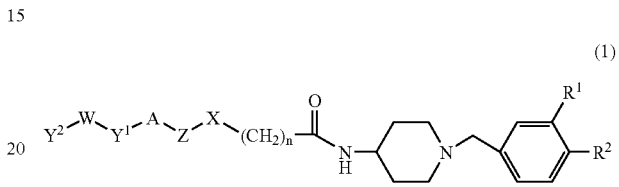

(1)

wherein W is heteroaryl, and other symbols are as defined above.

Method (9)

Various amine compounds can be synthesized by the following methods using a compound of the formula (21):

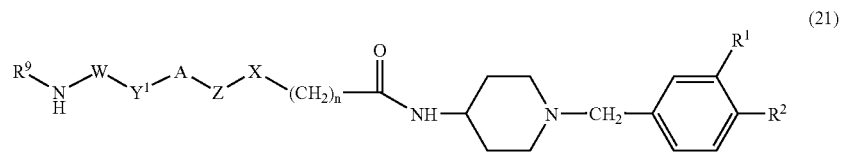

(21)

wherein $R^9$ is hydrogen atom, haloalkyl, alkyl or aryl and the symbols are as defined above.

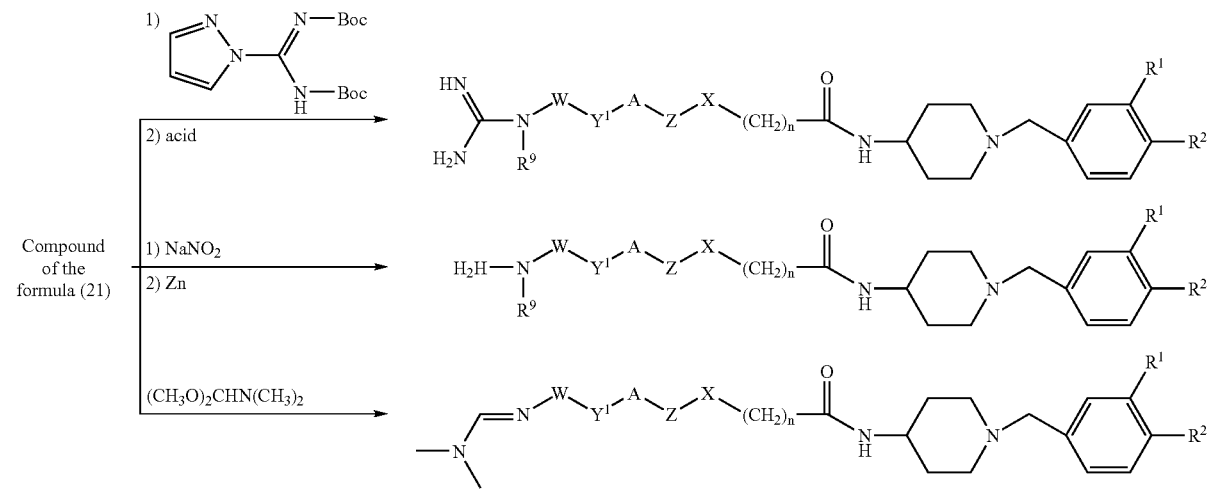

Synthesis of Guanidino Compound

A compound of the formula (21) or an acid addition salt thereof (hydrochloride, hydrobromide, sulfate, oxalate etc.) is reacted with a guanidinating agent such as S-methylthiourea, 1-(N,N'-di tert-butoxycarbonylamidino)pyrazole and the like in a suitable solvent that does not inhibit the reaction (dichloromethane, chloroform, dichloroethane, diethyl ether, THF, DMF or an optionally mixed solvent of these etc.).

When the protecting group is a Boc group, for example, the compound is reacted in an inert solvent such as acetonitrile, THF, 1,4-dioxane, ethyl acetate and the like using an acid such as hydrogen chloride or TFA and the like generally at 0° C. to 150° C. for 10 min to 24 hr for deprotection to give a compound of the formula (1):

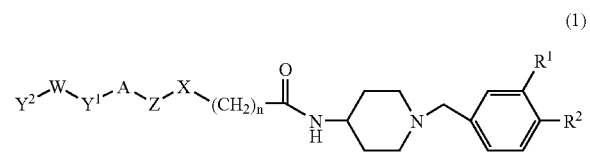
(1)

wherein $Y^2$ is guanidine and other substituents are as defined above.

Synthesis of Hydrazino Compound

A compound of the formula (21) or an acid addition salt thereof (hydrochloride, hydrobromide, sulfate, oxalate etc.) is reacted with sodium nitrite in an acidic solution of hydrochloric acid, acetic acid and the like generally at −30° C. to 100° C. for 10 min to 24 hr for nitrosation, and then reduced with a metal reagent such as zinc and the like in an acidic solution of hydrochloric acid, acetic acid or the like at 0° C. to 100° C. to give a compound of the formula (1):

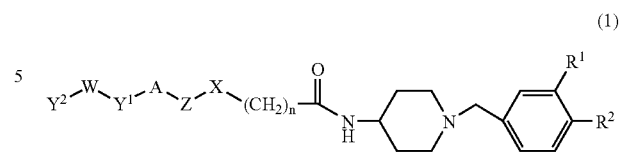
(1)

wherein $Y^2$ is hydrazino and other symbols are as defined above. The hydrazino compound can be also synthesized by a Rasching reaction using chloramine, and the like.

Synthesis of Aminomethyleneamino Compound

A compound of the formula (21) or an acid addition salt thereof (hydrochloride, hydrobromide, sulfate, oxalate etc.) is reacted with N,N-dimethylformamide diethylacetal in a suitable solvent that does not inhibit the reaction (methanol, ethanol, dichloromethane, chloroform, THF, DMF or an optionally mixed solvent of these etc.) generally at 0° C. to 100° C. for 10 min to 24 hr to give a compound of the formula (1):

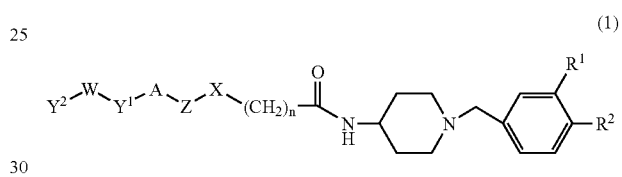
(1)

wherein $Y^2$ is aminomethyleneamino, and other symbols are as defined above.

Moreover, by a treatment of the aminomethyleneamino compound or a salt thereof with an amine (or a salt thereof (e.g., hydrochloride etc.)), a compound wherein $Y^2$ is iminomethylamino can be derived. That amine may be a mono-substituted amine, and when said mono-substituted amine is, for example, hydroxyamine, a compound wherein $Y^2$ is hydroxyiminomethylamino or a salt thereof can be obtained.

Method (10)

Various amine derivatives can be synthesized by the following methods using a compound of the formula (21):

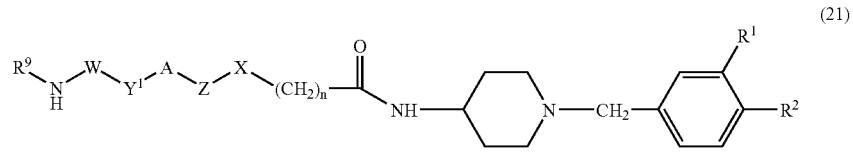
(21)

wherein R[9] is hydrogen atom, haloalkyl, alkyl or aryl and the symbols are as defined above.

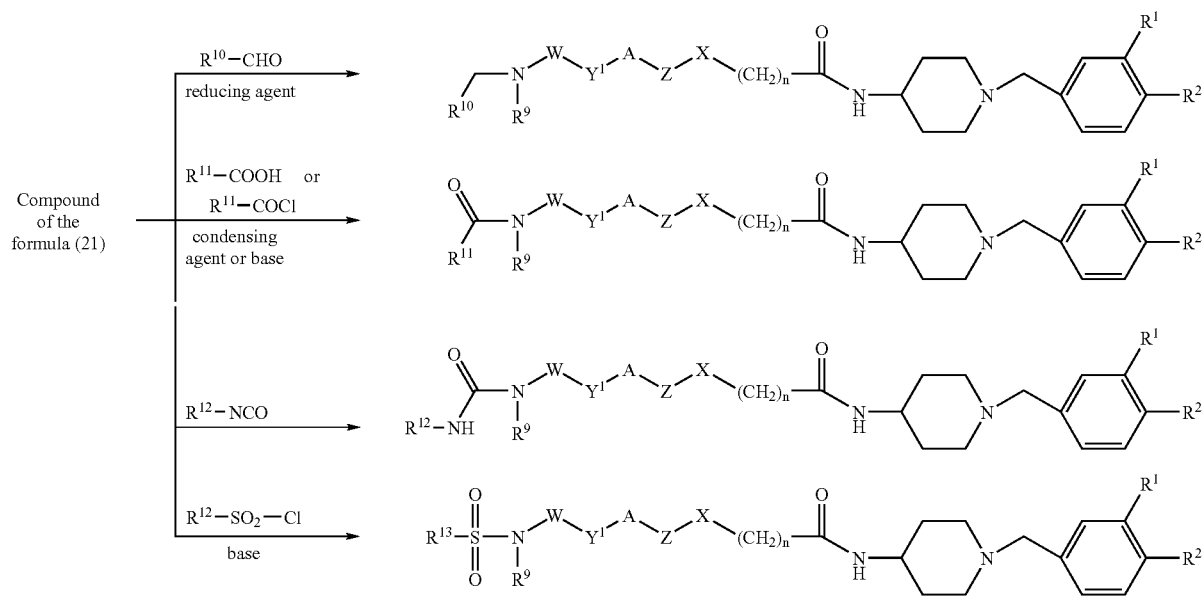

Synthesis of Alkylamino Compound

A compound of the formula (21) or an acid addition salt thereof (hydrochloride, hydrobromide, sulfate, oxalate etc.) is reacted with an aldehyde compound such as R[10]—CHO wherein R[10] is alkyl, and the like, in the presence of sodium borohydride, sodium cyanoborohydride, sodium triacetoxyborohydride and the like, in inert solvent such as methanol, ethanol, dichloromethane, THF, acetonitrile, 1,4-dioxane and the like, using, where necessary, an acidic catalyst such as acetic acid, p-toluenesulfonic acid, boron trifluoride-diethyl ether complex and the like generally at 0° C. to 100° C. for 10 min to 10 hr to give a compound of the formula (1):

(1)

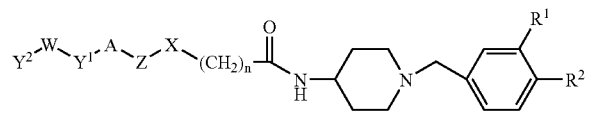

wherein Y[2] is alkylamino, and other symbols are as defined above.

Similarly, a compound of the formula (21) or a salt thereof wherein R[9] is a hydrogen atom is reacted with aminoalkylaldehyde or aminoalkylketone to give a compound wherein Y[2] is aminoalkylamino or a salt thereof.

Similarly, a compound of the formula (21) wherein R[9] is a hydrogen atom is reacted with a protected glyoxylic acid to give a compound wherein Y[2] is carboxymethylamino wherein the carboxyl group is protected, and the deprotection of this compound can derive a compound wherein Y[2] is carboxymethylamino.

Synthesis of Acylamino Compound

A compound of the formula (21) or an acid addition salt thereof (hydrochloride, hydrobromide, sulfate, oxalate etc.) is reacted with a carboxylic acid compound such as R[11]—COOH (wherein R[11] is alkyl, cycloalkyl, alkenyl, alkynyl, aryl, heteroaryl, aminoalkyl or a protected form thereof, nitrogen-containing cycloalkyl or a protected form thereof) and the like, optionally using a condensing agent used in Method (1), in an inert solvent such as acetonitrile, THF, dichloromethane, chloroform, DMF and the like generally at a temperature of −30° C. to 80° C., preferably −10° C. to 25° C., to give a compound of the formula (1):

(1)

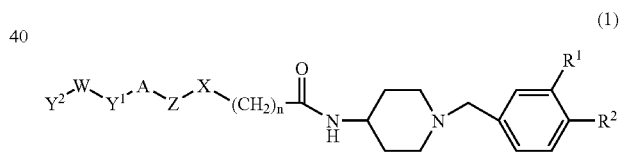

wherein Y[2] is acylamino, and other symbols are as defined above.

When a reactive derivative (acid chloride, acylimidazole etc.) of the carboxylic acid compound of R[11]—COOH (wherein R[11] is as defined above) is used, the reaction may also be carried out in a suitable solvent that does not inhibit the reaction (THF, dichloromethane, chloroform, benzene or an optionally mixed solvent of these etc.), in the presence of a tertiary amine such as triethylamine and the like or pyridine and the like, under ice-cooling or at room temperature for 1 to 24 hr to give a compound of the formula (1):

(1)

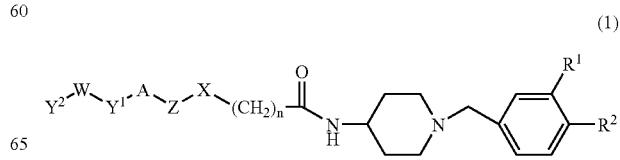

wherein $Y^2$ is acylamino, and other symbols are as defined above.

Synthesis of Urea Compound

A compound of the formula (21) or an acid addition salt thereof (hydrochloride, hydrobromide, sulfate, oxalate etc.) is reacted with an isocyanate compound such as $R^{12}$—NCO wherein $R^{12}$ is alkyl, and the like in a suitable solvent that does not inhibit the reaction (THF, dichloromethane, chloroform, benzene, diethyl ether, pyridine or an optionally mixed solvent of these etc.) at −10° C. to 100° C. for 1 to 24 hr to give a compound of the formula (1):

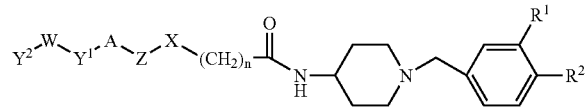

(1)

wherein $Y^2$ is —$NR^4CONR^5R^6$, and other symbols are as defined above.

Synthesis of Sulfonylamino (Sulfonamide) Compound

A compound of the formula (21) or an acid addition salt thereof (hydrochloride, hydrobromide, sulfate, oxalate etc.) is reacted with a sulfonylchloride compound such as $R^{13}$—$SO_2Cl$ wherein $R^{13}$ is alkyl, cycloalkyl, aryl, heteroaryl, aminoalkyl or a protected form thereof, nitrogen-containing cycloalkyl or a protected form thereof, and the like, in a suitable solvent that does not inhibit the reaction (THF, dichloromethane, chloroform, benzene, diethyl ether or an optionally mixed solvent of these etc.) at −10° C. to 100° C. for 1–24 hr to give a compound of the formula (1):

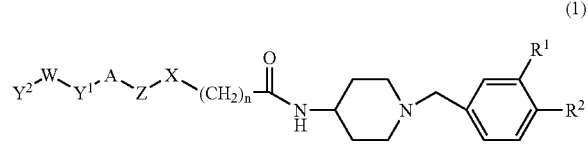

(1)

wherein $Y^2$ is sulfonylamino (sulfonamide), and other symbols are as defined above.

Method (11)

Synthesis of Amidine Compound

Using a compound of the formula (22):

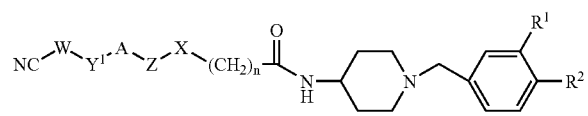

(22)

wherein the symbols are as defined above, and by adding $R^{14}$—NH—$R^{15}$ wherein $R^{14}$ and $R^{15}$ are each alkyl or phenyl at high pressure or in the presence of a Lewis acid such as aluminum chloride and the like or a base such as lanthanide, sodium hydride and the like, in a suitable solvent that does not inhibit the reaction (dimethyl sulfoxide, dioxane, diethylene glycol, dimethylether or an optionally mixed solvent of these etc.), or by adding lower alcohol such as ethanol and the like in the presence of an acid such as hydrogen chloride and the like to the compound of the formula (22) or an acid addition salt thereof (hydrochloride, hydrobromide, sulfate, oxalate etc.), and then performing a substitution reaction with $R^{14}$—NH—$R^{15}$ (4$^{th}$ edition, Courses in Experimental Chemistry 20, Organic Synthesis II, pp. 333–337), a compound of the formula (1):

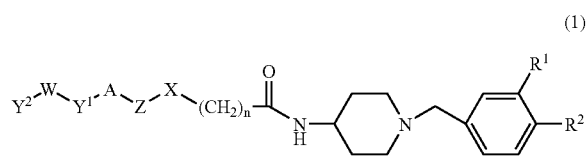

(1)

wherein $Y^2$ is amidine, and other symbols are as defined above, can be obtained.

Method (12)

A compound of the formula (1):

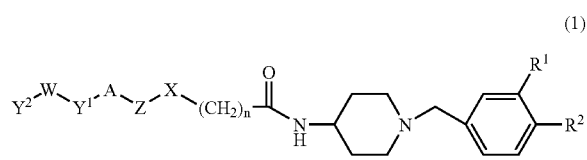

(1)

wherein X or Q in $Y^1$ is a sulfur atom and other symbols are as defined above, or an acid addition salt thereof (hydrochloride, hydrobromide, sulfate, oxalate etc.), which is prepared by any of the above-mentioned methods is reacted with m-chloroperbenzoic acid in dichloromethane under ice-cooling, or reacted with sodium metaperiodate in methanol at room temperature or under reflux, or reacted with aqueous hydrogen peroxide and the like in formic acid or acetic acid to give a compound of the formula (23-a):

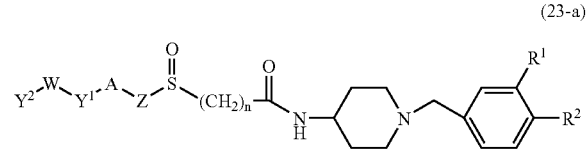

(23-a)

wherein $Y^1$ is —$(CH_2)_m$-Q- wherein Q is SO, m is an integer of 0 to 4, and other symbols are as defined above, or a compound of the formula (23-b):

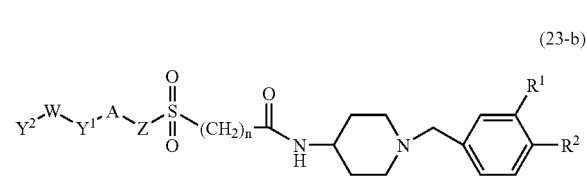

(23-b)

wherein $Y^1$ is —$(CH_2)_m$-Q- wherein Q is $SO_2$, m is an integer of 0 to 4, and other symbols are as defined above.

The compound (23-a) and (23-b) obtained by the above-mentioned method can be also synthesized by the following methods.

A compound of the formula (24):

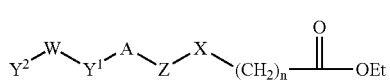
(24)

wherein X or Q is a sulfur atom, and other symbols are as defined above, or an acid addition salt thereof (hydrochloride, hydrobromide, sulfate, oxalate etc.) is reacted with m-chloroperbenzoic acid in dichloromethane under ice-cooling, or reacted with sodium metaperiodate in methanol at room temperature or under reflux, or reacted with aqueous hydrogen peroxide and the like in formic acid or acetic acid to give a compound of the formula (25-a):

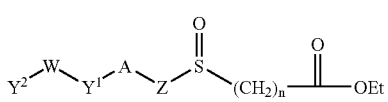
(25-a)

wherein $Y^1$ is —$(CH_2)_m$-Q- wherein Q is SO, m is an integer of 0 to 4, and other symbols are as defined above, or a compound of the formula (25-b):

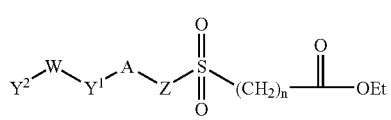
(25-b)

wherein $Y^1$ is —$(CH_2)_m$-Q- wherein Q is $SO_2$, m is an integer of to 4, and other symbols are as defined above.

These compounds are each react with an aqueous solution of sodium hydroxide, potassium hydroxide, potassium carbonate and the like, in a mixed solution of methanol, ethanol, THF and the like, at room temperature or under reflux for 1 to 24 hr to give a carboxylic acid compound. This is condensed with a compound of the formula (3), as shown in Method (1), to give a compound of the formula (23-a):

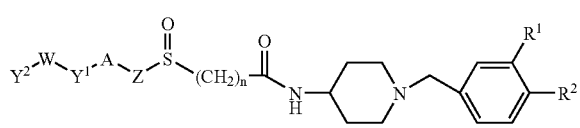
(23-a)

wherein $Y^1$ is —$(CH_2)_m$-Q- wherein Q is SO, m is an integer of 0 to 4, and other symbols are as defined above, or a compound of the formula (23-b):

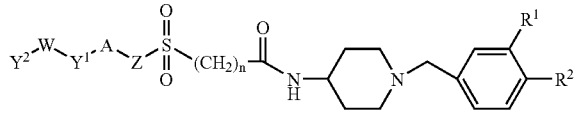
(23-b)

wherein $Y^1$ is —$(CH_2)_m$-Q- wherein Q is $SO_2$, m is an integer of 0 to 4, and other symbols are as defined above.

As a pharmaceutically acceptable salt of a compound of the formula (1), acid addition salts with inorganic acids or organic acids can be mentioned. By treating a compound of the formula (I) with inorganic acids (hydrochloric acid, hydrobromic acid, sulfuric acid, phosphoric acid, nitric acid etc.) or organic acids (acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphersulfonic acid, ascorbic acid etc.) according to a conventional method, a salt can be obtained. Furthermore, hydrates and solvates (ethanolate etc.) of a compound of the formula (1) are also encompassed in the present invention.

A compound of the present invention thus obtained can be isolated or purified by a conventional method such as recrystallization, column chromatography and the like. When the obtained product is a racemate, for example, it can be resolved into a desired optically active form by fractional recrystallization from salts with an optically active acid, or by passing through a column packed with an optically active carrier. The respective diastereomer can be separated by a means such as fractional crystallization, column chromatography and the like. They can be also obtained by the use of an optically active starting compound and the like. In addition, a stereoisomers can be isolated by recrystallization, column chromatography and the like.

When a benzylpiperidine compound of the present invention, an optical isomer thereof or a pharmaceutically acceptable salt thereof is used as a pharmaceutical agent, it can be orally or parenterally administered in the form of a pharmaceutical composition or a preparation (tablet, pill, capsule, granule, powder, syrup, emulsion, elixir, suspension, solution, injection, infusion, suppository etc.) obtained by mixing a compound of the present invention with a pharmaceutically acceptable carrier (excipient, binder, disintegrant, corrigent, flavor, emulsifier, diluent, dissolution aids etc.).

A pharmaceutical composition can be formulated into a preparation according to a conventional method. In the present specification, by parentaral is meant subcutaneous injection, intravenous injection, intramuscular injection, intraperitoneal injection, infusion and the like.

A solid administration dosage form for oral administration can be exemplified by those mentioned above, such as powder, granule, tablet, pill, capsule and the like. In such dosage form, the active ingredient compound can be mixed with at least one additive, such as sucrose, lactose, cellulose sugar, mannitol, multitol, dextran, starches, agar, arginates, chitins, chitosans, pectines, gum tragacanths, acasias, gelatins, collagens, casein, albumin, synthetic or semi-synthetic polymers or glycerols. Such product in such dosage form may contain a further additive (inert diluent, lubricants such as magnesium stearate and the like, preservatives such as parabens, sorbins and the like, antioxidants such as ascorbic acid, α-tocopherol, cysteine and the like, disintegrant, binder, thickener, buffer, sweetener, flavor, perfume etc.).

Furthermore, the tablets and pills may be produced with an enteric coating.

As a liquid for oral administration, a pharmaceutically acceptable emulsion, syrup, elixir, suspension, solution and the like can be mentioned, which may contain an inert diluent generally used in the art, such as water.

A preparation for injection (sterile aqueous suspension and oil suspension for injection, etc.) can be prepared using a suitable dispersing agent or wetting agent and a suspending agent according to a method known in the art. The sterile preparation for injection may be a sterile injectable solution or suspension using a diluent or solvent such as water and the like. As usable vehicle or solvent, water, Ringer solution, isotonic saline and the like can be mentioned. In addition, sterile involatile oil can be generally used as a solvent or suspending solvent. For this purpose, any involatile oil and fatty acid can be used, which is exemplified by natural, synthetic or semi-synthetic fatty oil or fatty acid, natural, synthetic or semi-synthetic monoglycerides, diglycerides and triglycerides.

The suppository for rectal administration can be produced by mixing the drug and suitable non-irritative aids, such as cocoa butter and polyethylene glycols, which are solid at normal temperature and liquid at a temperature in the rectum and melt in the rectum to release the drug, and the like.

The dose is determined taking into consideration of age, body weight, general health conditions, sex, diet, administration time, administration method, clearance rate, combination of drugs, the severity of the symptoms of patients then under treatment, and other factors. The compound of the present invention is low toxic and can be used safely. While the daily dose varies depending on the condition and body weight of the patients, the kind of the compound, administration route and the like, it is, for example, 0.01–1000 mg/kg body weight/day, preferably 0.05–500 mg/kg body weight/day, for oral administration in one to several portions a day. For parenteral administration, the compound is subcutaneously, intravenously, intramuscularly or intrarectally administered preferably at about 0.01–50 mg/kg body weight/day, preferably 0.01–20 mg/kg body weight/day.

BEST MODE FOR EMBODYING THE INVENTION

The present invention is explained in more detail in the following by referring to Starting Material Synthetic Examples, Examples and Experimental Examples, which are not to be construed as limitative.

The $^1$H-NMR spectra of the compounds were each measured at 300 MHz. The chemical shifts of $^1$H-NMR was measured using tetramethylsilane (TMS) as the internal standard and expressed as relative delta (δ) value in parts per million (ppm). For the coupling constant, obvious multiplicity is shown using s (singlet), d (doublet), t (triplet), q (quartet), m (multiplet), dd (doublet of doublets), brs (broad singlet) and he like in hertz (Hz). Column chromatography was performed sing silica gel manufactured by Fuji Silysia Chemical Ltd.

STARTING MATERIAL SYNTHETIC EXAMPLE 1

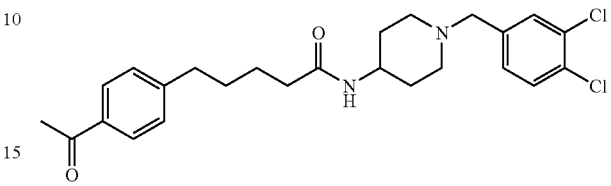

Synthesis of 5-(4-acetylphenyl)-N-[1-(3,4-dichlorobenzyl)piperidin-4-yl]valeramide 5-(4-Acetylphenyl)valeric acid (996 mg) and 4-amino-1-(3,4-dichlorobenzyl)piperidine dihydrochloride (1.50 g) were suspended in dichloromethane (40 mL), and triethylamine (1.26 mL) and EDC hydrochloride (953 mg) were added to the suspension. The suspension was stirred for 12 hrs. The reaction mixture was washed with water and then saturated brine and dried, and the solvent was evaporated under reduced pressure. Diethyl ether was added to the residue to crystallize to give the title compound (1.16 g) as a white solid.

$^1$H-NMR(CDCl$_3$) δ 1.34–1.47 (2H, m), 1.64–1.69 (4H, m), 1.88–1.91 (2H, m), 2.06–2.17 (4H, m), 2.58 (3H, s), 2.66–2.79 (4H, m), 3.42 (2H, s), 3.75–3.85 (1H, m), 5.24 (1H, d, J=8.1 Hz), 7.13 (1H, dd, J=8.1, 1.8 Hz), 7.25 (2H, d, J=8.4 Hz), 7.37 (1H, d, J=8.1 Hz), 7.42 (1H, d, J=1.8 Hz), 7.88 (2H, d, J=8.4 Hz)

STARTING MATERIAL SYNTHETIC EXAMPLE 2

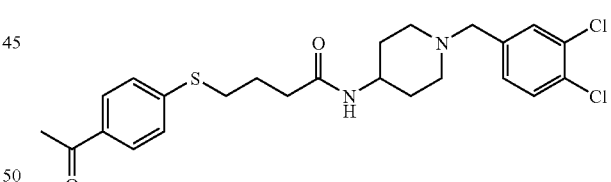

Synthesis of 4-(4-acetylphenylthio)-N-[1-(3,4-dichlorobenzyl)piperidin-4-yl]butylamide In the same manner as in Starting Material Synthetic Example 1, the title compound (1.55 g) was obtained as a white solid from 4-(4-acetylphenylthio)butyric acid (1.08 g) and 4-amino-1-(3,4-dichlorobenzyl)piperidine dihydrochloride (1.50 g).

$^1$H-NMR(CDCl$_3$) δ 1.35–1.48 (2H, m), 1.88–1.92 (2H, m), 2.02–2.16 (4H, m), 2.32 (2H, t, J=7.1 Hz), 2.57 (3H, s), 2.74–2.78 (2H, m), 3.06 (2H, t, J=7.1 Hz), 3.42 (2H, s), 3.75–3.85 (1H, m), 5.31 (1H, d, J=7.8 Hz), 7.13 (1H, dd, J=8.1, 1.8 Hz), 7.33 (2H, d, J=8.4 Hz), 7.37 (1H, d, J=8.1 Hz), 7.42 (1H, d, J=1.8 Hz), 7.86 (2H, d, J=8.4 Hz)

STARTING MATERIAL SYNTHETIC EXAMPLE 3

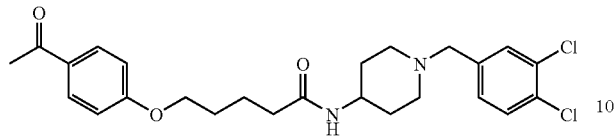

Synthesis of 5-(4-acetylphenyloxy)-N-[1-(3,4-dichlorobenzyl)piperidin-4-yl]valeramide In the same manner as in Starting Material Synthetic Example 1, the title compound (1.02 g) was obtained as a white solid from 5-(4-acetylphenyloxy)valeric acid (1.07 g) and 4-amino-1-(3,4-dichlorobenzyl)piperidine dihydrochloride (1.50 g).

$^1$H-NMR(CDCl$_3$) δ 1.36–1.49 (2H, m), 1.82–1.93 (6H, m), 2.07–2.16 (2H, m), 2.24 (2H, t, J=6.9 Hz), 2.55 (3H, s), 2.74–2.79 (2H, m), 3.42 (2H, s), 3.75–3.85 (1H, m), 4.04 (2H, t, J=6.0 Hz), 5.31 (1H, d, J=8.1 Hz), 6.91 (2H, d, J=6.9 Hz), 7.13 (1H, dd, J=8.1, 2.1 Hz), 7.37 (1H, d, J=8.1 Hz), 7.43 (1H, d, J=2.1 Hz), 7.92 (2H, d, J=6.9 Hz)

STARTING MATERIAL SYNTHETIC EXAMPLE 4

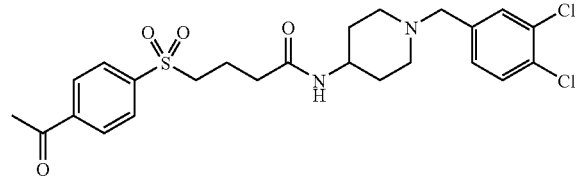

Synthesis of 4-(4-acetylphenylsulfonyl)-N-[1-(3,4-dichlorobenzyl)piperidin-4-yl]butylamide In the same manner as in Starting Material Synthetic Example 1, the title compound (1.61 g) was obtained as a white solid from 4-(4-acetylphenylsulfonyl)butyric acid (1.22 g) and 4-amino-1-(3,4-dichlorobenzyl)piperidine dihydrochloride (1.50 g)

$^1$H-NMR(CDCl$_3$) δ 1.38–1.49 (2H, m), 1.86–1.91 (2H, m), 2.02–2.14 (4H, m), 2.37 (2H, t, J=6.9 Hz), 2.67 (3H, s), 2.77–2.79 (2H, m), 3.21 (2H, t, J=7.2 Hz), 3.42 (2H, s), 3.75–3.85 (1H, m), 5.45 (1H, d, J=7.8 Hz), 7.14 (1H, dd, J=8.1, 1.8 Hz), 7.38 (1H, d, J=8.1 Hz), 7.42 (1H, d, J=1.8 Hz), 8.01 (2H, d, J=8.4 Hz), 8.13 (2H, d, J=8.4 Hz)

STARTING MATERIAL SYNTHETIC EXAMPLE 5

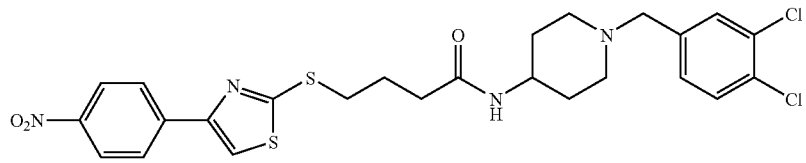

Synthesis of N-[1-(3,4-dichlorobenzyl)piperidin-4-yl]-4-[4-(4-nitrophenyl)thiazol-2-ylthio]butylamide In the same manner as in Starting Material Synthetic Example 1, the title compound (6.03 g) was obtained as a yellow-green solid from 4-[4-(4-nitrophenyl)thiazol-2-ylthio]butyric acid (6.00 g) and 4-amino-1-(3,4-dichlorobenzyl)piperidine dihydrochloride (6.14 g).

$^1$H-NMR(CDCl$_3$) δ 1.36–1.49 (2H, m), 1.88–1.92 (2H, m), 2.05–2.23 (4H, m), 2.37 (2H, t, J=7.2 Hz), 2.74–2.78 (2H, m), 3.73 (2H, t, J=6.9 Hz), 3.42 (2H, s), 3.74–3.87 (1H, m), 5.36 (1H, d, J=8.1 Hz), 7.13 (1H, dd, J=8.1, 2.1 Hz), 7.37 (1H, d, J=8.4 Hz), 7.42 (1H, d, J=2.1 Hz), 7.56 (1H, s), 8.03 (2H, d, J=8.8 Hz), 8.27 (2H, d, J=8.8 Hz)

STARTING MATERIAL SYNTHETIC EXAMPLE 6

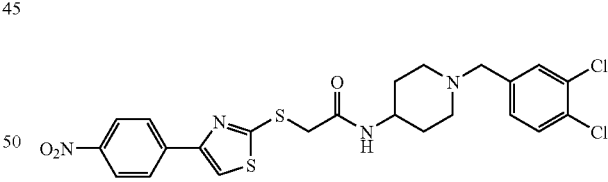

Synthesis of N-[1-(3,4-dichlorobenzyl)piperidin-4-yl]-[4-(4-nitrophenyl)thiazol-2-ylthio]acetamide In the same manner as in Starting Material Synthetic Example 1, the title compound (6.10 g) was obtained as a brown solid from [4-(4-nitrophenyl)thiazol-2-ylthio]acetic acid (5.48 g) and 4-amino-1-(3,4-dichlorobenzyl)piperidine dihydrochloride (6.14 g).

$^1$H-NMR(CDCl$_3$) δ 1.33–1.42 (2H, m), 1.79–1.88 (2H, m), 2.04–2.13 (2H, m), 2.58–2.63 (2H, m), 3.35 (2H, s), 3.77–3.86 (1H, m), 3.94 (2H, s), 6.95 (1H, d, J=7.4 Hz), 7.08 (1H, d, J=8.1 Hz), 7.33–7.36 (2H, m), 7.63 (1H, s), 8.02 (2H, d, J=8.9 Hz), 8.30 (2H, d, J=8.9 Hz)

STARTING MATERIAL SYNTHETIC EXAMPLE 7

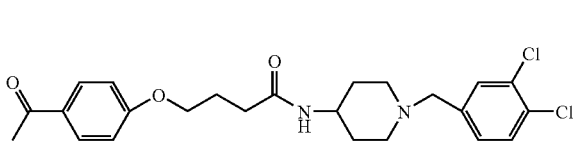

Synthesis of 4-(4-acetylphenyloxy)-N-[1-(3,4-dichlorobenzyl)piperidin-4-yl]butylamide 4-(4-Acetylphenyloxy)butyric acid (10 g) and 4-amino-1-(3,4-dichlorobenzyl)piperidine dihydrochloride (15 g) were suspended in DMF (200 mL), and triethylamine (19 mL), EDC hydrochloride (10.3 g) and HOBt (8.3 g) were added to the suspension. The suspension was stirred for 12 hr. The reaction mixture was washed with water and then saturated brine and dried, and the solvent was evaporated under reduced pressure. Diisopropyl ether was added to the residue to crystallize to give the title compound (18 g) as a white solid. melting point: 147° C.

STARTING MATERIAL SYNTHETIC EXAMPLE 8

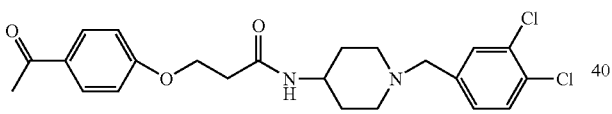

Synthesis of 3-(4-acetylphenyloxy)-N-[1-(3,4-dichlorobenzyl)piperidin-4-yl]propionamide 3-(4-Acetylphenyloxy)propionic acid (1.0 g) and 4-amino-1-(3,4-dichlorobenzyl)piperidine dihydrochloride (1.6 g) were suspended in DMF (50 mL), and triethylamine (1.3 mL), EDC hydrochloride (1.1 g) and HOBt (0.9 g) were added to the suspension. The suspension was stirred for 12 hrs. The reaction mixture was washed with water and then saturated brine and dried, and the solvent was evaporated under reduced pressure. Diisopropyl ether was added to the residue to crystallize to give the title compound (1.3 g) as a white solid.

$^1$H-NMR(DMSO-$d_6$) δ 1.30–1.49 (2H, m), 1.63–1.81 (2H, m), 2.02 (2H, t, J=9.0 Hz), 2.51 (3H, s), 2.55 (2H, t, J=6.1 Hz), 2.64–2.80 (2H, m), 3.45 (2H, s), 3.49–3.66 (1H, m), 4.26 (2H, t, J=6.1 Hz), 7.01 (2H, d, J=8.9 Hz), 7.29 (1H, dd, J=6.4, 1.7 Hz), 7.54 (1H, d, J=1.7 Hz), 7.58 (1H, d, J=6.4 Hz), 7.91 (2H, d, J=8.9 Hz), 7.93 (1H, brs)

STARTING MATERIAL SYNTHETIC EXAMPLE 9

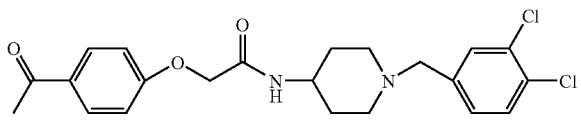

Synthesis of (4-acetylphenyloxy)-N-[1-(3,4-dichlorobenzyl)piperidin-4-yl]acetamide (4-Acetylphenyloxy)acetic acid (2.0 g) and 4-amino-1-(3,4-dichlorobenzyl)piperidine dihydrochloride (3.4 g) were suspended in DMF (50 mL), and triethylamine (2.9 mL), EDC hydrochloride (2.4 g) and HOBt (1.9 g) were added to the suspension. The suspension was stirred for 12 hrs. The reaction mixture was washed with water and then saturated brine and dried, and the solvent was evaporated under reduced pressure. Diisopropyl ether was added to the residue to crystallize to give the title compound (1.3 g) as a white solid. melting point: 113° C.

STARTING MATERIAL SYNTHETIC EXAMPLE 10

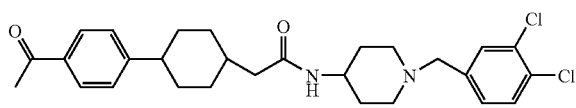

Synthesis of [4-(4-acetylphenyl)cyclohexyl]-N-[1-(3,4-dichlorobenzyl)piperidin-4-yl]acetamide

[4-(4-Acetylphenyl)cyclohexyl]acetic acid (2.0 g) and 4-amino-1-(3,4-dichlorobenzyl)piperidine dihydrochloride (2.5 g) were suspended in DMF (50 mL), and triethylamine (2.1 mL), EDC hydrochloride (1.6 g) and HOBt (1.3 g) were added to the suspension. The suspension was stirred for 12 hrs. The reaction mixture was washed with water and then saturated brine and dried, and the solvent was evaporated under reduced pressure. Diisopropyl ether was added to the residue to crystallize to give the title compound (2.2 g) as a white solid. melting point: 168° C.

STARTING MATERIAL SYNTHETIC EXAMPLE 11

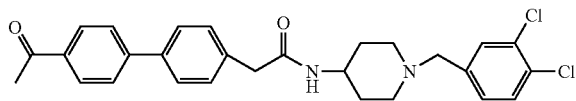

Synthesis of [4-(4-acetylphenyl)phenyl]-N-[1-(3,4-dichlorobenzyl)piperidin-4-yl]acetamide

[4-(4-Acetylphenyl)phenyl]acetic acid (2.0 g) and 4-amino-1-(3,4-dichlorobenzyl)piperidine dihydrochloride (2.5 g) were suspended in DMF (50 mL), and triethylamine (2.1 mL), EDC hydrochloride (1.6 g) and HOBt (1.3 g) were added to the suspension. The suspension was stirred for 12 hrs. The reaction mixture was washed with water and then saturated brine and dried, and the solvent was evaporated under reduced pressure. Diisopropyl ether was added to the residue to crystallize to give the title compound (2.5 g) as a white solid. melting point: 184° C.

STARTING MATERIAL SYNTHETIC EXAMPLE 12

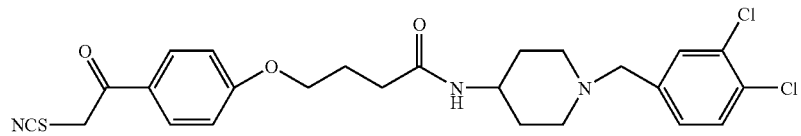

Synthesis of N-[1-(3,4-dichlorobenzyl)piperidin-4-yl]-4-(4-thiocyanatoacetylphenyloxy)butylamide The product (5.0 g) from Starting Material Synthetic Example 7 was dissolved in acetic acid (100 mL), and pyridinium tribromide (4.2 g) was added to the solution. The solution was stirred at 60° C. for 1 hr. The reaction solution was poured into 2 mol/L aqueous sodium hydroxide solution (500 mL), and extracted with ethyl acetate. The extract was washed with saturated brine and dried, and the solvent was evaporated under reduced pressure. The obtained residue was dissolved in acetonitrile (45 mL), and sodium thiocyanate (580 mg) was added to the solution. The mixture was stirred for 30 min, and the solvent was evaporated under reduced pressure. Ethyl acetate (100 mL) was added to the residue, and the mixture was washed with water and dried, and the solvent was evaporated under reduced pressure. The residue was purified by column chromatography (silica gel 120 g, chloroform:methanol=30:1–10:1) to give the title compound (1.91 g) as a brown amorphous solid.
ESI-MS(m/z)520

STARTING MATERIAL SYNTHETIC EXAMPLE 13

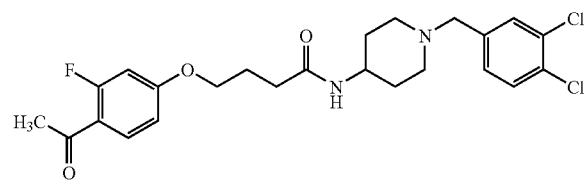

Synthesis of 4-(4-acetyl-3-fluorophenyloxy)-N-[1-(3,4-dichlorobenzyl)piperidin-4-yl]butylamide In the same manner as in Starting Material Synthetic Example 1, the title compound (4.01 g) was obtained as a white solid from 4-(4-acetyl-3-fluorophenyloxy)butyric acid (2.88 g) and 4-amino-1-(3,4-dichlorobenzyl)piperidine dihydrochloride (4.00 g).

$^1$H-NMR(CDCl$_3$) δ 1.36–1.48 (2H, m), 1.87–1.92 (2H, m), 2.08–2.18 (4H, m), 2.36 (2H, t, J=7.1 Hz), 2.59 (3H, d, J=5.1 Hz), 2.74–2.79 (2H, m), 3.42 (2H, s), 3.76–3.86 (1H, m), 4.06 (2H, t, J=6.0 Hz), 5.34 (1H, brd, J=7.5 Hz), 6.60 (1H, dd, J=13.2, 2.4 Hz), 6.73 (1H, dd, J=8.8, 2.4 Hz), 7.14 (1H, dd, J=8.1, 1.8 Hz), 7.37 (1H, d, J=8.1 Hz), 7.42 (1H, d, J=1.8 Hz), 7.87 (1H, t, J=8.8 Hz)

STARTING MATERIAL SYNTHETIC EXAMPLE 14

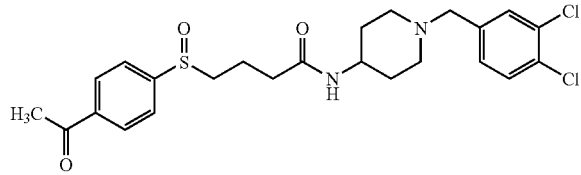

Synthesis of 4-(4-acetylphenylsulfinyl)-N-[1-(3,4-dichlorobenzyl)piperidin-4-yl]butylamide In the same manner as in Starting Material Synthetic Example 1, the title compound (1.68 g) was obtained as a white solid from 4-(4-acetylphenylsulfinyl)butyric acid (1.15 g) and 4-amino-1-(3,4-dichlorobenzyl)piperidine dihydrochloride (1.50 g).

$^1$H-NMR(CDCl$_3$) δ 1.43–1.49 (2H, m), 1.86–1.92 (2H, m), 2.01–2.17 (4H, m), 2.36 (2H, t, J=7.1 Hz), 2.65 (3H, s), 2.75–2.80 (2H, m), 2.80–2.90 (1H, m), 2.93–3.02 (1H, m), 3.43 (2H, s), 3.76–3.86 (1H, m), 5.62 (1H, brd, J=7.8 Hz), 7.14 (1H, dd, J=8.1, 1.8 Hz), 7.38 (1H, d, J=8.1 Hz), 7.43 (1H, d, J=1.8 Hz), 7.71 (2H, d, J=8.4 Hz), 8.10 (1H, d, J=8.4 Hz)

STARTING MATERIAL SYNTHETIC EXAMPLE 15

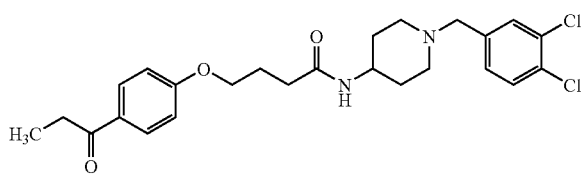

Synthesis of N-[1-(3,4-dichlorobenzyl)piperidin-4-yl]-4-(4-propionylphenyloxy)butylamide In the same manner as in Starting Material Synthetic Example 1, the title compound (2.14 g) was obtained as a white solid from 4-(4-propionylphenyloxy)butyric acid (1.28 g) and 4-amino-1-(3,4-dichlorobenzyl)piperidine dihydrochloride (1.80 g).

$^1$H-NMR(CDCl$_3$) δ 1.21 (3H, t, J=7.3 Hz), 1.42–1.47 (2H, m), 1.88–1.92 (2H, m), 2.10–2.19 (4H, m), 2.37 (2H, t, J=7.2 Hz), 2.76–2.79 (2H, m), 2.95 (2H, q, J=7.3 Hz), 3.44 (2H, s), 3.80–3.84 (1H, m), 4.07 (2H, t, J=5.9 Hz), 5.36 (1H, brd, J=8.1 Hz), 6.92 (2H, d, J=8.7 Hz), 7.15 (1H, brd, J=7.2 Hz), 7.38 (1H, d, J=8.1 Hz), 7.43 (1H, d, J=1.8 Hz), 7.94 (2H, d, J=8.7 Hz)

STARTING MATERIAL SYNTHETIC EXAMPLE 16

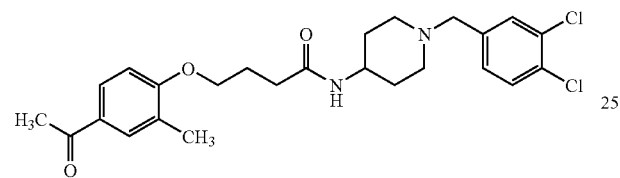

Synthesis of 4-(4-acetyl-2-methylphenyloxy)-N-[1-(3,4-dichlorobenzyl)piperidin-4-yl]butylamide In the same manner as in Starting Material Synthetic Example 1, the title compound (4.17 g) was obtained as a white solid from 4-(4-acetyl-2-methylphenyloxy)butyric acid-(2.84 g) and 4-amino-1-(3,4-dichlorobenzyl)piperidine dihydrochloride (4.00 g).

$^1$H-NMR(CDCl$_3$) δ 1.38–1.46 (2H, m), 1.87–1.91 (2H, m), 2.07–2.22 (4H, m), 2.25 (3H, s), 2.39 (2H, t, J=7.2 Hz), 2.55 (3H, s), 2.73–2.77 (2H, m), 3.41 (2H, s), 3.76–3.86 (1H, m), 4.08. (2H, t, J=6.0 Hz), 5.32 (1H, brd, J=7.8 Hz), 6.83 (1H, d, J=8.7 Hz), 7.13 (1H, dd, J=8.1, 1.8 Hz), 7.37 (1H, d, J=8.1 Hz), 7.42 (1H, d, J=1.8 Hz), 7.80–7.81 (2H, m)

STARTING MATERIAL SYNTHETIC EXAMPLE 17

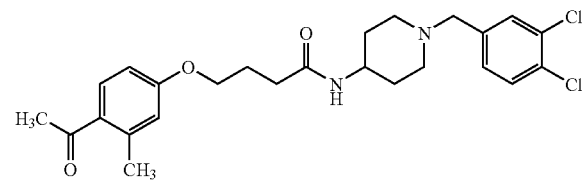

Synthesis of 4-(4-acetyl-3-methylphenyloxy)-N-[1-(3,4-dichlorobenzyl)piperidin-4-yl]butylamide In the same manner as in Starting Material Synthetic Example 1, the title compound (4.31 g) was obtained as a white solid from 4-(4-acetyl-3-methylphenyloxy)butyric acid (2.84 g) and 4-amino-1-(3,4-dichlorobenzyl)piperidine dihydrochloride (4.00 g).

$^1$H-NMR(CDCl$_3$) δ 1.39–1.48 (2H, m), 1.88–1.91 (2H, m), 2.09–2.17 (4H, m), 2.36 (2H, t, J=7.2 Hz), 2.54 (3H, s), 2.56 (3H, s), 2.74–2.78 (2H, m), 3.42 (2H, s), 3.76–3.86 (1H, m), 4.05 (2H, t, J=6.0 Hz), 5.35 (1H, brd, J=8.1 Hz), 6.73–6.76 (2H, m), 7.14 (1H, dd, J=8.1, 1.8 Hz), 7.37 (1H, d, J=8.1 Hz), 7.42 (1H, d, J=1.8 Hz), 7.74 (1H, d, J=9.6 Hz)

STARTING MATERIAL SYNTHETIC EXAMPLE 18

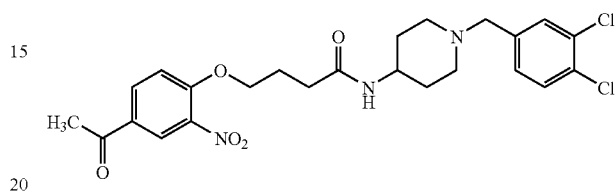

Synthesis of 4-(4-acetyl-2-nitrophenyloxy)-N-[1-(3,4-dichlorobenzyl)piperidin-4-yl]butylamide In the same manner as in Starting Material Synthetic Example 1, the title compound (4.04 g) was obtained as brown crystals from 4-(4-acetyl-2-nitrophenyloxy)butyric acid (3.21 g) and 4-amino-1-(3,4-dichlorobenzyl)piperidine dihydrochloride (4.00 g).

$^1$H-NMR(CDCl$_3$) δ 1.35–1.44 (2H, m), 1.80–1.85 (2H, m), 2.05–2.13 (2H, m), 2.19 (2H, quint, J=6.3 Hz), 2.43 (2H, t, J=6.9 Hz), 2.61 (3H, s), 2.68–2.72 (2H, m), 3.39 (2H, s), 3.76–3.81 (1H, m), 4.25 (2H, t, J=5.9 Hz), 5.66 (1H, brd, J=8.1 Hz), 7.12 (1H, dd, J=8.4, 2.1 Hz), 7.15 (1H, d, J=8.7 Hz), 7.36 (1H, d, J=8.4 Hz), 7.39 (1H, d, J=2.1 Hz), 8.15 (1H, dd, J=8.7, 2.4 Hz), 8.43 (1H, d, J=2.4 Hz)

STARTING MATERIAL SYNTHETIC EXAMPLE 19

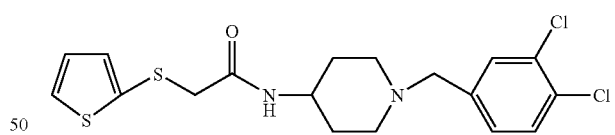

Synthesis of N-[1-(3,4-dichlorobenzyl)piperidin-4-yl]-(2-thienylthio)acetamide

In the same manner as in Starting Material Synthetic Example 1, the title compound (1.1 g) was obtained as a white solid from (2-thienylthio)acetic acid (1.5 g) and 4-amino-1-(3,4-dichlorobenzyl)piperidine dihydrochloride (3.0 g).

$^1$H-NMR(DMSO-d$_6$) δ 1.26–1.48 (2H, m), 1.60–1.77 (2H, m), 2.03 (2H, t, J=11.7 Hz), 2.69 (2H, d, J=11.7 Hz), 3.44 (2H, s), 3.46 (2H, s), 3.50–3.63 (1H, m), 6.98–7.08 (1H, m), 7.17 (1H, dd, J=3.6,–1.2 Hz), 7.28 (1H, dd, J=8.1, 1.8 Hz), 7.50–7.66 (3H, m), 7.82–7.98 (1H, m)

STARTING MATERIAL SYNTHETIC EXAMPLE 20

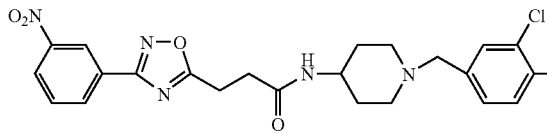

Synthesis of N-[1-(3,4-dichlorobenzyl)piperidin-4-yl]-3-[3-(3-nitrophenyl)-1,2,4-oxadiazol-5-yl]propanamide In the same manner as in Starting Material Synthetic Example 1, the title compound (2.2 g) was obtained as a pale-yellow solid from [3-(3-nitrophenyl)-1,2,4-oxadiazol-5-yl]propionic acid (2.0 g) and 4-amino-1-(3,4-dichlorobenzyl)piperidine dihydrochloride (2.5 g).

$^1$H-NMR(DMSO-d$_6$) δ 1.28–1.51 (2H, m), 1.62–1.80 (2H, m), 2.01 (2H, t, J=11.1 Hz), 2.64–2.81 (4H, m), 3.22 (2H, t, J=7.2 Hz), 3.43 (2H, s), 3.45–3.64 (1H, m), 7.27 (1H, dd, J=8.4, 1.8 Hz), 7.51 (1H, d, J=1.8 Hz), 7.57 (1H, d, J=8.1 Hz), 7.88 (1H, d, J=8.1 Hz), 7.96–8.05 (1H, m), 8.39–8.50 (2H, m), 8.68 (1H, d, J=1.8 Hz)

STARTING MATERIAL SYNTHETIC EXAMPLE 21

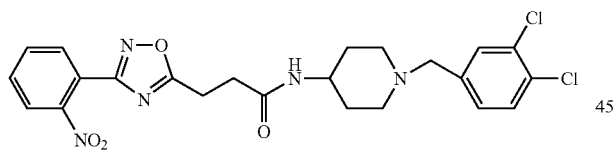

Synthesis of N-[1-(3,4-dichlorobenzyl)piperidin-4-yl]-3-[3-(2-nitrophenyl)-1,2,4-oxadiazol-5-yl]propanamide In the same manner as in Starting Material Synthetic Example 1, the title compound (1.2 g) was obtained as a pale-yellow solid from [3-(2-nitrophenyl)-1,2,4-oxadiazol-5-yl]propionic acid (0.9 g) and 4-amino-1-(3,4-dichlorobenzyl)piperidine dihydrochloride (1.1 g).

$^1$H-NMR(DMSO-d$_6$) δ 1.26–1.50 (2H, m), 1.65–1.80 (2H, m), 2.00 (2H, t, J=11.2 Hz), 2.68–2.80 (4H, m), 3.19 (2H, t, J=7.2 Hz), 3.44 (2H, s), 3.45–3.62 (1H, m), 7.28 (1H, dd, J=8.2, 1.8 Hz), 7.52 (1H, d, J=1.8 Hz), 7.57 (1H, d, J=8.2 Hz), 7.80–8.00 (3H, m), 8.06–8.16 (1H, m), 8.32 (1H, s)

STARTING MATERIAL SYNTHETIC EXAMPLE 22

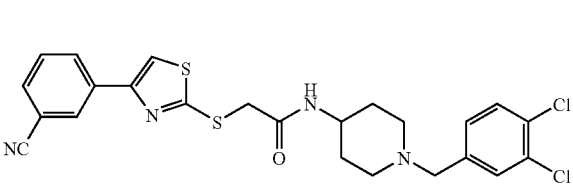

Synthesis of [4-(3-cyanophenyl)thiazol-2-ylthio]-N-[1-(3,4-dichlorobenzyl)piperidin-4-yl]acetamide In the same manner as in Starting Material Synthetic Example 1, the title compound (6.1 g) was obtained as a white solid from [4-(3-cyanophenyl)thiazol-2-ylthio]acetic acid (5.0 g) and 4-amino-1-(3,4-dichlorobenzyl)piperidine dihydrochloride (6.6 g).

$^1$H-NMR(CDCl$_3$) δ 1.30–1.44 (2H, m), 1.80–1.94 (2H, m), 2.02–2.15 (2H, m), 2.56–2.68 (2H, m), 3.32 (2H, s), 3.74–3.86 (1H, m), 3.91 (2H, s), 7.01–7.10 (2H, m), 7.31–7.36 (2H, m), 7.50 (1H, s), 7.55 (1H, d, J=7.8 Hz), 7.62–7.67 (1H, m), 8.05–8.10 (1H, m), 8.15 (1H, s)

STARTING MATERIAL SYNTHETIC EXAMPLE 23

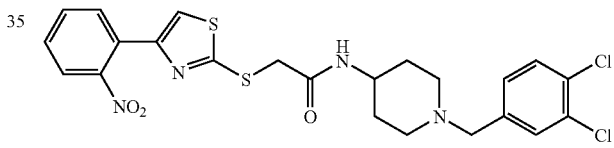

Synthesis of N-[1-(3,4-dichlorobenzyl)piperidin-4-yl]-[4-(2-nitrophenyl)thiazol-2-ylthio]acetamide In the same manner as in Starting Material Synthetic Example 1, the title compound (12.2 g) was obtained as a brown solid from [4-(2-nitrophenyl)thiazol-2-ylthio]acetic acid (7.1 g) and 4-amino-1-(3,4-dichlorobenzyl)piperidine dihydrochloride (7.9 g).

$^1$H-NMR(CDCl$_3$) δ 1.35–1.49 (2H, m), 1.75–1.85 (2H, m), 2.02–2.19 (2H, m), 2.59–2.70 (2H, m), 3.39 (2H, s), 3.69–3.83 (3H, m), 6.80–6.86 (1H, m), 7.03–7.11 (1H, m), 7.24–7.43 (3H, m), 7.49–7.70 (3H, m), 7.73–7.77 (1H, m)

STARTING MATERIAL SYNTHETIC EXAMPLE 24

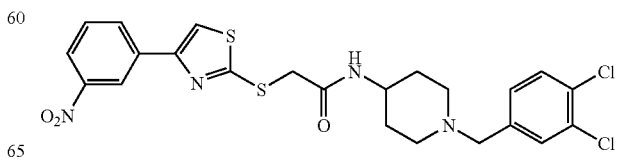

Synthesis of N-[1-(3,4-dichlorobenzyl)piperidin-4-yl]-[4-(3-nitrophenyl)thiazol-2-ylthio]acetamide In the same manner as in Starting Material Synthetic Example 1, the title compound (7.3 g) was obtained as a white solid from [4-(3-nitrophenyl)thiazol-2-ylthio]acetic acid (5.0 g) and 4-amino-1-(3,4-dichlorobenzyl)piperidine dihydrochloride (5.6 g).

¹H-NMR(CDCl₃) δ 1.35–1.44 (2H, m), 1.70–1.92 (2H, m), 2.08–2.20 (2H, m), 2.60–2.71 (2H, m), 3.36 (2H, s), 3.77–3.99 (1H, m), 3.93 (2H, s), 7.00–7.10 (2H, m), 7.20–7.26 (2H, m), 7.58 (1H, s), 7.59–7.66 (1H, m), 8.16–8.24 (2H, m), 8.68 (1H, s)

STARTING MATERIAL SYNTHETIC EXAMPLE 25

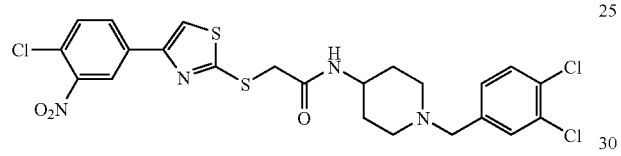

Synthesis of [4-(4-chloro-3-nitropheny)thiazol-2-ylthio]-N-[1-(3,4-dichlorobenzyl)piperidin-4-yl]acetamide 4-(4-Chloro-3-nitrophenyl)-2-mercaptothiazole (0.5 g) was dissolved in dimethylformamide (20 mL), and potassium carbonate (0.7 g) was added to the solution. Then, N-[1-(3,4-dichlorobenzyl)piperidin-4-yl]chloroacetamide (0.6 g) was added, and the mixture was stirred at room temperature for 3 hrs. Ethyl acetate was added to the reaction mixture, washed with water and saturated brine, and dried. The solvent was evaporated under reduced pressure, and the obtained residue was purified by silica gel column chromatography (chloroform:methanol=100:1) to give the title compound (0.7 g) as a yellow solid.

¹H-NMR(DMSO-d₆) δ 1.33–1.45 (2H, m), 1.65–1.71 (2H, m), 1.97–2.07 (2H, m), 2.64–2.73 (2H, m), 3.42 (2H, s), 3.50–3.61 (1H, m), 4.02 (2H, s), 7.24–7.30 (1H, m), 7.51–7.60 (2H, m), 7.85 (1H, d, J=8.4 Hz), 8.21–8.27 (2H, m), 8.31 (1H, s), 8.56–8.58 (1H, m)

STARTING MATERIAL SYNTHETIC EXAMPLE 26

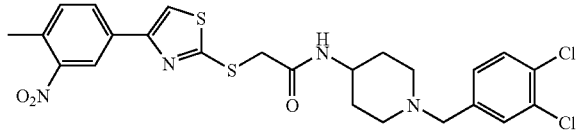

Synthesis of N-[1-(3,4-dichlorobenzyl)piperidin-4-yl]-[4-(4-methyl-3-nitrophenyl)thiazol-2-ylthio]acetamide In the same manner as in Starting Material Synthetic Example 25, the title compound (7.0 g) was obtained as a brown solid from 4-(4-methyl-3-nitrophenyl)-2-mercaptothiazole (5.0 g) and N-[1-(3,4-dichlorobenzyl)piperidin-4-yl]chloroacetamide (6.6 g).

¹H-NMR(DMSO-d₆) δ 1.32–1.48 (2H, m), 1.67–1.74 (2H, m), 1.98–2.08 (2H, m), 2.47–2.52 (3H, m), 2.62–2.72 (2H, m), 3.42 (2H, s), 3.48–3.61 (1H, m), 4.00 (2H, s), 7.25–7.30 (1H, m), 7.50–7.61 (3H, m), 8.14–8.27 (3H, m), 8.46–8.48 (1H, m)

STARTING MATERIAL SYNTHETIC EXAMPLE 27

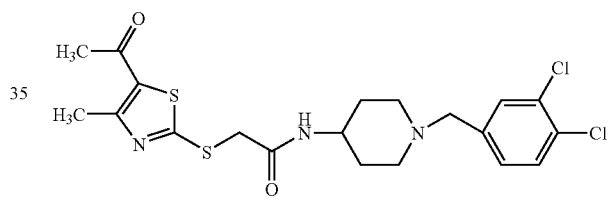

Synthesis of (5-acetyl-4-methylthiazol-2-ylthio)-N-[1-(3,4-dichlorobenzyl)piperidin-4-yl]acetamide In the same manner as in Starting Material Synthetic Example 1, the title compound (3.93 g) was obtained as pale-brown crystals from (5-acetyl-4-methylthiazol-2-ylthio)acetic acid (4.43 g) and 4-amino-1-(3,4-dichlorobenzyl)piperidine dihydrochloride (6.38 g).

¹H-NMR(CDCl₃) δ 1.36–1.46 (2H, m), 1.86–1.92 (2H, m), 2.08–2.16 (2H, m), 2.50 (3H, s), 2.66–2.72 (2H, m), 2.70 (3H, s), 3.40 (2H, s), 3.72–3.80 (1H, m), 3.82 (2H, s), 7.12 (1H, dd, J=8.1, 1.8 Hz), 7.20 (1H, d, J=7.5 Hz), 7.37 (1H, d, J=8.1 Hz), 7.41 (1H, d, J=1.8 Hz)

STARTING MATERIAL SYNTHETIC EXAMPLE 28

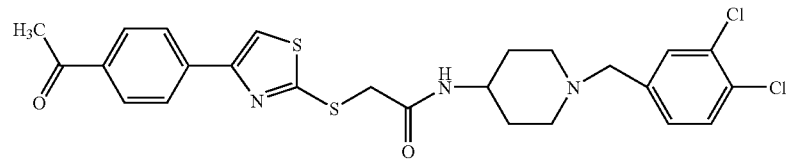

Synthesis of [4-(4-acetylphenyl)thiazol-2-ylthio]-N-[1-(3,4-dichlorobenzyl)piperidin-4-yl]acetamide In the same manner as in Starting Material Synthetic. Example 1, the title compound (1.23 g) was obtained as white crystals from [4-(4-acetylphenyl)thiazol-2-ylthio]acetic acid (1.22 g) and 4-amino-1-(3,4-dichlorobenzyl)piperidine dihydrochloride (1.38 g).

$^1$H-NMR(CDCl$_3$) δ 1.31–1.43 (2H, m), 1.80–1.86 (2H, m), 2.04–2.15 (2H, m), 2.52–2.56 (2H, m), 2.64 (3H, s), 3.29 (2H, s), 3.78–3.84 (1H, m), 3.92 (2H, s), 7.04 (1H, dd, J=8.4, 1.8 Hz), 7.17 (1H, d, J=8.1 Hz), 7.31 (1H, d, J=8.1 Hz), 7.33 (1H, d, J=8.4 Hz), 7.56 (1H, s), 7.95 (2H, d, J=8.4 Hz), 8.03 (2H, d, J=8.4 Hz)

STARTING MATERIAL SYNTHETIC EXAMPLE 29

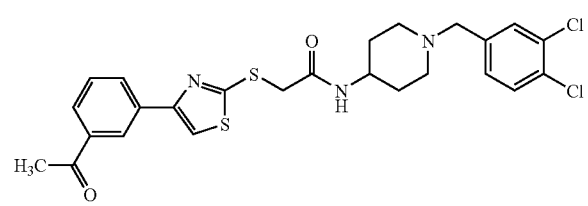

Synthesis of [4-(3-acetylphenyl)thiazol-2-ylthio]-N-[1-(3,4-dichlorobenzyl)piperidin-4-yl]acetamide In the same manner as in Starting Material Synthetic Example 1, the title compound (2.57 g) was obtained as a white solid from [4-(3-acetylphenyl)thiazol-2-ylthio]acetic acid (2.60 g) and 4-amino-1-(3,4-dichlorobenzyl)piperidine dihydrochloride (2.94 g).

$^1$H-NMR(CDCl$_3$) δ 1.32–1.43 (2H, m), 1.80–1.85 (2H, m), 2.02–2.11 (2H, m), 2.51–2.54 (2H, m), 2.67 (3H, s), 3.28 (2H, s), 3.77–3.84 (1H, m), 3.92 (2H, s), 7.04 (1H, dd, J=8.1, 1.8 Hz), 7.19 (1H, brd, J=8.1 Hz), 7.31 (1H, d, J=1.8 Hz), 7.33 (1H, d, J=8.1 Hz), 7.53 (1H, s), 7.56 (1H, t, J=7.8 Hz), 7.95 (1H, dt, J=7.8, 1.5 Hz), 8.08 (1H, dt, J=7.8, 1.5 Hz), 8.44 (1H, t, J=1.5 Hz)

STARTING MATERIAL SYNTHETIC EXAMPLE 30

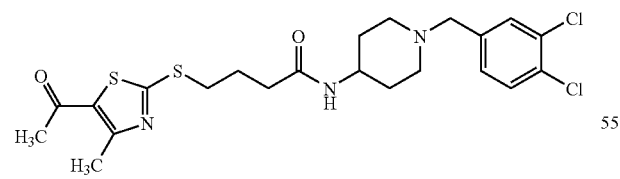

Synthesis of 4-(5-acetyl-4-methylthiazol-2-ylthio)-N-[1-(3,4-dichlorobenzyl)piperidin-4-yl]butylamide In the same manner as in Starting Material Synthetic Example 1, the title compound (12.6 g) was obtained as white crystals from 4-(5-acetyl-4-methylthiazol-2-ylthio) butyric acid (9.00 g) and 4-amino-1-(3,4-dichlorobenzyl) piperidine dihydrochloride (11.5 g).

$^1$H-NMR(CDCl$_3$) δ 1.39–1.50 (2H, m), 1.89–1.93 (2H, m), 2.08–2.18 (4H, m), 2.33 (2H, t, J=7.2 Hz), 2.48 (3H, s), 2.68 (3H, s), 2.75–2.79 (2H, m), 3.29 (2H, t, J=6.9 Hz), 3.42 (2H, s), 3.78–3.83 (1H, m), 5.40 (1H, brd, J=8.1 Hz), 7.13 (1H, dd, J=8.1, 1.8 Hz), 7.37 (1H, d, J=8.1 Hz), 7.42 (1H, d, J=1.8 Hz)

STARTING MATERIAL SYNTHETIC EXAMPLE 31

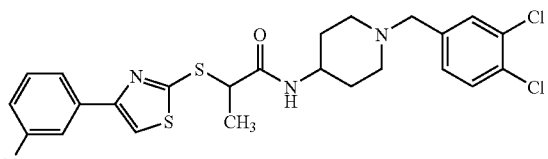

Synthesis of N-[1-(3,4-dichlorobenzyl)piperidin-4-yl]-2-[4-(3-nitrophenyl)thiazol-2-ylthio]propionamide In the same manner as in Starting Material Synthetic Example 1, the title compound (0.64 g) was obtained as white crystals from 2-[4-(3-nitrophenyl)thiazol-2-ylthio] propionic acid (1.73 g) and 4-amino-1-(3,4-dichlorobenzyl) piperidine dihydrochloride (1.85 g).

$^1$H-NMR(CDCl$_3$) δ 1.28–1.40 (2H, m), 1.64 (3H, d, J=7.3 Hz), 1.78–1.89 (2H, m), 2.03–2.10 (2H, m), 2.54–2.58 (2H, m), 3.30 (2H, s), 3.75–3.83 (1H, m), 4.42 (1H, q, J=7.3 Hz), 7.03–7.06 (2H, m), 7.32–7.34 (2H, m), 7.59 (1H, s), 7.64 (1H, t, J=8.0 Hz), 8.17–8.24 (2H, m), 8.70 (1H, t, J=2.0 Hz)

STARTING MATERIAL SYNTHETIC EXAMPLE 32

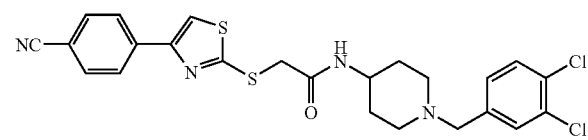

Synthesis of [4-(4-cyanophenyl)thiazol-2-ylthio]-N-[1-(3,4-dichlorobenzyl)piperidin-4-yl]acetamide In the same manner as in Starting Material Synthetic Example 1, the title compound (17.4 g) was obtained as a white solid from [4-(4-cyanophenyl)thiazol-2-ylthio]acetic acid (10 g) and 4-amino-1-(3,4-dichlorobenzyl)piperidine dihydrochloride (13.2 g).

$^1$H-NMR(CDCl$_3$) δ 1.44–1.60 (2H, m), 1.84–1.92 (2H, m), 2.18–2.30 (2H, m), 2.75–2.86 (2H, m), 3.49 (2H, s), 3.80–3.90 (1H, m), 3.93 (2H, s), 7.06–7.13 (2H, m), 7.28–7.38 (2H, m), 7.54 (1H, s), 7.65–7.72 (2H, m), 7.90–7.97 (2H, m)

STARTING MATERIAL SYNTHETIC EXAMPLE 33

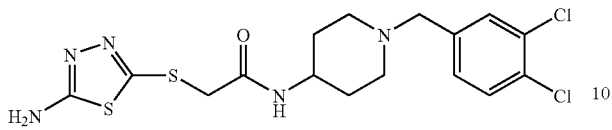

Synthesis of (2-amino-1,3,4-thiadiazole-5-ylthio)-N-[1-(3,4-dichlorobenzyl)piperidin-4-yl]acetamide In the same manner as in Starting Material Synthetic Example 25, the title compound (3.71 g) was obtained as a white powder from 2-amino-5-mercapto-1,3,4-thiadiazole (1.40 g) and N-[1-(3,4-dichlorobenzyl)piperidin-4-yl]chloroacetamide (3.36 g).

$^1$H-NNR(DMSO-$d_6$) δ 1.31–1.48 (2H, m), 1.67–1.74 (2H, m), 1.98–2.10 (2H, m), 2.64–2.76 (2H, m), 3.45 (2H, s), 3.45–3.60 (1H, m), 3.72 (2H, s), 7.22–7.31 (3H, m), 7.53–7.59 (2H, m), 8.06 (1H, d, J=7.5 Hz)

STARTING MATERIAL SYNTHETIC EXAMPLE 34

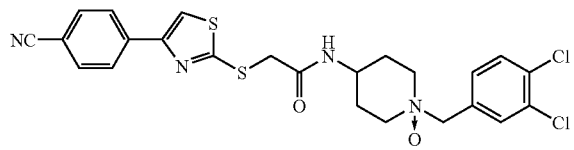

Synthesis of [4-(4-cyanophenyl)thiazol-2-ylthio]-N-[1-(3,4-dichlorobenzyl)-1-oxopiperidin-4-yl]acetamide In the same manner as in Starting Material Synthetic Example 25, the title compound (3.3 g) was obtained as a white solid from 4-(4-cyanophenyl)-2-mercaptothiazole (2.0 g) and N-[1-(3,4-dichlorobenzyl)piperidin-4-yl]chloroacetamide (3.2 g).

$^1$H-NMR(DMSO-$d_6$) δ 1.55–1.68 (2H, m), 2.05–2.21 (2H, m), 2.70–2.85 (2H, m), 3.22–3.40 (2H, m), 3.57–3.80 (1H, m), 4.03 (2H, s), 4.26 (2H, s), 7.51–7.59 (1H, m), 7.61–7.66 (1H, m), 7.86–7.96 (3H, m), 8.11–8.19 (1H, m), 8.30 (1H, s), 8.42–8.50 (1H, m)

STARTING MATERIAL SYNTHETIC EXAMPLE 35

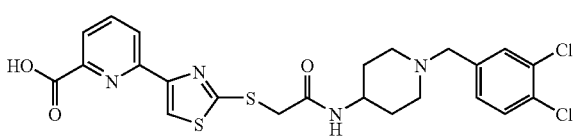

Synthesis of N-[1-(3,4-dichlorobenzyl)piperidin-4-yl]-[4-(6-carboxypyridin-2-yl)thiazol-2-ylthio]acetamide N-[1-(3,4-Dichlorobenzyl)piperidin-4-yl]-[4-(6-methoxycarbonylpyridin-2-yl)thiazol-2-ylthio]acetamide (330 mg) was suspended in a mixed solvent of methanol (5 mL), tetrahydrofuran (5 mL) and 1 mol/L aqueous sodium hydroxide solution (1.2 mL), and the suspension was stirred at room temperature for 5 hrs. The reaction mixture was neutralized by adding 1 mol/L hydrochloric acid, and saturated brine was added. The mixture was extracted with chloroform, and the extract was dried. Then, the solvent was evaporated to give the title compound (314 mg) as a slightly yellow powder.

ESI-MS(m/z): 537

STARTING MATERIAL SYNTHETIC EXAMPLE 36

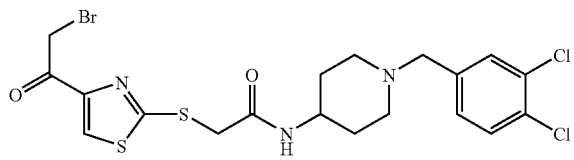

Synthesis of N-[1-(3,4-dichlorobenzyl)piperidin-4-yl]-[4-bromoacetylthiazol-2-ylthio]acetamide N-[1-(3,4-Dichlorobenzyl)piperidin-4-yl]-[4-carboxythiazol-2-ylthio]acetamide hydrochloride (4.97 g) was suspended in 1,4-dioxane (50 mL), and N-methylmorpholine (2.42 mL) and isobutyl chloroformate (1.44 mL) were added to the suspension under ice-cooling. The mixture was stirred at room temperature for 30 min. The reaction mixture was filtered, and a solution (20 mL) of diazomethane in ether was added to the filtrate under ice-cooling. The mixture was stirred at room temperature for 2 hrs. A 48% hydrobromic acid solution (5 mL) was added to the reaction mixture under ice-cooling, and the mixture was stirred at room temperature for 2 hrs. A saturated aqueous sodium hydrogen carbonate was added to the reaction mixture, and the mixture was extracted with ethyl acetate. The extract was washed with saturated brine and dried, and the solvent was evaporated to give the title compound (4.36 g) as slightly yellow solid.
ESI-MS(m/z): 536

STARTING MATERIAL SYNTHETIC EXAMPLE 37

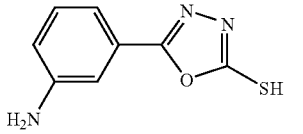

Synthesis of 5-(3-aminophenyl)-1,3,4-oxadiazole-2-thiol

3-Aminobenzhydrazide (5.76 g) was dissolved in ethanol (40 mL), and triethylamine (4.8 mL) and carbon disulfide (2.1 mL) were added to the solution. The mixture was heated under reflux for 4 hrs. The solvent was evaporated, and water was added. The precipitated solids were collected by filtration to give the title compound (5.06 g) as a pale-yellow powder.

$^1$H-NMR(DMSO-$d_6$) δ 3.2–3.5 (3H, m), 6.81–6.85 (1H, m), 7.03–7.06 (1H, m), 7.13–7.14 (1H, m), 7.22–7.28 (1H, m)

EXAMPLE 1

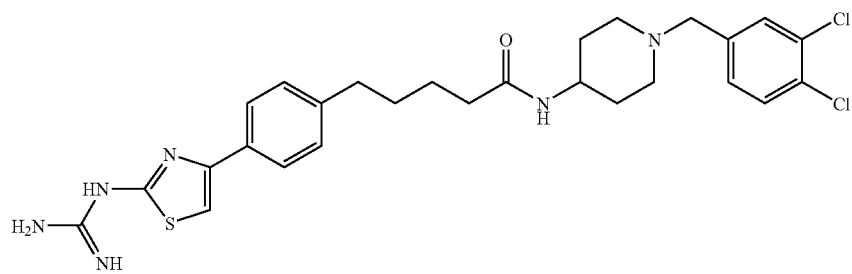

Synthesis of N-[1-(3,4-dichlorobenzyl)piperidin-4-yl]-5-[4-(2-guanidinothiazol-4-yl)phenyl]valeramide The product (500 mg) of Starting Material Synthetic Example 1 was dissolved in acetic acid (10 mL), and pyridinium tribromide (424 mg) was added to the solution. The mixture was stirred at 60° C. for 1 hr. The reaction mixture was poured into 2 mol/L aqueous sodium hydroxide solution (200 mL), and the mixture was extracted with ethyl acetate. The extract was washed with saturated brine and dried, and the solvent was evaporated under reduced pressure. The obtained residue was dissolved in ethanol (70 mL), and guanylthiourea (141 mg) was added. The mixture was heated under reflux for 12 hrs. The reaction mixture was concentrated under reduced pressure, and 1 mol/L aqueous sodium hydroxide solution (100 mL) was added. The mixture was extracted with chloroform. The extract was washed with saturated brine and dried, and the solvent was evaporated under reduced pressure. Chloroform and ethyl acetate were added to the obtained residue, and the resulting crystals were collected by filration to give the title compound (45 mg) as a brown solid.

$^1$H-NMR(DMSO-$d_6$) δ 1.31–1.42 (2H, m), 1.51–1.53 (4H, m), 1.67–1.70 (2H, m), 2.03–2.09 (4H, m), 2.55–2.57 (2H, m), 2.70–2.73 (2H, m), 3.39–3.45 (3H, m), 6.80–7.03 (2H, m), 7.09 (1H, s), 7.18 (2H, d, J=8.1 Hz), 7.29 (1H, d, J=8.2 Hz), 7.54 (1H, s), 7.58 (1H, d, J=8.2 Hz), 7.69–7.71 (1H, m), 7.72 (2H, d, J=8.1 Hz)

EXAMPLE 2

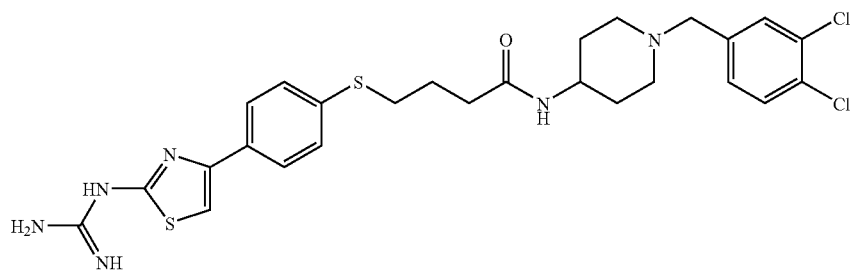

Synthesis of N-[1-(3,4-dichlorobenzyl)piperidin-4-yl]-4-[4-(2-guanidinothiazol-4-yl)phenylthio]butylamide In the same manner as in Example 1, the title compound (16 mg) was obtained as a brown solid from the product (610 mg) of Starting Material Synthetic Example 2.

$^1$H-NMR(DMSO-$d_6$) δ 1.35–1.41 (2H, m), 1.67–1.71 (2H, m), 1.78 (2H, quint, J=7.3 Hz), 1.98–2.05 (2H, m), 2.20 (2H, t, J=7.2 Hz), 2.69–2.73 (2H, m), 2.95 (2H, t, J=7.2 Hz), 3.44 (2H, s), 3.49–3.55 (1H, m), 6.89–6.93 (2H, m), 7.14 (1H, s), 7.28 (1H, dd, J=8.4, 1.8 Hz), 7.31 (2H, d, J=8.4 Hz), 7.53 (1H, d, J=1.8 Hz), 7.57 (1H, d, J=8.4 Hz), 7.76 (2H, d, J=8.4 Hz), 7.76–7.77 (1H, m)

EXAMPLE 3

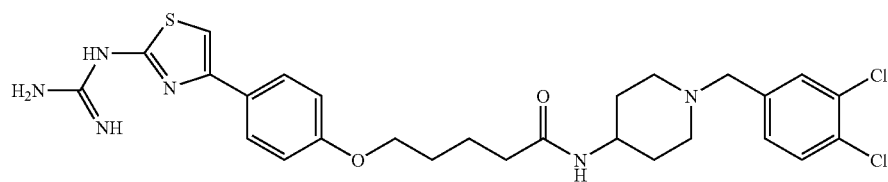

Synthesis of N-[1-(3,4-dichlorobenzyl)piperidin-4-yl]-5-[4-(2-guanidinothiazol-4-yl)phenyloxy]valeramide In the same manner as in Example 1, the title compound (4 mg) was obtained as a brown solid from the product (440 mg) of Starting Material Synthetic Example 3.

$^1$H-NMR(DMSO-$d_6$) δ 1.31–1.40 (2H, m), 1.54–1.80 (6H, m), 1.93–2.13 (4H, m), 2.65–2.78 (2H, m), 3.39–3.51 (3H, m), 3.96–3.99 (2H, m), 6.92 (2H, d, J=8.7 Hz), 7.00 (1H, s), 7.28–7.31 (1H, m), 7.54–7.60 (2H, m), 7.74 (2H, d, J=8.7 Hz), 7.89–7.93 (1H, m)

EXAMPLE 4

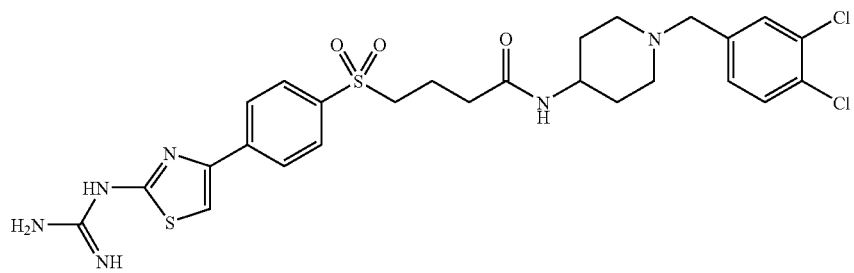

Synthesis of N-[1-(3,4-dichlorobenzyl)piperidin-4-yl]-4-[4-(2-guanidinothiazol-4-yl)phenylsulfonyl]butylamide In the same manner as in Example 1, the title compound (59 mg) was obtained as a brown solid from the product (620 mg) of Starting Material Synthetic Example 4.

$^1$H-NMR(DMSO-$d_6$) δ 1.28–1.38 (2H, m), 1.64–1.78 (4H, m), 1.95–2.03 (2H, m), 2.15 (2H, t, J=7.4 Hz), 2.54–2.71 (2H, m), 3.27–3.31 (2H, m), 3.40–3.48 (3H, m), 6.80–7.10 (3H, brs), 7.28 (1H, dd, J=8.3, 1.5 Hz), 7.48 (1H, s), 7.52 (1H, d, J=1.5 Hz), 7.57 (1H, d, J=8.3 Hz), 7.75 (1H, d, J=7.8 Hz), 7.85 (2H, d, J=8.4 Hz), 8.10 (2H, d, J=8.4 Hz)

EXAMPLE 5

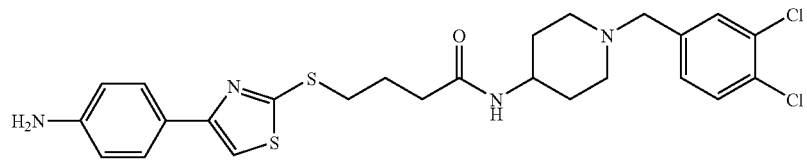

Synthesis of 4-[4-(4-aminophenyl)thiazol-2-ylthio]-N-[1-(3,4-dichlorobenzyl)piperidin-4-yl]butylamide hydrochloride The product (5.75 g) of Starting Material Synthetic Example 5 was dissolved in ethanol (200 mL), and stannous chloride anhydride (9.67 g) was added to the solution. The mixture was heated under reflux for 1 hr. The solvent was evaporated under reduced pressure and, 1 mol/L aqueous sodium hydroxide solution (100 mL) and chloroform (200 mL) were added. The mixture was stirred for 10 min and filtered through Celite. The chloroform layer of the filtrate was washed with saturated brine and dried, and the solvent was evaporated under reduced pressure. Ethyl acetate was added to the obtained residue, and the resulting crystals were collected by filtration to give the title compound (1.49 g) as a white solid.

$^1$H-NMR(DMSO-$d_6$) δ 1.63–1.69 (2H, m), 1.88–1.99 (4H, m), 2.24 (2H, t, J=7.2 Hz), 2.95–3.01 (2H, m), 3.21–3.26 (4H, m), 3.72–3.78 (1H, m), 4.24–4.26 (2H, brs), 5.31–5.46 (2H, brs), 6.59 (2H, d, J=8.7 Hz), 7.53–7.60 (4H, m), 7.75 (1H, d, J=8.1 Hz), 7.89 (1H, brs), 8.05 (1H, d, J=6.0 Hz), 10.23 (1H, brs)

EXAMPLE 6

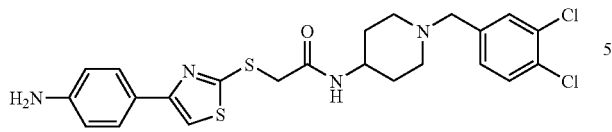

Synthesis of [4-(4-aminophenyl)thiazol-2-ylthio]-N-[1-(3,4-dichlorobenzyl)piperidin-4-yl]acetamide In the same manner as in Example 5, the title compound (993 mg) was obtained as a white solid from the product (5.86 g) of Starting Material Synthetic Example 6.

$^1$H-NMR(DMSO-$d_6$) δ 1.35–1.46 (2H, m), 1.70–1.73 (2H, m), 2.01–2.04 (2H, m), 2.66–2.70 (2H, m), 3.43 (2H, s), 3.53–3.58 (1H, m), 3.97 (2H, s), 5.31 (2H, brs), 6.58 (2H, d, J=8.7 Hz), 7.28. (1H, dd, J=8.3, 1.8 Hz), 7.52 (1H, d, J=1.8 Hz), 7.55–7.62 (4H, m), 8.20 (1H, d, J=7.5 Hz)

EXAMPLE 7

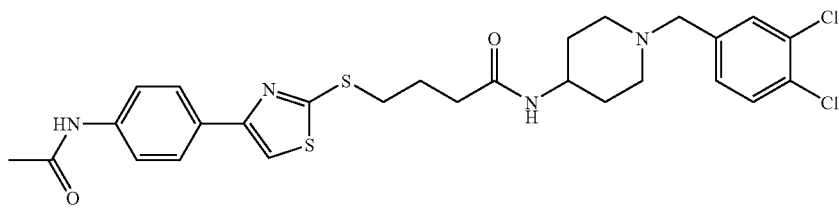

Synthesis of 4-[4-(4-acetylaminophenyl)thiazol-2-ylthio]-N-[1-(3,4-dichlorobenzyl)piperidin-4-yl] butylamide hydrochloride The product (106 mg) of Example 5 was dissolved in dichloromethane (80 mL), and triethylamine (30 μL) and acetyl chloride (15 μL) were added to the solution. The mixture was stirred at room temperature for 12 hrs. The reaction mixture was diluted with chloroform, washed with 0.1 mol/L sodium hydroxide and then saturated brine, and dried. The solvent was evaporated under reduced pressure, and the obtained residue was dissolved in ethanol (10 mL). 1 mol/L Hydrogen chloride diethyl ether solution (2 mL) was added, which was followed by filtration to give the title compound (62 mg) as a white amorphous solid.

$^1$H-NMR(DMSO-$d_6$) δ 1.66–1.73 (2H, m), 1.90–2.01 (4H, m), 2.06 (3H, s), 2.25 (2H, t, J=7.4 Hz), 2.55–2.98 (2H, m), 3.24–3.29 (4H, m), 3.70–3.80 (1H, m), 4.26 (2H, d, J=5.1 Hz), 7.54–7.58 (1H, m), 7.65 (2H, d, J=8.4 Hz), 7.75 (1H, d, J=8.4 Hz), 7.84 (2H, d, J=8.7 Hz), 7.89–7.90 (2H, m), 8.06–8.09 (1H, m), 10.09 (1H, brs), 10.40 (1H, brs)

EXAMPLE 8

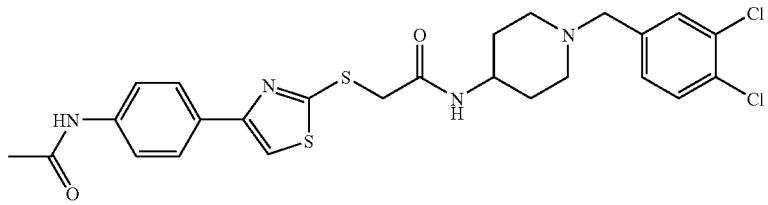

Synthesis of [4-(4-acetylaminophenyl)thiazol-2-ylthio]-N-[1-(3,4-dichlorobenzyl)piperidin-4-yl] acetamide hydrochloride In the same manner as in Example 7, the title compound (110 mg) was obtained as a white amorphous solid from the product (100 mg) of Example 6.

$^1$H-NMR(DMSO-$d_6$) δ 1.70–1.82 (2H, m), 1.90–1.95 (2H, m), 2.06 (3H, s), 2.73–3.06 (2H, m), 3.32–3.36 (2H, m), 4.02 (2H, s), 4.26 (2H, d, J=4.8 Hz), 7.56 (1H, d, J=8.3

Hz), 7.64 (2H, d, J=8.7 Hz), 7.75 (1H, d, J=8.3 Hz), 7.85 (2H, d, J=8.7 Hz), 7.88–7.90 (2H, m), 8.52 (1H, d, J=6.6 Hz), 10.08 (1H, brs), 10.45 (1H, brs)

EXAMPLE 9

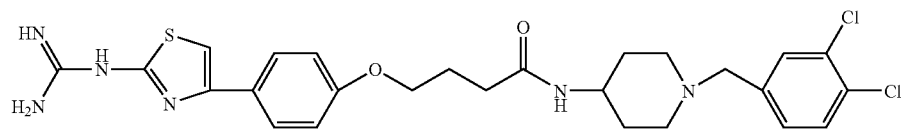

Synthesis of N-[1-(3,4-dichlorobenzyl)piperidin-4-yl]-4-[4-(2-guanidinothiazol-4-yl)phenyloxy]butylamide ½ fumarate ¼ hydrate The crystals obtained in the same manner as in Example 1 from the product (6.0 g) of Starting Material Synthetic Example 7 was treated in fumaric acid (1.6 g) and ethanol (60 ml) to give the title compound (4.8 g) as a white solid.
melting point: 258° C.

EXAMPLE 10

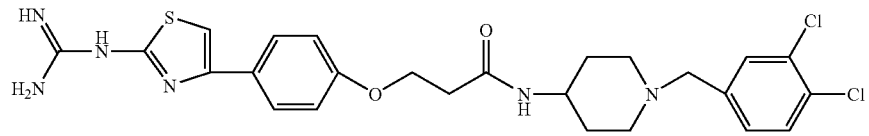

Synthesis of N-[1-(3,4-dichlorobenzyl)piperidin-4-yl]-3-[4-(2-guanidinothiazol-4-yl)phenyloxy]propionamide In the same manner as in Example 1, the title compound (520 mg) was obtained as a brown solid from the product (670 mg) of Starting Material Synthetic Example 8.

$^1$H-NMR(DMSO-$d_6$) δ 1.30–1.51 (2H, m), 1.62–1.82 (2H, m), 1.92–2.15 (2H, m), 2.48–2.64 (2H, m), 2.66–2.82 (2H, m), 3.46 (2H, s), 3.48–3.65 (1H, m), 4.18 (2H, t, J=6.3 Hz), 6.64–7.09 (3H, brs), 6.91 (2H, d, J=8.7 Hz), 6.94 (1H, s), 7.29 (1H, dd, J=8.1, 1.8 Hz), 7.54 (1H, d, J=1.8 Hz), 7.58 (1H, d, J=8.1 Hz), 7.73 (2H, d, J=8.7 Hz), 7.85–8.00 (1H, brs)

EXAMPLE 11

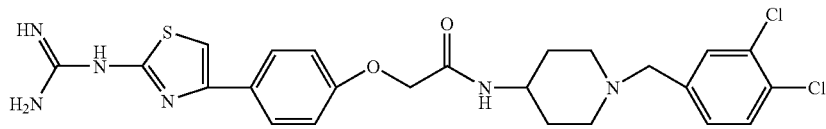

Synthesis of N-[1-(3,4-dichlorobenzyl)piperidin-4-yl]-[4-(2-guanidinothiazol-4-yl)phenyloxy]acetamide In the same manner as in Example 1, the title compound (800 mg) was obtained as a brown solid from the product (1.5 g) of Starting Material Synthetic Example 9. melting point: 182° C.

EXAMPLE 12

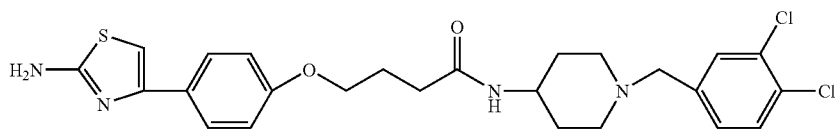

Synthesis of 4-[4-(2-aminothiazol-4-yl)phenyloxy]-N-[1-(3,4-dichlorobenzyl)piperidin-4-yl]butylamide In the same manner as in Example 1, the title compound (230 mg) was obtained as a brown solid from the product (500 mg) of Starting Material Synthetic Example 7 and thiourea (90 mg).

$^1$H-NMR(DMSO-$d_6$) δ 1.30–1.49 (2H, m), 1.62–1.78 (2H, m), 1.89–2.12 (4H, m), 2.18–2.32 (2H, m), 2.64–2.80 (2H, m), 3.44 (2H, s), 3.48–3.65 (1H, m), 3.97 (2H, t, J=6.3 Hz), 6.82 (1H, s), 6.91 (2H, d, J=8.8 Hz), 6.95–7.09 (1H, brs), 7.27 (1H, dd, J=6.4, 1.9 Hz), 7.52 (1H, d, J=1.9 Hz), 7.56 (1H, d, J=6.4 Hz), 7.71 (2H, d, J=8.8 Hz), 7.78–7.88 (1H, brs)

EXAMPLE 13

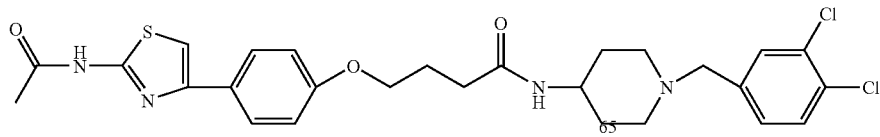

Synthesis of 4-[4-(2-acetamidethiazol-4-yl)phenyloxy]-N-[1-(3,4-dichlorobenzyl)piperidin-4-yl]butylamide In the same manner as in Example 1, the title compound (110 mg) was obtained as a brown solid from the product (500 mg) of Starting Material Synthetic Example 7 and N-acetylthiourea (140 mg).

$^1$H-NMR(DMSO-$d_6$) δ 1.28–1.50 (2H, m), 1.61–1.81 (2H, m), 1.89–2.31 (6H, m), 2.16 (3H, s), 2.60–2.89 (2H, m), 3.36 (2H, s), 3.47–3.68 (1H, m), 3.99 (2H, t, J=6.3 Hz), 6.96 (2H, d, J=8.7 Hz), 7.30 (1H, d, J=7.5 Hz), 7.41 (1H, s), 7.51–7.65 (2H, m), 7.70 (2H, d, J=8.7 Hz), 7.87–7.99 (1H, brs)

EXAMPLE 14

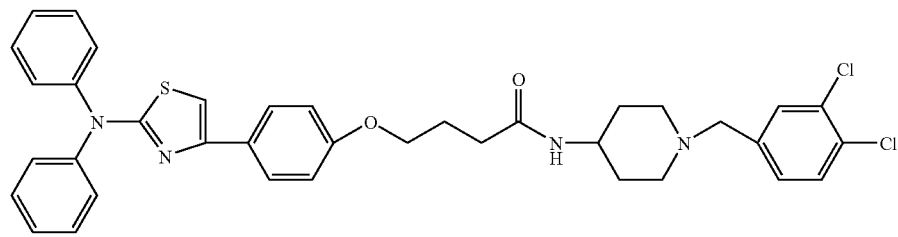

Synthesis of N-[1-(3,4-dichlorobenzyl)piperidin-4-yl]-4-[4-(2-diphenylaminothiazol-4-yl)phenyloxy]butylamide In the same manner as in Example 1, the title compound (480 mg) was obtained as a brown solid from the product (500 mg) of Starting Material Synthetic Example 7 and N,N-diphenylthiourea (270 mg).

$^1$H-NMR(DMSO-$d_6$) δ 1.28–1.74 (2H, m), 1.61–1.78 (2H, m), 1.88–2.15 (4H, m), 2.18–2.30 (2H, m), 2.63–2.80 (2H, m), 3.44 (2H, s), 3.48–3.63 (1H, m), 3.97 (2H, t, J=6.3 Hz), 6.81 (2H, d, J=8.7 Hz), 7.22 (1H, s), 7.25–7.61 (13H, m), 7.73 (2H, d, J=8.7 Hz), 7.75–7.88 (1H, brs)

EXAMPLE 15

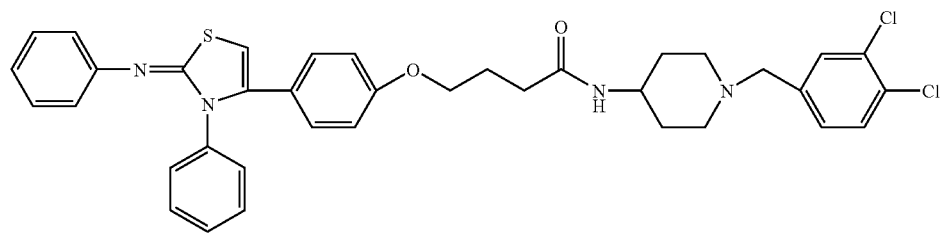

Synthesis of N-[1-(3,4-dichlorobenzyl)piperidin-4-yl]-4-[4-(3-phenyl-2-phenylimino-4-thiazolin-4-yl)phenyloxy]butylamide In the same manner as in Example 1, the title compound (350 mg) was obtained as a brown solid from the product (500 mg) of Starting Material Synthetic Example 7 and N,N'-diphenylthiourea (270 mg).

$^1$H-NMR(DMSO-d$_6$) δ 1.27–1.48 (2H, m), 1.64–1.79 (2H, m), 1.80–2.10 (4H, m), 2.13–2.31 (2H, m), 2.63–2.81 (2H, m), 3.44 (2H, s), 3.48–3.64 (1H, m), 3.89 (2H, t, J=6.3 Hz), 6.31 (1H, s), 6.76 (2H, d, J=8.7 Hz), 6.81 (2H, d, J=7.5 Hz), 6.98–7.13 (3H, m), 7.21–7.41 (8H, m), 7.48–7.64 (2H, m)

EXAMPLE 16

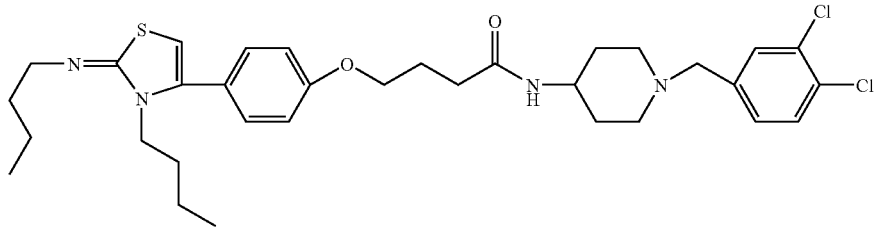

Synthesis of N-[1-(3,4-dichlorobenzyl)piperidin-4-yl]-4-[4-(3-normalbutyl-2-normalbutylimino-4-thiazolin-4-yl)phenyloxy]butylamide In the same manner as in Example 1, the title compound (340 mg) was obtained as a brown solid from the product (500 mg) of Starting Material Synthetic Example 7 and N,N'-dibutylthiourea (220 mg).

$^1$H-NMR(DMSO-d$_6$) δ 0.68 (3H, t, J=7.5 Hz), 0.91 (3H, t, J=7.5 Hz), 0.99–1.09 (2H, m), 1.28–1.49 (8H, m), 1.51–1.78 (4H, m), 1.87–2.10 (4H, m), 2.15–2.29 (2H, m), 2.61–2.80 (2H, m), 2.98 (2H, t, J=6.6 Hz), 3.44 (2H, s), 3.47–3.60 (1H, m), 3.60 (2H, t, J=6.3 Hz), 3.99 (2H, t, J=6.3 Hz), 5.97 (1H, s), 7.00 (2H, d, J=8.7 Hz), 7.27 (1H, dd, J=8.1, 2.1 Hz), 7.31 (2H, d, J=8.7 Hz), 7.53 (1H, d, J=2.1 Hz), 7.57 (1H, d, J=8.1 Hz), 7.72–7.85 (1H, brs)

EXAMPLE 17

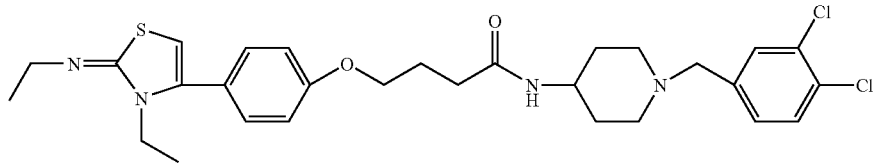

Synthesis of N-[1-(3,4-dichlorobenzyl)piperidin-4-yl]-4-[4-(3-ethyl-2-ethylimino-4-thiazolin-4-yl)phenyloxy]butylamide In the same manner as in Example 1, the title compound (70 mg) was obtained as a brown solid from the product (500 mg) of Starting Material Synthetic Example 7 and N,N'-diethylthiourea (160 mg).

$^1$H-NMR(DMSO-d$_6$) δ 0.98 (3H, t, J=6.9 Hz), 1.20 (3H, t, J=7.2 Hz), 1.28–1.50 (2H, m), 1.63–1.79 (2H, m), 1.86–2.10 (4H, m), 2.23 (2H, t, J=7.2 Hz), 2.66–2.80 (2H, m), 2.02 (2H, q, J=7.2 Hz), 3.44 (2H, s), 3.50–3.68 (1H, m), 3.60 (2H, q, J=6.9 Hz), 4.00 (2H, t, J=6.3 Hz), 5.98 (1H, s), 7.00 (2H, d, J=9.0 Hz), 7.27 (1H, dd, J=8.1, 1.8 Hz), 7.32 (2H, d, J=9.0 Hz), 7.53 (1H, d, J=1.8 Hz), 7.57 (1H, d, J=8.1 Hz), 7.74–7.82 (1H, brs)

EXAMPLE 18

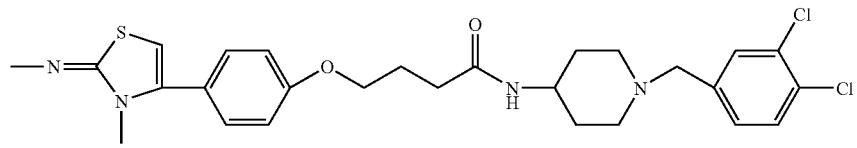

Synthesis of N-[1-(3,4-dichlorobenzyl)piperidin-4-yl]-4-[4-(3-methyl-2-methylimino-4-thiazolin-4-yl)phenyloxy]butylamide In the same manner as in Example 1, the title compound (190 mg) was obtained as-a brown solid from the product (500 mg) of Starting Material Synthetic Example 7 and N,N'-dimethylthiourea (120 mg).

$^1$H-NMR(DMSO-$d_6$) δ 1.30–1.51 (2H, m), 1.62–1.80 (2H, m), 1.87–2.12 (4H, m), 2.20–2.33 (2H, m), 2.13–2.30 (2H, m), 2.90 (3H, s), 3.10 (3H, s), 3.44 (2H, s), 3.49–3.63 (1H, m), 4.01 (2H, t, J=6.3 Hz), 6.05 (1H, s), 7.01 (2H, d, J=8.7 Hz), 7.28 (1H, dd, J=8.2, 1.8 Hz), 7.35 (2H, d, J=8.7 Hz), 7.52 (1H, d, J=1.8 Hz), 7.55 (1H, d, J=8.2 Hz), 7.73–7.87 (1H, brs)

EXAMPLE 19

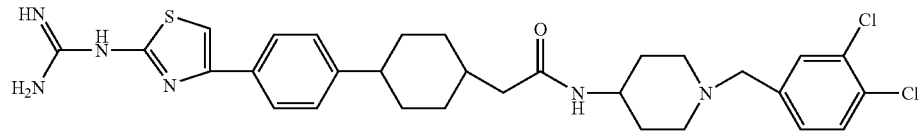

Synthesis of N-[1-(3,4-dichlorobenzyl)piperidin-4-yl]-[4-[4-(2-guanidinothiazol-4-yl)phenyl]cyclohexyl]acetamide In the same manner as in Example 1, the title compound (640 mg) was obtained as a brown solid from the product (1.0 g) of Starting Material Synthetic Example 10.

$^1$H-NMR(DMSO-$d_6$) δ 0.98–1.23 (2H, m), 1.20–1.60 (4H, m), 1.66–1.91 (7H, m), 1.92–2.08 (4H, m), 2.38–2.68 (1H, m), 2.65–2.81 (2H, m), 3.45 (2H, s), 3.50–3.67 (1H, m), 6.68–7.12 (3H, brs), 7.06 (1H, s), 7.22 (2H, d, J=8.4 Hz), 7.29 (1H, dd, J=8.1, 1.8 Hz), 7.53 (1H, d, J=1.8 Hz), 7.58 (1H, d, J=8.1 Hz), 7.71 (2H, d, J=8.4 Hz), 7.64–7.83 (1H, brs)

EXAMPLE 20

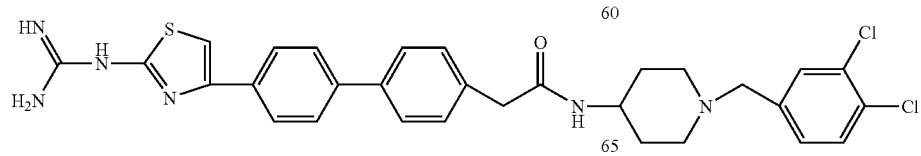

Synthesis of N-[1-(3,4-dichlorobenzyl)piperidin-4-yl]-[4-[4-(2-guanidinothiazol-4-yl)phenyl]phenyl]acetamide In the same manner as in Example 1, the title compound (920 mg) was obtained as a brown solid from the product (1.0 g) of Starting Material Synthetic Example 11.

$^1$H-NMR(DMSO-$d_6$) δ 1.61–1.89 (2H, m), 1.90–2.08 (2H, m), 2.88–3.17 (2H, m), 3.45 (2H, s), 3.71–3.90 (1H, m), 4.21–4.46 (2H, m), 7.36 (2H, d, J=7.8 Hz), 7.57 (1H, d, J=8.4 Hz), 7.65 (2H, d, J=8.1 Hz), 7.68–7.88 (3H, m), 7.91 (1H, s), 8.03 (2H, d, J=8.4 Hz), 8.24 (3H, m), 8.32–8.46 (1H, brs), 10.01–10.43 (1H, brs)

EXAMPLE 21

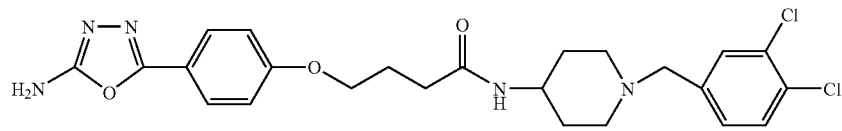

Synthesis of 4-[4-(5-amino-1,3,4-oxadiazol-2-yl)phenyloxy]-N-[1-(3,4-dichlorobenzyl)piperidin-4-yl]butylamide 4-[4-(5-Amino-1,3,4-oxadiazol-2-yl)phenyloxy]butyric acid (2.0 g) and 4-amino-1-(3,4-dichlorobenzyl)piperidine dihydrochloride (2.5 g) were suspended in DMF (50 mL), and triethylamine (2.1 mL), EDC hydrochloride (1.6 g) and HOBt (1.3 g) were added to the suspension. The mixture was stirred for 12 hrs. The reaction mixture was washed with water and then saturated brine, and dried, and the solvent was evaporated under reduced pressure. Diisopropyl ether was added to the residue to crystallize to give the title compound (2.3 g) as a white solid.

$^1$H-NMR(DMSO-$d_6$) δ 1.30–1.49 (2H, m), 1.62–1.81 (2H, m), 1.98–2.18 (4H, m), 2.18–2.34 (2H, m), 2.67–2.80 (2H, m), 3.45 (2H, s), 3.52–3.68 (1H, m), 4.02 (2H, t, J=6.3 Hz), 7.05 (2H, d, J=7.1 Hz), 7.13 (1H, s), 7.28 (1H, dd, J=8.2, 1.8 Hz), 7.53 (1H, d, J=1.8 Hz), 7.57 (1H, d, J=8.2 Hz), 7.71 (2H, d, J=7.1 Hz), 7.75–7.86 (1H, brs)

EXAMPLE 22

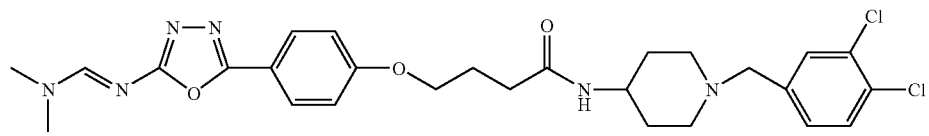

Synthesis of N-[1-(3,4-dichlorobenzyl)piperidin-4-yl]-4-[4-(5-dimethylaminomethyleneamino-1,3,4-oxadiazol-2-yl)phenyloxy]butylamide The product (920 mg) of Example 21 and N,N-dimethylformamide diethyl acetal (530 mg) were refluxed in methanol (30 mL) for 2 hrs, and the solvent was evaporated under reduced pressure. Diisopropyl ether was added to the residue to crystallize to give the title compound (740 mg) as a white solid.

$^1$H-NMR(DMSO-d$_6$) δ 1.28–1.51 (2H, m), 1.62–1.81 (2H, m), 1.90–2.12 (4H, m), 2.23 (2H, t, J=6.4 Hz), 2.64–2.80 (2H, m), 3.02 (3H, s), 3.17 (3H, s), 3.44 (2H, s), 3.50–3.65 (1H, m), 4.03 (2H, t, J=6.3 Hz), 7.01 (2H, d, J=8.7 Hz), 7.28 (1H, dd, J=8.1, 1.5 Hz), 7.52 (1H, d, J=1.5 Hz), 7.57 (1H, d, J=8.1 Hz), 7.71–7.92 (1H, brs), 7.83 (2H, d, J=8.7 Hz), 8.50 (1H, s)

EXAMPLE 23

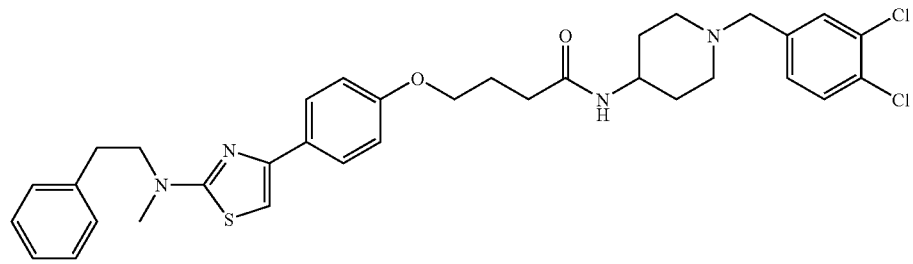

Synthesis of N-[1-(3,4-dichlorobenzyl)piperidin-4-yl]-4-[4-[2-(N-methylphenethylamino)thiazol-4-yl]phenyloxy]butylamide trifluoroacetate The compound (104 mg) of Starting Material Synthetic Example 12 was dissolved in tetrahydrofuran (7 mL), and N-methylphenethylamine (436 μL) was added to the solution. The mixture was stirred overnight at 60° C. The solvent was evaporated under reduced pressure, and the mixture was purified by Isolute Flush SIL (20 g, chloroform methanol=100:1) and then HPLC (Develosil C30-UG-5, 0.05% aqueous TFA:acetonitrile 2:8–0:10) to give the title compound (18.6 mg).

ESI-MS(m/z) : 637

EXAMPLE 24

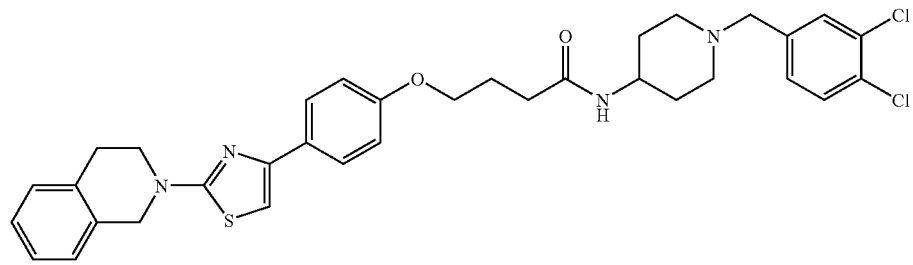

Synthesis of N-[1-(3,4-dichlorobenzyl)piperidin-4-yl]-4-[4-[2-(1,2,3,4-tetrahydroisoquinolin-2-yl)thiazol-4-yl]phenyloxy]butylamide trifluoroacetate In the same manner as in Example 23, the title compound was obtained from the product of Starting Material Synthetic Example 12 and 1,2,3,4-tetrahydroisoquinoline.

ESI-MS(m/z): 635

EXAMPLE 25

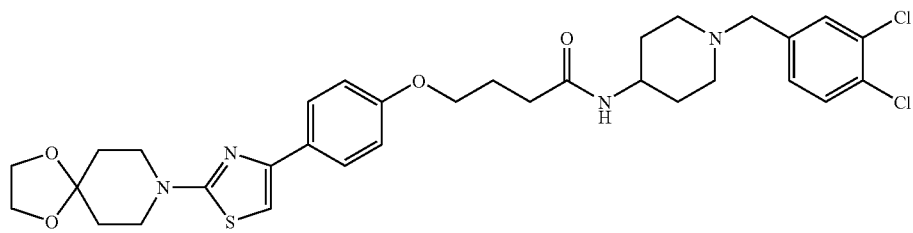

Synthesis of N-[1-(3,4-dichlorobenzyl)piperidin-4-yl]-4-[4-[2-(1,4-dioxa-8-azaspiro[4,5]decan-8-yl)thiazol-4-yl]phenyloxy]butylamide trifluoroacetate In the same manner as in Example 23, the title compound was obtained from the product of Starting Material Synthetic Example 12 and 1,4-dioxa-8-azaspiro[4,5]decane.

ESI-MS(m/z): 645

EXAMPLE 26

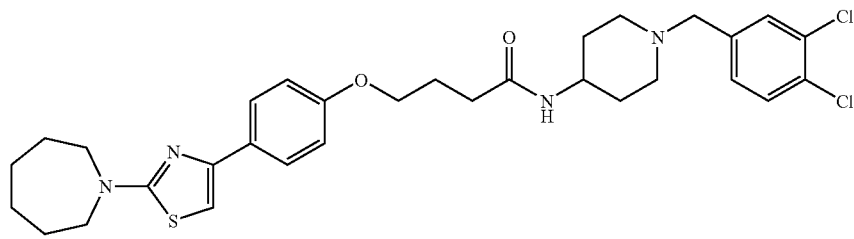

Synthesis of N-[1-(3,4-dichlorobenzyl)piperidin-4-yl]-4-[4-[2-(homopiperidin-1-yl)thiazol-4-yl)phenyloxy]butylamide trifluoroacetate In the same manner as in Example 23, the title compound was obtained from the product of Starting Material Synthetic Example 12 and homopiperidine. ESI-MS(m/z): 601

EXAMPLE 27

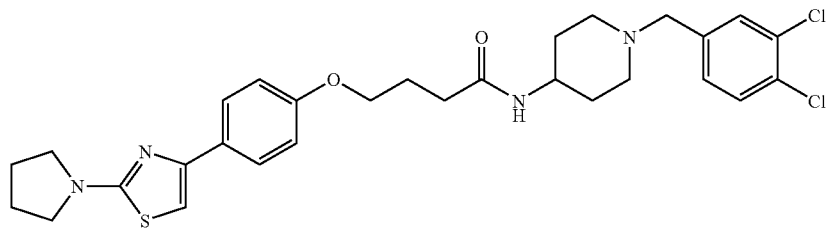

Synthesis of N-[1-(3,4-dichlorobenzyl)piperidin-4-yl]-4-[4-[2-(pyrrolidin-1-yl)thiazol-4-yl]phenyloxy]butylamide trifluoroacetate In the same manner as in Example 23, the title compound was obtained from the product of Starting Material Synthetic Example 12 and pyrrolidine. ESI-MS(m/z): 573

EXAMPLE 28

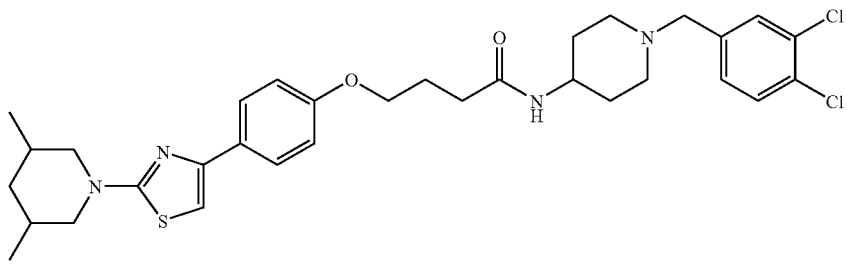

Synthesis of N-[1-(3,4-dichlorobenzyl)piperidin-4-yl]-4-[4-[2-(3,5-dimethylpiperidino)thiazol-4-yl]phenyloxy]butylamide trifluoroacetate In the same manner as in Example 23, the title compound was obtained from the product of Starting Material Synthetic Example 12 and 3,5-dimethylpiperidine. ESI-MS(m/z): 615

EXAMPLE 29

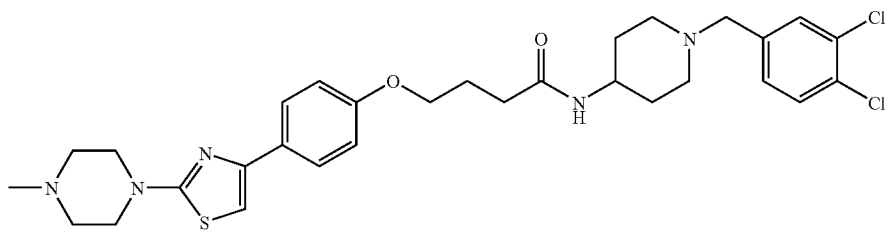

Synthesis of N-[1-(3,4-dichlorobenzyl)piperidin-4-yl]-4-[4-[2-(4-methylpiperazin-1-yl)thiazol-4-yl]phenyloxy]butylamide trifluoroacetate In the same manner as in Example 23, the title compound was obtained from the product of Starting Material Synthetic Example 12 and 1-methylpiperazine. ESI-MS(m/z): 602

EXAMPLE 30

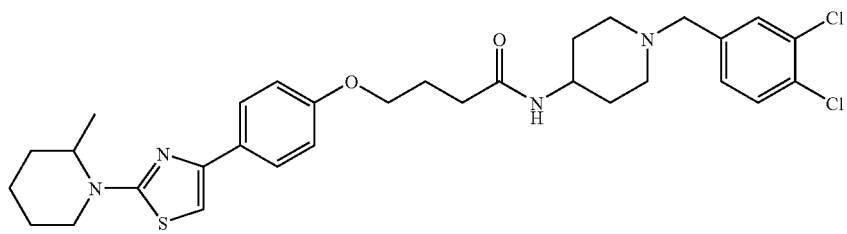

Synthesis of N-[1-(3,4-dichlorobenzyl)piperidin-4-yl]-4-[4-[2-(2-methylpiperidino)thiazol-4-yl]phenyloxy]butylamide trifluoroacetate In the same manner as in Example 23, the title compound was obtained from the product of Starting Material Synthetic Example 12 and 2-methylpiperidine. ESI-MS(m/z): 601

EXAMPLE 31

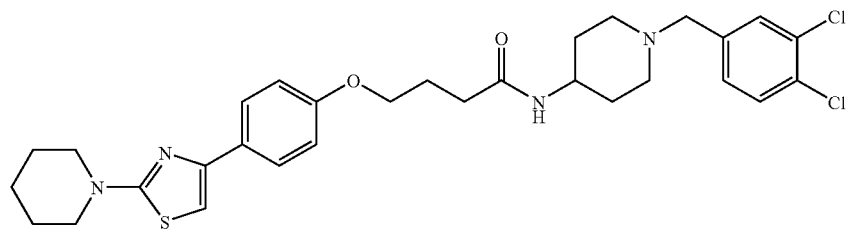

Synthesis of N-[1-(3,4-dichlorobenzyl)piperidin-4-yl]-4-[4-(2-piperidinothiazol-4-yl)phenyloxy]butylamide trifluoroacetate In the same manner as in Example 23, the title compound was obtained from the product of Starting Material Synthetic Example 12 and piperidine. ESI-MS(m/z): 587

EXAMPLE 32

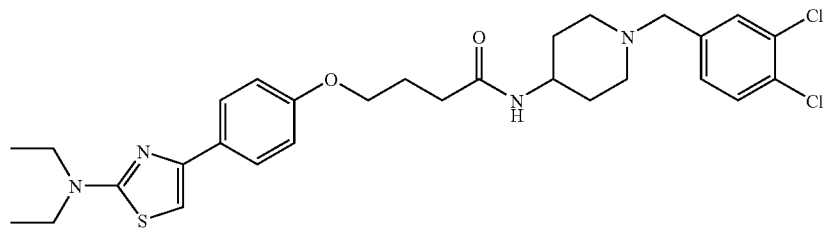

Synthesis of N-[1-(3,4-dichlorobenzyl)piperidin-4-yl]-4-[4-(2-diethylaminothiazol-4-yl)phenyloxy]butylamide trifluoroacetate In the same manner as in Example 23, the title compound was obtained from the product of Starting Material Synthetic Example 12 and diethylamine. ESI-MS(m/z): 575

EXAMPLE 33

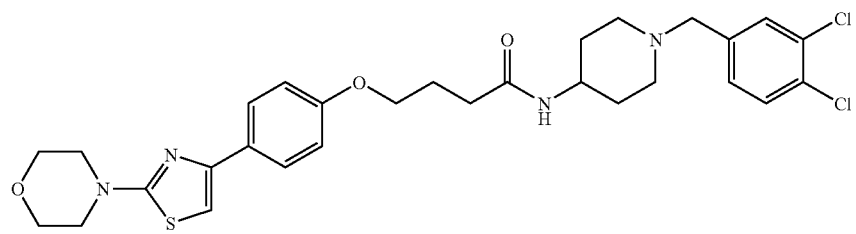

Synthesis of N-[1-(3,4-dichlorobenzyl)piperidin-4-yl]-4-[4-(2-morpholinothiazol-4-yl)phenyloxy]butylamide trifluoroacetate In the same manner as in Example 23, the title compound was obtained from the product of Starting Material Synthetic Example 12 and morpholine. ESI-MS(m/z): 589

EXAMPLE 34

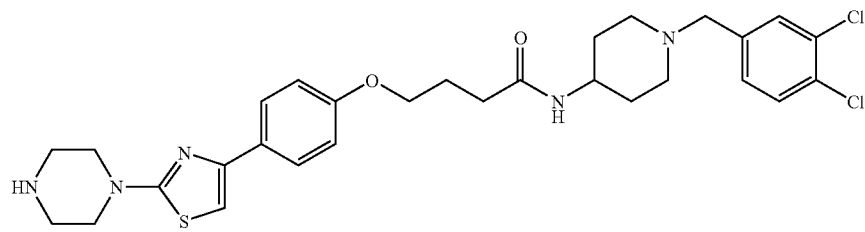

Synthesis of N-[1-(3,4-dichlorobenzyl)piperidin-4-yl]-4-[4-[2-(piperazin-1-yl)thiazol-4-yl]phenyloxy]butylamide trifluoroacetate In the same manner as in Example 23, 4-[4-[2-(4-tert-butoxycarbonylpiperazin-1-yl)thiazol-4-yl]phenyloxy]-N-[1-(3,4-dichlorobenzyl)piperidin-4-yl]butylamide trifluoroacetate was obtained from 1-tert-butoxycarbonylpiperazine, which is the product of Starting Material Synthetic Example 12. This compound was treated with trifluoroacetic acid to give the title compound. ESI-MS(m/z): 688

EXAMPLE 35

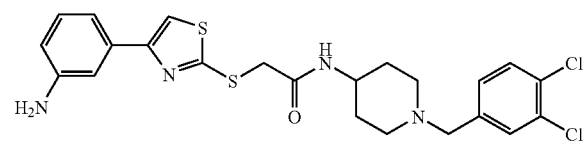

Synthesis of [4-(3-aminophenyl)thiazol-2-ylthio]-N-[1-(3,4-dichlorobenzyl)piperidin-4-yl]acetamide In the same manner as in Example 5, the title compound (4.8 g) was obtained as a white powder from the product (6.7 g) of Starting Material Synthetic Example 24 and tin(II) chloride (7.1 g).
$^1$H-NMR(CDCl$_3$) δ 1.37–1.52 (2H, m), 1.82–1.88 (2H, m), 2.05–2.15 (2H, m), 2.51–2.62 (2H, m), 3.28 (2H, s), 3.78–3.84 (1H, m), 3.85 (2H, s), 6.67–6.72 (1H, m), 7.03–7.08 (1H, m), 7.17–7.24 (3H, m), 7.31–7.37 (3H, m), 7.67–7.72 (1H, m)

EXAMPLE 36

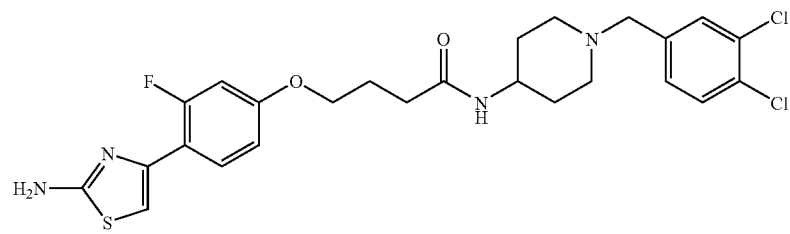

Synthesis of 4-[4-(2-aminothiazol-4-yl)-3-fluorophenyloxy]-N-[1-(3,4-dichlorobenzyl)piperidin-4-yl]butylamide dihydrochloride The residue obtained from the product (1.93 g) of Starting Material Synthetic Example 13 and thiourea (305 mg) by a method similar to the method of Example 1 was dissolved in methanol (30 mL), and a 1 mol/L hydrogen chloride diethyl ether solution (5 mL) was added to the solution. The solvent was evaporated to give the title compound (152 mg) as a brown amorphous solid.

$^1$H-NMR(DMSO-d$_6$) δ 1.65–1.75 (2H, m), 1.87–1.95 (4H, m), 2.23 (2H, t, J=7.2 Hz), 2.95–3.03 (2H, m), 3.31–3.35 (2H, m), 3.68–3.80 (1H, m), 4.01 (2H, t, J=6.3 Hz), 4.26 (1H, d, J=4.5 Hz), 6.83–6.94 (2H, m), 7.57 (1H, dd, J=8.1, 1.8 Hz), 7.75 (1H, d, J=8.1 Hz), 7.75–7.85 (1H, m), 7.92 (1H, d, J=1.8 Hz), 8.06 (1H, d, J=7.5 Hz), 10.52 (1H, brs)

EXAMPLE 37

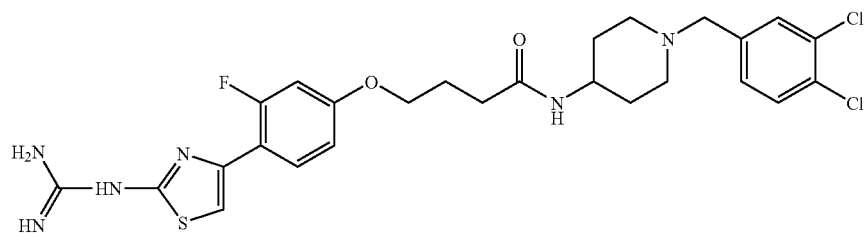

Synthesis of N-[1-(3,4-dichlorobenzyl)piperidin-4-yl]-4-[3-fluoro-4-(2-guanidinothiazol-4-yl)phenyloxy]butylamide In the same manner as in Example 1, the title compound (191 mg) was obtained as brown crystals from the product (1.93 g) of Starting Material Synthetic Example 13.

$^1$H-NMR(DMSO-$d_6$) δ 1.32–1.42 (2H, m), 1.68–1.72 (2H, m), 1.88–2.06 (4H, m), 2.23 (2H, t, J=7.4 Hz), 2.69–2.73 (2H, m), 3.45 (2H, s), 3.50–3.59 (1H, m), 4.00 (2H, t, J=6.3 Hz), 6.79–6.92 (6H, m), 7.28 (1H, dd, J=8.1, 1.8 Hz), 7.53 (1H, d, J=1.8 Hz), 7.57 (1H, d, J=8.1 Hz), 7.78 (1H, d, J=7.5 Hz), 7.87 (1H, t, J=9.2 Hz)

EXAMPLE 38

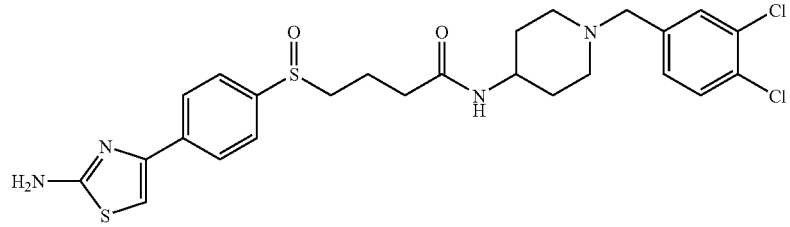

Synthesis of 4-[4-(2-aminothiazol-4-yl)phenylsulfinyl]-N-[1-(3,4-dichlorobenzyl)piperidin-4-yl]butylamide In the same manner as in Example 1, the title compound (51 mg) was obtained as brown crystals from the product (0.60 g) of Starting Material Synthetic Example 14 and thiourea (0.11 g)

$^1$H-NMR(DMSO-$d_6$) δ 1.30–1.39 (2H, m), 1.64–1.68 (3H, m), 1.79–1.85 (1H, m), 1.96–2.03 (2H, m), 2.16 (2H, t, J=7.4 Hz), 2.67–2.71 (2H, m), 2.74–2.80 (1H, m), 2.89–2.94 (1H, m), 3.39–3.50 (1H, m), 3.43 (2H, s), 7.13 (2H, s), 7.19 (1H, s), 7.28 (1H, dd, J=8.2, 1.8 Hz), 7.52 (1H, d, J=1.7 Hz), 7.57 (1H, d, J=8.2 Hz), 7.62 (2H, d, J=8.4 Hz), 7.76 (1H, d, J=7.7 Hz), 7.98 (2H, d, J=8.4 Hz)

EXAMPLE 39

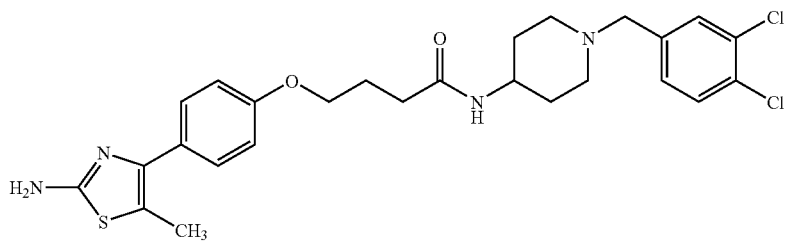

Synthesis of 4-[4-(2-amino-5-methylthiazol-4-yl)phenyloxy]-N-[1-(3,4-dichlorobenzyl)piperidin-4-yl]butylamide In the same manner as in Example 1, the title compound (465 mg) was obtained as a brown amorphous solid from the product (1.05 g) of Starting Material Synthetic Example 15 and thiourea (167 mg).

$^1$H-NMR(DMSO-$d_6$) δ 1.31–1.43 (2H, m), 1.68–1.71 (2H, m), 1.90–2.05 (4H, m), 2.23 (2H, t, J=7.4 Hz), 2.28 (3H, s), 2.69–2.72 (2H, m), 3.44 (2H, s), 3.51–3.56 (1H, m), 3.96 (2H, t, J=6.3 Hz), 6.71 (2H, s), 6.92 (2H, d, J=8.7 Hz), 7.28 (1H, dd, J=8.1, 1.8 Hz), 7.47 (2H, d, J=8.7 Hz), 7.53 (1H, d, J=1.8 Hz), 7.57 (1H, d, J=8.1 Hz), 7.78 (1H, d, J=7.8 Hz)

EXAMPLE 40

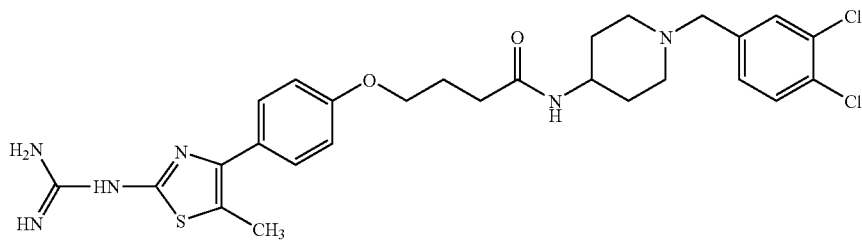

Synthesis of N-[1-(3,4-dichlorobenzyl)piperidin-4-yl]-4-[4-(2-guanidino-5-methylthiazol-4-yl)phenyloxy]butylamide In the same manner as in Example 1, the title compound (316 mg) was obtained as a brown amorphous solid from the product (1.05 g) of Starting Material Synthetic Example 15.

$^1$H-NMR(DMSO-$d_6$) δ 1.32–1.42 (2H, m), 1.68–1.72 (2H, m), 1.88–2.06 (4H, m), 2.23 (2H, t, J=7.4 Hz), 2.31 (3H, s), 2.70–2.73 (2H, m), 3.45 (2H, s), 3.49–3.57 (1H, m), 3.98 (2H, t, J=6.3 Hz), 6.82 (3H, brs), 6.95 (2H, d, J=8.7 Hz), 7.29 (1H, dd, J=8.1, 1.8 Hz), 7.49 (2H, d, J=8.7 Hz), 7.53 (1H, d, J=1.8 Hz), 7.58 (1H, d, J=8.1 Hz), 7.78 (1H, d, J=7.8 Hz)-

EXAMPLE 41

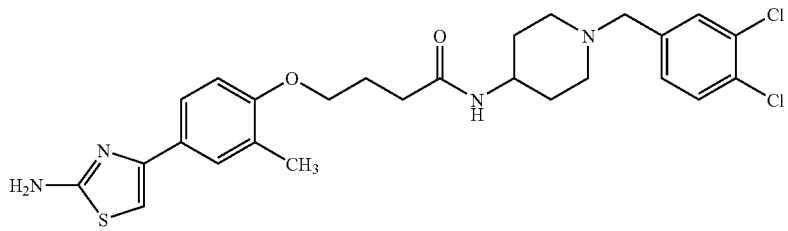

Synthesis of 4-[4-(2-aminothiazol-4-yl)-2-methylphenyloxy]-N-[1-(3,4-dichlorobenzyl)piperidin-4-yl]butylamide In the same manner as in Example 1, the title compound (337 mg) was obtained as a brown amorphous solid from the product (1.95 g) of Starting Material Synthetic Example 16 and thiourea (311 mg).

$^1$H-NMR(DMSO-$d_6$) δ 1.32–1.42 (2H, m), 1.68–1.71 (2H, m), 1.89–2.05 (4H, m), 2.17 (3H, s), 2.25 (2H, t, J=7.5 Hz), 2.68–2.72 (2H, m), 3.44 (2H, s), 3.50–3.57 (1H, m), 3.96 (2H, t, J=6.2 Hz), 6.78 (1H, s), 6.87 (1H, d, J=8.1 Hz), 6.97 (2H, s), 7.28 (1H, dd, J=8.4, 1.8 Hz), 7.52–7.59 (4H, m), 7.77 (1H, d, J=7.5 Hz)

EXAMPLE 42

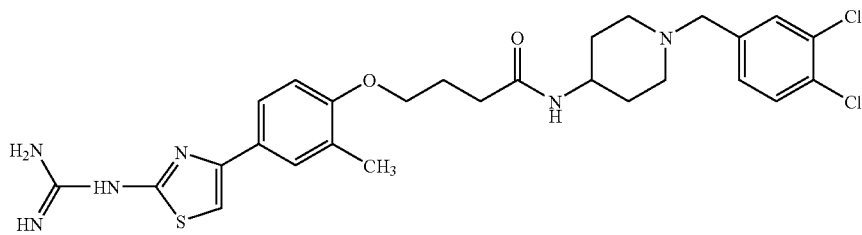

Synthesis of N-[1-(3,4-dichlorobenzyl)piperidin-4-yl]-4-[4-(2-guanidinothiazol-4-yl)-2-methylphenyloxy]butylamide In the same manner as in Example 1, the title compound (275 mg) was obtained as brown crystals from the product (1.95 g) of Starting Material Synthetic Example 16.

$^1$H-NMR(DMSO-$d_6$) δ 1.31–1.43 (2H, m), 1.68–1.71 (2H, m), 1.91–2.05 (4H, m), 2.20 (3H, s), 2.26 (2H, t, J=7.4 Hz), 2.68–2.72 (2H, m), 3.44 (2H, s), 3.52–3.56 (1H, m), 3.97 (2H, t, J=6.3 Hz), 6.87 (3H, brs), 6.89 (1H, d, J=9.0 Hz), 6.94 (1H, s), 7.28 (1H, dd, J=8.1, 1.8 Hz), 7.52–7.60 (4H, m), 7.77 (1H, d, J=7.5 Hz)

EXAMPLE 43

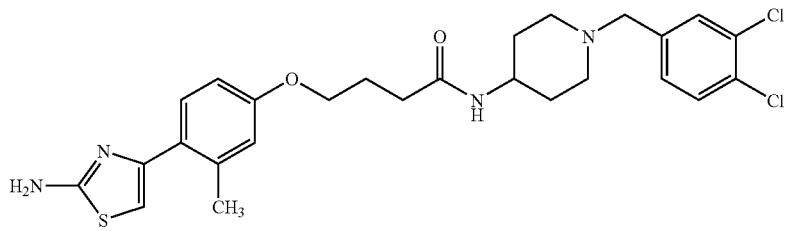

Synthesis of 4-[4-(2-aminothiazol-4-yl)-3-methylphenyloxy]-N-[1-(3,4-dichlorobenzyl)piperidin-4-yl]butylamide In the same manner as in Example 1, the title compound (529 mg) was obtained as brown crystals from the product (2.02 g) of Starting Material Synthetic Example 17 and thiourea (322 mg).

$^1$H-NMR(DMSO-$d_6$) δ 1.32–1.41 (2H, m), 1.68–1.71 (2H, m), 1.89–2.05 (4H, m), 2.22 (2H, t, J=7.4 Hz), 2.38 (3H, s), 2.69–2.73 (2H, m), 3.44 (2H, s), 3.50–3.57 (1H, m), 3.95 (2H, t, J=6.3 Hz), 6.47 (1H, s), 6.72–6.77 (2H, m), 6.92 (2H, s), 7.28 (1H, dd, J=8.4, 1.8 Hz), 7.46 (1H, d, J=8.4 Hz), 7.53 (1H, d, J=1.8 Hz), 7.58 (1H, d, J=8.4 Hz), 7.77 (1H, d, J=7.5 Hz)

EXAMPLE 44

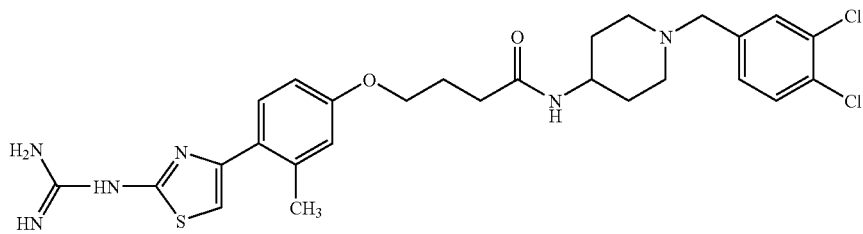

Synthesis of N-[1-(3,4-dichlorobenzyl)piperidin-4-yl]-4-[4-(2-guanidinothiazol-4-yl)-3-methylphenyloxy]butylamide In the same manner as in Example 1, the title compound (725 mg) was obtained as a brown amorphous solid from the product (2.02 g) of Starting Material Synthetic Example 17.

$^1$H-NMR(DMSO-$d_6$) δ 1.32–1.43 (2H, m), 1.69–1.72 (2H, m), 1.87–2.07 (4H, m), 2.22 (2H, t, J=7.2 Hz), 2.37 (3H, s), 2.70–2.74 (2H, m), 3.46 (2H, s), 3.52–3.56 (1H, m), 3.96 (2H, t, J=6.3 Hz), 6.65 (1H, s), 6.74–6.78 (2H, m), 6.79 (3H, brs), 7.29 (1H, dd, J=8.1, 1.8 Hz), 7.43 (1H, d, J=8.4 Hz), 7.53 (1H, d, J=1.8 Hz), 7.58 (1H, d, J=8.1 Hz), 7.77 (1H, d, J=7.5 Hz)

EXAMPLE 45

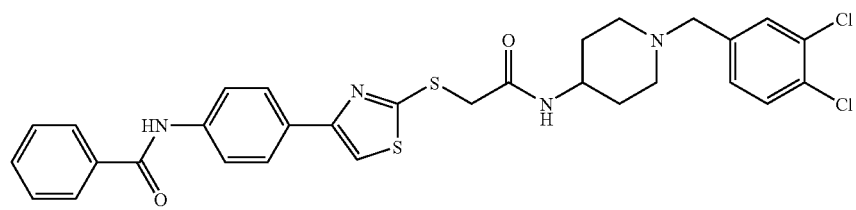

Synthesis of [4-(4-benzoylaminophenyl)thiazol-2-ylthio]-N-[1-(3,4-dichlorobenzyl)piperidin-4-yl]acetamide The product (400 mg) of Example 6 was dissolved in dichloromethane (100 mL), and triethylamine (132 μL) and benzoyl chloride (110 μL) were added to the solution. The mixture was stirred at room temperature for 2 hrs, and triethylamine (132 μL) and benzoyl chloride (110 μL) were added again. The mixture was stirred at room temperature for 2 hrs. The reaction mixture was diluted with chloroform and washed with 0.1 mol/L sodium hydroxide and then saturated brine, and dired. The solvent was evaporated under reduced pressure, and the residue was dissolved in tetrahydrofuran (100 mL), methanol (100 mL) and 1 mol/L sodium hydroxide (50 mL). The mixture was stirred at room temperature for 30 min. The organic solvent was evaporated under reduced pressure, and the residue was extracted with chloroform. The chloroform layer was washed with saturated brine and dried. The solvent was evaporated under reduced pressure, and the residue was crystallized from diethyl ether to give the title compound (361 mg) as brown crystals.

$^1$H-NMR(CDCl$_3$) δ 1.33–1.46 (2H, m), 1.81–1.86 (2H, m), 2.06–2.14 (2H, m), 2.50–2.54 (2H, m), 3.29 (2H, s), 3.79–3.87 (1H, m), 3.90 (2H, s), 7.06 (1H, dd, J=8.1, 1.8 Hz), 7.32 (2H, d, J=8.1 Hz), 7.38–7.41 (2H, m), 7.75–7.59 (3H, m), 7.76 (2H, d, J=8.7 Hz), 7.87–7.92 (5H, m)

EXAMPLE 46

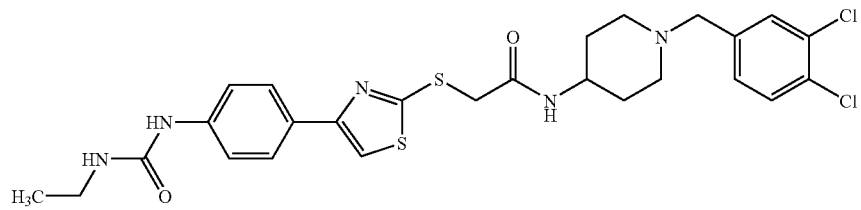

Synthesis of N-[1-(3,4-dichlorobenzyl)piperidin-4-yl]-{4-[4-(3-ethylureido)phenyl]thiazol-2-ylthio}acetamide The product (400 mg) of Example 6 was dissolved in pyridine (25 mL), and ethyl isocyanate (75 μL) was added to the solution. The mixture was stirred overnight at 100° C., and the solvent was evaporated. 1 mol/L Sodium hydroxide (100 mL) was added to the residue, and the mixture was extracted with chloroform. The chloroform layer was washed with saturated brine and dried. The solvent was evaporated under reduced pressure, and the residue was recrystallized from ethyl acetate and diethyl ether to give the title compound (242 mg) as brown crystals.

$^1$H-NMR(DMSO-d$_6$) δ 1.06 (3H, t, J=7.2 Hz), 1.36–1.46 (2H, m), 1.70–1.73 (2H, m), 2.00–2.07 (2H, m), 2.65–2.69 (2H, m), 3.07–3.16 (2H, m), 3.43 (2H, s), 3.53–3.58 (1H, m), 3.99 (2H, s), 6.13 (1H, t, J=5.6 Hz), 7.28 (1H, dd, J=8.4, 1.8 Hz), 7.45 (1H, d, J=8.7 Hz), 7.52 (1H, d, J=1.8 Hz), 7.58 (1H, d, J=8.4 Hz), 7.79 (2H, d, J=8.7 Hz), 7.80 (1H, s), 8.22 (1H, d, J=7.5 Hz)

EXAMPLE 47

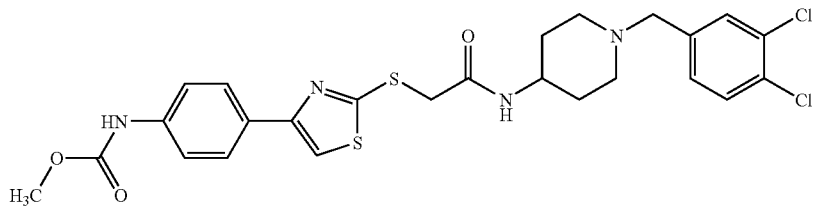

Synthesis of N-[1-(3,4-dichlorobenzyl)piperidin-4-yl]-[4-(4-methoxycarbonylaminophenyl)thiazol-2-ylthio]acetamide The product (400 mg) of Example 6 was dissolved in methylene chloride (100 mL), and triethylamine (132 μL) and methyl chloroformate (73 μL) were added to the solution. The mixture was stirred at 60° C. for 2 hrs. Triethylamine (132 μL) and methyl chloroformate (73 μL) were added again, and the mixture was stirred overnight at 60° C. The reaction mixture was washed with sodium hydroxide and saturated brine, and dried, and the solvent was evaporated under reduced pressure. The residue was purified by HPLC (Develosil C30-UG-5, 0.05% aqueous TFA:acetonitrile 2:8–0:10) to give the title compound (20 mg) as white crystals.

$^1$H-NMR(DMSO-d$_6$) δ 1.39–1.45 (2H, m), 1.69–1.73 (2H, m), 1.99–2.06 (2H, m), 2.65–2.69 (2H, m), 3.43 (2H, s), 3.54–3.58 (1H, m), 3.68 (3H, s), 3.99 (2H, s), 7.28 (1H, d, J=7.8 Hz), 7.50–7.59 (4H, m), 7.84–7.87 (3H, m), 8.22 (1H, d, J=7.5 Hz), 9.77 (1H, s)

EXAMPLE 48

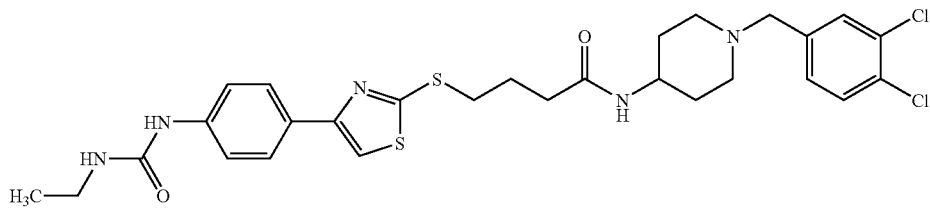

Synthesis of N-[1-(3,4-dichlorobenzyl).piperidin-4-yl]-4-{4-[4-(3-ethylureido)phenyl]thiazol-2-ylthio}butylamide In the same manner as in Example 46, the title compound (36 mg) was obtained as white crystals from the product (110 mg) of Example 5.

$^1$H-NMR(DMSO-d$_6$) δ 1.05 (3H, t, J=7.2 Hz), 1.33–1.40 (2H, m), 1.67–1.71 (2H, m), 1.93–2.04 (4H, m), 2.23 (2H, t, J=7.2 Hz), 2.68–2.72 (2H, m), 3.09–3.13 (2H, m), 3.25 (2H, t, J=7.2 Hz), 3.44 (2H, s), 3.51–3.56 (1H, m), 6.13 (1H, t, J=5.6 Hz), 7.28 (1H, dd, J=8.1, 1.8 Hz), 7.45 (2H, d, J=8.7 Hz), 7.53 (1H, d, J=1.8 Hz), 7.57 (1H, d, J=8.1 Hz), 7.76–7.83 (4H, m), 8.55 (1H, s)

EXAMPLE 49

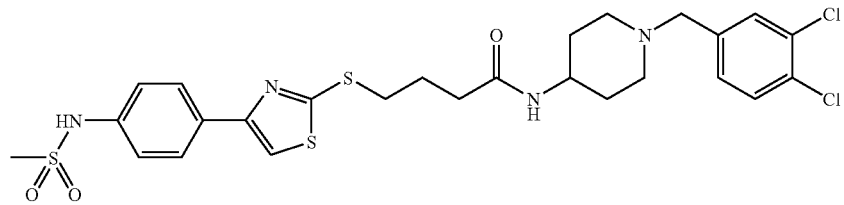

Synthesis of N-[1-(3,4-dichlorobenzyl)piperidin-4-yl]-4-[4-(4-methylsulfonylaminophenyl)thiazol-2-ylthio]butylamide hydrochloride A free base of the title compound was obtained from the product (150 mg) of Example 5 and methanesulfonyl chloride by a method similar to Example 45. This residue was dissolved in chloroform (25 mL) and methanol (25 mL), and a 1 mol/L hydrogen chloride diethyl ether solution (5 mL) was added to the solution. The solvent was evaporated to give the title compound (84 mg) as a brown amorphous solid.

$^1$H-NMR(DMSO-d$_6$) δ 1.68–1.76 (2H, m), 1.89–2.01 (4H, m), 2.25 (2H, t, J=7.2 Hz), 2.96–3.00 (2H, m), 3.03 (3H, s), 3.24–3.34 (4H, m), 3.72–3.78 (1H, m), 4.26 (2H, d, J=5.1 Hz), 7.27 (2H, d, J=8.7 Hz), 7.57 (1H, dd, J=8.4, 1.8 Hz), 7.75 (1H, d, J=8.4 Hz), 7.88 (2H, d, J=8.7 Hz), 7.92–7.94 (2H, m), 8.09 (1H, d, J=7.2 Hz), 9.91 (1H, s), 10.55 (1H, brs)

EXAMPLE 50

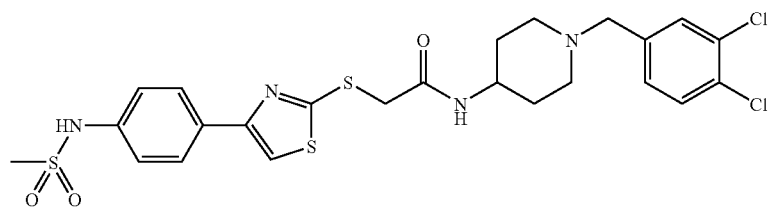

Synthesis of N-[1-(3,4-dichlorobenzyl)piperidin-4-yl]-[4-(4-methylsulfonylaminophenyl)thiazol-2-ylthio]acetamide hydrochloride In the same manner as in Example 49, the title compound (84 mg) was obtained as a brown amorphous solid from the product (220 mg) of Example 6.

$^1$H-NMR(DMSO-d$_6$) δ 1.79–1.94 (4H, m), 2.98–3.02 (2H, m), 3.30–3.35 (2H, m), 3.75–3.82 (1H, m), 4.01 (2H, s), 4.26 (2H, d, J=5.1 Hz), 7.26 (2H, d, J=8.7 Hz), 7.59 (1H, dd, J=8.1, 1.8 Hz), 7.74 (1H, d, J=8.1 Hz), 7.88 (2H, d, J=8.7 Hz), 7.92–7.94 (2H, m), 8.55 (1H, d, J=7.2 Hz), 9.89 (1H, s), 10.83 (1H, brs)

EXAMPLE 51

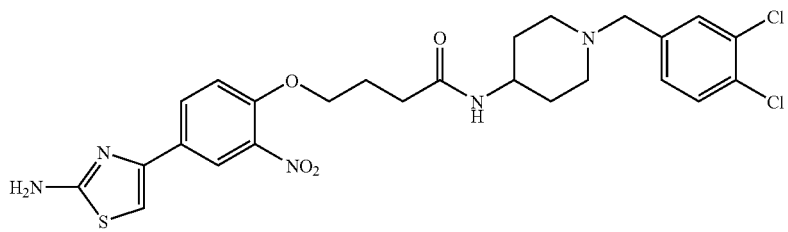

Synthesis of 4-[4-(2-aminothiazol-4-yl)-2-nitrophenyloxy]-N-[1-(3,4-dichlorobenzyl)piperidin-4-yl] butylamide The title compound (210 mg) was obtained as yellow crystals from the product (1.88 g) of Starting Material Synthetic Example 18 and thiourea (282 mg) by a method similar to Example 1.

$^1$H-NMR(DMSO-$d_6$) δ 1.31–1.43 (2H, m), 1.68–1.71 (2H, m), 1.92–2.04 (4H, m), 2.23 (2H, t, J=7.3 Hz), 2.68–2.72 (2H, m), 3.44 (2H, s), 3.48–3.56 (1H, m), 4.17 (2H, t, J=6.2 Hz), 7.10 (1H, s), 7.14 (2H, s), 7.28 (1H, dd, J=8.2, 1.9 Hz), 7.36 (1H, d, J=8.8 Hz), 7.53 (1H, d, J=1.9 Hz), 7.57 (1H, d, J=8.2 Hz), 7.77 (1H, d, J=7.6 Hz), 8.04 (1H, dd, J=8.8, 2.2 Hz), 8.26 (1H, d, J=2.2 Hz)

EXAMPLE 52

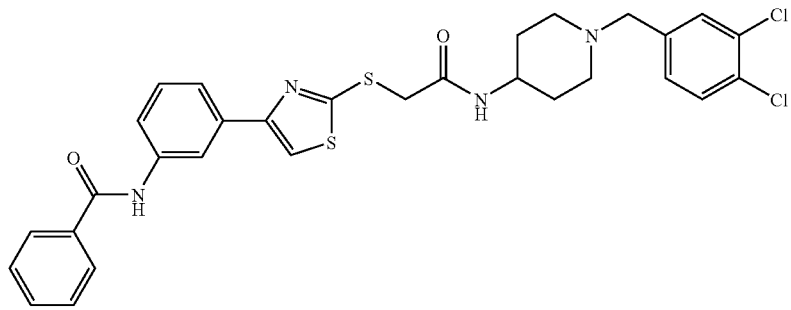

Synthesis of [4-(3-benzoylaminophenyl)thiazol-2-ylthio]-N-[1-(3,4-dichlorobenzyl)piperidin-4-yl] acetamide hydrochloride The title compound (360 mg) was obtained as a brown amorphous solid from the product (300 mg) of Example 35 and benzoyl chloride (103 μL) by a method similar to Example 7.

$^1$H-NMR(DMSO-$d_6$) δ 1.72–1.79 (2H, m), 1.93–1.97 (2H, m), 2.96–3.04 (2H, m), 3.78–3.84 (1H, m), 4.02 (2H, s), 4.26 (1H, d, J=4.5 Hz), 7.42–7.65 (6H, m), 7.74–7.76 (2H, m), 7.90–8.01 (4H, m), 8.34 (1H, s), 8.53 (1H, d, J=7.2 Hz), 10.36 (1H, s), 10.42 (1H, brs)

EXAMPLE 53

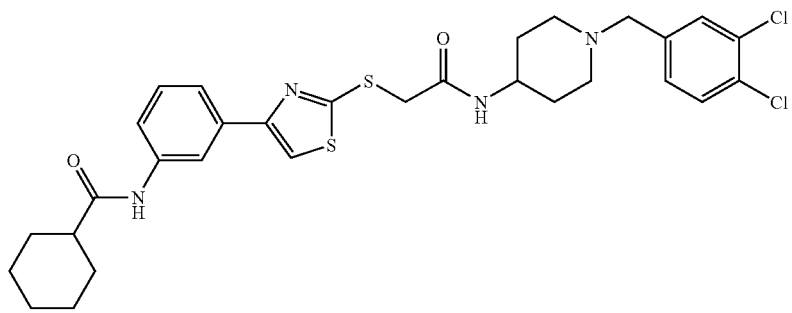

Synthesis of [4-(3-cyclohexylcarbonylaminophenyl)thiazol-2-ylthio]-N-[1-(3,4-dichlorobenzyl)piperidin-4-yl]acetamide The title compound (181 mg) was obtained as white crystals from the product (300 mg) of Example 35 and cyclohexanecarbonyl chloride (103 µL) by a method similar to Example 7.

$^1$H-NMR(DMSO-$d_6$) δ 1.19–1.43 (7H, m), 1.67–1.82 (7H, m), 1.99–2.05 (2H, m), 2.31–2.35 (1H, m), 2.65–2.68 (2H, m), 3.42 (2H, s), 3.55–3.59 (1H, m), 3.99 (2H, s), 7.26–7.36 (2H, m), 7.52–7.62 (4H, m), 7.91 (1H, s), 8.16–8.21 (2H, m), 9.89 (1H, s)

EXAMPLE 54

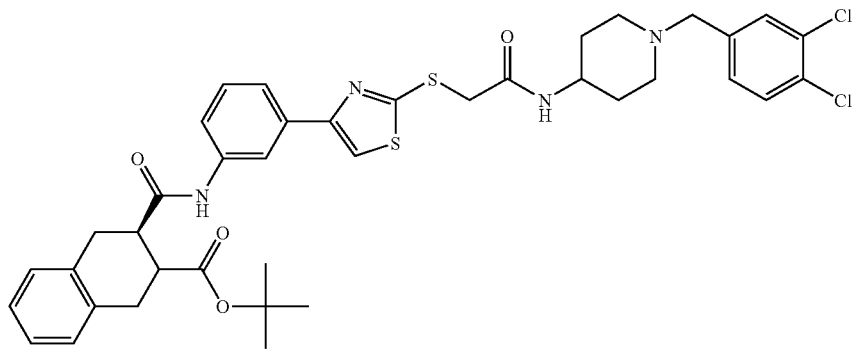

Synthesis of {4-[3-(2-tert-butoxycarbonyl-(S)-1,2,3,4-tetrahydroisoquinolin-3-ylcarbonylamino)phenyl]thiazol-2-ylthio}-N-[1-(3,4-dichlorobenzyl)piperidin-4-yl]acetamide the product (508 mg) of Example 35, 2-tert-butoxycarbonyl-(S)-1,2,3,4-tetrahydroisoquinoline-3-carboxylic acid (277 mg) and 1-hydroxybenzotriazole monohydrate (153 mg) were dissolved in methylene chloride (60 mL), and 1-ethyl-3-(3'-dimethylaminopropyl)carbodiimide hydrochloride (192 mg) was added to the solution. The mixture was stirred overnight. The reaction mixture was washed with water and saturated brine, and dried. The solvent was evaporated under reduced pressure, and the obtained residue was purified by silica gel column chromatography (chloroform:methanol=99:1–95:5) to give the title compound (690 mg) as a yellow amorphous solid.

¹H-NMR(CD₃) δ 1.31–1.41 (2H, m), 1.64 (9H, s), 1.75–1.79 (2H, m), 2.03–2.10 (2H, m), 2.43–2.47 (2H, m), 3.14–3.33 (2H, m), 3.24 (2H, s), 3.77–3.82 (1H, m), 3.89 (2H, s), 4.66 (2H, s), 7.01 (1H, dd, J=8.4, 2.1 Hz), 7.18–7.36 (9H, m), 7.40 (1H, s), 7.59 (1H, d, J=8.7 Hz)

EXAMPLE 55

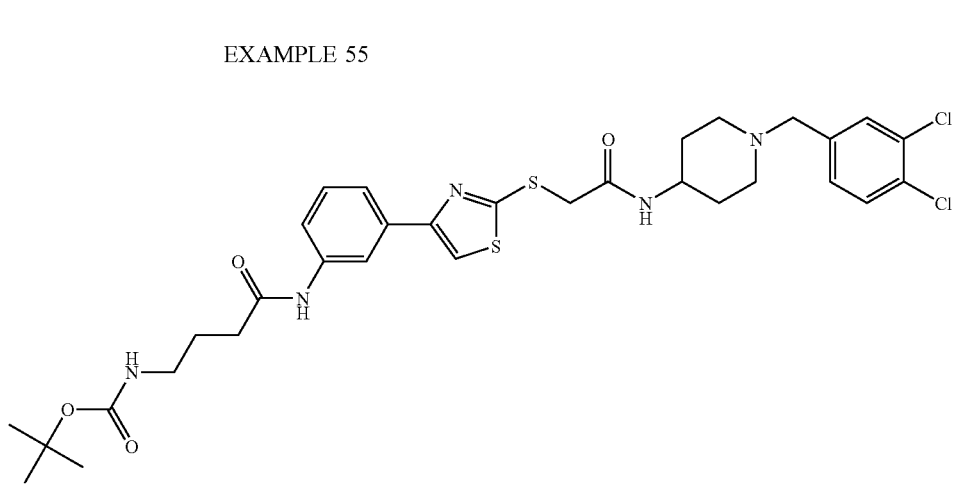

Synthesis of (4-{3-[4-(tert-butoxycarbonylamino)-butylamide]phenyl}thiazol-2-ylthio)-N-[1-(3,4-dichlorobenzyl)piperidin-4-yl]acetamide The title compound (594 mg) was obtained as a yellow amorphous solid from the product (508 mg) of Example 35 and 4-(tert-butoxycarbonylamino)butyric acid (203 mg) by a method similar to Example 54.

¹H-NMR(CDCl₃) δ 1.37–1.42 (2H, m), 1.47 (9H, s), 1.77–1.80 (2H, m), 1.85–1.91 (2H, m), 2.05–2.11 (2H, m), 2.39–2.46 (4H, m), 3.24–3.28 (4H, m), 3.78–3.82 (1H, m), 3.90 (2H, s), 4.88 (1H, brs), 7.03 (1H, dd, J=8.4, 1.8 Hz), 7.31–7.44 (5H, m), 7.56–7.61 (2H, m), 8.32 (1H, brs), 9.09 (1H, brs)

EXAMPLE 56

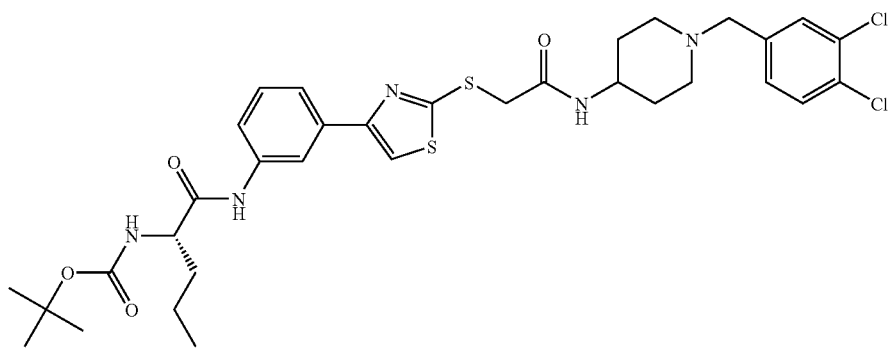

Synthesis of (4-{3-[N-(tert-butoxycarbonyl)-L-nor-valylamino]phenyl}thiazol-2-ylthio)-N-[1-(3,4-dichlorobenzyl)piperidin-4-yl]acetamide The title compound (654 mg) was obtained as a yellow amorphous solid from the product (508 mg) of Example 35 and N-(tert-butoxycarbonyl)-L-norvaline (217 mg) by a method similar to Example 54.

¹H-NMR(CDCl₃) δ 0.95 (3H, t, J=7.4 Hz), 1.37–1.46 (2H, m), 1.46 (9H, s), 1.59–1.63 (1H, m), 1.78–1.82 (1H, m), 1.89–1.93 (1H, m), 2.04–2.08 (2H, m), 2.52–2.56 (2H, m), 3.23 (1H, d, J=13.2 Hz), 3.33 (1H, d, J=13.2 Hz), 3.81–3.85 (1H, m), 3.87 (1H, d, J=15.0 Hz), 3.95 (1H, d, J=15.0 Hz), 4.18–4.23 (1H, m), 5.38–5.41 (1H, brs), 7.05 (1H, dd, J=8.4, 1.8 Hz), 7.32–7.39 (5H, m), 7.42 (1H, s), 7.58 (1H, d, J=6.6 Hz), 8.25 (1H, s), 8.47 (1H, brs)

EXAMPLE 57

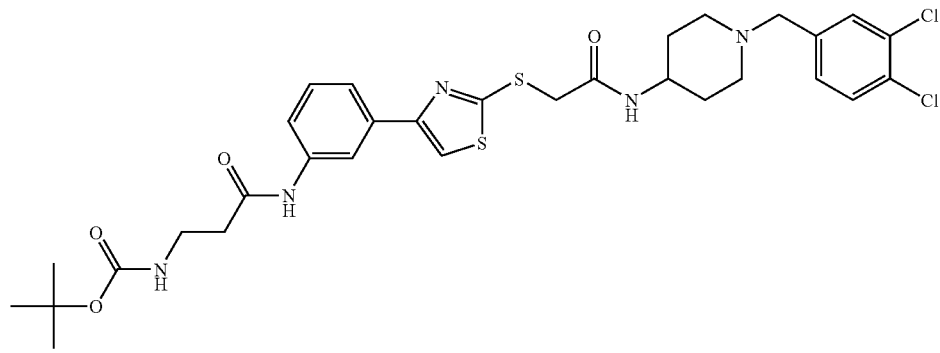

Synthesis of (4-{3-[3-(tert-butoxycarbonylamino)-propionamide]phenyl}thiazol-2-ylthio)-N-[1-(3,4-dichlorobenzyl)piperidin-4-yl]acetamide The title compound (468 mg) was obtained as a yellow amorphous solid from the product (508 mg) of Example 35 and N-(tert-butoxycarbonylamino)propionic acid (189 mg) by a method similar to Example 54.

¹H-NMR(CDCl₃) δ 1.40–1.43 (2H, m), 1.49 (9H, s), 1.77–1.81 (2H, m), 2.03–2.10 (2H, m), 2.53–2.55 (2H, m), 2.66 (2H, t, J=5.9 Hz), 3.30 (2H, s), 3.49 (2H, q, J=6.1 Hz), 3.79–3.82 (1H, m), 3.91 (2H, s), 5.52 (1H, brs), 7.05 (1H, d, J=8.1 Hz), 7.32–7.46 (6H, m), 7.58 (1H, d, J=7.5 Hz), 8.03 (1H, brs), 8.31 (1H, brs)

EXAMPLE 58

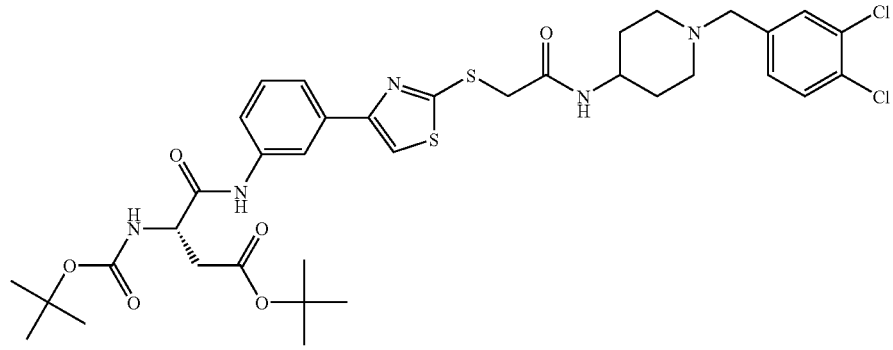

Synthesis of (4-{3-[3-(tert-butoxycarbonyl)-2-(tert-butoxycarbonylamino)-(S)-propionamide] phenyl}thiazol-2-ylthio)-N-[1-(3,4-dichlorobenzyl) piperidin-4-yl]acetamide The title compound (694 mg) was obtained as a yellow amorphous solid from the product. (508 mg) of Example 35 and N-(tert-butoxycarbonyl)-L-aspartic acid 4-tert-butyl ester (289 mg) by a method similar to Example 54.

¹H-NMR(CDCl₃) δ 1.39–1.41 (2H, m), 1.46 (9H, s), 1.48 (9H, s), 1.79–1.84 (2H, m), 2.06–2.13 (2H, m), 2.51–2.55 (2H, m), 2.71 (1H, dd, J=16.8, 6.6 Hz), 2.90 (1H, dd, J=16.8, 4.5 Hz), 3.29 (1H, d, J=13.2 Hz), 3.30 (1H, d, J=13.2 Hz), 3.80–3.90 (1H, m), 3.90 (2H, s), 4.61–4.65 (1H, m), 5.98 (H, brs), 7.05 (1H, dd, J=8.1, 1.8 Hz), 7.32–7.43 (6H, m), 7.61–7.63 (1H, m), 8.18 (1H, s), 8.80 (1H, s)

EXAMPLE 59

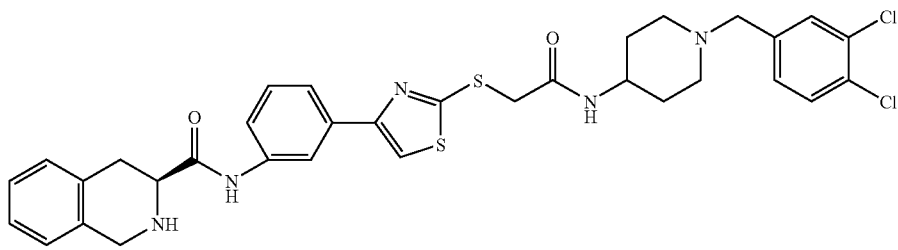

Synthesis of N-[1-(3,4-dichlorobenzyl)piperidin-4-yl]-{4-[3-((S)-1,2,3,4-tetrahydroisoquinolin-3-ylcarbonylamino)phenyl]thiazol-2-ylthio}acetamide Trifluoroacetic acid (5 mL) was added to the product (667 mg) of Example 54, and the mixture was stirred at room temperature for 1 hr. The reaction mixture was diluted with chloroform (100 mL), and the mixture was washed with 1 mol/L sodium hydroxide and saturated brine, and dried. The solvent was evaporated under reduced pressure to give the title compound (362 mg) as a white amorphous solid.

¹H-NMR(CDCl₃) δ 1.36–1.44 (2H, m), 1.78–1.83 (2H, m), 2.03–2.10 (2H, m), 2.47–2.50 (2H, m), 2.93 (1H, dd, J=16.5, 10.5 Hz), 3.24 (2H, s), 3.36 (1H, dd, J=16.5, 5.4 Hz), 3.68–3.73 (1H, m), 3.79–3.83 (1H, m), 3.92 (2H, s), 4.04 (1H, d, J=16.2 Hz), 4.06 (1H, d, J=16.2 Hz), 7.02 (1H, dd, J=8.1, 1.8 Hz), 7.09–7.10 (1H, m), 7.20–7.22 (3H, m), 7.28–7.30 (2H, m), 7.35–7.39 (1H, m), 7.41 (1H, t, J=8.1. Hz), 7.46 (1H, s), 7.55–7.56 (1H, m), 7.61–7.64 (1H, m), 8.27 (1H, t, J=1.8 Hz), 9.50 (1H, s)

EXAMPLE 60

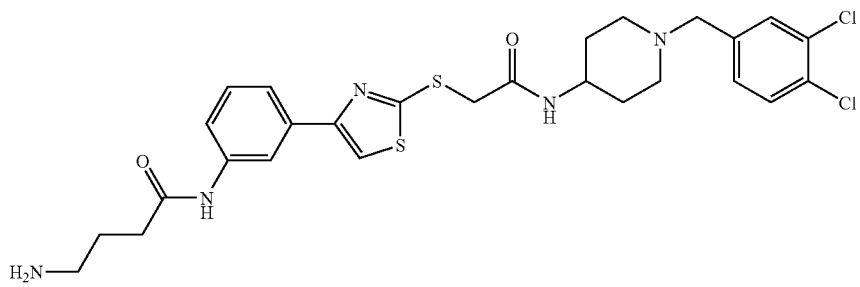

Synthesis of {4-[3-(4-aminobutylamide)phenyl]thiazol-2-ylthio}-N-[1-(3,4-dichlorobenzyl)piperidin-4-yl]acetamide The title compound (24 mg) was obtained as white crystals from the product (551 mg) of Example 55 by a method similar to Example 59.

$^1$H-NMR(CDCl$_3$) δ 1.36–1.39 (2H, m), 1.72–1.76 (2H, m), 1.90–1.93 (1H, m), 1.99–2.03 (2H, m), 2.45–2.47 (2H, m), 2.88–2.91 (2H, m), 3.24 (2H, s), 3.74–3.78 (1H, m), 3.89 (2H, s), 7.01 (1H, d, J=8.1 Hz), 7.29–7.38 (5H, m), 7.47–7.55 (2H, m), 8.15 (1H, brs), 9.37 (1H, brs)

EXAMPLE 61

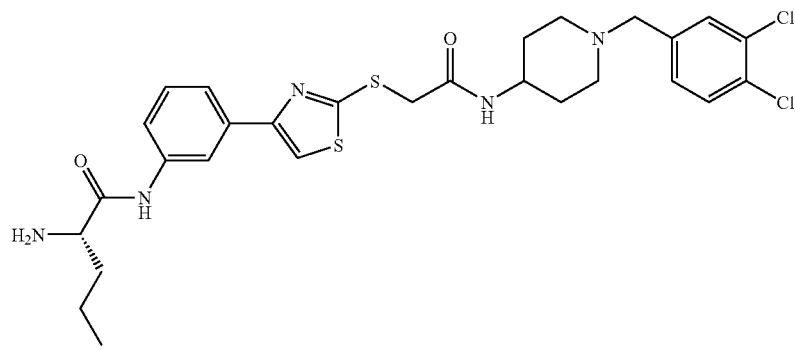

Synthesis of N-[1-(3,4-dichlorobenzyl)piperidin-4-yl]-{4-[3-(L-norvalylamino)phenyl]thiazol-2-ylthio}acetamide The title compound (379 mg) was obtained as white crystals from the product (630 mg) of Example 56 by a method similar to Example 59.

$^1$H-NMR(CDCl$_3$) δ 0.97 (3H, t, J=7.4 Hz), 1.37–1.58 (5H, m), 1.78–1.83 (2H, m), 1.89–1.96 (1H, m), 2.05–2.11 (2H, m), 2.46–2.48 (2H, m), 3.25 (2H, s), 3.49–3.53 (1H, m), 3.78–3.82 (1H, m), 3.91 (2H, s), 7.04 (1H, dd, J=8.1, 1.8 Hz), 7.31–7.34 (1H, m), 7.37–7.43 (1H, m), 7.46 (1H, s), 7.54–7.57 (1H, m), 7.59–7.63 (1H, m), 8.26 (1H, t, J=1.8 Hz), 9.66 (1H, s)

EXAMPLE 62

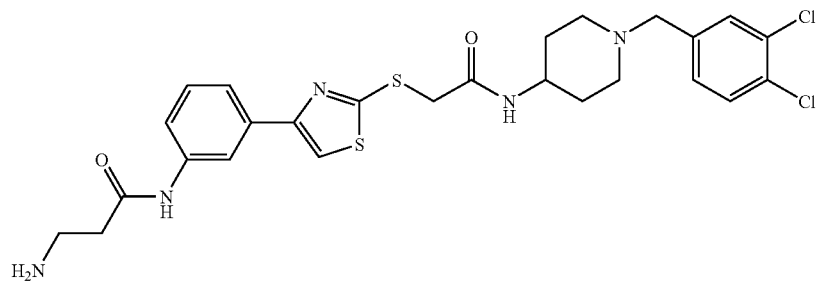

Synthesis of {4-[3-(3-aminopropionamide)phenyl]thiazol-2-ylthio}-N-[1-(3,4-dichlorobenzyl)piperidin-4-yl]acetamide The title compound (135 mg) was obtained as a yellow amorphous solid from the product (431 mg) of Example 57 by a method similar to Example 59.

$^1$H-NMR(CDCl$_3$) δ 1.33–1.45 (2H, m), 1.79–1.83 (2H, m), 2.04–2.12 (2H, m), 2.47–2.51 (4H, m), 3.14 (2H, t, J=5.7 Hz), 3.26 (2H, s), 3.79–3.83 (1H, m), 3.90 (2H, s), 7.04 (1H, dd, J=8.1, 1.8 Hz), 7.32–7.40 (4H, m), 7.44 (1H, s), 7.51 (1H, d, J=8.7 Hz), 7.58 (1H, d, J=7.8 Hz), 8.18 (1H, s), 10.36 (1H, s)

EXAMPLE 63

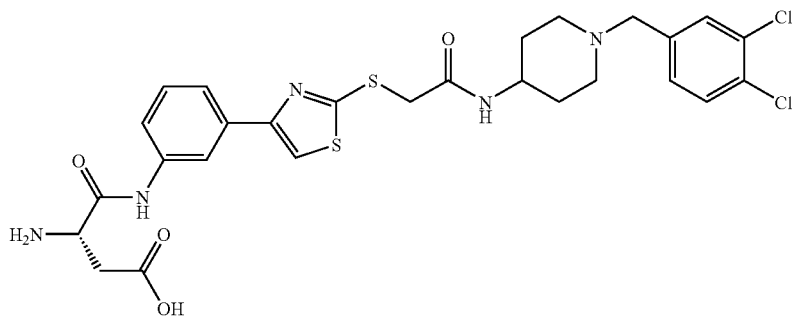

Synthesis of {4-[3-(L-α-aspartylamino)phenyl]thiazol-2-ylthio}-N-[1-(3,4-dichlorobenzyl)piperidin-4-yl]acetamide The title compound (633 mg) was obtained as a white amorphous solid from the product (508 mg) of Example 58 by a method similar to Example 59.

$^1$H-NMR(CDCl$_3$) δ 1.65–1.69 (2H, m), 1.92–1.96 (2H, m), 2.86 (1H, dd, J=17.4, 7.8 Hz), 2.96–3.04 (2H, m), 3.29–3.39 (4H, m), 3.78–3.82 (1H, m), 4.02 (2H, s), 4.25 (2H, s), 7.40–7.50 (2H, m), 7.63–7.79 (3H, m), 7.97 (1H, s), 8.11 (1H, s), 8.44–8.50 (2H, m), 10.60 (1H, s)

EXAMPLE 64

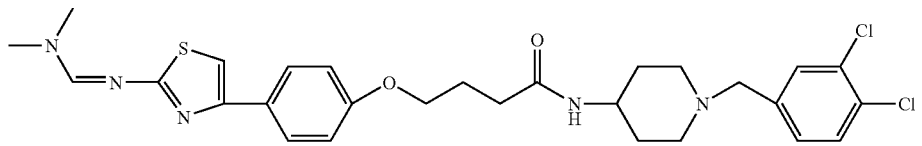

Synthesis of N-[1-(3,4-dichlorobenzyl)piperidin-4-yl]-4-[4-(2-dimethylaminomethyleneaminothiazol-4-yl)phenyloxy]butylamide The product (5.0 g) of Example 12 and N,N-dimethylformamide diethylacetal (1.5 g) in methanol (50 mL) were refluxed for 2 hrs, and the solvent was evaporated. The residue was purified by silica gel column chromatography (chloroform:methanol=40:1–20:1) to give the title compound (3.2 g) as a white solid.

$^1$H-NMR(DMSO-d$_6$) δ 1.28–1.48 (2H, m), 1.62–1.79 (2H, m), 1.89–2.11 (4H, m), 2.23 (2H, t, J=7.5 Hz), 2.60 (2H, d, J=11.7 Hz), 2.93 (3H, s), 3.13 (3H, s), 3.44 (2H, s), 3.50–3.67 (1H, m), 3.97 (2H, t, J=6.3 Hz), 6.93 (2H, d, J=8.7 Hz), 7.24 (1H, s), 7.28 (1H, dd, J=8.1, 1.8 Hz), 7.52 (1H, d, J=1.8 Hz), 7.57 (1H, d, J=8.1 Hz), 7.72–7.87 (1H, m), 7.79 (2H, d, J=8.7 Hz), 8.34 (1H, s)

EXAMPLE 65

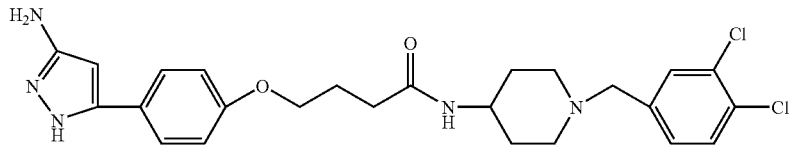

Synthesis of 4-[4-(3-aminopyrazol-5-yl)phenyloxy]-N-[1-(3,4-dichlorobenzyl)piperidin-4-yl]butylamide The product (2.4 g) of Starting Material Synthetic Example 7 and N,N-dimethylformamide diethylacetal (2.3 g) in methanol (50 mL) were refluxed for 2 hrs, and the solvent was evaporated. Hydroxyamine hydrochloride (0.7 g), methanol (60 mL) and water (20 mL) were added to the residue, and the mixture was heated overnight. The solvent was evaporated. Hydrazine (0.5 g) and methanol (20 mL) were added to the residue, and the mixture was again heated overnight. The solvent was evaporated. The residue was purified by silica gel column chromatography (chloroform:methanol=40:1–20:1) to give the title compound (0.2 g) as a white solid.

$^1$H-NMR(DMSO-$d_6$) δ 1.31–1.50 (2H, m), 1.66–1.80 (2H, m), 1.89–2.10 (4H, m), 2.22 (2H, t, J=7.4 Hz), 2.61–2.80 (2H, m), 3.44 (2H, s), 3.50–3.62 (1H, m), 3.96 (2H, t, J=6.0 Hz), 4.40–4.64 (1H, m), 6.80–7.03 (2H, m), 7.28 (1H, dd, J=8.1, 1.8 Hz), 7.51–7.68 (4H, m), 7.77 (1H, d, J=7.8 Hz)

EXAMPLE 66

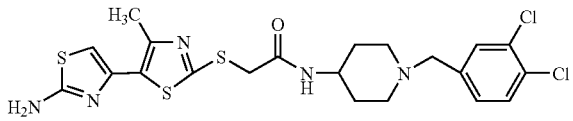

Synthesis of [5-(2-aminothiazol-4-yl)-4-methylthiazol-2-ylthio]-N-[1-(3,4-dichlorobenzyl)piperidin-4-yl]acetamide The title compound (90 mg) was obtained as a brown powder from the product (1 g) of Starting Material Synthetic Example 27 and thiourea by a method similar to Example 1.

$^1$H-NMR(DMSO-$d_6$) δ 1.39–1.46 (2H, m), 1.69–1.72 (2H, m), 2.01–2.08 (2H, m), 2.45 (3H, s), 2.66–2.70 (2H, m), 3.44 (2H, s), 3.51–3.57 (1H, m), 3.89 (2H, s), 6.67 (1H, s), 7.19 (2H, s), 7.28 (1H, dd, J=8.2, 1.8 Hz), 7.53 (1H, d, J=1.8 Hz), 7.58 (1H, d, J=8.2 Hz), 8.15 (1H, d, J=7.5 Hz)

EXAMPLE 67

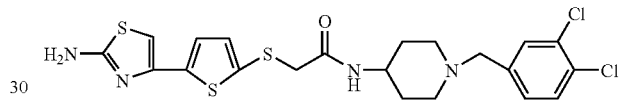

Synthesis of [5-(2-aminothiazol-4-yl)thiophen-2-ylthio]-N-[1-(3,4-dichlorobenzyl)piperidin-4-yl]acetamide The product (0.7 g) of Starting Material Synthetic Example 19 was added to a solution of aluminum chloride (0.7 g) and chloracetyl chloride (0.4 mL) in dichloromethane (30 mL), and the mixture was stirred at room temperature for 1 hr. The reaction mixture was poured into water and extracted with chloroform. The solvent was evaporated. Thiourea (0.1 g) and ethanol (50 mL) were added to the residue, and the mixture was refluxed overnight. By the same treatment as in Example 1, the title compound (0.2 g) was obtained as a pale-yellow amorphous solid.

$^1$H-NMR(DMSO-$d_6$) δ 1.30–1.49 (2H, m), 1.61–1.80 (2H, m), 1.96–2.12 (2H, m), 2.60–2.78 (2H, m), 3.43 (2H, s), 3.47 (2H, s), 3.54–3.66 (1H, m), 6.88 (1H, s), 7.09 (1H, d, J=3.7 Hz), 7.20 (2H, m), 7.23–7.31 (1H, m), 7.27 (1H, d, J=3.7 Hz), 7.47–7.60 (2H, m), 7.88–7.98 (1H, m)

EXAMPLE 68

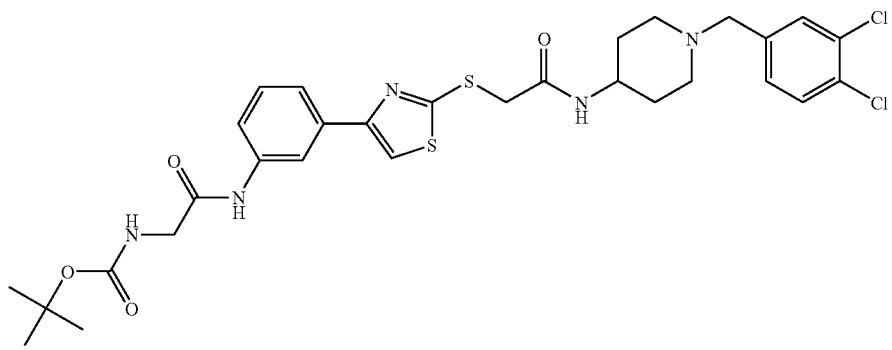

Synthesis of (4-{3-[N-(tert-butoxycarbonyl)glycylamino]phenyl}thiazol-2-ylthio)-N-[1-(3,4-dichlorobenzyl)piperidin-4-yl]acetamide The product (0.3 g) of Example 35, N-(tert-butoxycarbonyl)glycine (0.1 g) and 1-hydroxybenzotriazole monohydrate (0.1 g) were dissolved in methylene chloride (30 mL), and 1-ethyl-3-(3'-dimethylaminopropyl) carbodiimide hydrochloride (0.12 g) was added to the solution. The mixture was stirred overnight. The reaction mixture was washed with water and saturated brine, and dried. The solvent was evaporated under reduced pressure, and the obtained residue was purified by silica gel column chromatography (chloroform:methanol=99:1–95:5) to give the title compound (0.4 g) as a yellow amorphous solid.

$^1$H-NMR(DMSO-d$_6$) δ 1.30–1.64 (11H, m), 1.64–1.81 (2H, m), 1.95–2.12 (2H, m), 2.62–2.78 (2H, m), 3.43 (2H, s), 3.50–3.69 (1H, m), 3.73 (2H, d, J=6.3 Hz), 3.99 (2H, s), 7.06 (1H, t, J=6.3 Hz), 7.27 (1H, dd, J=8.1, 2.1 Hz), 7.36 (1H, t, J=8.1 Hz), 7.48–7.69 (4H, m), 7.93 (1H, s), 8.11 (1H, s), 8.15–8.27 (1H, m), 10.02 (1H, s)

EXAMPLE 69

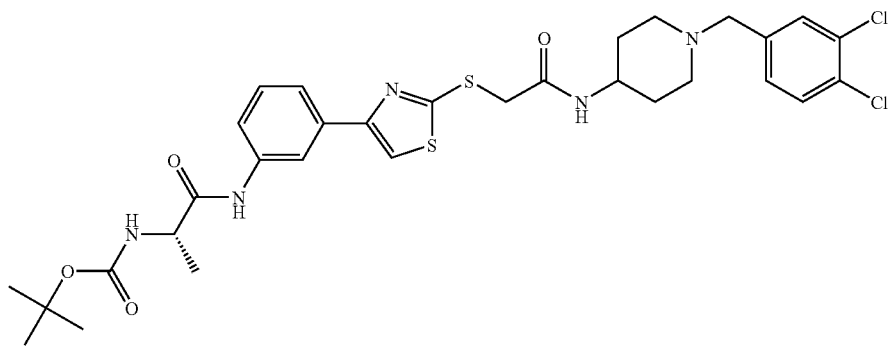

Synthesis of (4-{3-[N-(tert-butoxycarbonyl)-L-alanylamino]phenyl}thiazol-2-ylthio)-N-[1-(3,4-dichlorobenzyl)piperidin-4-yl]acetamide The title compound (4.0 g) was obtained as a white powder from the product (3.0 g) of Example 35 and N-(tert-butoxycarbonyl)-L-alanine (2.3 g) by a method similar to Example 54.

$^1$H-NMR(CDCl$_3$) δ 1.45–1.53 (14H, m), 1.75–1.88 (2H, m), 2.01–2.15 (2H, m), 2.47–2.65 (2H, m), 3.30 (2H, dd, J=1.2, 6.7 Hz), 3.76–3.85 (1H, m), 3.82–3.97 (2H, m), 4.30–4.40 (1H, m), 5.45 (1H, brs), 7.06 (1H, d, J=8.1 Hz), 7.28–7.45 (6H, m), 7.57 (1H, d, J=7.3 Hz), 8.24 (1H, s), 8.71 (1H, s)

EXAMPLE 70

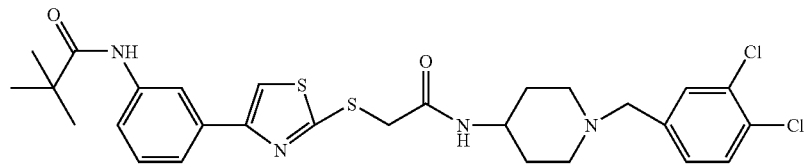

Synthesis of {4-[3-(tert-butylcarbonylamino)phenyl]thiazol-2-ylthio}-N-[1-(3,4-dichlorobenzyl)piperidin-4-yl]acetamide To a solution of the product (0.3 g) of Example 35 and triethylamine (0.16 g) in dichloromethane (30 mL) was added pivaloyl chloride (0.07 g), and the mixture was stirred for 1 hr. The reaction mixture was treated in the same manner as in Example 54 to give the title compound (262 mg) as a pale-yellow amorphous solid.

$^1$H-NMR(DMSO-d$_6$) δ 1.25 (9H, s), 1.34–1.56 (2H, m), 1.64–1.82 (2H, m), 1.98–2.17 (2H, m), 2.62–2.83 (2H, m), 3.42 (2H, s), 3.53–3.72 (1H, m), 4.01 (2H, s), 7.26 (1H, dd, J=8.1, 1.8 Hz), 7.35 (1H, t, J=7.8 Hz), 7.48–7.67 (3H, m), 7.69–7.77 (1H, m), 7.93 (1H, s), 8.15–8.32 (2H, m), 9.32 (1H, s)

EXAMPLE 71

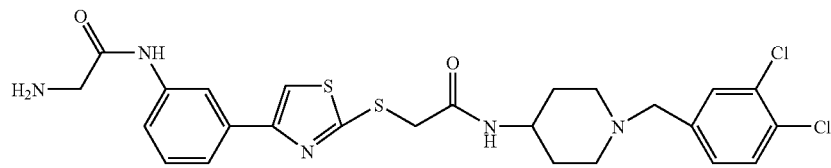

Synthesis of N-[1-(3,4-dichlorobenzyl)piperidin-4-yl]-{4-[3-(glycylamino)phenyl]thiazol-2-ylthio}acetamide The title compound (160 mg) was obtained as white crystals from the product (0.3 g) of Example 68 by a method similar to Example 59.

$^1$H-NMR(DMSO-d$_6$) δ 1.35–1.53 (2H, m), 1.63–1.81 (2H, m), 1.92–2.10 (2H, m), 2.60–2.79 (2H, m), 3.34 (2H, s), 3.42 (2H, s), 3.52–3.70 (1H, m), 4.01 (2H, s), 7.26 (1H, dd, J=8.1, 1.8 Hz), 7.37 (1H, t, J=7.8 Hz), 7.47–7.68 (3H, m), 7.72 (1H, d, J=8.1 Hz), 7.95 (1H, s), 8.15 (1H, s), 8.21–8.35 (1H, m)

EXAMPLE 72

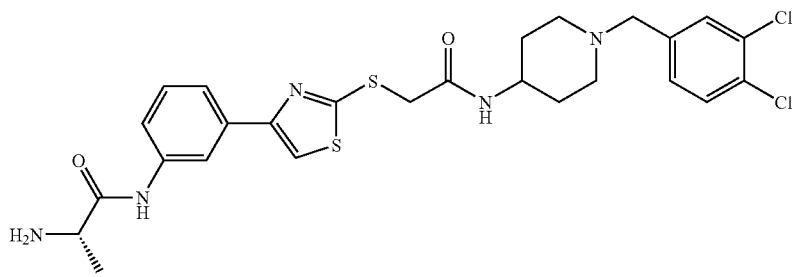

Synthesis of {4-[3-(L-alanylamino)phenyl]thiazol-2-ylthio}-N-[1-(3,4-dichlorobenzyl)piperidin-4-yl]acetamide The title compound (2.4 g) was obtained as a white powder from the product (3.0 g) of Example 69 by a method similar to Example 59.

$^1$H-NMR(CDCl$_3$) δ 1.31–1.44 (2H, m), 1.45 (3H, d, J=7.2 Hz), 1.77–1.83 (2H, m), 2.02–2.12 (2H, m), 2.43–2.58 (2H, m), 3.25 (2H, s), 3.59–3.68 (1H, m), 3.75–3.91 (1H, m), 3.91 (2H, s), 7.03 (1H, dd, J=1.8, 8.1 Hz), 7.38–7.50 (5H, m), 7.52–7.64 (2H, m), 8.26 (1H, s), 9.64 (1H, brs)

EXAMPLE 73

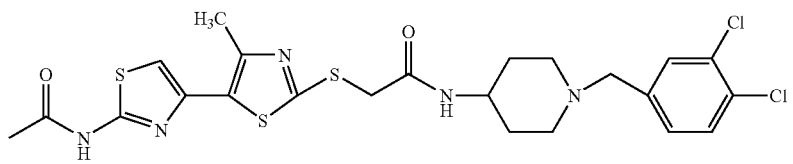

Synthesis of [5-(2-acetamidethiazol-4-yl)-4-methylthiazol-2-ylthio]-N-[1-(3,4-dichlorobenzyl)piperidin-4-yl]acetamide The title compound (20 mg) was obtained as a brown amorphous solid from the product (1 g) of Starting Material Synthetic Example 27 and acetylthiourea by a method similar to Example 1.

$^1$H-NMR(DMSO-d$_6$) δ 1.37–1.44 (2H, m), 1.69–1.73 (2H, m), 2.00–2.07 (2H, m), 2.15 (3H, s), 2.54 (3H, s), 2.67–2.71 (2H, m), 3.44 (2H, s), 3.51–3.57 (1H, m), 3.93 (2H, s), 7.26–7.30 (2H, m), 7.52 (1H, d, J=1.8 Hz), 7.57 (1H, d, J=8.2 Hz), 8.16 (1H, d, J=7.6 Hz)

EXAMPLE 74

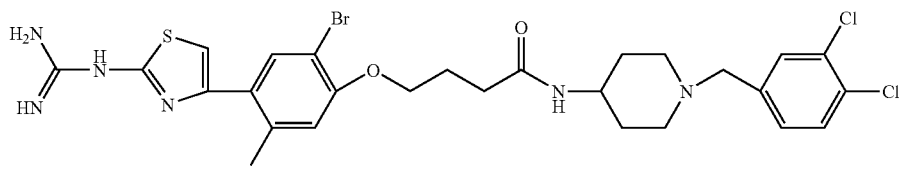

Synthesis of 4-[2-bromo-4-(2-guanidinothiazol-4-yl)-5-methylphenyloxy]-N-[1-(3,4-dichlorobenzyl)piperidin-4-yl]butyrylamide difumarate The oil obtained from the product (3.0 g) of Starting Material Synthetic Example 17 by a method similar to Example 1 was treated with fumaric acid in acetone to give the title compound (66 mg) as pale-brown crystals.

¹H-NMR(DMSO-d₆) δ 1.31–1.50 (2H, m), 1.64–1.78 (2H, m), 1.89–2.15 (4H, m), 2.20–2.87 (2H, m), 2.38 (3H, s), 2.67–2.80 (2H, m), 3.48 (2H, s), 3.58–3.72 (1H, m), 4.06 (2H, t, J=6.2 Hz), 6.62 (4H, s), 6.80 (1H, s), 6.84–7.20 (3H, m), 7.00 (1H, s), 7.29 (1H, dd, J=8.4, 1.8 Hz), 7.52–7.62 (2H, m), 7.66 (1H, s), 7.71–7.88 (1H, m)

EXAMPLE 75

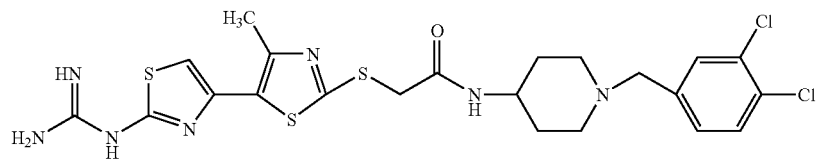

Synthesis of N-[1-(3,4-dichlorobenzyl)piperidin-4-yl]-[5-(2-guanidinothiazol-4-yl)-4-methylthiazol-2-ylthio]acetamide The title compound (61 mg) was obtained as a brown powder from the product (1 g) of Starting Material Synthetic Example 27 and guanidinothiourea by a method similar to Example 1.

¹H-NMR(DMSO-d₆) δ 1.37–1.44 (2H, m), 1.70–1.73 (2H, m), 2.01–2.09 (2H, m), 2.47 (3H, s), 2.67–2.71 (2H, m), 3.45 (2H, s), 3.54–3.57 (1H, m), 3.91 (2H, s), 6.84 (1H, s), 6.89 (4H, brs), 7.29 (1H, dd, J=8.1, 1.8 Hz), 7.53 (1H, d, J=1.8 Hz), 7.58 (1H, d, J=8.1 Hz), 8.18 (1H, d, J=7.5 Hz)

EXAMPLE 76

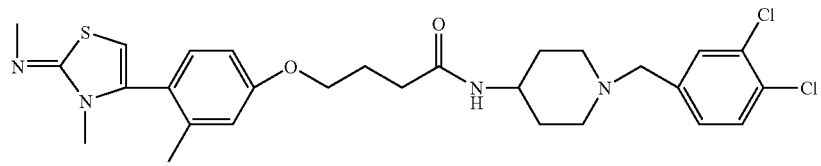

Synthesis of N-[1-(3,4-dichlorobenzyl)piperidin-4-yl]-4-[4-(3-methyl-2-methylimino-4-thiazolidin-4-yl)-3-methylphenyloxy]butylamide trifumarate The oil obtained from the product (1.0 g) of Starting Material Synthetic Example 17 by a method similar to Example 1 was treated with fumaric acid in acetone to give the title compound (567 mg) as a brown oil.

¹H-NMR(DMSO-d₆) δ 1.40–1.60 (2H, m), 1.70–1.87 (2H, m), 1.89–2.06 (2H, m), 2.14 (3H, s), 2.20–2.38 (4H, m), 2.75–2.94 (2H, m), 3.03 (3H, s), 3.14 (3H, s), 3.51–3.73 (3H, m), 4.01 (2H, t, J=6.3 Hz), 6.61 (6H, s), 6.73 (1H, s), 6.82–7.00 (2H, m), 7.21 (1H, d, J=8.4 Hz), 7.34 (1H, dd, J=8.3, 1.6 Hz), 7.60 (1H, dd, J=5.0, 3.4 Hz), 7.85–7.98 (1H, m)

EXAMPLE 77

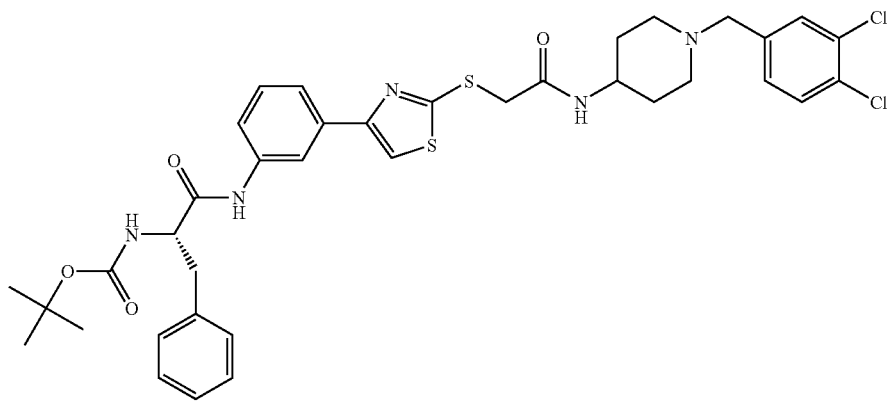

Synthesis of (4-{3-[N-(tert-butoxycarbonyl)-L-phenylalanylamino]phenyl}thiazol-2-ylthio)-N-[1-(3,4-dichlorobenzyl)piperidin-4-yl]acetamide The title compound (0.42 g) was obtained as white crystals from the product (0.51 g) of Example 35 and N-(tert-butoxycarbonyl)-L-phenylalanine (0.53 g) by a method similar to Example 54.

$^1$H-NMR(DMSO-d$_6$) δ 1.20–1.49 (11H, m), 1.67–1.80 (2H, m), 1.92–2.11 (2H, m), 2.55–2.72 (2H, m), 2.72–2.90 (1H, m), 2.91–3.09 (1H, m), 3.42 (2H, s), 3.50–3.65 (1H, m), 3.58 (2H, s), 4.25–4.42 (1H, m), 7.05–7.41 (8H, m), 7.48–7.71 (4H, m), 7.95 (1H, s), 8.10 (1H, s), 8.15–8.28 (1H, m), 10.16 (1H, s)

EXAMPLE 78

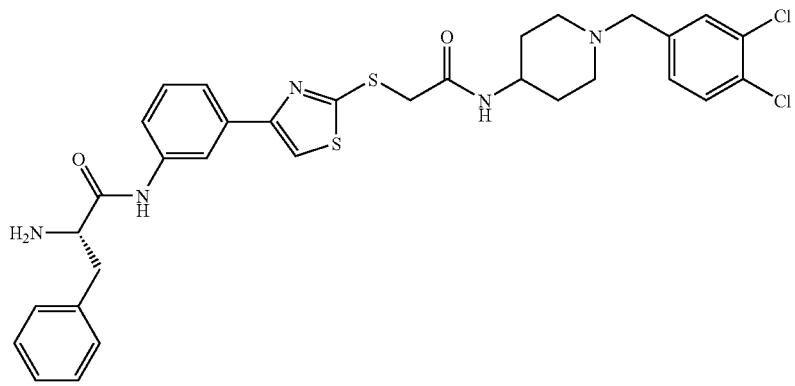

Synthesis of N-[1-(3,4-dichlorobenzyl)piperidin-4-yl]-{4-[3-(L-phenylalanylamino)phenyl]thiazol-2-ylthio}acetamide The title compound (0.25 g) was obtained as white crystals from the product (0.4 g) of Example 77 by a method similar to Example 59.

$^1$H-NMR(DMSO-d$_6$) δ 1.34–1.56 (2H, m), 1.62–1.83 (2H, m), 1.95–2.15 (2H, m), 2.60–2.81 (3H, m), 3.00–3.10 (1H, m), 3.42 (2H, s), 3.50–3.71 (2H, m), 4.00 (2H, s), 7.08–7.44 (7H, m), 7.48–7.75 (4H, m), 7.95 (1H, s), 8.12 (1H, s), 8.21–8.30 (1H, m), 9.60–10.38 (1H, m)

EXAMPLE 79

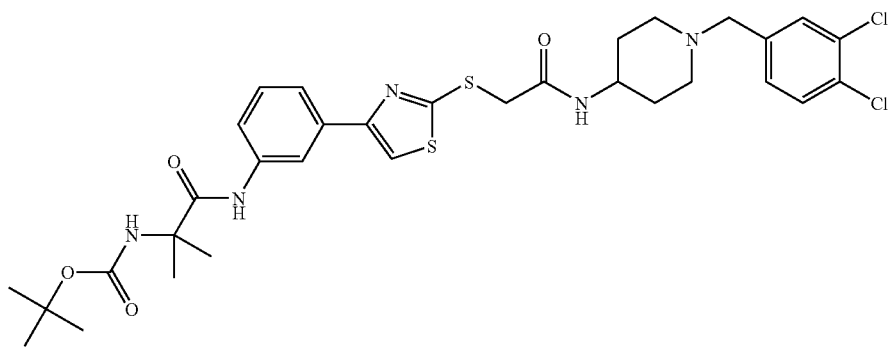

Synthesis of (4-{3-[α-(tert-butoxycarbonylamino)-isobutylamide]phenyl}thiazol-2-ylthio)-N-[1-(3,4-dichlorobenzyl)piperidin-4-yl]acetamide The title compound (0.47 g) was obtained as white crystals from the product (0.51 g) of Example 35 and N-(tert-butoxycarbonylamino)isobutyric acid (0.41 g) by a method similar to Example 54.

$^1$H-NMR(DMSO-$d_6$) δ 1.10–1.54 (17H, m), 1.70–1.80 (2H, m), 1.92–2.11 (2H, m), 2.61–2.78 (2H, m), 3.43 (2H, s), 3.50–3.68 (1H, m), 3.99 (2H, s), 6.83–7.07 (1H, m), 7.22–7.40 (2H, m), 7.48–7.74 (3H, m), 7.90 (1H, s), 8.11–8.30 (2H, m), 9.52 (1H, s)

EXAMPLE 80

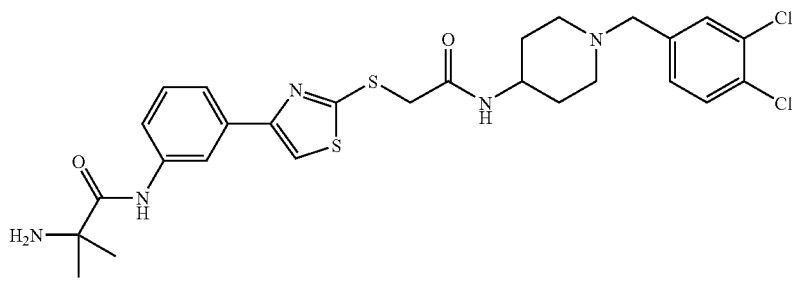

Synthesis of (4-[3-(α-aminoisobutylamide)phenyl]thiazol-2-ylthio}-N-[1-(3,4 4-dichlorobenzyl)piperidin-4-yl]acetamide The title compound (0.05 g) was obtained as white crystals from the product (0.3 g) of Example 79 by a method similar to Example 59.

$^1$H-NMR(DMSO-$d_6$) δ 1.32 (6H, s), 1.38–1.59 (2H, m), 1.68–1.85 (2H, m), 1.91–2.13 (2H, m), 2.62–2.80 (2H, m), 3.41 (2H, s), 3.50–3.69 (1H, m), 4.02 (2H, s), 7.25 (1H, dd, J=8.2, 1.7 Hz), 7.37 (1H, t, J=8.0 Hz), 7.50 (1H, d, J=1.7 Hz), 7.56 (1H, d, J=8.2 Hz), 7.63 (1H, d, J=7.8 Hz), 7.76 (1H, dd, J=8.0, 0.7 Hz), 7.97 (1H, s), 8.19 (1H, s), 8.21–8.30 (1H, m)

EXAMPLE 81

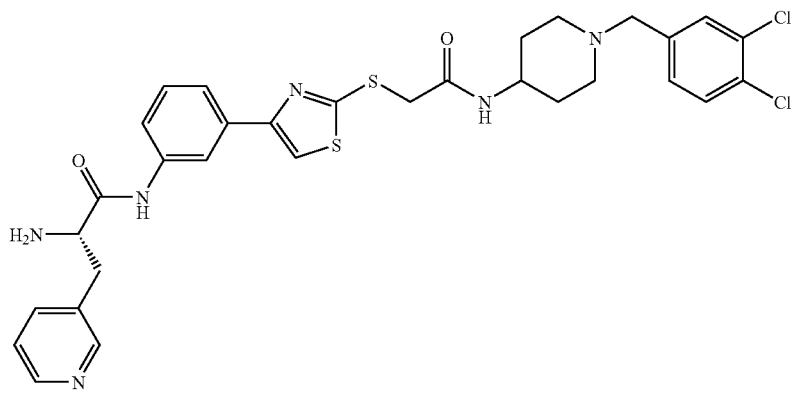

Synthesis of N-[1-(3,4-dichlorobenzyl)piperidin-4-yl]-{4-[3-(L-3-pyridylalanylamino)phenyl]thiazol-2-ylthio}acetamide The compound obtained from the product (0.51 g) of Example 35 and N-tert-butoxycarbonyl-L-3-pyridylalanine (0.53 g) by a method similar to Example 54 was treated in the same manner as in Example 59 to give the title compound (0.19 g) as a white amorphous solid.

$^1$H-NMR(DMSO-d$_6$) δ 1.34–1.65 (2H, m), 1.66–1.80 (2H, m), 1.95–2.12 (2H, m), 2.62–2.75 (2H, m), 2.80–2.96 (2H, m), 3.00–3.23 (1H, m), 3.42 (2H, s, 3.54–3.72 (1H, m), 3.85–4.00 (1H, m), 4.03 (2H, s), 7.07–7.20 (1H, m), 7.22–7.44 (3H, m), 7.45–7.72 (4H, m), 7.77 (1H,d, J=7.9 Hz), 7.96 (1H, d, J=7.6 Hz), 8.11 (1H, d, J=7.9 Hz), 8.20–8.30 (1H, m), 8.88–9.13 (2H, m)

EXAMPLE 82

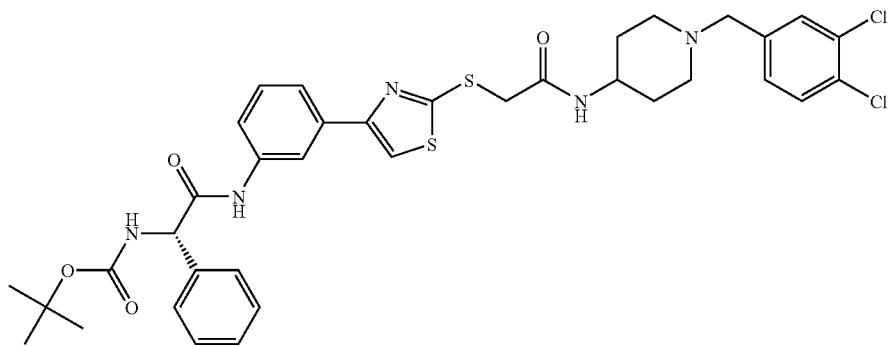

Synthesis of (4-{3-[N-(tert-butoxycarbonyl)-(S)-phenylglycylamino]phenyl}thiazol-2-ylthio)-N-[1-(3,4-dichlorobenzyl)piperidin-4-yl]acetamide The title compound (0.38 g) was obtained as a white amorphous solid from the product (0.51 g) of Example 35 and N-(tert-butoxycarbonyl)-(S)-phenylglycine (0.50 g) by a method similar to Example 54.

$^1$H-NMR(DMSO-d$_6$) δ 1.20–1.50 (9H, m), 1.64–1.80 (2H, m), 1.95–2.11 (2H, m), 2.61–2.79 (2H, m), 3.42 (2H, s), 3.50–3.68 (1H, m), 3.98 (1H, s), 5.30–5.45 (1H, m), 7.23–7.40 (5H, m), 7.49–7.70 (6H, m), 7.94 (1H, s), 8.10 (1H, s), 8.20–8.28 (1H, m), 10.35 (1H, s)

EXAMPLE 83

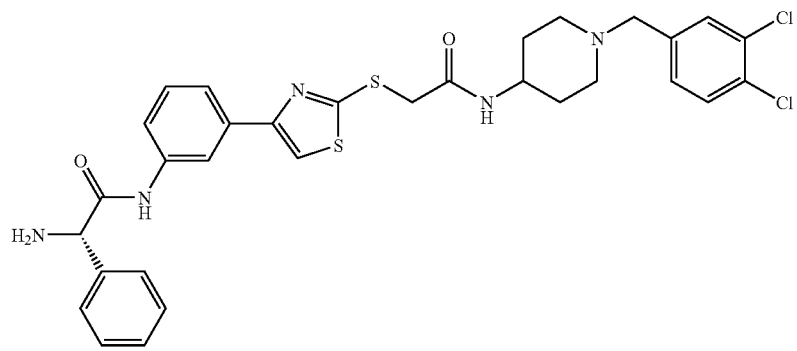

Synthesis of N-[1-(3,4-dichlorobenzyl)piperidin-4-yl]-{4-[3-((S)-phenylglycylamino)phenyl) thiazol-2-ylthio}acetamide The title compound (0.21 g) was obtained as a white amorphous solid by treating the product (0.28 g) of Example 82 in the same manner as in Example 59.

$^1$H-NMR(DMSO-$d_6$) δ 1.35–1.58 (2H, m), 1.67–1.86 (2H, m), 1.92–2.12 (2H, m), 2.62–2.81 (2H, m), 3.41 (2H, s), 3.50–3.70 (1H, m), 4.01 (2H, s), 4.58 (1H, s), 7.19–7.44 (5H, m), 7.45–7.78 (6H, m), 7.94 (1H, s), 8.17 (1H, s), 8.20–8.31 (1H, m), 9.75–10.60 (1H, m)

EXAMPLE 84

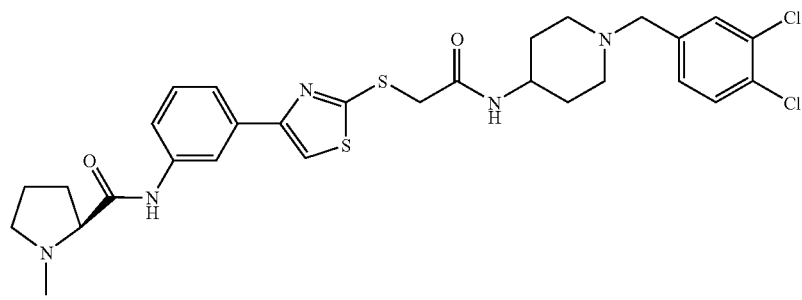

Synthesis of N-[1-(3,4-dichlorobenzyl)piperidin-4-yl]-{4-[3-(N-methyl-L-prolylamino)phenyl]thiazol-2-ylthio}acetamide The title compound (0.34 g) was obtained as a white amorphous solid from the product (0.51 g) of Example 35 and N-methyl-L-proline (0.29 g) by a method similar to Example 54.

$^1$H-NMR(DMSO-$d_6$) δ 1.32–1.51 (2H, m), 1.65–1.90 (6H, m), 1.97–2.28 (3H, m), 2.36 (3H, s), 2.68–2.78 (2H, m), 2.90–3.18 (3H, m), 3.44–3.50 (2H, m), 3.51–3.70 (1H, m), 3.98 (2H, d, J=6.3 Hz), 5.05–5.20 (1H, m), 6.43–6.74 (1H, m), 7.04–7.19 (1H, m), 7.22–7.41 (2H, m), 7.48–7.86 (3H, m), 8.13–8.30 (2H, m), 9.74 (1H, s)

EXAMPLE 85

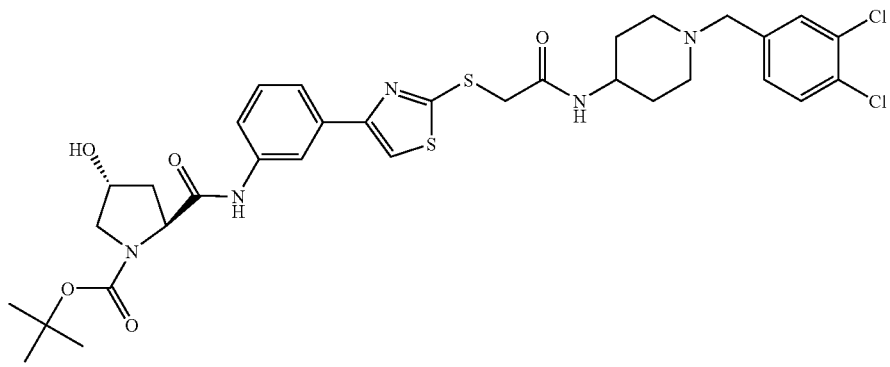

Synthesis of (4-{3-[1-(tert-butoxycarbonyl)-3-hydroxy-L-prolylamino]phenyl}thiazol-2-ylthio)-N-[1-(3,4-dichlorobenzyl)piperidin-4-yl]acetamide The title compound (0.43 g) was obtained as a white amorphous solid from the product (0.51 g) of Example 35 and N-(tert-butoxycarbonyl)-3-hydroxy-L-proline (0.46 g) by a method similar to Example 54.

$^1$H-NMR(DMSO-d$_6$) δ 1.23–1.60 (11H, m), 1.70–1.87 (4H, m), 1.90–2.21 (4H, m), 2.64–2.80 (2H, m), 2.98–3.12 (4H, m), 3.46 (2H, s), 3.50–3.66 (1H, m), 3.98 (2H, s), 4.30–4.44 (1H, m), 5.08 (1H, d, J=3.0 Hz), 7.25–7.43 (2H, m), 7.50–7.75 (4H, m), 7.92 (1H, s), 8.11–8.30 (2H, m), 10.14 (1H, s)

EXAMPLE 86

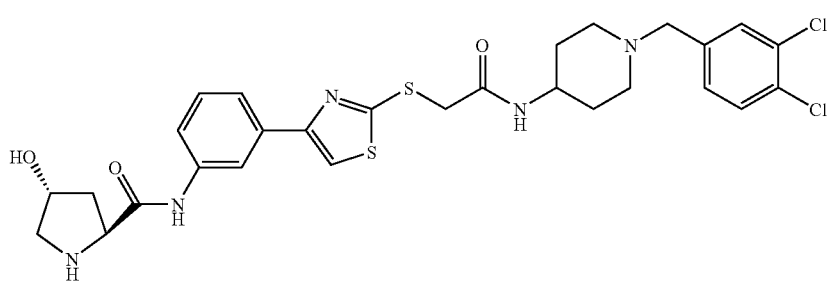

Synthesis of N-[1-(3,4-dichlorobenzyl)piperidin-4-yl]-{4-[3-(3-hydroxy-L-prolylamino)phenyl]thiazol-2-ylthio}acetamide The title compound (0.35 g) was obtained as a white amorphous solid from the product (0.33 g) of Example 85 by a method similar to Example 59.

$^1$H-NMR(DMSO-d$_6$) δ 1.31–1.64 (2H, m), 1.60–1.91 (4H, m), 1.93–2.17 (4H, m), 2.61–2.80 (2H, m), 3.42 (2H, s), 3.51–3.75 (1H, m), 3.89–4.10 (1H, m), 4.12 (2H, s), 4.27 (1H, s), 4.65–5.10 (1H, m), 7.26 (1H, dd, J=8.4, 1.8 Hz), 7.37 (1H, t, J=7.8 Hz), 7.50 (1H, d, J=1.5 Hz), 7.56 (1H, d, J=8.4 Hz), 7.63 (1H, d, J=8.1 Hz), 7.74 (1H, d, J=7.8 Hz), 7.97 (1H, s), 8.15 (1H, s), 8.34–8.35 (1H, m), 10.14 (1H, s)

EXAMPLE 87

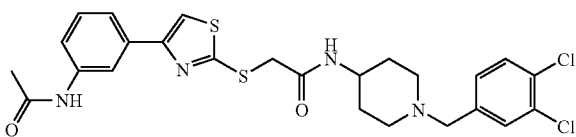

Synthesis of [4-(3-acetylamidephenyl)thiazol-2-ylthio]-N-[1-(3,4-dichlorobenzyl)piperidin-4-yl]acetamide The product (500 mg) of Example 35 was dissolved in methylene chloride (50 mL), and dimethylaminopyridine (180 mg) was added to the solution. Then, acetic anhydride (100 μL) was added, and the mixture was stirred for 1 hr. The reaction mixture was washed with water, saturated aqueous sodium hydrogen carbonate solution and saturated brine. The solvent was evaporated under reduced pressure, and the obtained residue was recrystallized from ethyl acetate and hexane to give the title compound (453 mg) as a white powder $^1$H-NMR(CDCl$_3$) δ 1.33–1.49 (2H, m), 1.77–1.84 (2H, m), 2.02–2.12 (2H, m), 2.20 (3H, s), 2.49–2.56 (2H, m), 3.28 (2H, s), 3.77–3.86 (1H, m), 3.90 (2H, s), 7.05 (1H, dd, J=1.8, 8.4 Hz), 7.30–7.42 (4H, m), 7.43 (1H, s), 7.49–7.52 (2H, m), 7.58 (1H, d, J=7.8 Hz), 8.10 (1H, s)

EXAMPLE 88

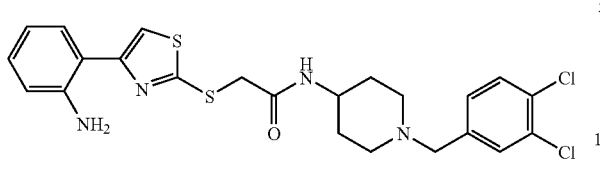

Synthesis of [4-(2-aminophenyl)thiazol-2-ylthio]-N-[1-(3,4-dichlorobenzyl)piperidin-4-yl]acetamide The title compound (6.6 g) was obtained as a white powder from the product (11.3 g) of Starting Material Synthetic Example 23 and tin(II) chloride (11.9 g) by a method similar to Example 5.

$^1$H-NMR(CDCl$_3$) δ 1.30–1.43 (2H, m), 1.75–1.83 (2H, m), 2.03–2.13 (2H, m), 2.48–2.58 (2H, m), 3.28 (2H, s), 3.74–3.84 (1H, m), 6.87–6.93 (1H, m), 7.06 (1H, dd, J=1.8, 8.4 Hz), 7.13–7.19 (1H, m), 7.32 (1H, s), 7.34–7.36 (2H, m), 7.41–7.45 (1H, m)

EXAMPLE 89

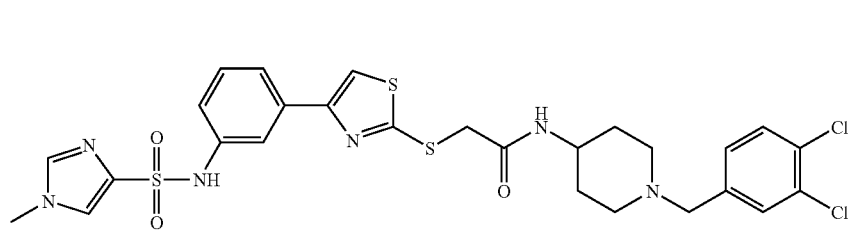

Synthesis of N-[1-(3,4-dichlorobenzyl)piperidin-4-yl]-{4-[3-(1-methyl-1H-imidazole-4-sulfonamide)phenyl]thiazol-2-ylthio}acetamide The title compound (210 mg) was obtained as a white powder from the product (500 mg) of Example 35 and 1-methyl-1H-imidazole-4-sulfonic acid (540 mg) by a method similar to Example 45.

$^1$H-NMR(DMSO-d$_6$) δ 1.33–1.49 (2H, m), 1.69–1.77 (2H, m), 1.98–2.07 (2H, m), 2.64–2.70 (2H, m), 3.42 (2H, s), 3.50–3.63 (1H, m), 3.99 (2H, s), 7.27 (1H, dd, J=1.8, 8.1 Hz), 7.43 (1H, t, J=8.1 Hz), 7.51 (1H, d, J=1.8 Hz), 7.55 (1H, s), 7.57–7.60 (2H, m), 7.67–7.73 (2H, m), 7.97 (1H, s), 8.09 (1H, dd, J=1.8, 7.5 Hz), 8.20 (1H, d, J=7.5 Hz), 8.26 (1H, s), 8.54 (1H, dd, J=1.8, 8.1 Hz), 10.73 (1H, s)

EXAMPLE 90

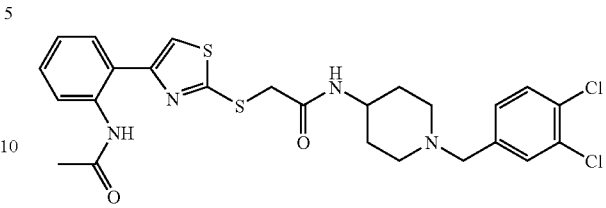

Synthesis of [4-(2-acetylamidephenyl)thiazol-2-ylthio]-N-[1-(3,4-dichlorobenzyl)piperidin-4-yl]acetamide The title compound (490 mg) was obtained as a white powder from the product (500 mg) of Example 88 and acetic anhydride (100 μL) by a method similar to Example 87.

$^1$H-NMR(CDCl$_3$) δ 1.30–1.43 (2H, m), 1.54–1.69 (5H, m), 1.76–1.87 (2H, m), 2.02–2.14 (2H, m), 2.52–2.66 (2H, m), 3.32 (2H, s), 3.71–3.84 (1H, m), 3.88 (2H, s), 6.47–6.58 (1H, m), 7.04–7.13 (2H, m), 7.3–7.46 (4H, m), 7.53 (1H, d, J=7.5 Hz), 8.03–8.45 (1H, m), 10.26 (1H, brs)

EXAMPLE 91

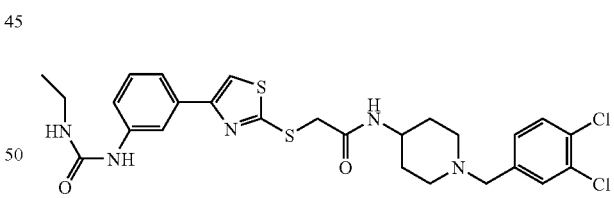

Synthesis of N-[1-(3,4-dichlorobenzyl)piperidin-4-yl]-{4-[3-(3-ethylureido)phenyl]thiazol-2-ylthio}acetamide The title compound (402 mg) was obtained as a white powder from the product (500 mg) of Example 35 and ethylisocyanate (940 μL) by a method similar to Example 46.

$^1$H-NMR(DMSO-d$_6$) δ 1.06 (3H, t, J=7.0 Hz), 1.36–1.48 (2H, m), 1.70–1.75 (2H, m), 2.03 (2H, t, J=10.8 Hz), 2.64–2.70 (2H, m), 3.08–3.17 (2H, m), 3.42 (2H, s), 3.54–3.65 (1H, m), 3.98 (2H, s), 6.08 (1H, t, J=5.4 Hz), 7.21–7.56 (6H, m), 7.85 (1H, s), 7.93 (1H, s), 8.18 (1H, d, J=7.2 Hz), 8.50 (1H, s)

EXAMPLE 92

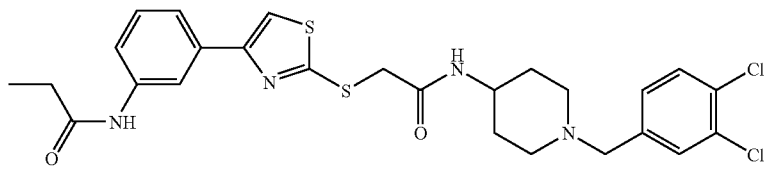

Synthesis of N-[1-(3,4-dichlorobenzyl)piperidin-4-yl]-[4-(3-propionamidephenyl)thiazol-2-ylthio]acetamide The title compound (287 mg) was obtained as a white powder from the product (280 mg) of Example 35 and propionyl chloride (58 µL) by a method similar to Example 45.

$^1$H-NMR(CDCl$_3$) δ 1.26 (3H, t, J=7.5 Hz), 1.36–1.48 (2H, m), 1.73–1.84 (2H, m), 2.43 (2H, q, J=7.5 Hz), 2.50–2.58 (2H, m), 3.30 (2H, s), 3.76–3.86 (1H, m), 3.90 (2H, s), 7.06 (1H, dd, J=1.6, 8.1 Hz), 7.31–7.44 (4H, m), 7.43 (1H, s), 7.49–7.59 (3H, m), 8.16 (1H, s)

EXAMPLE 93

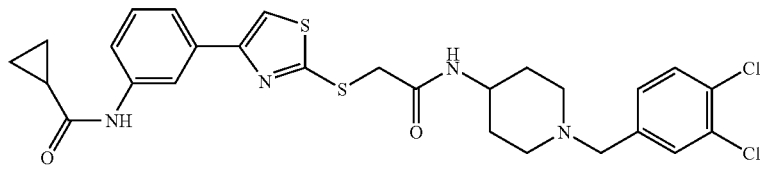

Synthesis of [4-(3-cyclopropanecarboxyamidephenyl)thiazol-2-ylthio]-N-[1-(3,4-dichlorobenzyl)piperidin-4-yl]acetamide The title compound (295 mg) was obtained as a white powder from the product (290 mg) of Example 35 and cyclopropylcarbonyl chloride (62 µL) by a method similar to Example 45.

$^1$H-NMR(CDCl$_3$) δ 0.82–0.90 (2H, m), 1.08–1.12 (2H, m), 1.34–1.48 (2H, m), 1.50–1.65 (1H, m), 1.74–1.86 (2H, m), 2.04–2.15 (2H, m), 3.28 (2H, s), 3.77–3.88 (1H, m), 3.90 (2H, s), 7.05 (1H, dd, J=1.8, 8.1 Hz), 7.30–7.51 (6H, m), 7.57 (1H, d, J=7.5 Hz), 7.68 (1H, s), 8.17 (1H, s)

EXAMPLE 94

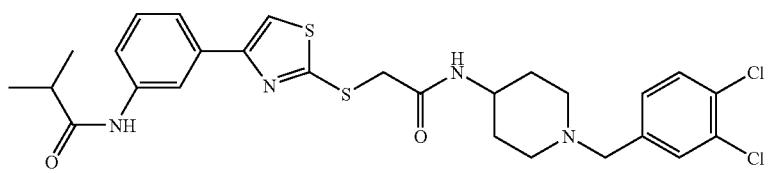

Synthesis of N-[1-(3,4-dichlorobenzyl)piperidin-4-yl]-[4-(3-isobutylamidephenyl)thiazol-2-ylthio]acetamide The title compound (296 mg) was obtained as a white powder from the product (300 mg) of Example 35 and isobutyryl chloride (74 µL) by a method similar to Example 45.

¹H-NMR(CDCl₃) δ 1.26 (3H, s), 1.28 (3H, s), 1.35–1.44 (2H, m) 1.76–1.85 (2H, m), 2.03–2.11 (2H, m), 2.45–2.58 (2H, m), 3.27 (2H, s), 3.76–3.86 (1H, m), 3.91 (2H, s), 7.04 (1H, dd, J=1.8, 8.1 Hz), 7.30–7.50 (7H, m), 7.59 (1H, d, J=7.8 Hz), 8.21 (1H, s)

EXAMPLE 95

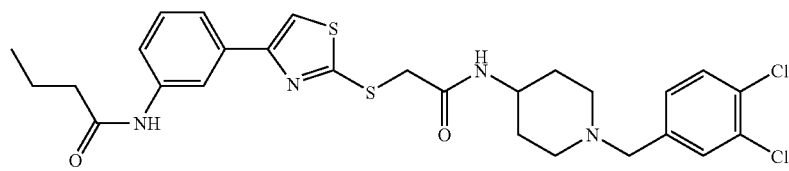

Synthesis of [4-(3-butylamidephenyl)thiazol-2-ylthio]-N-[1-(3,4-dichlorobenzyl)piperidin-4-yl]acetamide The title compound (300 mg) was obtained as a white powder from the product (280 mg) of Example 35 and butanecarbonyl chloride (68 μL) by a method similar to Example 45.

¹H-NMR(CDCl₃) δ 1.01 (3H, t, J=7.4 Hz), 1.32–1.45 (2H, m), 1.73–1.84 (4H, m), 2.02–2.12 (2H, m), 2.36 (2H, t, J=7.4 Hz), 2.47–2.52 (2H, m), 3.27 (2H, s), 3.73–3.89 (1H, m), 3.90 (2H, s), 7.04 (1H, dd, J=1.6, 8.3 Hz), 7.22–7.52 (7H, m), 7.58 (1H, d, J=7.4 Hz), 8.16 (1H, s)

EXAMPLE 96

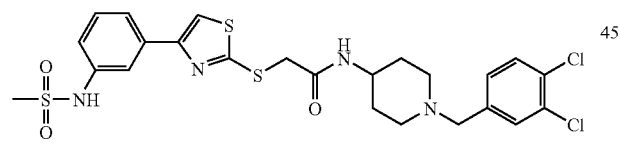

Synthesis of N-[1-(3,4-dichlorobenzyl)piperidin-4-yl]-[4-(3-methanesulfonamidephenyl)thiazol-2-ylthio]acetamide hydrochloride The residue obtained from the product (500 mg) of Example 35 and methanesulfonyl chloride (242 mg) by a method similar to Example 45 was purified by silica gel column chromatography (chloroform:methanol=100:1–30:1). Then, after dissolving in chloroform (2 mL) and methanol (2 mL), a 1 mol/L hydrochloric acid/ether solution (1 mL) was added, and the mixture was stirred for 1 min. The solvent was evaporated under reduced pressure to give the title compound (260 mg) as a white amorphous solid.

¹H-NMR(DMSO-d₆) δ 1.70–1.92 (4H, m), 2.08 (3H, m), 2.94–3.05 (2H, m), 3.31–3.36 (2H, m), 3.76–3.82 (1H, m), 4.09 (2H, s), 4.26 (2H, d, J=4.8 Hz), 7.21 (1H, d, J=7.8 Hz), 7.40 (1H, t, J=7.8 Hz), 7.57 (1H, d, J=7.8 Hz), 7.66 (1H, d, J=7.8 Hz), 7.73–7.76 (2H, m), 7.91 (1H, s), 7.97 (1H, s), 8.53 (1H, d, J=7.5 Hz), 9.80 (1H, s), 10.58 (1H, brs)

EXAMPLE 97

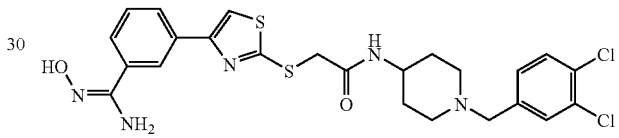

Synthesis of N-[1-(3,4-dichlorobenzyl)piperidin-4-yl]-{4-[3-(N²-hydroxyamidino)phenyl]thiazol-2-ylthio}acetamide The product (1.15 g) of Starting Material Synthetic Example 22 and potassium carbonate (570 mg) were dissolved in ethanol (30 mL), and hydroxyamine hydrochloride (460 mg) was added to the solution. After stirring at room temperature for 4 hrs, water was added to the reaction mixture. The mixture was extracted with chloroform, washed with saturated brine, and dried. The solvent was evaporated under reduced pressure, and the obtained residue was purified by silica gel column chromatography (chloroform:methanol=100:1–20:1) to give the title compound (970 mg) as a white amorphous solid.

¹H-NMR(CDCl₃) δ 1.86–1.93 (2H, m), 2.08–2.35 (4H, m), 2.96–3.03 (2H, m), 3.49 (2H, s), 3.74 (2H, s), 3.84–3.97 (1H, m), 4.85 (2H, brs), 7.19 (1H, dd, J=1.8, 8.2 Hz), 7.38–7.50 (5H, m), 7.62–7.67 (1H, m), 7.74 (1H, d, J=8.2 Hz), 8.50 (1H, s)

EXAMPLE 98

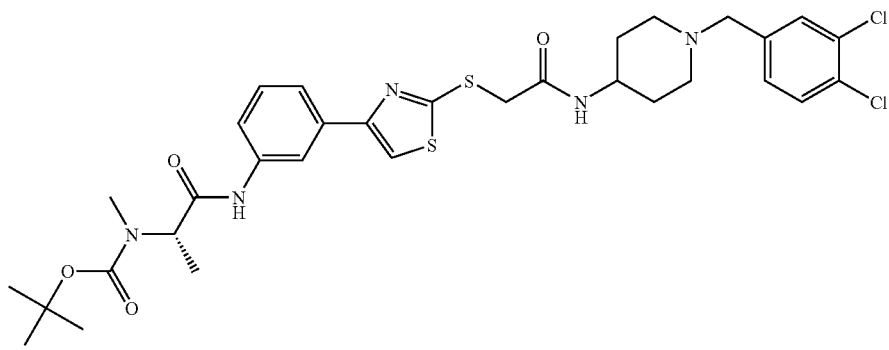

Synthesis of (4-{3-[N-(tert-butoxycarbonyl)-N-methyl-L-alanylamino]phenyl)thiazol-2-ylthio)-N-[1-(3,4-dichlorobenzyl)piperidin-4-yl]acetamide The title compound (670 mg) was obtained as a white amorphous solid from the product (500 mg) of Example 35 and N-(tert-butoxycarbonyl)-N-methyl-L-alanine (340 mg) by a method similar to Example 54.

$^1$H-NMR(CDCl$_3$) δ 1.36–1.53 (5H, m), 1.53 (9H, s), 1.75–1.88 (2H, m), 2.02–2.11 (2H, m), 2.43–2.54 (2H, m), 2.88 (3H, s), 3.25 (2H, s), 3.74–3.85 (1H, m), 3.90 (2H, s), 4.86 (1H, brs), 7.03 (1H, dd, J=1.5, 8.1 Hz), 7.29–7.45 (6H, m), 7.53 (1H, d, J=7.3 Hz), 8.13 (1H, s), 8.82 (1H, brs)

EXAMPLE 99

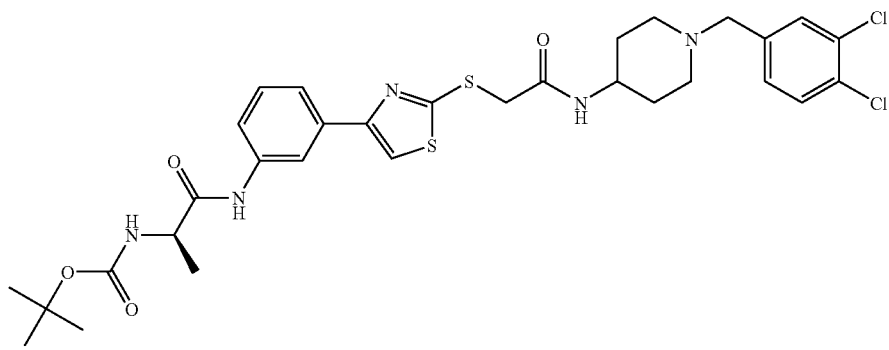

Synthesis of (4-{3-[N-(tert-butoxycarbonyl)-D-alanylamino]phenyl}thiazol-2-ylthio)-N-[1-(3,4-dichlorobenzyl)piperidin-4-yl]acetamide The title compound (630 mg) was obtained as a white powder from the product (500 mg) of Example 35 and -N-(tert-butoxycarbonyl)-D-alanine (310 mg) by a method similar to Example 54.

$^1$H-NMR(CDCl$_3$) δ 1.45–1.53 (14H, m), 1.75–1.88 (2H, m), 2.01–2.15 (2H, m), 2.47–2.65 (2H, m), 3.30 (2H, dd, J=1.2, 6.7 Hz), 3.76–3.85 (1H, m), 3.82–3.97 (2H, m), 4.30–4.40 (1H, m), 5.45 (1H, brs), 7.06 (1H, d, J=8.1 Hz), 7.28–7.45 (6H, m), 7.57 (1H, d, J=7.3 Hz), 8.24 (1H, s), 8.71 (1H, s)

EXAMPLE 100

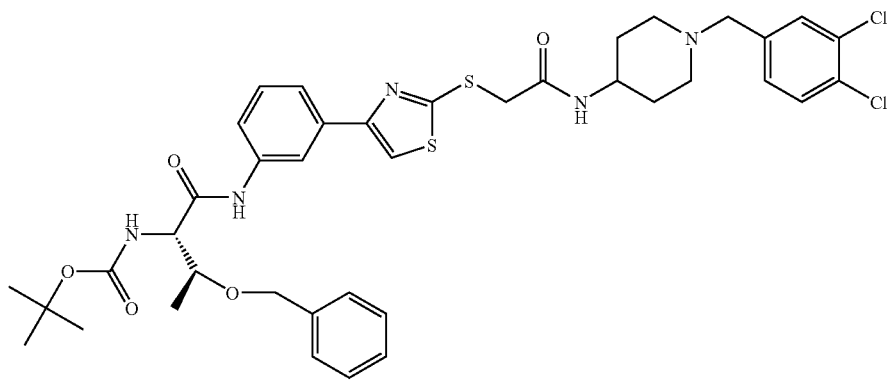

Synthesis of (4-{3-[O-benzyl-N-(tert-butoxycarbonyl)-L-threonylamino]phenyl}thiazol-2-ylthio)-N-[1-(3,4-dichlorobenzyl)piperidin-4-yl]acetamide The title compound (670 mg) was obtained as a white powder from the product (500 mg) of Example 35 and O-benzyl-N-(tert-butoxycarbonyl)-L-threonine (550 mg) by a method similar to Example 54.

$^1$H-NMR(CDCl$_3$) δ 1.22 (3H, d, J=6.1 Hz), 1.34–1.50 (11H, m), 1.75–1.84 (2H, m), 2.03–2.20 (2H, m), 2.44–2.58 (2H, m), 3.28 (2H, s), 3.73–3.85 (1H, m), 3.88 (2H, s), 4.20–4.28 (1H, m), 4.45–4.52 (1H, m), 4.59–4.73 (2H, m), 5.63–5.67 (1H, m), 7.00–7.07 (1H, m), 7.27–7.40 (1H, m), 7.59–7.64 (1H, m), 8.06 (1H, s), 8.64 (1H, brs)

EXAMPLE 101

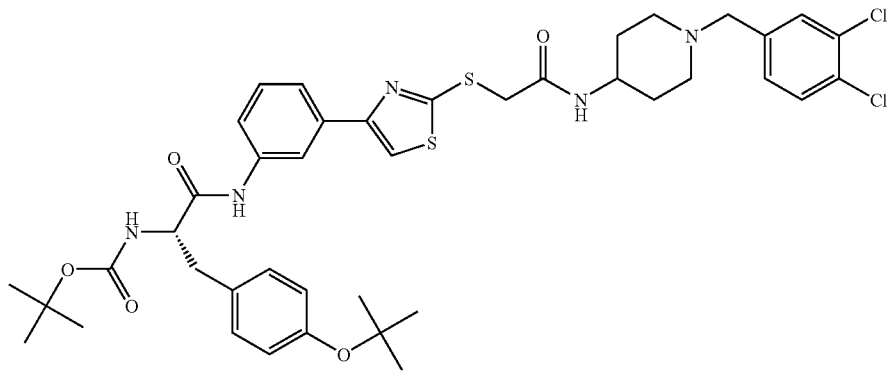

Synthesis of (4-{3-[N-(tert-butoxycarbonyl)-O-(tert-butyl)-L-tyrosylamino]phenyl}thiazol-2-ylthio)-N-[1-(3,4-dichlorobenzyl)piperidin-4-yl]acetamide The title compound (780 mg) was obtained as a white powder from the product (500 mg) of Example 35 and N-(tert-butoxycarbonyl)-O-(tert-butyl)-L-tyrosine (635 mg) by a method similar to Example 54.

$^1$H-NMR(CDCl$_3$) δ 1.31 (9H, s), 1.42 (9H, s), 1.75–1.87 (2H, m), 2.02–2.12 (2H, m), 2.47–2.61 (2H, m), 3.10 (2H, d, J=7.1 Hz), 3.27 (1H, d, J=13.5 Hz), 3.29 (1H, d, J=13.5 Hz), 3.75–3.87 (1H, m), 3.90 (2H, s), 4.45 (1H, d, J=6.1 Hz), 5.36 (1H, brs), 6.93 (2H, d, J=8.3 Hz), 7.04 (1H, dd, J=1.7, 8.1 Hz), 7.15 (2H, d, J=8.3 Hz), 7.27–7.38 (5H, m), 7.43 (1H, s), 7.56–7.62 (1H, m), 8.00 (2H, s)

EXAMPLE 102

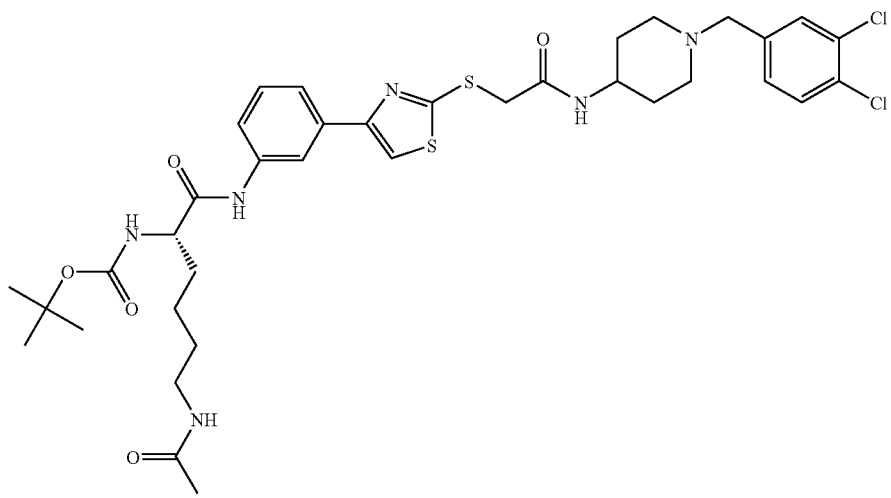

Synthesis of (4-{3-[N'-acetyl-N-(tert-butoxycarbonyl)-L-lysylamino]phenyl}thiazol-2-ylthio)-N-[1-(3,4-dichlorobenzyl)piperidin-4-yl]acetamide The title compound (750 mg) was obtained as a white powder from the product (500 mg) of Example 35 and N'-acetyl-N-(tert-butoxycarbonyl)-L-lysin (570 mg) by a method similar to Example 54.

$^1$H-NMR(CDCl$_3$) δ 1.38–1.60 (15H, m), 1.65–1.86 (2H, m), 1.91–2.01 (4H, m), 2.02–2.14 (2H, m), 2.50–2.63 (2H, m), 3.88 (1H, d, J=15.1 Hz), 3.92 (1H, d, J=15.1 Hz), 4.21–4.32 (1H, m), 5.48–5.60 (1H, m), 5.69–5.78 (1H, m), 7.03–7.09 (1H, m), 7.33–7.46 (5H, m), 7.51–7.60 (2H, m), 8.22 (1H, s), 8.91 (1H, brs)

EXAMPLE 103

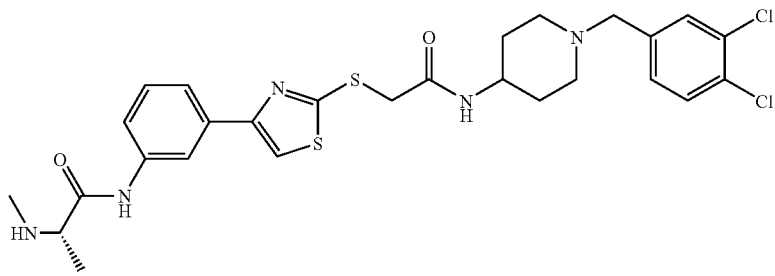

Synthesis of {4-[3-(N-methyl-L-alanylamino)phenyl]thiazol-2-ylthio}-N-[1-(3,4-dichlorobenzyl)piperidin-4-yl]acetamide The title compound (150 mg) was obtained as a white powder from the product (600 mg) of Example 98 by a method similar to Example 59.

$^1$H-NMR(CDCl$_3$) δ 1.32–1.49 (5H, m), 1.77–1.83 (2H, m), 2.02–2.11 (2H, m), 2.42–2.59 (5H, m), 3.18 (1H, q, J=6.9 Hz), 3.25 (2H, s), 3.76–2.87 (1H, m), 3.91 (2H, s), 7.02–7.06 (1H, m), 7.29–7.44 (4H, m), 7.46 (1H, s), 7.52–7.64 (2H, m), 8.27 (1H, s), 9.44 (1H, s)

EXAMPLE 104

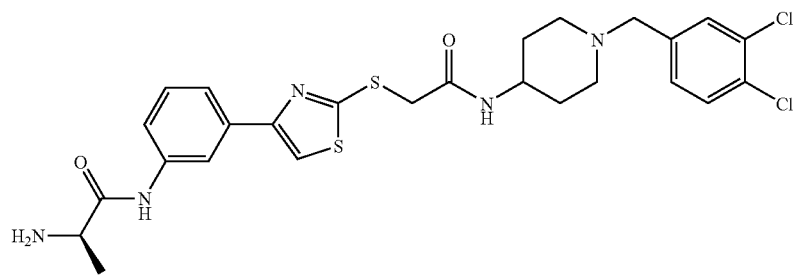

Synthesis of (4-[3-(D-alanylamino)phenyl]thiazol-2-ylthio)-N-[1-(3,4-dichlorobenzyl)piperidin-4-yl)acetamide The title compound (400 mg) was obtained as a white powder from the product (600 mg) of Example 99 by a method similar to Example 59.

$^1$H-NMR(CDCl$_3$) δ 1.31–1.44 (2H, m), 1.45 (3H, d, J=7.2 Hz), 1.77–1.83 (2H, m), 2.02–2.12 (2H, m), 2.43–2.58 (2H, m), 3.25 (2H, s), 3.59–3.68 (1H, m), 3.75–3.91 (1H, m), 3.91 (2H, s), 7.03 (1H, dd, J=1.8, 8.1 Hz), 7.38–7.50 (5H, m), 7.52–7.64 (2H, m), 8.26 (1H, s), 9.64 (1H, brs)

EXAMPLE 105

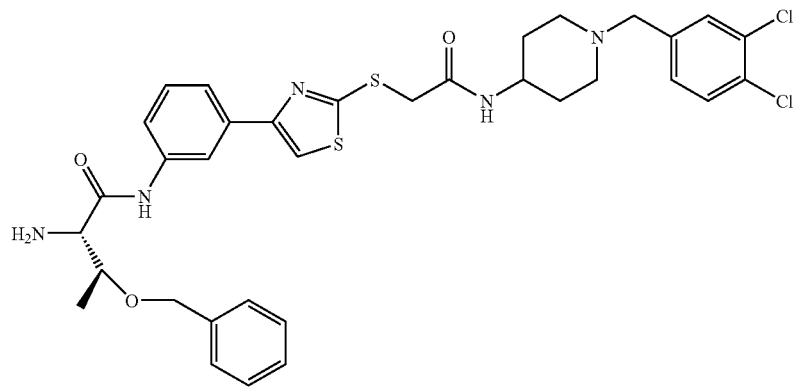

Synthesis of {4-[3-(O-benzyl-L-threonylamino)phenyl]thiazol-2-ylthio}-N-[1-(3,4-dichlorobenzyl)piperidin-4-yl]acetamide The title compound (400 mg) was obtained as a white amorphous solid from the product (500 mg) of Example 100 by a method similar to Example 59.

$^1$H-NMR(CDCl$_3$) δ 1.31 (3H, d, J=6.3 Hz), 1.36–1.47 (2H, m), 1.76–1.84 (2H, m), 2.01–2.11 (2H, m), 2.43–2.60 (2H, m), 3.23 (2H, s), 3.28–3.36 (1H, m), 3.78–3.85 (1H, m), 3.90 (2H, s), 4.32–4.40 (1H, m), 4.42–4.64 (2H, m), 7.00–7.04 (1H, m), 7.26–7.43 (10H, m), 7.54–7.66 (2H, m), 8.19 (1H, s), 9.82 (1H, s)

EXAMPLE 106

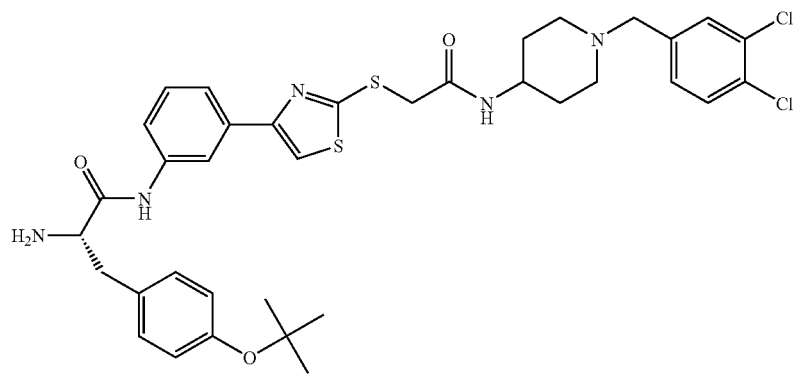

Synthesis of (4-{3-[O-(tert-butyl)-L-tyrosylamino]phenyl}thiazol-2-ylthio)-N-[1-(3,4-dichlorobenzyl)piperidin-4-yl]acetamide The title compound (400 mg) was obtained as a white amorphous solid from the product (540 mg) of Example 101 by a method similar to Example 59.

$^1$H-NMR(CDCl$_3$) δ 1.28–1.44 (2H, m), 1.52–1.86 (11H, m), 2.02–2.14 (2H, m), 2.50–2.63 (2H, m), 2.88–2.99 (1H, m), 3.05–3.14 (1H, m), 3.28 (2H, dd, J=13.4, 15.5 Hz), 3.69–3.84 (2H, m), 3.94 (2H, dd, J=15.5, 19.9 Hz), 6.74 (2H, d, J=8.4 Hz), 7.01–7.08 (3H, m), 7.27–7.33 (3H, m), 7.39 (1H, d, J=7.9 Hz), 7.42 (1H, s), 7.52–7.57 (1H, m), 7.66–7.71 (1H, m), 7.92 (1H, s), 9.20 (1H, s)

EXAMPLE 107

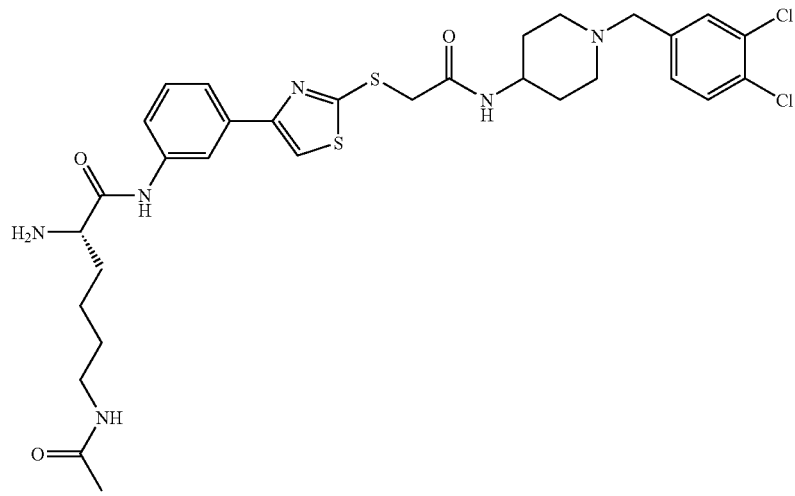

Synthesis of (4-[3-(N'-acetyl-L-lysylamino)phenyl]thiazol-2-ylthio}-N-[1-(3,4-dichlorobenzyl)piperidin-4-yl]acetamide The title compound (450 mg) was obtained as a white amorphous solid from the product (600 mg) of Example 102 by a method similar to Example 59.

$^1$H-NMR(CDCl$_3$) δ 1.33–1.73 (7H, m), 1.76–1.87 (2H, m), 1.90–2.01 (4H, m), 2.03–2.14 (2H, m), 2.43–2.56 (2H, m), 3.22–3.34 (4H, m), 3.47–3.54 (1H, m), 3.73–3.87 (1H, m), 3.91 (2H, s), 5.64 (1H, brs), 7.04 (1H, dd, J=1.8, 8.1 Hz), 7.30–7.47 (5H, m), 7.55–7.64 (2H, m), 8.22 (1H, s), 9.67 (1H, s)

EXAMPLE 108

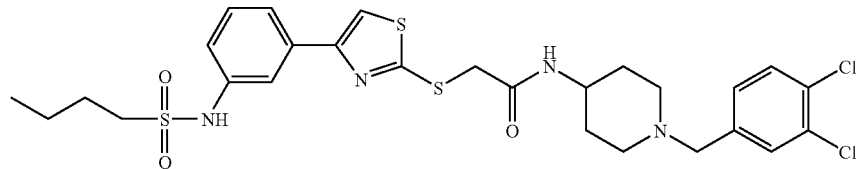

Synthesis of [4-(3-butanesulfonamidephenyl)thiazol-2-ylthio]-N-[1(3,4-dichlorobenzyl)piperidin-4-yl]acetamide The title compound (400 mg) was obtained as a white amorphous solid from the product (500 mg) of Example 35 and butanesulfonyl chloride (260 μL) by a method similar to Example 45.

$^1$H-NMR(CDCl$_3$) δ 0.87 (3H, t, J=7.3 Hz), 1.32–1.50 (4H, m), 1.76–1.89 (4H, m), 2.00–2.11 (2H, m), 2.55–2.64 (2H, m), 3.12 (2H, t, J=7.8 Hz), 3.33 (2H, s), 3.28–3.70 (1H, m), 3.89 (2H, s), 7.07 (1H, d, J=8.1 Hz), 7.28–7.45 (6H, m), 7.60 (1H, d, J=7.5 Hz), 7.79 (1H, s)

EXAMPLE 109

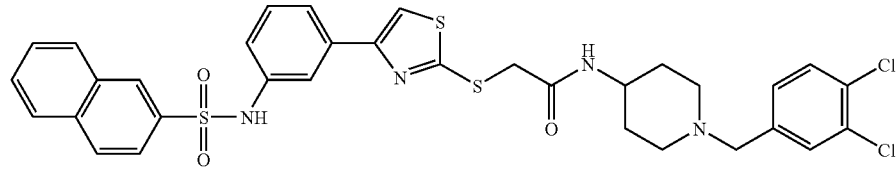

Synthesis of N-[1-(3,4-dichlorobenzyl)piperidin-4-yl]-{4-[3-(2-naphthalenesulfonamide)phenyl]thiazol-2-ylthio}acetamide The title compound (460 mg) was obtained as a white amorphous solid from the product (500 mg) of Example 35 and 2-naphthalenesulfonyl chloride (450 mg) by a method similar to Example 45.

$^1$H-NMR(CDCl$_3$) δ 1.32–1.44 (2H, m), 1.77–1.83 (2H, m), 1.98–2.05 (2H, m), 2.54–2.59 (2H, m), 3.32 (2H, s), 3.71–3.85 (1H, m), 3.79 (2H, s), 7.05 (1H, d, J=8.1 Hz), 7.22–7.36 (5H, m), 7.49–7.69 (5H, m), 7.76–7.90 (4H, m), 8.41 (1H, s)

EXAMPLE 110

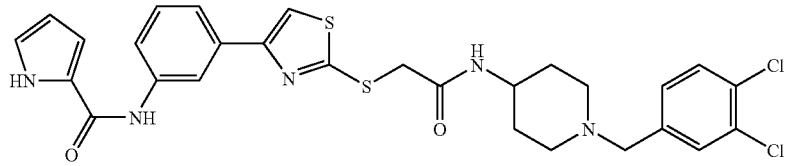

Synthesis of N-[1-(3,4-dichlorobenzyl)piperidin-4-yl]-{4-[3-(pyrrol-2-ylcarboxamide)phenyl]thiazol-2-ylthio}acetamide The title compound (430 mg) was obtained as a white powder from the product (500 mg) of Example 35 and pyrrole-2-carboxylic acid (130 mg) by a method similar to Example 54.

$^1$H-NMR(DMSO-$d_6$) δ 1.35–1.70 (2H, m), 1.70–1.73 (2H, m), 1.99–2.06 (2H, m), 2.64–2.68 (2H, m), 3.41 (2H, s), 3.55–3.60 (1H, m), 3.99 (2H, s), 6.16–6.18 (1H, m), 6.96–6.98 (1H, m), 7.09–7.12 (1H, m), 7.24–7.27 (1H, m), 7.38 (1H, t, J=7.9 Hz), 7.51 (1H, d, J=1.8 Hz), 7.54–7.62 (2H, m), 7.81–7.84 (1H, m), 7.94 (1H, s), 8.20–8.23 (2H, m), 9.83 (1H, s), 11.66 (1H, brs)

EXAMPLE 111

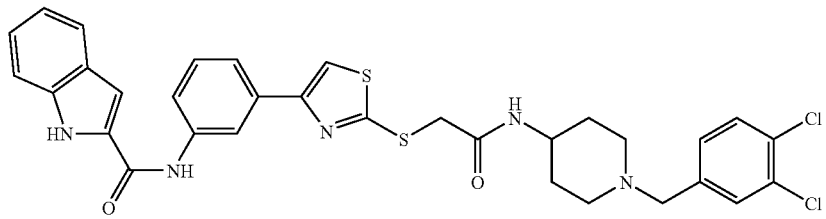

Synthesis of N-[1-(3,4-dichlorobenzyl)piperidin-4-yl]-{4-[3-(indole-2-carboxyamide)phenyl]thiazol-2-ylthio}acetamide The title compound (440 mg) was obtained as a white powder from the product (500 mg) of Example 35 and indole-2-carboxylic acid (193 mg) by a method similar to Example 54.

$^1$H-NMR(CDCl$_3$) δ 1.35–1.47 (2H, m), 1.80–1.84 (2H, m), 2.00–2.10 (2H, m), 2.48–2.52 (2H, m), 3.24 (2H, s), 3.77–3.86 (1H, m), 3.92 (2H, s), 6.99 (1H, dd, J=1.8, 8.2 Hz), 7.07 (1H, m), 7.16–7.21 (1H, m), 7.25–7.35 (2H, m), 7.43–7.48 (3H, m), 7.60–7.71 (3H, m), 8.09 (1H, s), 8.27 (1H, brs), 9.32 (1H, s)

EXAMPLE 112

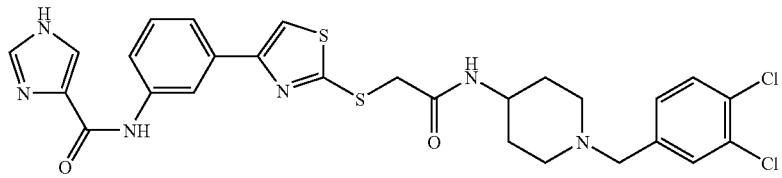

Synthesis of N-[1-(3,4-dichlorobenzyl)piperidin-4-yl]-{4-[3-(4-imidazolecarboxamide)phenyl]thiazol-2-ylthio}acetamide The residue obtained from the product (500 mg) of Example 35 and imidazole-4-carboxylic acid (135 mg) by a method similar to Example 54 was purified by HPLC (Develosil C30-UG-5, 0.05% aqueous TFA:acetonitrile 2:8–0:10) to give the title compound (180 mg) as a white amorphous solid.

$^1$H-NMR(CDCl$_3$) δ 1.28–1.47 (2H, m), 1.78–1.83 (2H, m), 2.00–2.07 (2H, m), 2.45–2.49 (2H, m), 3.22 (2H, s), 3.75–3.85 (1H, m), 3.92 (2H, s), 6.99 (1H, dd, J=1.8, 8.1 Hz), 7.29 (1H, s), 7.38–7.49 (3H, m), 7.57–7.68 (3H, m), 7.73 (1H, s), 8.32 (1H, s), 9.21 (1H, s), 11.08 (1H, brs)

EXAMPLE 113

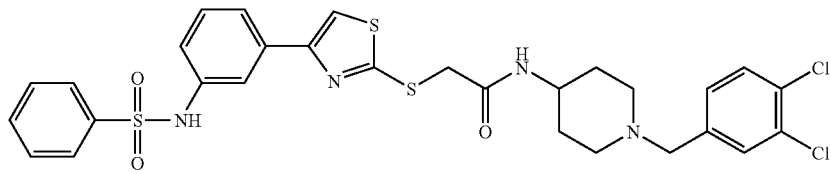

Synthesis of [4-(3-benzenesulfonamidephenyl)thiazol-2-ylthio]-N-[1-(3,4-dichlorobenzyl)piperidin-4-yl]acetamide The title compound (170 mg) was obtained as a white amorphous solid from the product (500 mg) of Example 35 and benzenesulfonyl chloride (253 mg) by a method similar to Example 45.

$^1$H-NMR(CDCl$_3$) δ 1.34–1.47 (2H, m), 1.80–1.86 (2H, m), 2.01–2.10 (2H, m), 2.53–2.68 (2H, m), 3.37 (2H, s), 3.76–3.85 (1H, m), 3.83 (2H, s), 7.08 (1H, dd, J=1.8, 8.1 Hz), 7.18–7.22 (1H, m), 7.26–7.44 (6H, m), 7.47–7.63 (5H, m), 7.77–7.82 (2H, m)

EXAMPLE 114

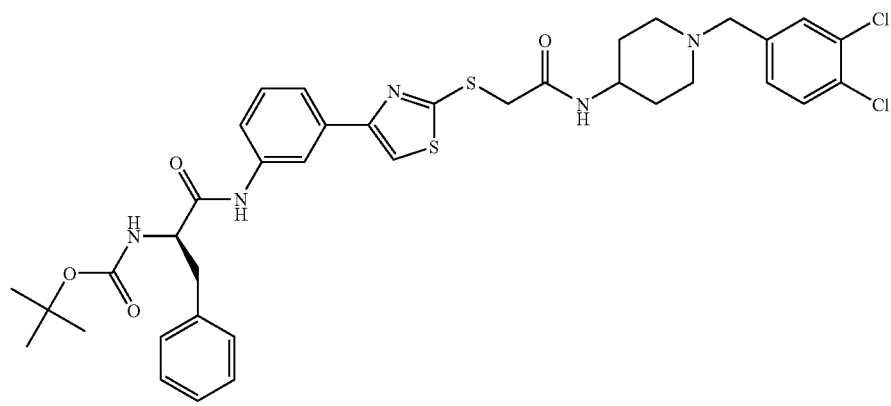

Synthesis of (4-{3-[N-(tert-butoxycarbonyl)-D-phenylalanylamino]phenyl thiazol-2-ylthio)-N-[1-(3,4-dichlorobenzyl)piperidin-4-yl]acetamide The title compound (710 mg) was obtained as a yellow amorphous solid from the product (510 mg) of Example 35 and N-(tert-butoxycarbonyl)-D-phenylalanine (265 mg) by a method similar to Example 54.

ESI-MS(m/z): 754

EXAMPLE 115

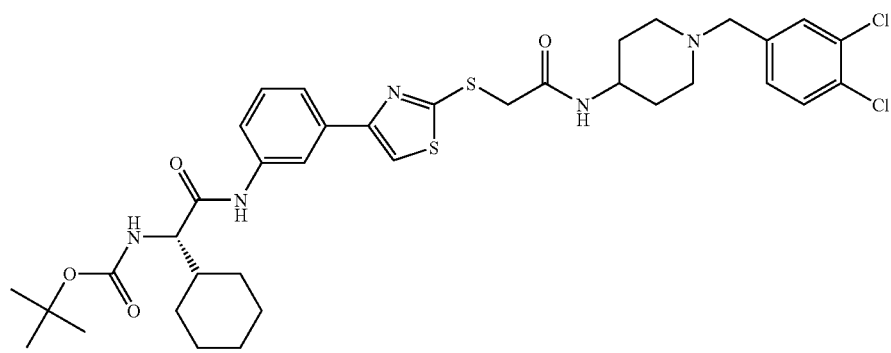

Synthesis of (4-(3-[N-(tert-butoxycarbonyl)-L-2-cyclohexylglycylamino]phenyl}thiazol-2-ylthio)-N-[1-(3,4-dichlorobenzyl)piperidin-4-yl]acetamide The title compound (741 mg) was obtained as a yellow amorphous solid from the product (510 mg) of Example 35 and N-(tert-butoxycarbonyl)-L-2-cyclohexylglycine (257 mg) by a method similar to Example 54.

ESI-MS(m/z): 746

EXAMPLE 116

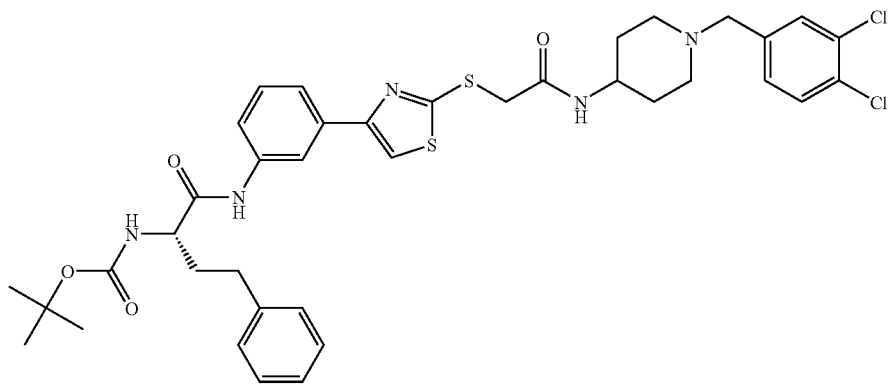

Synthesis of (4-{3-[N-(tert-butoxycarbonyl)-L-homophenylalanylamino]phenyl}thiazol-2-ylthio)-N-[1-(3,4-dichlorobenzyl)piperidin-4-yl]acetamide The title compound (699 mg) was obtained as a yellow amorphous solid from the product (510 mg) of Example 35 and N-(tert-butoxycarbonyl)-L-homophenylalanine (279 mg) by a method similar to Example 54.

ESI-MS(m/z): 768

EXAMPLE 117

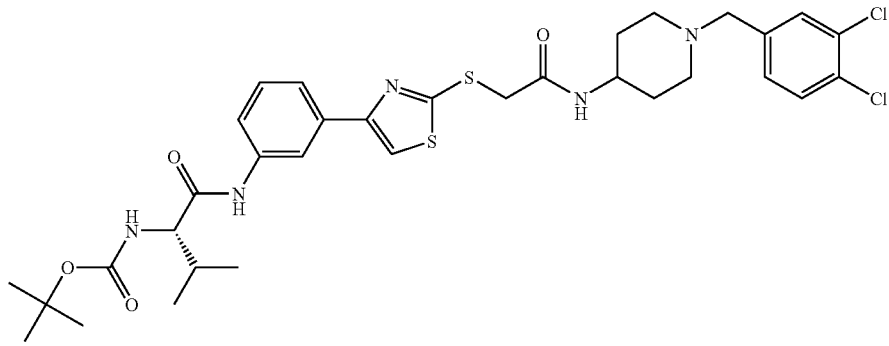

Synthesis of (4-{3-[N-(tert-butoxycarbonyl)-L-valylamino]phenyl}thiazol-2-ylthio)-N-[1-(3,4-dichlorobenzyl)piperidin-4-yl]acetamide The title compound (670 mg) was obtained as a yellow amorphous solid from the product (510 mg) of Example 35 and N-(tert-butoxycarbonyl)-L-valine (217 mg) by a method similar to Example 54.

ESI-MS(m/z): 706

EXAMPLE 118

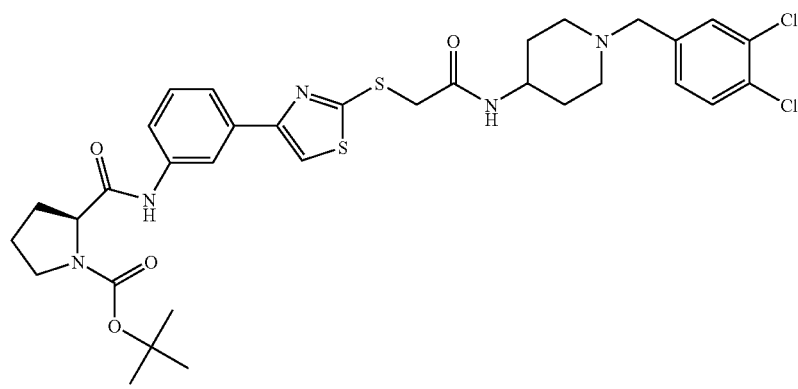

Synthesis of (4-{3-[N-(tert-butoxycarbonyl)-L-pro-lylamino]phenyl}thiazol-2-ylthio)-N-[1-(3,4-dichlorobenzyl)piperidin-4-yl]acetamide The title compound (521 mg) was obtained as a yellow amorphous solid from the product (510 mg) of Example 35 and N-(tert-butoxycarbonyl)-L-proline (215 mg) by a method similar to Example 54.

ESI-MS(m/z): 704

EXAMPLE 119

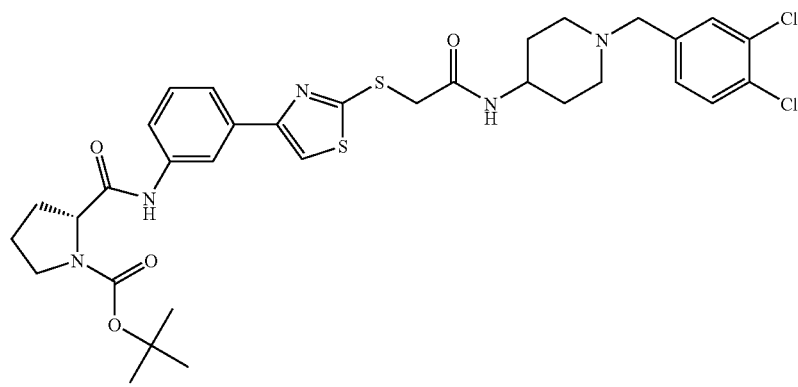

Synthesis of (4-{3-[N-(tert-butoxycarbonyl)-D-pro-lylamino]phenyl}thiazol-2-ylthio)-N-[1-(3,4-dichlorobenzyl)piperidin-4-yl]acetamide The title compound (628 mg) was obtained as a yellow amorphous solid from the product (510 mg) of Example 35 and N-(tert-butoxycarbonyl)-D-proline (215 mg) by a method similar to Example 54.

ESI-MS(m/z): 704

EXAMPLE 120

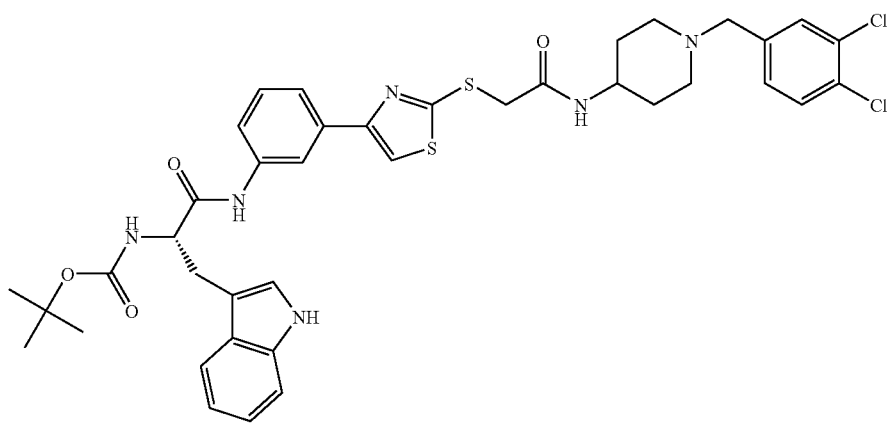

Synthesis of (4-{3-[N-(tert-butoxycarbonyl)-L-tryptophylamino]phenyl}thiazol-2-ylthio)-N-[1-(3,4-dichlorobenzyl)piperidin-4-yl]acetamide The title compound (486 mg) was obtained as a yellow amorphous solid from the product (510 mg) of Example 35 and N-(tert-butoxycarbonyl)-L-tryptophan (304 mg) by a method similar to Example 54.

ESI-MS(m/z): 793

EXAMPLE 121

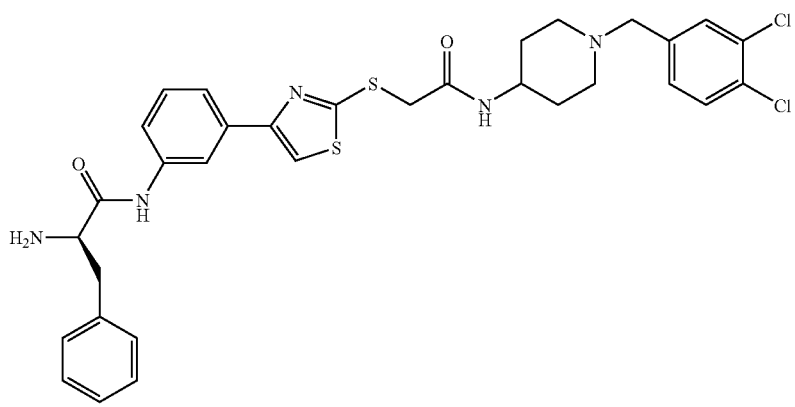

Synthesis of N-[1-(3,4-dichlorobenzyl)piperidin-4-yl]-{4-[3-(D-phenylalanylamino)phenyl]thiazol-2-ylthio}acetamide The title compound (381 mg) was obtained as a white powder from the product (570 mg) of Example 114 by a method similar to Example 59.
ESI-MS(m/z): 654

EXAMPLE 122

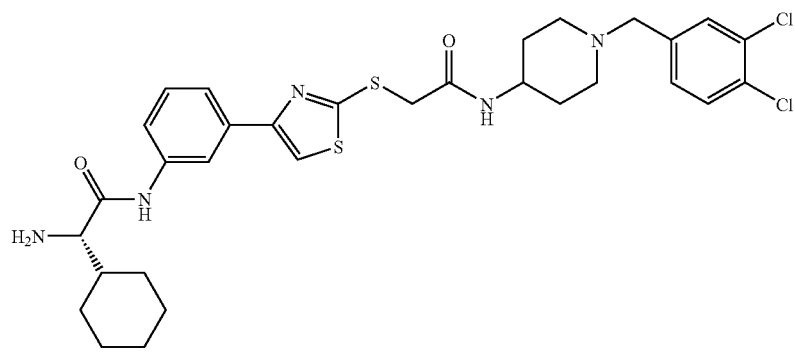

Synthesis of {4-[3-(L-2-cyclohexylglycylamino)phenyl]thiazol-2-ylthio}-N-[1-(3,4-dichlorobenzyl)piperidin-4-yl]acetamide The title compound (343 mg) was obtained as a white powder from the product (595 mg) of Example 115 by a method similar to Example 59.

ESI-MS(m/z): 646

EXAMPLE 123

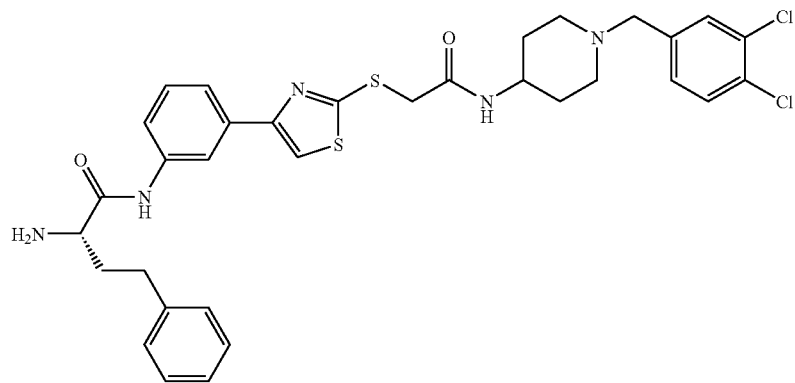

Synthesis of N-[1-(3,4-dichlorobenzyl)piperidin-4-yl]-{4-[3-(L-homophenylalanylamino)phenyl]thiazol-2-ylthio}acetamide The title compound (345 mg) was obtained as a white powder from the product (569 mg) of Example 116 by a method similar to Example 59.

ESI-MS(m/z): 668

EXAMPLE 124

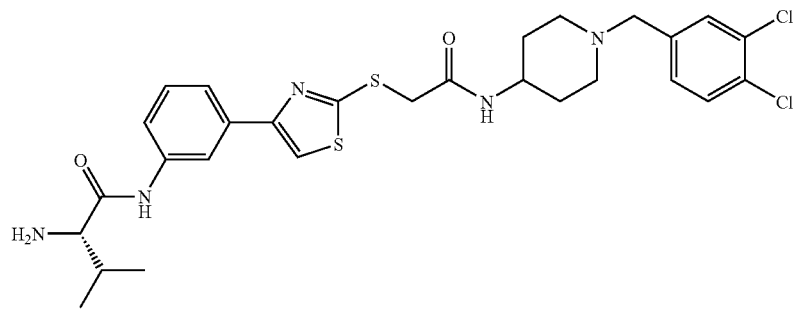

Synthesis of N-[1-(3,4-dichlorobenzyl)piperidin-4-yl]-{4-[3-(L-valylamino)phenyl]thiazol-2-ylthio}acetamide The title compound (139 mg) was obtained as a white powder from the product (521 mg) of Example 117 by a method similar to Example 59.
ESI-MS(m/z): 606

EXAMPLE 125

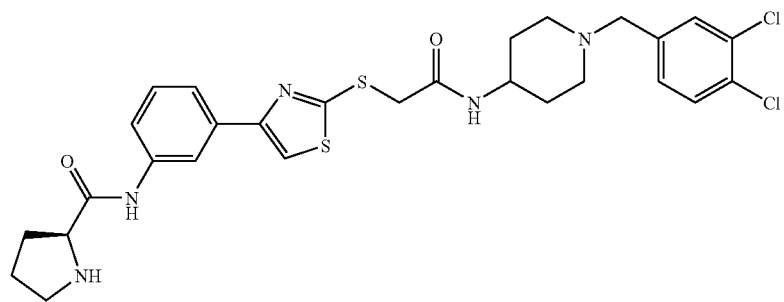

Synthesis of N-[1-(3,4-dichlorobenzyl)piperidin-4-yl]-{4-[3-(L-prolylamino)phenyl]thiazol-2-ylthio}acetamide The title compound (246 mg) was obtained as a white powder from the product (361 mg) of Example 118 by a method similar to Example 59.
ESI-MS(m/z): 604

EXAMPLE 126

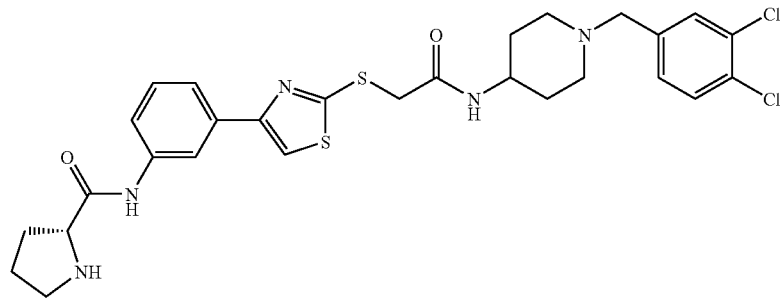

Synthesis of N-[1-(3,4-dichlorobenzyl)piperidin-4-yl]-(4-[3-(D-prolylamino)phenyl]thiazol-2-ylthio}acetamide The title compound (153 mg) was obtained as a white powder from the product (438 mg) of Example 119 by a method similar to Example 59.
ESI-MS(m/z): 604

EXAMPLE 127

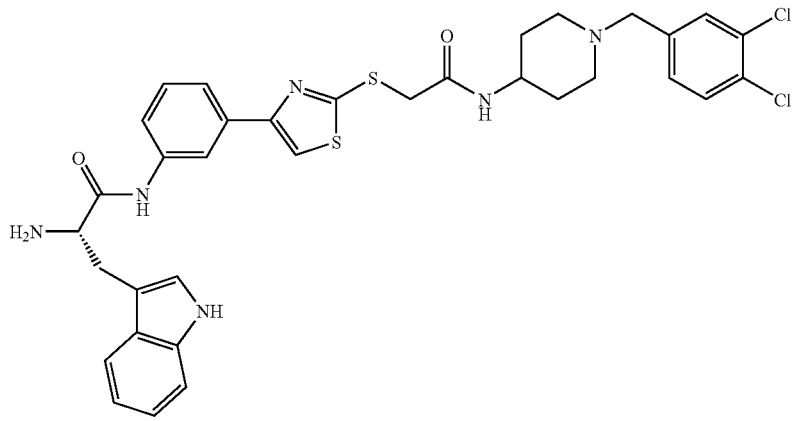

Synthesis of N-[1-(3,4-dichlorobenzyl)piperidin-4-yl]-{4-[3-(L-tryptophylamino)phenyl]thiazol-2-ylthio}acetamide The title compound (129 mg) was obtained as a yellow amorphous solid from the product (338 mg) of Example 120 by a method similar to Example 59.
ESI-MS(m/z): 693

EXAMPLE 128

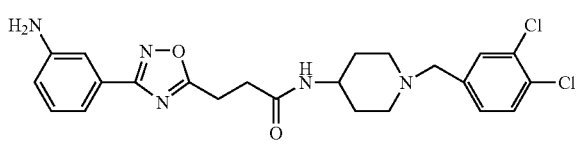

Synthesis of 3-[3-(3-aminophenyl)-1,2,4-oxadiazol-5-yl]-N-[1-(3,4-dichlorobenzyl)piperidin-4-yl]propanamide The product (2.0 g) of Starting Material Synthetic Example 20, ammonium chloride (1.2 g), iron powder (0.8 g), THF (10 mL), methanol (10 mL) and water (10 mL) were refluxed for 3 hrs. The reaction mixture was filtered through Celite with heating, and the solvent was evaporated. The obtained residue was purified by silica gel column chromatography (chloroform:methanol=80:1–40:1) to give the title compound (0.2 g) as white crystals.
$^1$H-NMR(DMSO-$d_6$) δ 1.31–1.50 (2H, m), 1.62–1.76 (2H, m), 1.91–2.11 (2H, m), 2.60–2.82 (4H, m), 3.14 (2H, t, J=7.2 Hz), 3.43 (2H, s), 3.48–3.67 (1H, m), 5.39 (2H, s), 6.67–6.78 (1H, m), 7.05–7.27 (3H, m), 7.28 (1H, dd, J=8.1, 1.8 Hz), 7.50–7.67 (2H, m), 7.89–8.00 (1H, m)

EXAMPLE 129

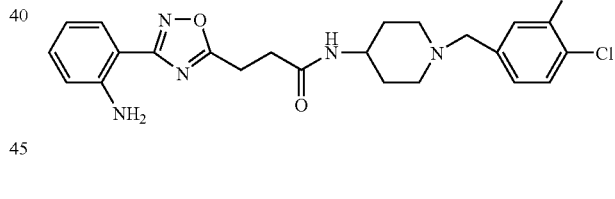

Synthesis of 3-[3-(2-aminophenyl)-1,2,4-oxadiazol-5-yl]-N-[1-(3,4-dichlorobenzyl)piperidin-4-yl]propanamide The product (1.0 g) of Starting Material Synthetic Example 21, ammonium chloride (0.6 g), iron powder (0.4 g), THF (5 mL), methanol (5 mL) and water (5 mL) were refluxed for 3 hrs. The reaction mixture was filtered through Celite with heating, and the solvent was evaporated. The obtained residue was purified by silica gel column chromatography (chloroform:methanol=80:1–40:1) to give the title compound (0.1 g) as white crystals.
$^1$H-NMR(DMSO-$d_6$) δ 1.15–1.36 (2H, m), 1.42–1.65 (2H, m), 1.71–1.98 (2H, m), 2.17–2.65 (6H, m), 3.26 (2H, s), 3.32–3.61 (1H, m), 6.80–6.92 (1H, m), 7.05–7.20 (2H, m), 7.21–7.32 (1H, m), 7.33–7.49 (3H, m), 7.51–7.80 (3H, m)

EXAMPLE 130

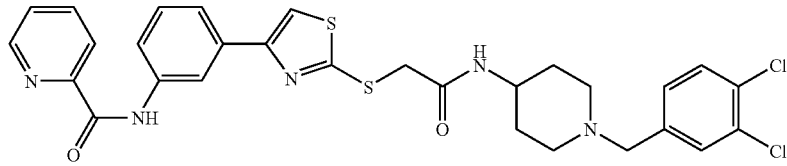

Synthesis of N-[1-(3,4-dichlorobenzyl)piperidin-4-yl]-{4-[3-(pyridin-2-ylcarboxyamide)phenyl]thiazol-2-ylthio}acetamide The product (500 mg) of Example 35 and picoline acid (245 mg) were dissolved in tetrahydrofuran (10 mL), and triethylamine (140 μL) and diethyl cyanophosphonate (180 μL) were added to the solution. The mixture was stirred at room temperature for 1 hr. The reaction mixture was diluted with chloroform, washed with saturated brine, and then saturated aqueous sodium hydrogen carbonate solution, and dried. The solvent was evaporated under reduced pressure, and the residue was purified by silica gel column chromatography (chloroform:methanol=100:1–20:1) to give the title compound (480 mg) as a white amorphous solid.

$^1$H-NMR(CDCl$_3$) δ 1.35–1.48 (2H, m), 1.78–1.86 (2H, m), 2.02–2.11 (2H, m), 2.41–2.53 (2H, m), 3.22 (2H, s), 3.77–3.87 (2H, m), 3.93 (2H, s), 6.99 (1H, dd, J=1.8, 8.2 Hz), 7.28 (2H, s), 7.42–7.53 (4H, m), 7.65 (1H, d, J=7.7 Hz), 7.74–7.79 (1H, m), 7.93 (1H, dt, J=1.8, 7.7 Hz), 8.31 (1H, d, J=7.7 Hz), 8.40 (1H, t, J=1.8 Hz), 8.60–8.64 (1H, m), 10.15 (1H, s)

EXAMPLE 131

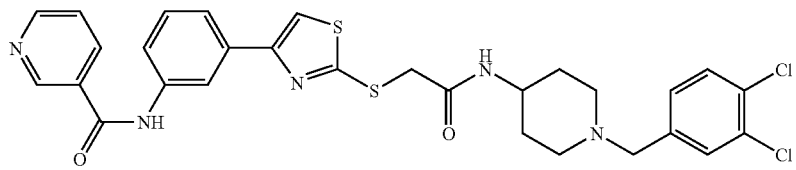

Synthesis of N-[1-(3,4-dichlorobenzyl)piperidin-4-yl]-{4-[3-(pyridin-3-ylcarboxamide)phenyl]thiazol-2-ylthio}acetamide The title compound (540 mg) was obtained as a white powder from the product (500 mg) of Example 35 and nicotinic. acid (245 mg) by a method similar to Example 130.

$^1$H-NMR(CDCl$_3$) δ 1.37–1.51 (2H, m), 1.74–1.86 (2H, m), 2.03–2.13 (2H, m), 2.50–2.63 (2H, m), 3.30 (2H, s), 3.74–3.87 (1H, m), 3.90 (2H, s), 7.01–7.06.(1H, m), 7.30–7.37 (3H, m), 7.42–7.49 (3H, m), 7.62–7.74 (2H, m), 8.20–8.28 (2H, m), 8.36 (1H, brs), 8.76–8.81 (1H, m), 9.14 (1H, d, J=1.8 Hz)

EXAMPLE 132

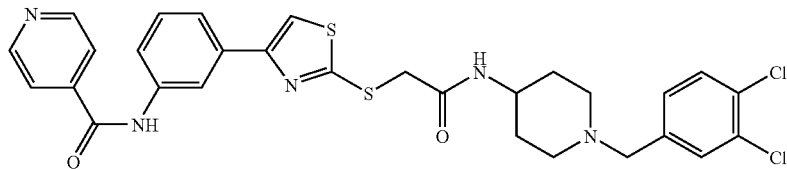

Synthesis of N-[1-(3,4-dichlorobenzyl)piperidin-4-yl]-[4-(3-isonicotinoylaminophenyl)thiazol-2-ylthio]acetamide The title compound (410 mg) was obtained as a white powder from the product (500 mg) of Example 35 and isonicotinic acid (245 mg) by a method similar to Example 130.

$^1$H-NMR(CDCl$_3$) δ 1.38–1.50 (2H, m), 1.79–1.88 (2H, m), 2.02–2.11 (2H, m), 2.48–2.59 (2H, m), 3.28 (2H, s), 3.73–3.86 (1H, m), 3.91 (2H, s), 7.01–7.07 (1H, m), 7.30–7.35 (3H, m), 7.46 (1H, t, J=7.8 Hz), 7.47 (1H, s), 7.64 (1H, d, J=7.8 Hz), 7.69–7.78 (3H, m), 8.23 (1H, s), 8.39 (1H, brs), 8.87–8.86 (2H, m)

EXAMPLE 133

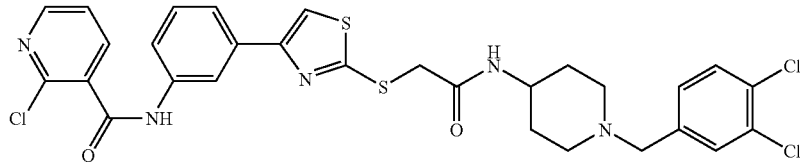

Synthesis of (4-[3-(2-chloronicotinoylamino)phenyl]thiazol-2-ylthio}-N-[1-(3,4-dichlorobenzyl)piperidin-4-yl]acetamide The title compound (440 mg) was obtained as a white powder from the product (500 mg) of Example 35 and 2-chloronicotinic acid (234 mg) by a method similar to Example 130.

$^1$H-NMR(DMSO-d$_6$) δ 1.35–1.47 (2H, m), 1.67–1.76 (2H, m), 1.97–2.08 (2H, m), 2.60–2.69 (2H, m), 3.40 (2H, s), 3.51–3.62 (1H, m), 4.01 (2H, s), 7.23 (1H, dd, J=1.8, 8.1 Hz), 7.40–7.48 (2H, m), 7.55 (1H, d, J=8.1 Hz), 7.71 (1H, d, J=8.1 Hz), 7.90–7.95 (1H, m), 7.97 (1H, s), 8.23 (1H, d, J=7.8 Hz), 8.44 (1H, s), 8.82 (1H, t, J=1.8 Hz), 8.94 (1H, d, J=2.1 Hz), 9.32 (1H, d, J=1.5 Hz), 10.77 (1H, s)

EXAMPLE 134

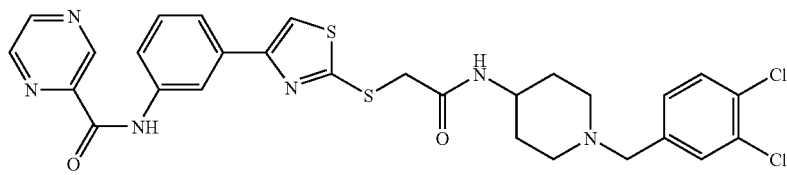

Synthesis of N-[1-(3,4-dichlorobenzyl)piperidin-4-yl]-[4-(3-pyrazinecarboxyamidephenyl)thiazol-2-ylthio]acetamide The title compound (330 mg) was obtained as a white powder from the product (500 mg) of Example 35 and pyrazinecarboxylic acid (184 mg) by a method similar to Example 130.

$^1$H-NMR(DMSO-$d_6$) δ 1.32–1.46 (2H, m), 1.67–1.77 (2H, m), 1.98–2.07 (2H, m), 2.64–2.70 (2H, m), 3.42 (2H, s), 3.50–3.63 (1H, m), 3.99 (2H, s), 7.27 (1H, dd, J=1.8, 8.1 Hz), 7.43 (1H, t, J=8.1 Hz), 7.51 (1H, d, J=1.8 Hz), 7.55 (1H, s), 7.57–7.60 (2H, m), 7.67–7.73 (2H, m), 7.97 (1H, s), 8.09 (1H, dd, J=1.8, 7.5 Hz), 8.20 (1H, d, J=7.5 Hz), 8.26 (1H, s), 8.54 (1H, dd, J=1.8, 8.1 Hz), 10.73 (1H, s)

EXAMPLE 135

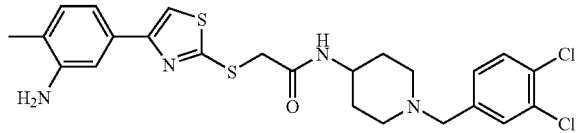

Synthesis of [4-(3-amino-4-methylphenyl)thiazol-2-ylthio]-N-[1-(3,4-dichlorobenzyl)piperidin-4-yl]acetamide The title compound (5.6 g) was obtained as a white powder from the product (6.8 g) of Starting Material Synthetic Example 26 and reduced iron (4 g) by a method similar to Example 128.

$^1$H-NMR(DMSO-$d_6$) δ 1.35–1.47 (2H, m), 1.66–1.76 (2H, m), 1.98–2.07 (5H, m), 2.64–2.70 (2H, m), 3.42 (2H, s), 3.50–3.61 (1H, m), 3.96 (2H, s), 4.89 (2H, brs), 6.95 (1H, d, J=7.8 Hz), 7.03 (2H, dd, J=1.6, 7.5 Hz), 7.18 (1H, d, J=1.6 Hz), 7.27 (1H, dd, J=1.8, 8.1 Hz), 7.51 (1H, d, J=1.8 Hz), 7.57 (1H, d, J=8.1 Hz), 7.72 (1H, s), 8.20 (1H, d, J=7.5 Hz)

EXAMPLE 136

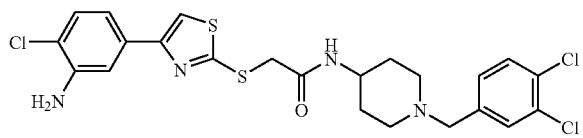

Synthesis of [4-(3-amino-4-chlorophenyl)thiazol-2-ylthio]-N-[1-(3,4-dichlorobenzyl)piperidin-4-yl]acetamide The title compound (460 mg) was obtained as a white powder from the product (680 mg) of Starting Material Synthetic Example 25 and reduced iron (370 mg) by a method similar to Example 128.

$^1$H-NMR(DMSO-$d_6$) δ 1.34–1.46 (2H, m), 1.67–1.75 (2H, m), 1.98–2.08 (2H, m), 2.63–2.72 (2H, m), 3.42 (2H, s), 3.48–3.59 (1H, m), 3.97 (2H, s), 5.42 (2H, s), 7.09 (1H, dd, J=2.0, 8.2 Hz), 7.21–7.32 (2H, m), 7.39 (1H, d, J=2.0 Hz), 7.51–7.60 (2H, m), 7.85 (1H, s), 8.19–8.23 (1H, m)

EXAMPLE 137

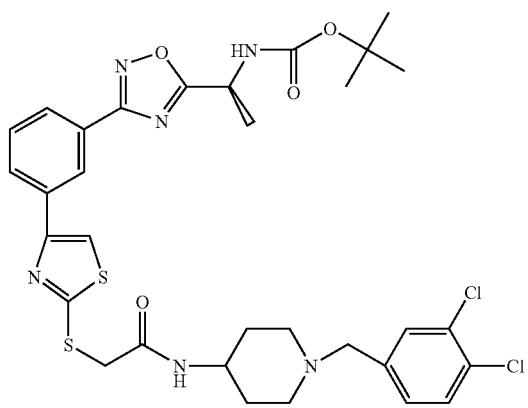

Synthesis of (S)-(4-{3-[5-(1-tert-butoxycarbonylaminoethyl)-1,2,4-oxadiazol-3-yl]phenyl}thiazol-2-ylthio)-N-[1-(3,4-dichlorobenzyl)piperidin-4-yl]acetamide The crude product obtained from the product (0.5 g) of Example 97 and N-(tert-butoxycarbonyl)-L-alanine (0.17 g) by a method similar to Example 54 in the presence of dioxane (30 mL) and molecular sieves 4A (1.5 g) was refluxed for 3 hrs, and filtered through Celite. The filtrate was concentrated, and the obtained residue was purified by silica gel column chromatography (chloroform:methanol=80:1–40:1) to give the title compound (0.49 g) as a white amorphous solid.

$^1$H-NMR(DMSO-$d_6$) δ 1.32–1.53 (11H, m), 1.53 (3H, d, J=7.2 Hz), 1.75–1.80 (2H, m), 1.96–2.15 (2H, m), 2.63–2.81 (2H, m), 3.45 (2H, s), 3.50–3.67 (1H, m), 4.02 (2H, s), 4.91–5.08 (1H, m), 7.27 (1H, d, J=8.4 Hz), 7.51–7.72 (3H, m), 7.75–7.89 (1H, m), 7.97 (1H, d, J=7.8 Hz), 8.15 (1H, d, J=7.5 Hz), 8.20 (1H, s), 8.25–8.82 (1H, m), 8.52 (1H, s)

EXAMPLE 138

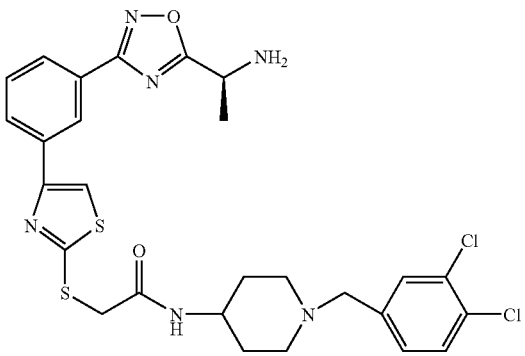

Synthesis of (S)-(4-(3-[5-(1-aminoethyl)-1,2,4-oxadiazol-3-yl]phenyl}thiazol-2-ylthio)-N-[1-(3,4-dichlorobenzyl)piperidin-4-yl]acetamide fumarate The oil obtained from the product (0.4 g) of Example 137 by a method similar to Example 59 was treated with fumaric acid in acetone to give the title compound (0.3 g) as white crystals.

$^1$H-NMR(DMSO-d$_6$) δ 1.31–1.57 (2H, m), 1.53 (3H, d, J=6.9 Hz), 1.68–1.81 (2H, m), 2.00–2.13 (2H, m ), 2.62–2.80 (2H, m), 3.46 (2H, s), 3.50–3.65 (1H, m), 4.02 (2H, )}, 4.40 (1H, q, J=6.9 Hz), 6.62 (2H, s), 7.28 (1H, dd, J=8.4, 1.8 Hz), 7.48–7.71 (3H, m), 7.99 (1H, d, J=7.8 Hz), 8.15 (1H, d, J=7.8 Hz), 8.20 (1H, s), 8.24–8.32 (1H, m), 8.55 (1H, s)

EXAMPLE 139

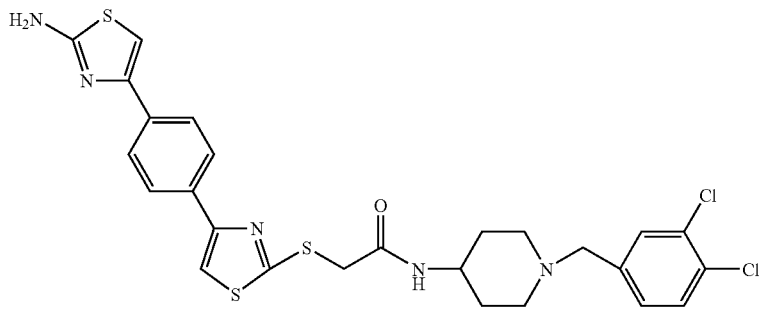

Synthesis of {4-[4-(2-aminothiazol-4-yl)phenyl]thiazol-2-ylthio}-N-[1-(3,4-dichlorobenzyl)piperidin-4-yl]acetamide The title compound (11 mg) was obtained as a brown powder from the product (0.5 g) of Starting Material Synthetic Example 28 and thiourea by a method similar to Example 1.

$^1$H-NMR(DMSO-d$_6$) δ 1.38–1.47 (2H, m), 1.70–1.74 (2H, m), 2.00–2.07 (2H, m), 2.66–2.69 (2H, m), 3.42 (2H, s), 3.54–3.58 (1H, m), 4.02 (2H, s), 7.09 (3H, m), 7.28 (1H, d, J=8.1 Hz), 7.51 (1H, s), 7.55 (1H, d, J=8.1 Hz), 7.85 (2H, d, J=8.7 Hz), 7.94 (2H, d, J=8.7 Hz), 8.02 (1H, s), 8.25 (1H, d, J=6.9 Hz)

EXAMPLE 140

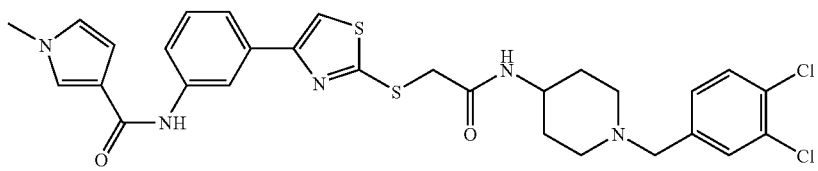

Synthesis of N-[1-(3,4-dichlorobenzyl)piperidin-4-yl]-{4-[3-(1-methylpyrrol-3-ylcarboxamide)phenyl]thiazol-2-ylthio}acetamide The title compound (441 mg) was obtained as a white powder from the product (500 mg) of Example 35 and 1-methylpyrrole-3-carboxylic acid (150 mg) by a method similar to Example 54.

$^1$H-NMR(DMSO-$d_6$) δ 1.34–1.48 (2H, m), 1.67–1.76 (2H, m), 1.97–2.06 (2H, m), 2.62–2.70 (2H, m), 3.41 (2H, s), 3.49–3.63 (1H, m), 3.88 (3H, s), 3.99 (2H, s), 6.07–6.11 (1H, m), 6.99–7.03 (1H, m), 7.05–7.09 (1H, m), 7.26 (1H, dd, J=8.2,–1.9 Hz), 7.36 (1H, t, J=8.2 Hz), 7.50 (1H, d, J=1.9 Hz), 7.56 (1H, d, J=8.2 Hz), 7.57–7.63 (1H, m), 7.70–7.76 (1H, m), 7.93 (1H, s), 8.18–8.25 (2H, m), 9.82 (1H, s)

EXAMPLE 141

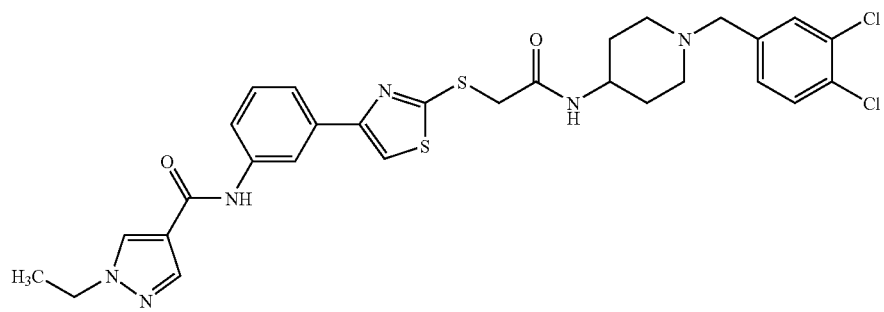

Synthesis of N-[1-(3,4-dichlorobenzyl)piperidin-4-yl]-{4-[3-(1-ethylpyrazol-4-ylcarboxyamide)phenyl]thiazol-2-ylthio}acetamide The title compound (0.36 g) was obtained as a white amorphous solid from the product (1.8 g) of Example 35 and 1-ethylpyrazol-4-ylcarboxylic acid (0.5 g) by a method similar to Example 54.

$^1$H-NMR(DMSO-$d_6$) δ 1.37–1.53 (2H, m), 1.44 (3H, t, J=7.3 Hz), 1.74–1.77 (2H, m), 1.99–2.06 (2H, m), 2.66–2.70 (2H, m), 3.47 (2H, s), 3.57–3.66 (1H, m), 4.05 (2H, s), 4.22 (2H, q, J=7.3 Hz), 7.25 (1H, dd, J=8.2, 1.7 Hz), 7.42 (1H, t, J=7.9 Hz), 7.49 (1H, d, J=1.7 Hz), 7.54 (1H, d, J=8.2 Hz), 7.65–7.67 (1H, m), 7.84–7.87 (1H, m), 7.97 (1H, s), 8.12 (1H, s), 8.25–8.27 (2H, m), 8.43 (1H, s), 9.96 (1H, s)

EXAMPLE 142

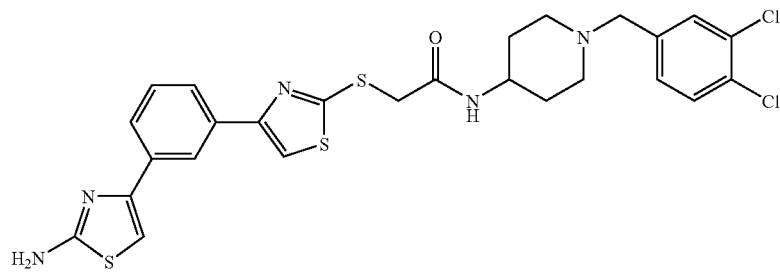

Synthesis of {4-[3-(2-aminothiazol-4-yl)phenyl]thiazol-2-ylthio}-N-[1-(3,4-dichlorobenzyl)piperidin-4-yl]acetamide The title compound (86 mg) was obtained as a white powder from the product (500 mg) of Starting Material Synthetic Example 35 and thiourea by a method similar to Example 1.

$^1$H-NMR(DMSO-$d_6$) δ 1.42–1.53 (2H, m), 1.76–1.79 (2H, m), 2.05–2.12 (2H, m), 2.70–2.74 (2H, m), 3.48 (2H, s), 3.59–3.65 (1H, m), 4.07 (2H, s), 7.18 (3H, s), 7.33 (1H, dd, J=8.2, 1.8 Hz), 7.49 (1H, t, J=7.7 Hz), 7.57 (1H, d, J=1.8 Hz), 7.63 (1H, d, J=8.2 Hz), 7.84 (1H, d, J=7.9 Hz), 7.88 (1H, d, J=7.8 Hz), 8.09 (1H, s), 8.30 (1H, d, J=7.5 Hz), 8.41 (1H, s)

EXAMPLE 143

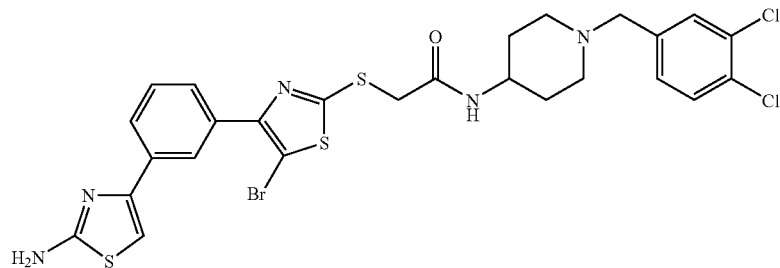

Synthesis of {4-[3-(2-aminothiazol-4-yl)phenyl]-5-bromothiazol-2-ylthio}-N-[1-(3,4-dichlorobenzyl)piperidin-4-yl]acetamide The title compound (33 mg), as well as the, compound of Example 142, was obtained as a white powder from the product (500 mg) of Starting Material Synthetic Example 35 and thiourea by a method similar to Example 1.

$^1$H-NMR(DMSO-$d_6$) δ 1.38–1.46 (2H, m), 1.70–1.75 (2H, m), 1.95–2.15 (2H, m), 2.71–2.75 (2H, m), 3.47 (2H, brs), 3.58–3.62 (1H, m), 3.99 (2H, s), 7.08–7.11 (3H, m), 7.30 (1H, d, J=7.5 Hz), 7.47 (1H, t, J=7.8 Hz), 7.56–7.62 (2H, m), 7.72–7.75 (1H, m), 7.83–7.86 (1H, m), 8.24 (1H, brd), 8.29 (1H, t, J=1.5 Hz)

EXAMPLE 144

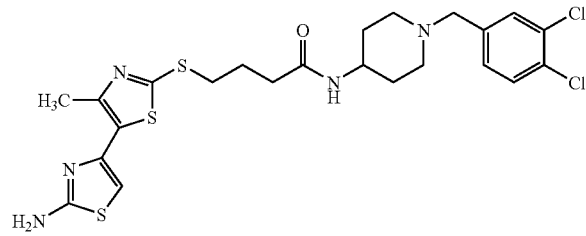

Synthesis of 4-[5-(2-aminothiazol-4-yl)-4-methylthiazol-2-ylthio]-N-[1-(3,4-dichlorobenzyl)piperidin-4-yl]butylamide The title compound (0.47 g) was obtained as a brown amorphous solid from the product (1 g) of Starting Material Synthetic Example 30 and thiourea by a method similar to Example 1.

$^1$H-NMR(DMSO-d$_6$) δ 1.33–1.43 (2H, m), 1.68–1.71 (2H, m), 1.88–2.05 (4H, m), 2.20 (2H, t, J=7.4 Hz), 2.46 (3H, s), 2.69–2.73 (2H, m), 3.15 (2H, t, J=7.2 Hz), 3.44 (2H, s), 3.50–3.54 (1H, m), 6.67 (1H, s), 7.20 (2H, s), 7.28 (1H, dd, J=8.1, 1.8 Hz), 7.53 (1H, d, J=1.8 Hz), 7.57 (1H, d, J=8.1 Hz), 7.79 (1H, d, J=7.5 Hz)

EXAMPLE 145

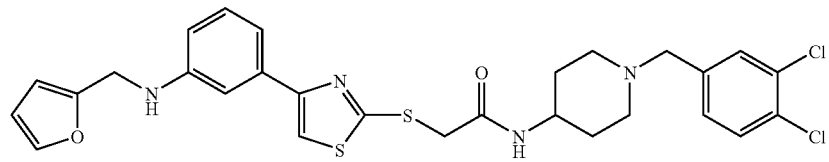

Synthesis of N-[1-(3,4-dichlorobenzyl)piperidin-4-yl]-{4-[3-(2-furylmethylamino)phenyl]thiazol-2-ylthio}acetamide The product (254 mg) of Example 35 and furfural (41 μL) were suspended in dichloromethane (5 mL), and acetic acid (29 μL) and sodium triacetoxyborohydride (212 mg) were added to the suspension. The mixture was stirred at room temperature for 3 hrs. Saturated aqueous sodium hydrogen carbonate was added, and the mixture was extracted with chloroform. The extract was washed with saturated brine and dried, and the solvent was. evaporated. The obtained residue was recrystallized from a mixed solvent of ethyl acetate and diisopropyl ether to give the title compound (260 mg) as a yellow powder.

$^1$H-NMR(DMSO-d$_6$) δ 1.30–1.46 (2H, m), 1.62–1.78 (2H, m), 1.91–2.08 (2H, m), 2.57–2.70 (2H, m), 3.40 (2H, s), 3.51–3.55 (1H, m), 3.96 (2H, s), 4.27 (1H, d, J=5.7 Hz), 6.14 (1H, m), 6.29–6.35 (2H, m), 6.60–6.02 (1H, m), 7.09–7.11 (2H, m), 7.20–7.26 (2H, m), 7.49–7.56 (3H, m), 7.83 (1H, s), 8.18 (1H, d, J=6.9 Hz)

EXAMPLE 146

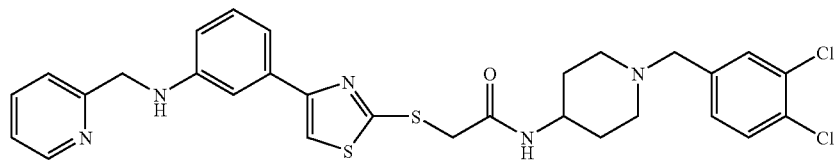

Synthesis of N-[1-(3,4-dichlorobenzyl)piperidin-4-yl]-{4-[3-(2-pyridylmethylamino)phenyl]thiazol-2-ylthio}acetamide hydrochloride A free base of the title compound was obtained from the product (508 mg) of Example 35 and 2-pyridinecarbaldehyde (48 μL) by a method similar to Example 145. The obtained residue was dissolved in ethyl acetate, and a 4 mol/L hydrogen chloride—ethyl acetate solution was added to the solution. The resulting crystals were collected by filtration to give the title compound (306 mg) as a slight yellow powder.

$^1$H-NMR(DMSO-d$_6$) δ 1.74–1.99 (4H, m), 2.89–3.10 (2H, m), 3.04–3.38 (2H, m), 3.77–3.81 (1H, m), 3.99 (2H, s), 4.26 (2H, s), 4.78 (2H, s), 6.58–6.62 (1H, m), 7.15–7.24 (3H, m), 7.62–7.66 (1H, m), 7.70–7.74 (1H, m), 7.84–8.00 (5H, m), 8.42–8.46 (1H, m), 8.60 (1H, d, J=7.2 Hz), 8.78–8.82 (1H, m), 11.30 (1H, brs)

EXAMPLE 147

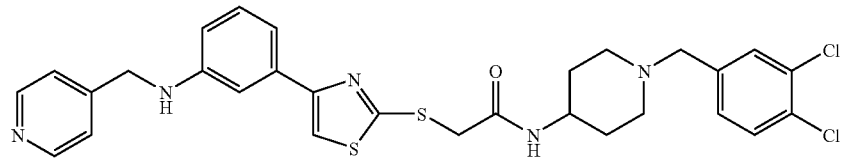

Synthesis of N-[1-(3,4-dichlorobenzyl)piperidin-4-yl]-(4-[3-(4-pyridylmethylamino)phenyl]thiazol-2-ylthio)acetamide hydrochloride The title compound (385 mg) was obtained as a slight yellow powder from the product (508 mg) of Example 35 and 4-pyridinecarbaldehyde (48 μL) by a method similar to Example 146.

$^1$H-NMR(DMSO-d$_6$) δ 1.77–1.96 (4H, m), 2.83–3.04 (2H, m), 3.05–3.33 (2H, m), 3.73–3.77 (1H, m), 3.96 (2H, s), 4.23 (2H, s), 4.67 (2H, s), 6.46–6.50 (1H, m), 7.09–7.16 (3H, m), 7.61 (1H, d, J=8.4 Hz), 7.71 (1H, d, J=8.4 Hz), 7.81–8.85 (1H, m), 7.94–8.02 (3H, m), 8.31 (1H, s), 8.60 (1H, d, J=7.2 Hz), 8.83 (2H, d, J=6.3 Hz), 11.38 (1H, brs)

EXAMPLE 148

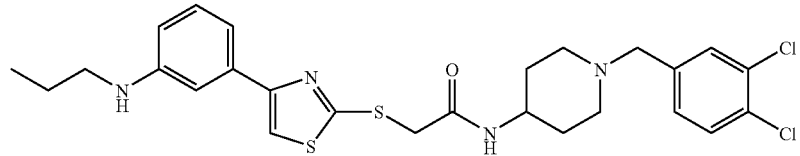

Synthesis of N-[1-(3,4-dichlorobenzyl)piperidin-4-yl]-[4-(3-propylaminophenyl)thiazol-2-ylthio]acetamide hydrochloride The title compound (115 mg) was obtained as a white powder from the product (254 mg) of Example 35 and propionaldehyde (40 μL) by a method similar to Example 146.

$^1$H-NMR(DMSO-d$_6$) δ 0.95 (3H, t, J=7.5 Hz), 1.66 (2H, q, J=7.5 Hz), 1.78–1.96 (4H, m), 2.90–3.07 (2H, m), 3.15–3.34 (5H, m), 4.01 (2H, s), 4.25 (2H, s), 7.05–7.19 (1H, m), 7.34–7.43 (1H, m), 7.59–7.62 (2H, m), 7.72–7.75 (2H, m), 7.96 (1H, d, J=1.8 Hz), 8.01 (1H, s), 8.59 (1H, d, J=7.2 Hz), 11.00 (1H, brs)

EXAMPLE 149

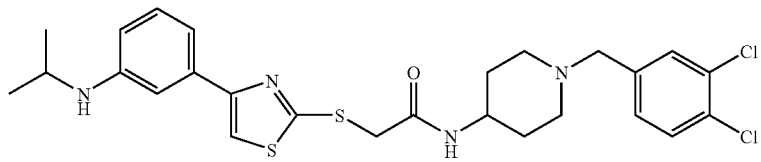

Synthesis of N-[1-(3,4-dichlorobenzyl)piperidin-4-yl]-{4-[3-(2-propylamino)phenyl]thiazol-2-ylthio}acetamide hydrochloride The title compound (265 mg) was obtained as a white powder from the product (254 mg) of Example 35 and acetone (40 μL) by a method similar to Example 146.

$^1$H-NMR(DMSO-$d_6$) δ 1.29 (6H, d, J=6.3 Hz), 1.78–1.92 (4H, m), 2.90–3.06 (2H, m), 3.28–3.32 (2H, m), 3.68–3.85 (2H, m), 4.03 (2H, s), 4.25 (2H, s), 7.50–7.74 (4H, m), 7.98–8.16 (4H, m), 8.66 (1H, d, J=7.5 Hz), 11.17 (1H, brs)

EXAMPLE 150

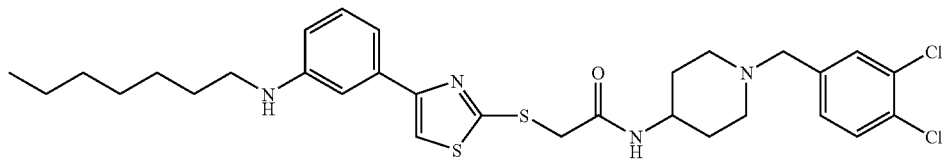

Synthesis of N-[1-(3,4-dichlorobenzyl)piperidin-4-yl]-[4-(3-heptylaminophenyl)thiazol-2-ylthio]acetamide hydrochloride The title compound (120 mg) was obtained as a white powder from the product (254 mg) of Example 35 and heptanal (77 μL) by a method similar to Example 146.

$^1$H-NMR(DMSO-$d_6$) δ 0.80 (3H, t, J=7.5 Hz), 0.98–1.48 (10H, m), 1.56–2.03 (6H, m), 2.84–3.04 (2H, m), 3.05–3.34 (3H, m), 3.64–3.82 (1H, m), 4.00 (2H, s), 4.23 (2H, s), 7.31–8.08 (8H, m), 8.64 (1H, d, J=7.2 Hz), 8.01 (1H, s), 8.59 (1H, d, J=7.2 Hz), 11.50 (1H, brs)

EXAMPLE 151

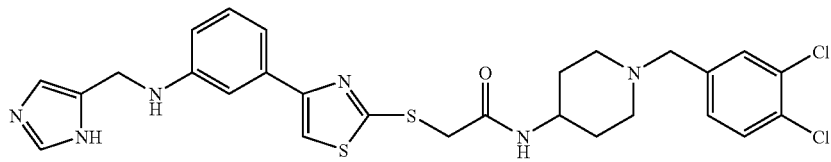

Synthesis of N-[1-(3,4-dichlorobenzyl)piperidin-4-yl]-{4-[3-(imidazol-4-yl-methylamino)phenyl]thiazol-2-ylthio}acetamide dihydrochloride The title compound (239 mg) was obtained as a white powder from the product, (507 mg) of Example 35 and 4-imidazolecarbaldehyde (96 mg) by a method similar to Example 146.

¹H-NMR(DMSO-d₆) δ 1.76–2.18 (4H, m), 2.9.1–3.20 (2H, m), 3.22–3.38 (2H, m), 3.69–3.88 (1H, m), 4.02 (2H, s), 4.27 (2H, s), 4.46 (2H, s), 6.72–6.77 (1H, m), 7.15–7.42 (3H, m), 7.56–7.77 (3H, m), 7.91–8.03 (2H, m), 8.68 (1H, d, J=7.2 Hz), 9.07 (1H, s), 11.31–11.58. (1H, brs), 14.38–14.62 (1H, brs), 14.70–15.04 (1H, brs)

EXAMPLE 152

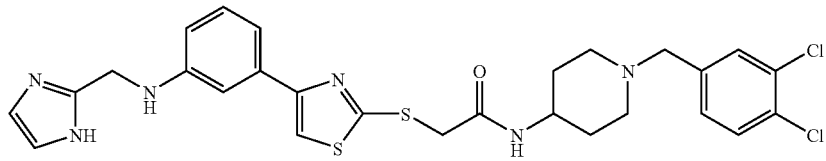

Synthesis of N-[1-(3,4-dichlorobenzyl)piperidin-4-yl]-{4-[3-(imidazol-2-yl-methylamino)phenyl]thiazol-2-ylthio}acetamide dihydrochloride The title compound (107 mg) was obtained as a white powder from the product (507 mg) of Example 35 and 2-imidazolecarbaldehyde (96 mg) by a method similar to Example 146.

¹H-NMR(DMSO-d₆) δ 1.76–2.13 (4H, m), 2.88–3.20 (2H, m), 3.21–3.38 (2H, m), 3.68–3.87 (1H, m), 4.01 (2H, s), 4.26 (2H, s), 4.72 (2H, s), 6.57–6.70 (1H, m), 7.09–7.33 (3H, m), 7.50–7.78 (4H, m), 8.00 (2H, s), 8.64 (1H, d, J=7.2 Hz), 11.22–11.52 (1H, brs), 13.18–13.45 (2H, brs)

EXAMPLE 153

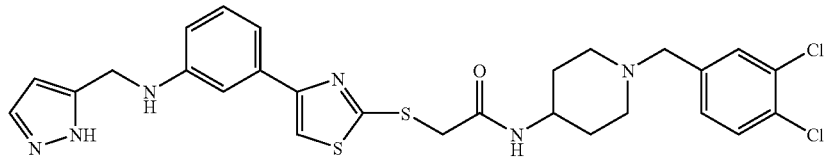

Synthesis of N-[1-(3,4-dichlorobenzyl)piperidin-4-yl]-{4-[3-(pyrazol-3-yl-methylamino)phenyl]thiazol-2-ylthio}acetamide hydrochloride The title compound (317 mg) was obtained as a white powder from the product (507 mg) of Example 35 and 3-pyrazolecarbaldehyde (96 mg) by a method similar to Example 146.

¹H-NMR(DMSO-d₆) δ 1.78–2.10 (4H, m), 2.90–3.38 (4H, m), 3.69–3.88 (1H, m), 4.01 (2H, s), 4.26 (2H, s) 4.46 (2H, s), 6.39 (1H, s), 6.92–7.00 (1H, m), 7.22–7.38 (1H, m), 7.47 (1H, d, J=7.3 Hz), 7.55–7.69 (2H, m), 7.70–7.80 (2H, m), 7.94–8.03 (2H, m), 8.60 (1H, d, J=7.2 Hz), 11.01–11.35 (1H, brs)

EXAMPLE 154

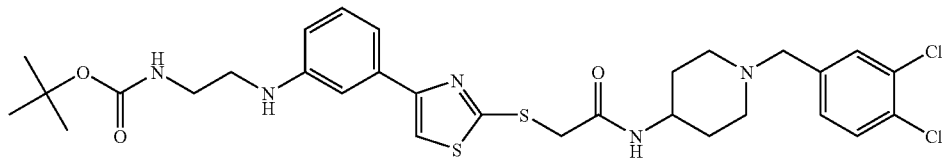

Synthesis of {4-[3-(2-tert-butoxycarbonylaminoethylamino)-phenyl]thiazol-2-ylthio}-N-[1-(3,4-dichlorobenzyl)piperidin-4-yl]acetamide The residue obtained from the product (508 mg) of Example and tert-butoxycarbonylaminoacetaldehyde (159 mg) by a method similar to Example 145 was purified by silica gel column chromatography to give the title compound (325 mg) as a white amorphous solid.

ESI-MS(m/z): 650

EXAMPLE 155

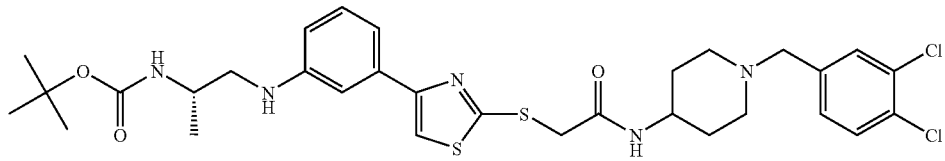

Synthesis of (S)-{4-[3-(2-tert-butoxycarbonylamino-2-methylethylamino)phenyl]thiazol-2-ylthio}-N-[1-(3,4-dichlorobenzyl)piperidin-4-yl]acetamide The title compound (526 mg) was obtained as a white amorphous solid from the product (508 mg) of Example 35 and tert-butoxycarbonylalanine aldehyde (173 mg) by a method similar to Example 154.

ESI-MS(m/z): 664

EXAMPLE 156

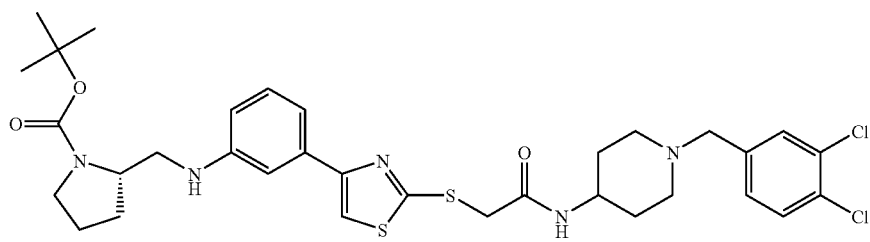

Synthesis of (S)-{4-[3-(N-tert-butoxycarbonylpyrro-
lidin-2-ylmethylamino)phenyl]thiazol-2-ylthio}-N-
[1-(3,4-dichlorobenzyl)piperidin-4-yl]acetamide The title compound (665 mg) was obtained as a white amorphous solid from the product (508 mg) of Example 35 and tert-butoxycarbonylproline aldehyde (187 μL) by a method similar to Example 154.

ESI-MS(m/z): 690

EXAMPLE 157

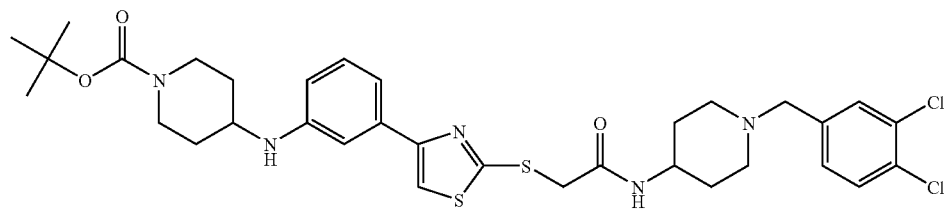

Synthesis of {4-[3-(N-tert-butoxycarbonylpiperidin-
4-yl-amino)phenyl]thiazol-2-ylthio}-N-[1-(3,4-
dichlorobenzyl)piperidin-4-yl]acetamide The title compound (634 mg) was obtained as a white amorphous solid from the product (508 mg) of Example 35 and 1-tert-butoxycarbonyl-4-piperidinone (199 mg) by a method similar to Example 154.

ESI-MS(m/z): 690

EXAMPLE 158

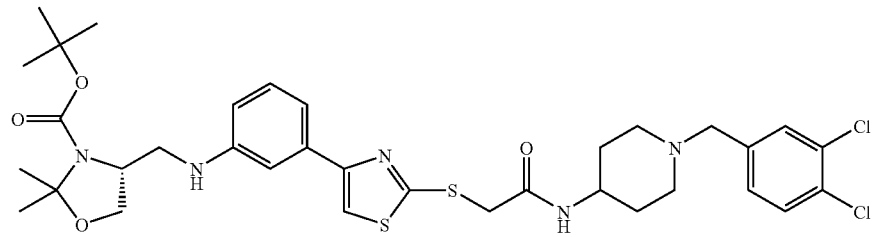

Synthesis of (R)-{4-[3-(3-tert-butoxycarbonyl-2,2-
dimethyloxazolidin-4-ylmethylamino)phenyl]thia-
zol-2-ylthio}-N-[1-(3,4-dichlorobenzyl)piperidin-4-
yl]acetamide The title compound (639 mg) was obtained as a white amorphous solid from the product (508 mg) of Example 35 and N-tert-butoxycarbonyl-2,2-dimethyloxazolidine-4-alde-
hyde (216 μL) by a method similar to Example 154.

$^1$H-NMR(DMSO-d$_6$) δ 1.41 (6H, s), 1.46 (9H, s), 1.50–1.53 (2H, m), 1.63–1.78 (2H, m), 1.93–2.09 (2H, m), 2.58–2.71 (2H, m), 2.88–3.04 (1H, m), 3.41 (2H, s), 3.46–3.62 (1H, m), 3.78–4.07 (6H, m), 6.04–6.13 (1H, m), 6.59–6.69 (1H, m), 7.02–7.16 (2H, m), 7.20–7.32 (2H, m), 7.50–7.58 (2H, m), 7.81–7.90 (1H, m), 8.09–8.21 (1H, m)

EXAMPLE 159

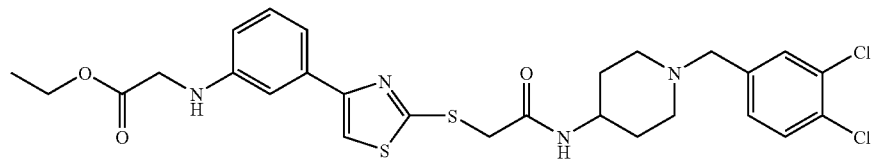

Synthesis of N-[1-(3,4-dichlorobenzyl)piperidin-4-yl]-[4-(3-ethoxycarbonylmethylaminophenyl)thiazol-2-ylthio]acetamide The title compound (615 mg) was obtained as a white powder from the product (1.02 g) of Example 35 and a solution (1.0 g) of ethyl glyoxylate in toluene by a method similar to Example 154.

$^1$H-NMR(DMSO-$d_6$) δ 1.20 (3H, t, J=6.9 Hz), 1.36–1.46 (2H, m), 1.70–1.73 (2H, m), 2.00–2.07 (2H, m), 2.65–2.69 (2H, m), 3.42 (2H, s), 3.50–3.64 (1H, m), 3.94 (2H, d, J=6.3 Hz), 3.98 (2H, s), 6.03 (1H, t, J=6.3 Hz), 6.53–6.56 (1H, m), 7.10–7.15 (3H, m), 7.26–7.29 (1H, m), 7.51–7.58 (2H, m), 7.86 (1H, s), 8.20 (1H, d, J=7.5 Hz)

EXAMPLE 160

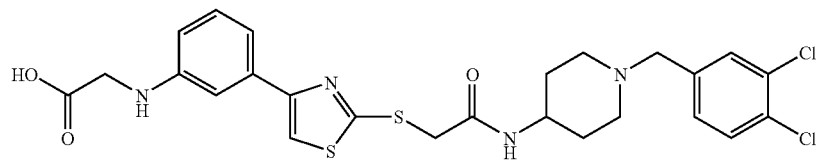

Synthesis of N-[1-(3,4-dichlorobenzyl)piperidin-4-yl]-[4-(3-carboxymethylaminophenyl)thiazol-2-ylthio]acetamide The product (515 mg), of Example 159 was suspended in a mixed solvent of methanol (2 mL), tetrahydrofuran (2 mL) and a 1 mol/L aqueous sodium hydroxide solution (2 mL), and the suspension was stirred at room temperature for 2.5 hrs. The reaction mixture was neutralized by adding conc. hydrochloric acid, and saturated brine was added. The mixture was extracted with a mixed solvent of chloroform-methanol. The extract was dried, and the solvent was evaporated. Ethyl acetate was added to crystallize to give the title compound (456 mg) as a pink powder.

$^1$H-NMR(DMSO-$d_6$) δ 1.49–1.67 (2H, m), 1.73–1.89 (2H, m), 2.32–2.51 (2H, m), 2.80–2.99 (2H, m), 3.56–3.81 (1H, m), 3.86 (2H, s), 3.99 (2H, s), 6.50–6.60 (1H, m), 7.08–7.21 (3H, m), 7.39 (1H, d, J=7.8 Hz), 7.62 (1H, s), 7.66 (2H, d, J=7.8 Hz), 7.86 (1H, s), 8.31 (1H, d, J=7.5 Hz)-

EXAMPLE 161

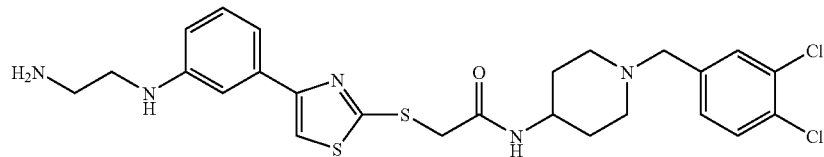

Synthesis of (4-[3-(2-aminoethylamino)phenyl]thiazol-2-ylthio}-N-[1-(3,4-dichlorobenzyl)piperidin-4-yl]acetamide dihydrochloride The product (238 mg) of Example 154 was dissolved in ethyl acetate (1 mL), and a 4 mol/L hydrogen chloride-ethyl acetate solution (0.55 mL) was added to the solution under ice-cooling. The mixture was stirred at room temperature for 20 hrs, and the resulting solids were collected by filtration to give the title compound (201 mg) as a white powder.

$^1$H-NMR(DMSO-$d_6$) δ 1.76–1.97 (4H, m), 2.91–3.09 (4H, m), 3.12–3.49 (4H, m), 3.69–3.88 (1H, m), 4.01 (2H, s), 4.26 (2H, d, J=4.5 Hz), 6.64–6.76 (1H, m), 7.15–7.40 (3H, m), 7.56–7.68 (1H, m), 7.71–7.75 (1H, m), 7.90–8.09 (2H, m), 8.13–8.28 (3H, brs), 8.62 (1H, d, J=7.5 Hz), 11.09–11.38 (1H, brs)

EXAMPLE 162

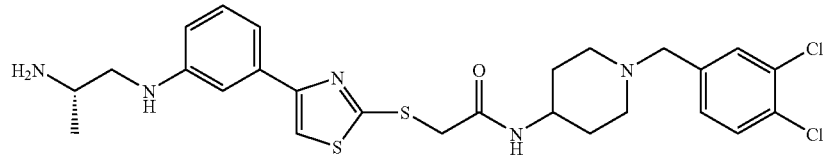

Synthesis of (S)-[4-(3-(2-amino-2-methyl-ethylamino)phenyl)thiazol-2-ylthio]-N-[1-(3,4-dichlorobenzyl)piperidin-4-yl]acetamide dihydrochloride The title compound (437 mg) was obtained as a white powder from the product (462 mg) of Example 155 by a method similar to Example 161.

$^1$H-NMR(DMSO-$d_6$) δ 1.28 (3H, d, J=6.3 Hz), 1.78–1.96 (4H, m), 2.90–3.09 (2H, m), 3.11–3.48 (5H, m), 3.70–3.85 (1H, m), 4.02 (2H, s), 4.26 (2H, d, J=3.9 Hz), 6.61–6.70 (1H, m), 7.09–7.36 (3H, m), 7.55–7.66 (1H, m), 7.71–7.75 (1H, m), 7.93–7.99 (2H, m), 8.14–8.27 (3H, brs), 8.63 (1H, d, J=7.5 Hz), 11.09–11.39 (1H, brs)

EXAMPLE 163

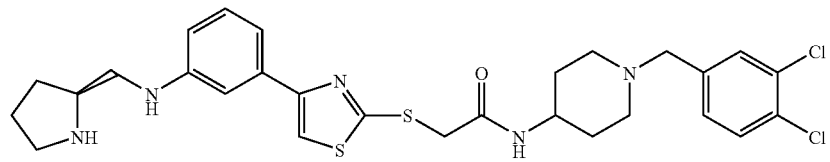

Synthesis of (S)-[4-(3-(pyrrolidin-2-yl-methylamino)phenyl)thiazol-2-ylthio]-N-[1-(3,4-dichlorobenzyl)piperidin-4-yl]acetamide dihydrochloride The title compound (645 mg) was obtained as a white powder from the product (665 mg) of Example 156 by a method similar to Example 161.

$^1$H-NMR(DMSO-$d_6$) δ 1.64–2.18 (8H, m), 2.91–3.58 (8H, m), 3.64–3.90 (2H, m), 4.02 (2H, s), 4.27 (2H, d, J=4.8 Hz), 6.67–6.75 (1H, m), 7.12–7.38 (3H, m), 7.53–7.68 (1H, m), 7.69–7.77 (1H, m), 7.92–8.00 (2H, m), 8.61 (1H, d, J=7.5 Hz), 9.13–9.31 (1H, brs), 9.54–9.71 (1H, brs), 11.17–11.39 (1H, brs)

EXAMPLE 164

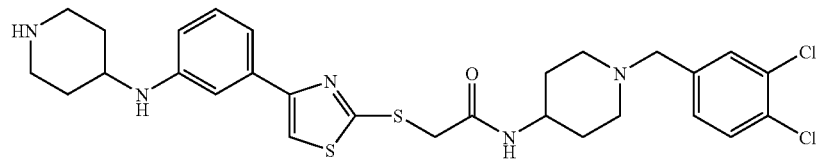

Synthesis of [4-(3-(piperidin-4-yl-amino)phenyl)thiazol-2-ylthio]-N-[1-(3,4-dichlorobenzyl)piperidin-4-yl]acetamide dihydrochloride The title compound (544 mg) was obtained as a white powder from the product (634 mg) of Example 157 by a method similar to Example 161.

$^1$H-NMR(DMSO-$d_6$) δ 1.50–2.18 (8H, m), 2.81–3.40 (8H, m), 3.69–3.86 (2H, m), 4.02 (2H, s), 4.26 (2H, d, J=4.5 Hz), 6.96–7.12 (1H, m), 7.28–7.42 (1H, m), 7.45–7.79 (4H, m), 7.89–8.00 (2H, m), 8.68 (1H, d, J=7.5 Hz), 8.86–9.06 (1H, brs), 9.10–9.29 (1H, brs), 11.10–11.35 (1H, brs)

EXAMPLE 165

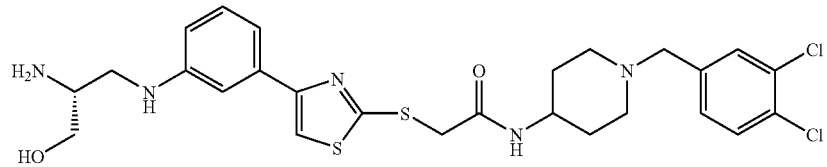

Synthesis of (R)-[4-(3-(2-amino-3-hydroxypropylamino)phenyl)-thiazol-2-ylthio]-N-[1-(3,4-dichlorobenzyl)piperidin-4-yl]acetamide dihydrochloride The product (639 mg) of Example 158 was dissolved in methanol (3 mL), and conc. hydrochloric acid (1 mL) was added to the solution. The mixture was stirred at room temperature for 3 days. Saturated aqueous sodium hydrogen carbonate was added to the reaction mixture and extracted with chloroform.

The extract was washed with saturated brine, and dried, and the solvent was evaporated. The residue purified by silica gel column chromatography, and the obtained residue was dissolved in ethanol (1 mL). A 4 mol/L Hydrogen chloride-ethyl acetate solution (1.5 mL) was added, and the resulting precipitates were collected by filtration to give the title compound (322 mg) as a white powder.

$^1$H-NMR(DMSO-d$_6$) δ 1.73–2.12 (4H, m), 2.89–3.09 (2H, m), 3.11–3.45 (5H, m), 3.58–3.89 (3H, m), 4.01 (2H, s), 4.26 (2H, d, J=4.8 Hz), 6.61–6.71 (1H, m), 7.10–7.39 (3H, m), 7.55–7.68 (1H, m), 7.70–7.77 (1H, m), 7.93–8.01 (2H, m), 8.09–8.31 (3H, brs), 8.62 (1H, d, J=7.2 Hz), 11.08–11.37 (1H, brs)

EXAMPLE 166

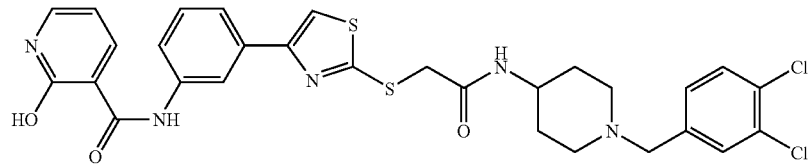

Synthesis of N-[1-(3,4-dichlorobenzyl)piperidin-4-yl]-{4-[3-(2-hydroxypyridin-3-ylcarboxyamide)phenyl]thiazol-2-ylthio}acetamide The residue obtained from the product (500 mg) of Example 35 and 2-hydroxynicotinic acid (275 mg) by a method similar to Example 130 was purified by HPLC (Develosil C30-UG-5, 0.05% aqueous TFA:acetonitrile 2:8–0:10) to give the title compound (90 mg) as a white powder.

$^1$H-NMR(DMSO-d$_6$) δ 1.30–1.43 (2H, m), 1.62–1.72 (2H, m), 1.91–2.02 (2H, m), 2.56–2.64 (2H, m), 3.32–3.60 (3H, m), 3.95 (2H, s), 6.50–6.56 (1H, m), 7.18–7.22 (1H, m), 7.31 (1H, t, J=7.8 Hz), 7.44 (1H, s), 7.48–7.52 (1H, m), 7.62 (1H, d, J=7.8 Hz), 7.69 (1H, d, J=7.8 Hz), 7.69–7.79 (1H, m), 7.99 (1H, s), 8.10 (1H, s), 8.15–8.19 (1H, m), 8.40–8.44 (1H, m), 12.25 (1H, s)

EXAMPLE 167

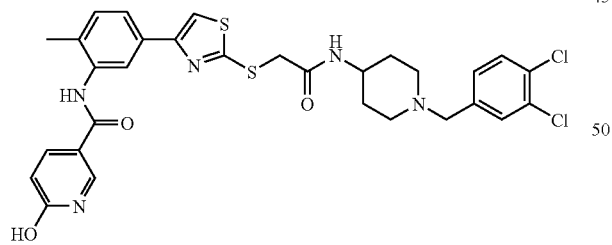

Synthesis of N-[1-(3,4-dichlorobenzyl)piperidin-4-yl]-{4-[3-(2-hydroxypyridin-5-ylcarboxyamide)-4-methylphenyl]thiazol-2-ylthio}acetamide The title compound (160 mg) was obtained as a white powder from the product (300 mg) of Example 135 and 6-hydroxynicotinic acid (275 mg) by a method similar to Example 130.

$^1$H-NMR(DMSO-d$_6$) δ 1.31–1.50 (2H, m), 1.67–1.74 (2H, m), 1.95–2.06 (2H, m), 2.22 (3H, s), 2.62–2.70 (2H, m), 3.41 (2H, s), 3.48–3.63 (1H, m), 3.98 (2H, s), 6.38–6.43 (1H, m), 7.24–7.34 (2H, m), 7.51 (1H, s), 7.54–7.59 (1H, m), 7.72–7.76 (1H, m), 7.82 (1H, s), 7.95–7.99 (1H, m), 8.16–8.23 (2H, m), 9.74 (1H, s), 12.08 (1H, brs)

EXAMPLE 168

Synthesis of N-[1-(3,4-dichlorobenzyl)piperidin-4-yl]-(4-[3-(2-hydroxypyridin-3-ylcarboxyamide)-4-methylphenyl]thiazol-2-ylthio}acetamide The residue obtained from the product (300 mg) of Example 135 and 2-hydroxynicotinic acid (275 mg) by a method similar to Example 130 was purified by HPLC (Develosil C30-UG-5, 0.05% aqueous TFA:acetonitrile 2:8–0:10) to give the title compound (30 mg) as a white powder.

$^1$H-NMR(DMSO-d$_6$) δ 1.37–1.48 (2H, m), 1.67–1.74 (2H, m), 1.97–2.07 (2H, m), 2.35 (3H, s), 2.61–2.68 (2H, m), 3.41 (2H, s), 3.46–3.64 (1H, m), 3.98 (2H, s), 6.55–6.61 (1H, m), 7.23–7.32 (2H, m), 7.50 (1H, s), 7.54–7.61 (2H, m), 7.82–7.86 (1H, m), 7.89 (1H, s), 8.18–8.22 (1H, m), 8.45–8.50 (1H, m), 8.83 (1H, s), 12.26 (1H, s)

EXAMPLE 169

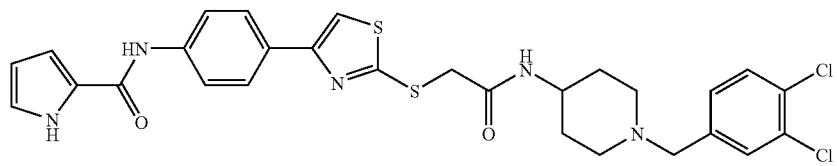

Synthesis of N-[1-(3,4-dichlorobenzyl)piperidin-4-yl]-{4-[4-(pyrrol-2-ylcarboxamide)phenyl]thiazol-2-ylthio}acetamide Pyrrole-2-carboxylic acid (130 mg) was dissolved in dioxane (2 mL), and 4M-HCl/dioxane (290 μL) was added to the solution. Then thionyl chloride (420 μL) and a catalytic amount of dimethylformamide were added, and the mixture was stirred at room temperature. for 1 hr. The solvent was evaporated under reduced pressure, and the residue was dissolved in pyridine (5 mL). The product (500 mg) of Example was added to the solution, and the mixture was stirred at room temperature for 23 hrs. The solvent was evaporated under reduced pressure and extracted with chloroform. The chloroform layer was washed with a saturated brine and a saturated aqueous sodium hydrogen carbonate solution, and dried over sodium sulfate. The solvent was evaporated under reduced pressure, and the residue was crystallized from chloroform/diisopropyl ether to give the title compound (0.5 g) as a white powder.

$^1$H-NMR(DMSO-$d_6$) δ 1.36–1.49 (2H, m), 1.68–1.75 (2H, m), 1.98–2.09 (2H, m), 2.63–2.71 (2H, m), 3.42 (2H, s), 3.51–3.67 (1H, m), 4.00 (2H, s), 6.16–6.20 (1H, m), 6.97–6.99 (1H, m), 7.00–7.10 (1H, m), 7.24–7.30 (1H, m), 7.49–7.58 (2H, m), 7.82 (2H, d, J=9.0 Hz), 7.88–7.94 (3H, m), 8.24 (1H, d, J=7.5 Hz), 9.85 (1H, s), 11.68 (1H, brs)

EXAMPLE 170

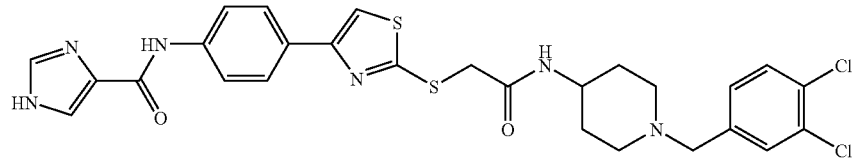

Synthesis of N-[1-(3,4-dichlorobenzyl)piperidin-4-yl]-{4-[4-(4-imidazolecarboxamide)phenyl]thiazol-2-ylthio}acetamide The title compound (1.5 g) was obtained as a white powder from the product (1.5 g) of Example 6 and imidazole-4-carboxylic acid (0.4 g) by a method similar to Example 169.

$^1$H-NMR(DMSO-$d_6$) δ 1.36–1.48 (2H, m), 1.68–1.75 (2H, m), 1.98–2.09 (2H, m), 2.63–2.71 (2H, m), 3.42 (2H, s), 3.50–3.62 (1H, m), 4.00 (2H, s), 7.28 (1H, d, J=8.4 Hz), 7.51 (1H, s), 7.56 (1H, d, J=8.4 Hz), 7.80–8.02 (7H, m), 8.24 (1H, d, J=7.2 Hz), 9.93 (1H, s), 12.67 (1H, brs)

EXAMPLE 171

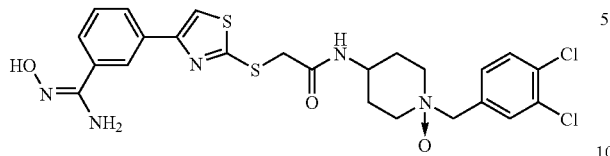

Synthesis of N-[1-(3,4-dichlorobenzyl)-1-oxopiperidin-4-yl]-{4-[3-(N²-hydroxyamidino)phenyl]thiazol-2-ylthio}acetamide The product (130 mg) of Example 97 was dissolved in dichloromethane (10 mL), and m-chloroperbenzoic acid (56 mg) was added to the solution. The mixture was stirred at room temperature for 4 hrs, and water was added to the reaction mixture. The mixture was extracted with chloroform, then washed with saturated brine and a saturated aqueous sodium hydrogen carbonate solution, and dried. The solvent was evaporated under reduced pressure, and the obtained residue was crystallized from chloroform to give the title compound (90 mg) as a white powder.

$^1$H-NMR(DMSO-d$_6$) δ 1.62–1.68 (2H, m), 2.51–2.65 (2H, m), 2.90–2.95 (2H, m), 3.30–3.39 (2H, m), 3.60–3.71 (1H, m), 3.98 (2H, s), 4.33 (2H, s), 5.65 (2H, s), 7.37–7.44 (1H, m), 7.51–7.59 (2H, m), 7.65–7.69 (1H, m), 7.78–7.88 (2H, m), 7.98 (1H, s), 8.27 (1H, s), 8.39–8.43 (1H, m), 12.09 (1H, s)

EXAMPLE 172

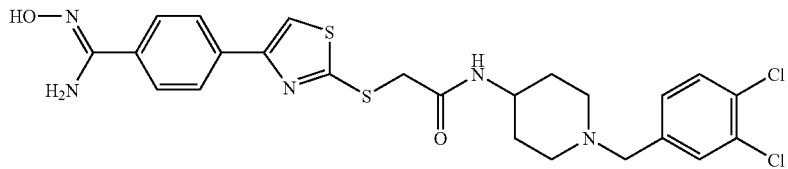

Synthesis of N-[1-(3,4-dichlorobenzyl)piperidin-4-yl]-{4-[4-(N²-hydroxyamidino)phenyl]thiazol-2-ylthio}acetamide The title compound (0.3 g) was obtained as a white solid from the product (2 g) of Starting Material Synthetic Example 32 by a method similar to Example 97.

$^1$H-NMR(DMSO-d$_6$) δ 1.36–1.50 (2H, m), 1.68–1.78 (2H, m), 2.00–2.11 (2H, m), 2.63–2.71 (2H, m), 3.42 (2H, s), 3.50–3.61 (1H, m), 4.01 (2H, s), 5.84 (2H, s), 7.27 (1H, dd, J=1.9, 8.2 Hz), 7.51 (1H, d, J=1.9 Hz), 7.57 (1H, d, J=8.2 Hz), 7.74 (2H, d, J=8.5 Hz), 7.94 (2H, d, J=8.5 Hz), 8.05 (1H, s), 8.21 (1H, d, J=7.4 Hz), 9.67 (1H, s)

EXAMPLE 173

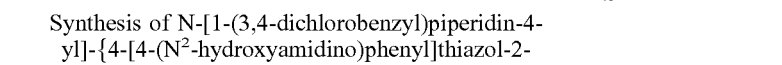

Synthesis of N-[1-(3,4-dichlorobenzyl)piperidin-4-yl]-{4-[3-(dimethylaminomethyleneamino)phenyl]thiazol-2-ylthio}acetamide The product (0.5 g) of Example 35 was dissolved in toluene (20 mL), and N,N-dimethylformamide dimethylacetal (160 μL) was added to the solution. The mixture was stirred for 5 hrs. The solvent was evaporated under reduced pressure, and the obtained residue was extracted with ethyl acetate, then washed with saturated brine, and dried. The solvent was evaporated under reduced pressure, and the obtained residue was crystallized from ethyl acetate/hexane to give the title compound (150 mg) as a white powder.

$^1$H-NMR(DMSO-d$_6$) δ 1.35–1.50 (2H, m), 1.67–1.75 (2H, m), 1.96–2.08 (2H, m), 2.63–2.72 (2H, m), 2.91 (3H, brs), 3.00 (3H, brs), 3.42 (2H, s), 3.49–3.61 (1H, m), 4.00 (2H, s), 6.85–6.90 (1H, m), 7.21–7.29 (2H, m), 7.45–7.61 (4H, m), 7.77 (1H, s), 7.97 (1H, s), 8.24 (1H, d, J=7.2 Hz)

EXAMPLE 174

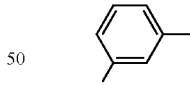

Synthesis of N-[1-(3,4-dichlorobenzyl)piperidin-4-yl]-{4-[3-(hydroxyiminomethylamino)phenyl]thiazol-2-ylthio}acetamide The product (100 mg) of Example 173 was dissolved in methanol (10 mL), and hydroxyamine hydrochloride (15 mg) was added to the solution. The mixture was stirred for 30 hrs. The solvent was evaporated under reduced pressure, and the obtained residue was extracted with chloroform, then washed with saturated brine, and dried. The solvent was evaporated under reduced pressure, and the obtained residue was purified by silica gel column chromatography (chloroform:methanol=100:1–20:1) to give the title compound (90 mg) as a white amorphous solid.

$^1$H-NMR(DMSO-d$_6$) δ 1.36–1.50 (2H, m), 1.63–1.77 (2H, m), 1.96–2.10 (2H, m), 2.60–2.71 (2H, m), 3.41 (2H, s), 3.49–3.63 (1H, m), 4.01 (2H, s), 7.09–7.33 (3H, m), 7.40–7.62 (4H, m), 7.72 (1H, s), 7.96 (1H, s), 8.16–8.22 (1H, m), 8.53–8.65 (1H, m), 9. 89 (1H, s)

EXAMPLE 175

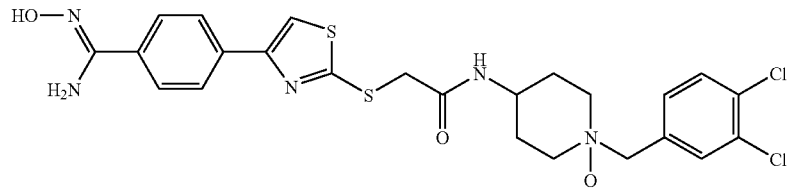

Synthesis of N-[1-(3,4-dichlorobenzyl)-1-oxopiperidin-4-yl]-{4-[4-(N$^2$-hydroxyamidino)phenyl]thiazol-2-ylthio}acetamide The title compound (0.19 g) was obtained as a white powder from the product (0.16 g) of Starting Material Synthetic Example 34 by a method similar to Example 97.

$^1$H-NMR(DMSO-d$_6$) δ 1.55–1.63 (2H, m), 2.05–2.24 (2H, m), 2.73–2.86 (2H, m), 3.25–3.40 (2H, m), 3.59–3.75 (1H, m), 4.02 (2H, s), 4.28 (2H, s), 5.86 (2H, brs), 7.53 (1H, dd, J=1.3, 8.2), 7.63 (1H, d, J=8.2), 7.73 (2H, d, J=8.3), 7.88 (1H, d, J=1.3), 7.93 (2H, d, J=8.3), 7.93 (2H, d, J=8.3), 8.06 (1H, s), 8.51 (1H, d, J=7.4), 9.87 (1H, s)

EXAMPLE 176

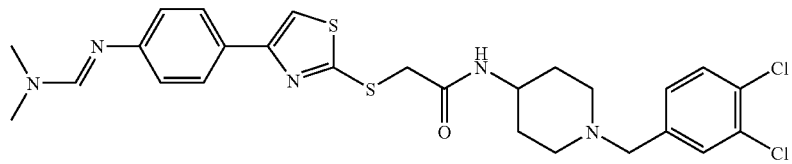

Synthesis of N-[1-(3,4-dichlorobenzyl)piperidin-4-yl]-{4-[4-(dimethylaminomethyleneamino)phenyl]thiazol-2-ylthio}acetamide The title compound (0.4 g) was obtained as a white powder from the product (0.5 g) of Example 6 by a method similar to Example 173.

$^1$H-NMR(DMSO-d$_6$) δ 1.32–1.50 (2H, m), 1.65–1.89 (2H, m), 1.94–2.09 (2H, m), 2.62–2.73 (2H, m), 2.92 (3H, s), 3.01 (3H, s), 3.42 (2H, s), 3.48–3.83 (1H, m), 3.99 (2H, s), 6.90–7.00 (2H, m), 7.23–7.32 (1H, m), 7.50–7.60 (2H, m), 7.70–7.90 (4H, m), 8.20–8.28 (1H, m)-

EXAMPLE 177

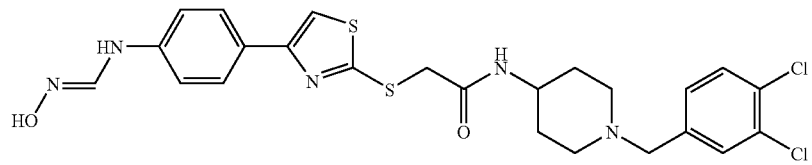

Synthesis of N-[1-(3,4-dichlorobenzyl)piperidin-4-yl]-{4-[4-(hydroxyiminomethylamino)phenyl]thiazol-2-ylthio}acetamide hydrochloride N-[1-(3,4-Dichlorobenzyl)piperidin-4-yl]-{4-[4-(hydroxyiminomethylamino)phenyl]thiazol-2-ylthio} acetamide (0.15 g) was obtained as a pale yellow oil from the product (0.2 g) of Example 176 by a method similar to Example 174. Then the compound was dissolved in methanol (2 mL), and a 4 mol/L hydrochloric acid/ethyl acetate solution (68 μL) was added to the solution. The mixture was stirred for 40 min. The solvent was evaporated under reduced pressure to give the title compound (0.13 g) as a white powder.

$^1$H-NMR(DMSO-$d_6$) δ 1.64–2.02 (4H, m), 2.92–3.14 (2H, m), 3.20–3.35 (2H, m), 3.68–3.83 (1H, m), 4.00 (2H, s), 4.25 (2H, s), 7.17–7.27 (2H, m), 7.49–7.61 (2H, m), 7.70–7.82 (4H, m), 7.86–7.91 (1H, m), 8.44–8.53 (1H, m), 8.63–8.77 (1H, m), 9.93 (1H, s)

EXAMPLE 178

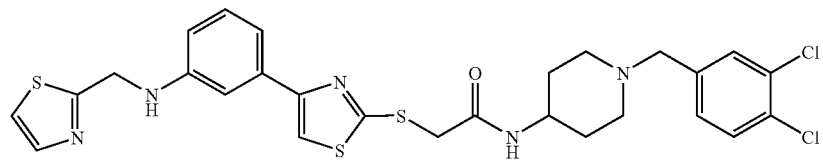

Synthesis of N-[1-(3,4-dichlorobenzyl)piperidin-4-yl]-{4-[3-(thiazol-2-ylmethylamino)phenyl]thiazol-2-ylthio}acetamide hydrochloride The title compound (224 mg) was obtained as a slightly yellow powder from the product (254 mg) of Example 35 and 2-thiazolecarbaldehyde (51 μL) by a method similar to Example 146.

$^1$H-NMR(DMSO-$d_6$) δ 1.71–2.12 (4H, m), 2.87–3.08 (2H, m), 3.10–3.37 (2H, m), 3.66–3.88 (1H, m), 4.00 (2H, s), 4.25 (2H, s), 4.69 (2H, s), 6.60 (1H, d, J=6.9 Hz), 7.12–7.35 (3H, m), 7.57–7.86 (5H, m), 7.89–8.01 (1H, m), 8.62 (1H, d, J=7.2 Hz), 11.30 (1H, brs)-

EXAMPLE 179

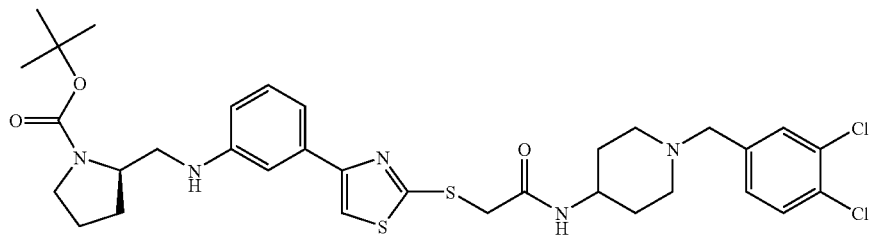

Synthesis of (R)-{4-[3-(N-tert-butoxycarbonylpyrrolidin-2-ylmethylamino)phenyl]thiazol-2-ylthio}-N-[1-(3,4-dichlorobenzyl)piperidin-4-yl]acetamide The title compound (302 mg) was obtained as a white amorphous solid from the product (254 mg) of Example 35 and (R)-tert-butoxycarbonylproline aldehyde (94 μL) by a method similar to Example 154.

ESI-MS(m/z) :690

EXAMPLE 180

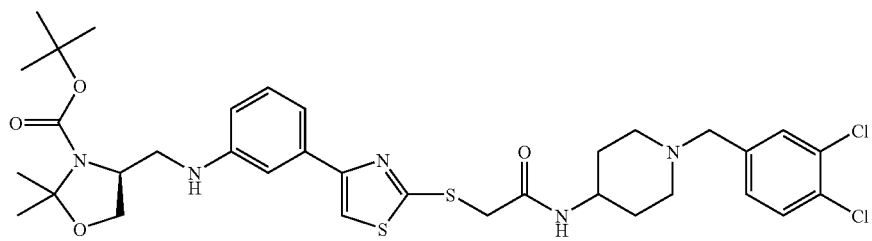

Synthesis of (S)-{4-[3-(3-tert-butoxycarbonyl-2,2-dimethyloxazolidin-4-ylmethylamino)phenyl]thiazol-2-ylthio}-N-[1-(3,4-dichlorobenzyl)piperidin-4-yl]acetamide The title compound (278 mg) was obtained as a white amorphous solid from the product (254 mg) of Example 35 and (S)-N-tert-butoxycarbonyl-2,2-dimethyloxazolidine-4-aldehyde (108 μL) by a method similar to Example 154.

$^1$H-NMR(DMSO-$d_6$) δ 1.41 (6H, s), 1.46 (9H, s), 1.50–1.53 (2H, m), 1.63–1.78 (2H, m), 1.93–2.09 (2H, m), 2.58–2.71 (2H, m), 2.88–3.04 (1H, m), 3.41 (2H, s), 3.46–3.62 (1H, m), 3.78–4.07 (6H, m), 6.04–6.13 (1H, m), 6.59–6.69 (1H, m), 7.02–7.16 (2H, m), 7.20–7.32 (2H, m), 7.50–7.58 (2H, m), 7.81–7.90 (1H, m), 8.09–8.21 (1H, m)

EXAMPLE 181

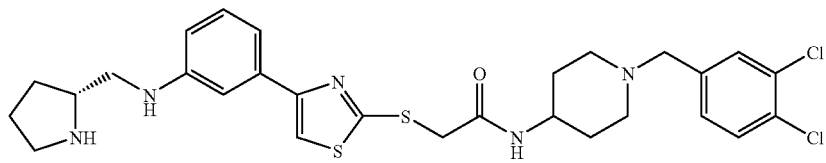

Synthesis of (R)-[4-(3-(pyrrolidin-2-ylmethylamino)phenyl)-thiazol-2-ylthio]-N-[1-(3,4-dichlorobenzyl)piperidin-4-yl]acetamide dihydrochloride The product (300 mg) of Example 179 was dissolved in a mixed solvent of trifluoroacetic acid (0.5 mL) and methylene chloride (0.5 mL), and the mixture was stirred at room temperature for 15 hrs. The reaction mixture was diluted with chloroform, and saturated aqueous sodium hydrogen carbonate as added. The aqueous layer was extracted with chloroform. The combined extract was washed with saturated brine and dried, and the solvent was evaporated. The obtained residue was dissolved in ethanol (1 mL), and a 4 mol/L hydrogen chloride-ethyl acetate solution (0.5 mL) was added. The resulting precipitate was collected by filtration to give the title compound (224 mg) as a white powder.

$^1$H-NMR(DMSO-$d_6$) δ 1.64–2.18 (8H, m), 2.91–3.58 (8H, m), 3.64–3.90 (2H, m), 4.02 (2H, s), 4.27 (2H, d, J=4.8 Hz), 6.67–6.75 (1H, m), 7.12–7.38 (3H, m), 7.53–7.68 (1H, m), 7.69–7.77 (1H, m), 7.92–8.00 (2H, m), 8.61 (1H, d, J=7.5 Hz), 9.13–9.31 (1H, brs), 9.54–9.71 (1H, brs), 11.17–11.39 (1H, brs)

EXAMPLE 182

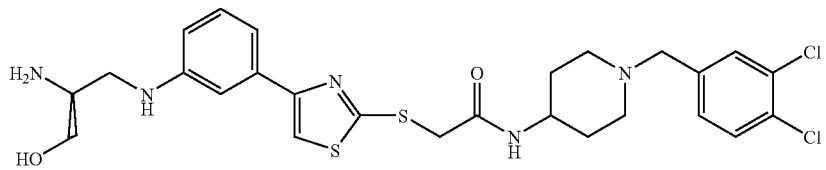

Synthesis of (S)-[4-(3-(2-amino-3-hydroxypropylamino)phenyl)thiazol-2-ylthio]-N-[1-(3,4-dichlorobenzyl)piperidin-4-yl]acetamide dihydrochloride The product (275 mg) of Example 180 was dissolved in a mixed solvent of trifluoroacetic acid (0.5 mL) and water (0.5 mL), and the mixture was stirred at room temperature for 2 days. The reaction mixture was diluted with chloroform, and saturated aqueous sodium hydrogen carbonate was added. The aqueous layer was extracted with chloroform. The combined extract was washed with saturated brine and dried, and the solvent was evaporated. The obtained residue was dissolved in ethanol (0.5 mL), and a 4 mol/L hydrogen chloride-ethyl acetate solution (0.3 mL) was added. The resulting precipitate was collected by filtration to give the title compound (42 mg) as a white powder.

$^1$H-NMR(DMSO-$d_6$) δ 1.73–2.12 (4H, m), 2.89–3.09 (2H, m), 3.11–3.45 (5H, m), 3.58–3.89 (3H, m), 4.01 (2H, s), 4.26 (2H, d, J=4.8 Hz), 6.61–6.71 (1H, m), 7.10–7.39 (3H, m), 7.55–7.68 (1H, m), 7.70–7.77 (1H, m), 7.93–8.01 (2H, m), 8.09–8.31 (3H, brs), 8.62 (1H, d, J=7.2 Hz), 11.08–11.37 (1H, brs)

EXAMPLE 183

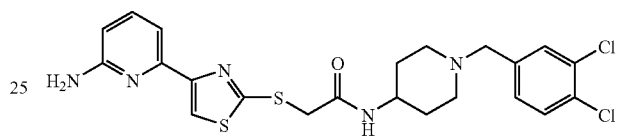

Synthesis of [4-(6-aminopyridin-2-yl)thiazol-2-ylthio]-N-[1-(3,4-dichlorobenzyl)piperidin-4-yl]acetamide dihydrochloride The product (230 mg) of Starting Material Synthetic Example 35 was dissolved in dioxane (4 mL), and triethylamine (38 μL) and diphenylphosphoryl azide (92 μL) were added to the solution. The mixture was stirred at 100° C. for 1 hr. Water (1 mL) was added to the reaction mixture, and the mixture was stirred at 100° C. for 3 hrs. Saturated aqueous sodium hydrogen carbonate was added to the reaction mixture, and the mixture was extracted with ethyl acetate. The extract was washed with saturated brine. After drying, the solvent was evaporated. The residue was purified by silica gel column chromatography, and the obtained residue was dissolved in chloroform (2 mL). A 4 mol/L Hydrogen chloride—ethyl acetate solution (0.2 mL) was added, and the obtained solution was concentrated to dryness to give the title compound (128 mg) as a slightly yellow powder.

$^1$H-NMR(DMSO-$d_6$) δ 1.72–2.05 (4H, m), 2.87–3.08 (2H, m), 3.20–3.36 (2H, m), 3.68–3.81 (1H, m), 3.97 (2H, s), 4.24 (2H, s), 6.90–7.00 (1H, m), 7.45 (1H, d, J=7.4 Hz), 7.59–7.60 (1H, m), 7.73 (1H, d, J=8.2 Hz), 7.83–8.00 (2H, m), 8.39–8.58 (3H, brs), 8.67 (1H, s), 8.80 (1H, d, J=7.2 Hz), 10.90 (1H, brs)

EXAMPLE 184

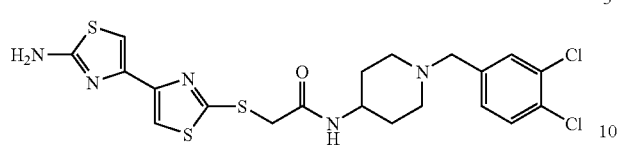

Synthesis of [4-(2-aminothiazol-4-yl)thiazol-2-ylthio]-N-[1-(3,4-dichlorobenzyl)piperidin-4-yl]acetamide The product (2.18 g) of Starting Material Synthetic Example 36 and thiourea (339 mg) were suspended in ethanol (20 mL). The suspension was heated under reflux for 40 min. The reaction mixture was concentrated under reduced pressure, and saturated aqueous sodium hydrogen carbonate was added to the residue. The mixture was extracted with a mixed solvent of chloroform-methanol. The extract was washed with saturated brine and dried. The solvent was evaporated, and the residue was purified by silica gel column chromatography to give the title compound (302 mg) as a slightly yellow powder.

$^1$H-NMR(DMSO-d$_6$) δ 1.32–1.48 (2H, m), 1.63–1.79 (2H, m), 1.92–2.08 (2H, m), 2.60–2.73 (2H, m), 3.43 (2H, s), 3.45–3.61 (1H, m), 3.95 (2H, s), 6.94 (1H, s), 7.09 (2H, brs), 7.22–7.30 (1H, m), 7.44–7.59 (3H, m), 8.17 (1H, d, J=7.2 Hz)

EXAMPLE 185

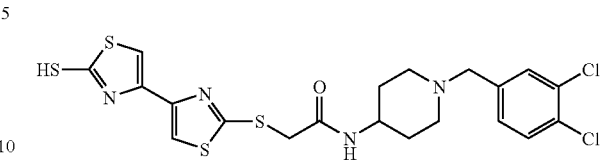

Synthesis of N-[1-(3,4-dichlorobenzyl)piperidin-4-yl]-[4-(2-mercaptothiazol-4-yl)thiazol-2-ylthio]acetamide The product (240 mg) of Starting Material Synthetic Example 36 and ammonium thiocarbamate (98 mg) were suspended in ethanol (10 mL), and the suspension was stirred at room temperature for 30 min and heated under reflux for 2 hrs. The reaction mixture was concentrated under reduced pressure, and water was added to the residue. The mixture was extracted with a mixed solvent of chloroform-methanol. The extract was washed with saturated brine and dried. The solvent was evaporated to give the title compound (177 mg) as a brown powder.

$^1$H-NMR(DMSO-d$_6$) δ 1.43–1.69 (2H, m), 1.71–1.93 (2H, m), 2.84–3.06 (2H, m), 3.17–3.44 (2H, m), 3.52–3.88 (3H, m), 4.01 (2H, s), 7.33 (1H, s), 7.35–7.43 (1H, m), 7.56–7.77 (2H, m), 8.08 (1H, s), 8.35 (1H, d, J=6.3 Hz)

EXAMPLE 186

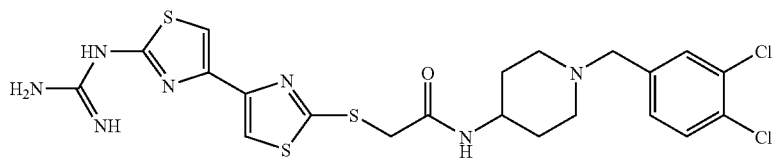

Synthesis of N-[1-(3,4-dichlorobenzyl)piperidin-4-yl]-[4-(2-guanidinothiazol-4-yl)thiazol-2-ylthio]acetamide The product (269 mg) of Starting Material Synthetic Example 36 and guanylthiourea (59 mg) were suspended in ethanol (2.5 mL), and the suspension was heated under reflux for 2.5 hrs. The reaction mixture was concentrated under reduced pressure, and the residue was washed with ethyl acetate to give the title compound (304 mg) as a slightly yellow powder.

$^1$H-NMR(DMSO-d$_6$) δ 1.44–1.69 (2H, m), 1.76–1.94 (2H, m), 2.50–2.90 (2H, m), 2.91–3.18 (2H, m), 3.58–3.77 (1H, m,), 4.01 (2H, s), 4.04 (2H, s), 7.25 (1H, s), 7.26–7.48 (5H, m), 7.58–7.78 (2H, m), 7.95 (1H, s), 8.38 (1H, d, J=6.3 Hz), 10.35 (1H, brs)

EXAMPLE 187

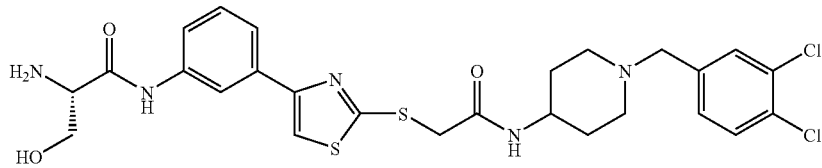

Synthesis of (S)-{4-[3-(2-amino-3-hydroxypropanoylamino)-phenyl]thiazol-2-ylthio}-N-[1-(3,4-dichlorobenzyl)piperidin-4-]acetamide.

The residue obtained from the product (1.78 g) of Example 35 and N-tert-butoxycarbonyl-(R)-2,2-dimethyloxazolidine-4-carboxylic acid (1.04 g) by a method similar to Example 54 was treated by a method similar to Example 182 to give the title compound (80 mg) as a-white amorphous solid.

$^1$H-NMR(DMSO-d$_6$) δ 1.38–1.49 (2H, m), 1.63–1.78 (2H, m), 1.93–2.10 (2H, m), 2.60–2.75 (2H, m), 3.42 (2H, s), 3.51–3.65 (7H, m), 4.01 (2H, s), 4.77–5.02 (1H, brs), 7.27 (1H, dd, J=1.9, 8.3 Hz), 7.34 (1H, t, J=7.9 Hz), 7.51–7.64 (3H, m), 7.72–7.79 (1H, m), 7.95 (1H, s), 8.19 (1H, s), 8.25 (1H, d, J=7.5 Hz)

EXAMPLE 188

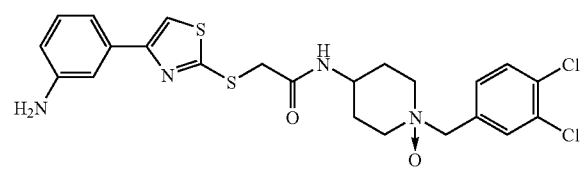

Synthesis of [4-(3-aminophenyl)thiazol-2-ylthio]-N-[1-(3,4-dichlorobenzyl)-1-oxopiperidin-4-yl]acetamide The title compound (0.23 g) was obtained as a white powder from the product (0.5 g) of Example 35 by a method similar to Example 171.

$^1$H-NMR(DMSO-d$_6$) δ 1.54–1.69 (2H, m), 2.07–2.22 (2H, m), 2.76–2.83 (2H, m), 3.23–3.40 (2H, m), 3.56–3.75 (1H, m), 3.94 (2H, s), 4.27 (2H, s), 5.18 (2H, brs), 6.50–6.58 (1H, m), 6.99–7.09 (2H, m), 7.14 (1H, s), 7.49–7.56 (1H, m), 7.59–7.67 (1H, m), 7.78 (1H, s), 7.87 (1H, s), 8.37–8.44 (1H, m)

EXAMPLE 189

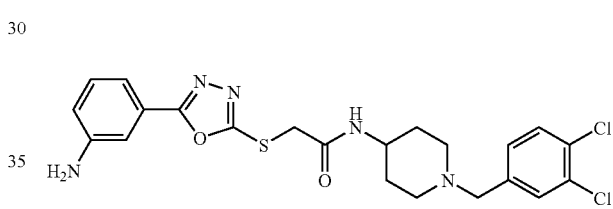

Synthesis of N-[1-(3,4-dichlorobenzyl)piperidin-4-yl]-[5-(3-minophenyl)-1,3,4-oxadiazol-2-ylthio]acetamide dihydrochloride A base form of the title compound (410 mg) was obtained as a pale-yellow oil from the product (203 mg) of Starting Material Synthetic Example 37 by a method similar to Starting Material Synthetic Example 25. Thereto was added hydrochloric acid-ethyl acetate, and the solvent was evaporated to give the title compound as a pale-yellow amorphous solid.

ESI-MS(m/z): 492(M+1)

$^1$H-NMR(DMSO-d$_6$) δ 1.90–2.00 (2H, m), 2.45–2.55 (2H, m), 2.90–3.00 (2H, m), 3.20–3.30 (2H, m), 3.70–3.80 (1H, m), 4.07 (2H, s), 4.25 (2H, s), 7.10–7.15 (1H, m), 7.40–7.50 (2H, m), 7.50–7.55 (1H, m), 7.55–7.63 (1H, m), 7.71–7.75 (1H, m), 7.97 (1H, s), 8.60–8.63 (1H, m), 11.1–11.2 (4H, m)

EXAMPLE 190

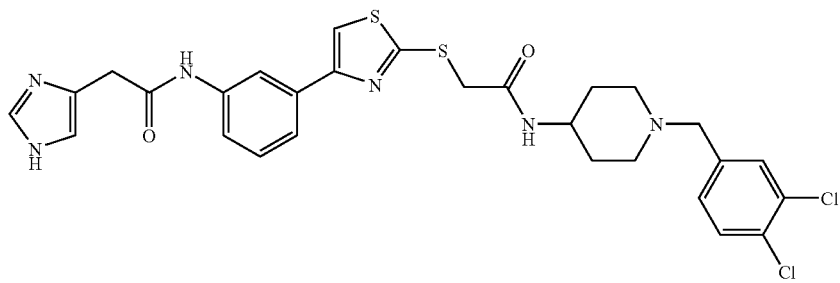

Synthesis of N-[1-(3,4-dichlorobenzyl)piperidin-4-yl]-{4-[3-(imidazol-4-ylacetamide)phenyl]thiazol-2-ylthio}acetamide The title compound was obtained from the product of Example 35 and 4-imidazoleacetic acid by a method similar to Example 54.

$^1$H-NMR(DMSO-$d_6$) δ 1.36–1.47 (2H, m), 1.70–1.73 (2H, m), 2.00–2.06 (2H, m), 2.66–2.69 (2H, m), 3.43 (2H, s), 3.55–3.59 (1H, m), 3.59 (2H, s), 3.99 (2H, s), 6.93 (1H, brs), 7.26–7.38 (2H, m), 7.52–7.64 (5H, m), 7.93 (1H, s), 8.13–8.23 (2H, m), 10.19 (1H, brs)

EXAMPLE 191

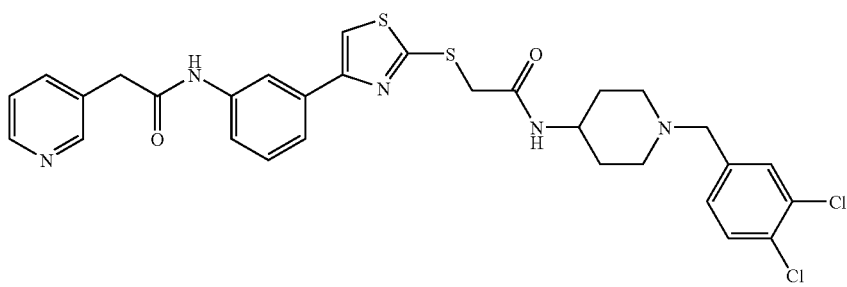

Synthesis of N-[1-(3,4-dichlorobenzyl)piperidin-4-yl]-{4-[3-(pyridin-3-ylacetamide)phenyl]thiazol-2-ylthio}acetamide The title compound was obtained from the product of Example 35 and 3-pyridineacetic acid by a method similar to Example 54.

$^1$H-NMR(DMSO-$d_6$) δ 1.40–1.46 (2H, m), 1.70–1.74 (2H, m), 1.99–2.06 (2H, m), 2.66–2.69 (2H, m), 3.42 (2H, s), 3.50–3.58. (H, m), 3.37 (2H, s), 3.99 (2H, s), 7.28–7.39 (3H, m), 7.51–7.63 (4H, m), 7.72–7.78 (1H, m), 7.94 (1H, s), 8.14–8.32 (2H, m), 8.46–8.55 (2H, m), 10.37 (1H, s)

EXAMPLE 192

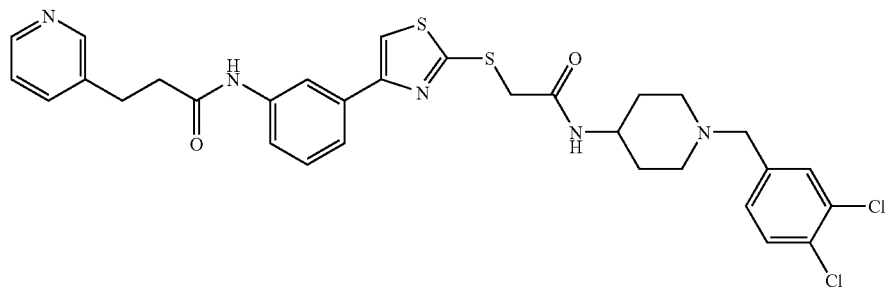

Synthesis of N-[1-(3,4-dichlorobenzyl)piperidin-4-
yl]-(4-{3-[3-(3-pyridyl)propionylamino]
phenyl}thiazol-2-ylthio)acetamide The title compound was obtained from the product of Example 35 and 3-(3-pyridine)butyric acid by a method similar to Example 54.

$^1$H-NMR(DMSO-$d_6$) δ 1.40–1.47 (2H, m), 1.71–1.74 (2H, m), 2.00–2.06 (2H, m), 2.66–2.71 (4H, m), 2.92–2.95 (2H, m), 3.41 (2H, s), 3.51–3.61 (1H, m), 4.00 (2H, s), 7.25–7.37 (4H, m), 7.51–7.67 (4H, m), 7.93 (1H, s), 8.10–8.23 (2H, m), 8.40–8.50 (2H, m), 10.04 (1H, m)

EXAMPLE 193

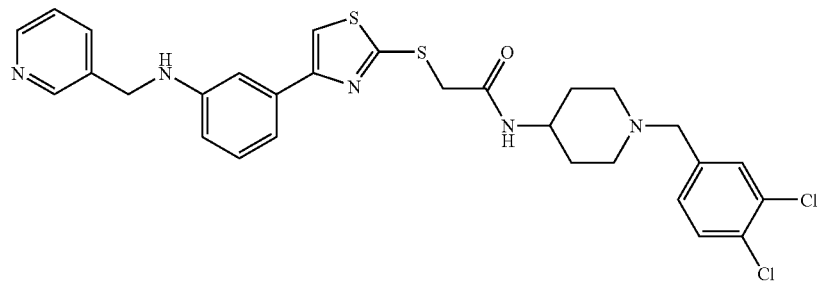

Synthesis of N-[1-(3,4-dichlorobenzyl)piperidin-4-
yl]-{4-[3-(pyridin-3-ylmethylamino)phenyl]thiazol-
2-ylthio]acetamide The title compound was obtained from the product of Example 35 and 3-pyridinecarbaldehyde by a method similar to Example 146.

$^1$H-NMR(DMSO-$d_6$) δ 1.39–1.47 (2H, m), 1.70–1.73 (2H, m), 1.99–2.06 (2H, m), 2.65–2.69 (2H, m), 3.40 (2H, s), 3.50–3.60 (1H, m), 3.98 (2H, s), 4.35 (2H, d, J=6.0 Hz), 6.37 (1H, t, J=6.0 Hz), 6.57–6.58 (1H, m), 7.0–7.36 (5H, m), 7.51–7.58 (2H, m), 7.76–7.79 (1H, m), 7.84 (1H, s), 8.22–8.63 (3H, m)

EXAMPLE 194

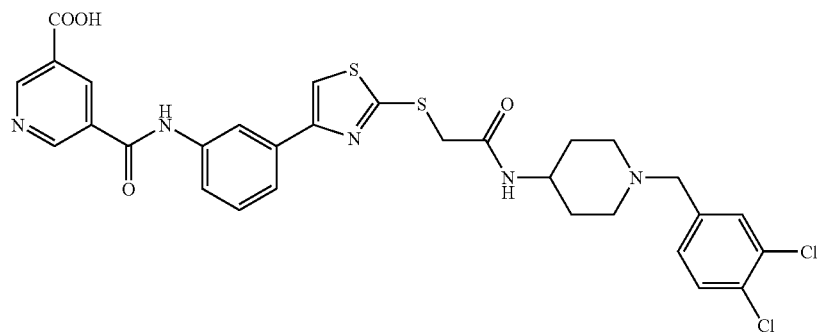

Synthesis of {4-[3-(5-carboxynicotinoyl)aminophenyl]thiazol-2-ylthio}-N-[1-(3,4-dichlorobenzyl)piperidin-4-yl]acetamide The title compound was obtained from the product of Example 35 and 3,5-pyridinedicarboxylic acid by a method similar to Example 54.

$^1$H-NMR(DMSO-d$_6$) δ 1.42–1.48 (2H, m), 1.71–1.75 (2H, m), 2.02–2.09 (2H, m), 2.67–2.71 (2H, m), 3.41 (2H, s), 3.50–3.60 (1H, m), 4.01 (2H, s), 7.25–7.85 (6H, m), 7.99 (1H, s), 8.22–8.30 (2H, m), 8.81 (1H, d, J=2.1 Hz), 9.21–9.28 (2H, m), 10.71 (1H, s)

The following compounds are synthesized by methods described in the above-mentioned Examples, or methods analogous to the above-mentioned methods.

[4-(2-aminopyridin-5-yl)thiazol-2-ylthio]-N-[1-(3,4-dichlorobenzyl)piperidin-4-yl]acetamide:

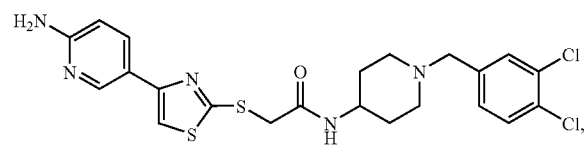

[4-(2-aminopyridin-4-yl)thiazol-2-ylthio]-N-[1-(3,4-dichlorobenzyl)piperidin-4-yl]acetamide:

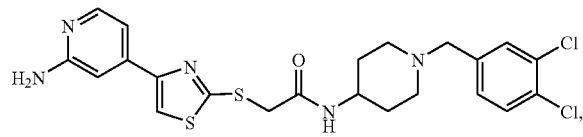

[4-(3-aminopyridin-5-yl)thiazol-2-ylthio]-N-[1-(3,4-dichlorobenzyl)piperidin-4-yl]acetamide:

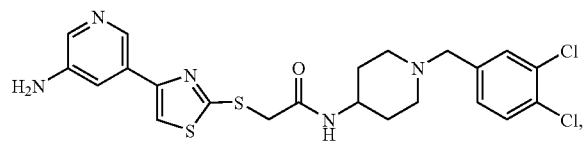

[3-(3-aminophenyl)1,2,4-thiadiazol-5-ylthio]-N-[1-(3,4-dichlorobenzyl)piperidin-4-yl]acetamide:

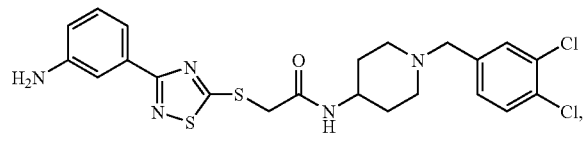

(R)-{4-[3-(2-amino-2-methyl-ethylamino)phenyl]thiazol-2-ylthio}-N-[1-(3,4-dichlorobenzyl)piperidin-4-yl]acetamide:

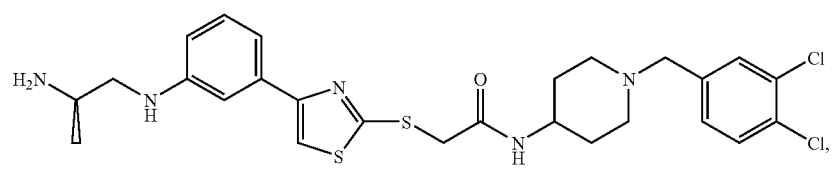

[2-(3-aminophenyl)1,3,4-oxadiazol-5-ylthiol-N-[1-(3,4-dichlorobenzyl)-1-oxopiperidin-4-yl]acetamide:

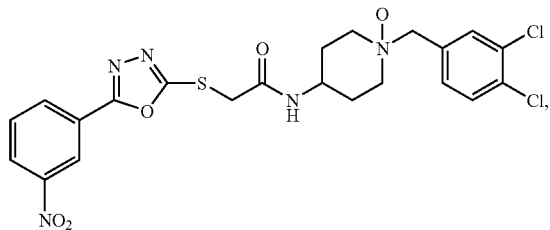

[2-(3-aminophenyl)1,3,4-thiadiazol-5-ylthio]-N-[1-(3,4-dichlorobenzyl)piperidin-4-yl]acetamide:

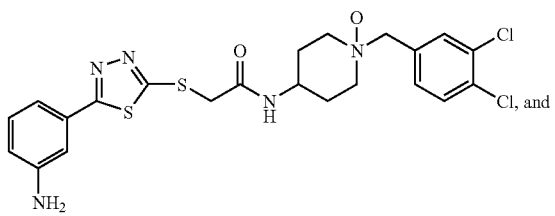

[2-(3-aminophenyl)1,3,4-thiadiazol-5-ylthio]-N-[1-(3,4-dichlorobenzyl)-1-oxopiperidin-4-yl]acetamide:

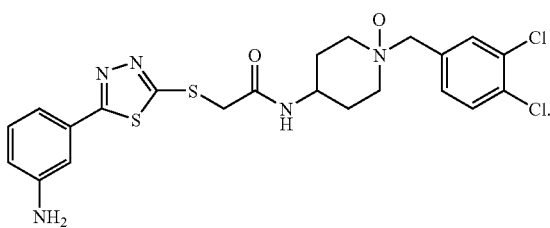

EXPERIMENTAL EXAMPLE 1

Assay for Binding Inhibitory Activity Between Chemokine and Human Eosinophil

Human eosinophil was separated from the anticoagulation treated peripheral blood of a healthy subject by CD16 negative selection method (e.g., J. Immunol. Methods, vol., 145, pp. 105–110, 1991). The separated eosinophil ($2 \times 10^5$), 50 pmol/L [$^{125}$I]-eotaxin (2000 Ci/mmoL, manufactured by AmershamPharmacia Biotech) and a test compound were mixed in 0.1 mL of a binding buffer (50 mmol/L HEPES, 1 mmol/L CaCl$_2$, 5 mmol/L MgCl$_2$, 0.5% bovine serum albumin (BSA), 0.1% sodium azide, pH 7.6), and the mixture was incubated at 25° C. for 1 hr in a multiscreen plate (manufactured by Millipore Corporation). After the completion of the incubation, the reaction mixture in the multiscreen plate was filtered in vacuo and washed with 0.6 mL of a cold washing buffer (50 mmol/L HEPES, 1 mmol/L CaCl$_2$, 5 mmol/L MgCl$_2$, 0.5 mol/L NaCl, 0.1% sodium azide, pH 7.6), and the radioactivity on the filter was measured. In this assay, the compound of the present invention showed a binding inhibitory activity for chemokine. The IC$_{50}$ values (concentration of a test compound necessary for decreasing the binding between [$^{125}$I]-eotaxin and human eosinophil by 50%) of some of the compounds of the present invention were as follows.

TABLE 1

| Compound | IC$_{50}$ (nmol/L) |
|---|---|
| Example 1 | 6 |
| 2 | 4 |
| 6 | 11 |
| 9 | 4 |
| 18 | 41 |

EXPERIMENTAL EXAMPLE 2

Effect on Intracellular Calcium Concentration

The effect of the compound of the present invention on intracellular calcium in eosinophil in the peripheral blood of a healthy subject on stimulation with CCL11 was elavuated by the following method.

Eosinophil separated from the peripheral blood of a healthy subject was suspended in a buffer for measurement (10 mmol/L HEPES, and 0.5% bovine serum albumin-containing hanks' balanced salt solution), and the suspension was incubated in the presence of 5 µmol/L of Fura-2 AM (manufactured by Dojindo Laboratories) at 37° C. for 45 min. After the completion of incubation, the cells were washed three times with the buffer for measurement to remove Fura-2 AM not-incorporated into the cells.

The cell suspension was adjusted to the final concentration of $1 \times 10^6$ cells/mL with the buffer for measurement and preserved in a dark place until measurement. The intracellular calcium was measured using FDSS6000 manufactured by Hamamatsu Photonics K.K. That is, a cell suspension (0.1 mL) loaded with Fura-2 AM was placed in a 96 well plate for measurement, and the plate was set on FDSS6000. The fluorescence intensities due to excitation lights at wavelengths 340 nm and 380 nm were measured. The ratio of the fluorescence intensities corresponding to the excitation lights at these two wavelengths was determined to calculate the intracellular calcium concentration. As an agonist, CCL11 (0.3 nmol/L) was used, which is a CCR3 selective ligand. The antagonism was determined in terms of 50 % inhibition value (IC$_{50}$) of the increase in the intracellular calcium concentration ?by the treatment of eosinophil with various concentrations of the compound of the present invention 5 min before stimulation with the agonist.

TABLE 2

| Compound | IC$_{50}$ (nmol/L) |
|---|---|
| Example 9 | 6 |

EXPERIMENTAL EXAMPLE 3

Effect on Antigen-Induced Eosinophil Infiltration Model

The effect of the compound of the present invention in vivo was evaluated using a mouse ovalbumin (OVA)-induced eosinophil infiltration model. The model was prepared according to the method of Das et al. (Clin. Exp. Immunol., vol. 117, pp. 223–229, 1999). Namely, female BALB/c mouse was actively sensitized by two times, every other week, of subcutaneous administration of OVA adsorbed on aluminum hydroxide gel (Alum) (100 μg OVA in 3.3 mg Alum/mouse), and 1 week after the final sensitization, OVA was intraperitoneally challenged (10 μg/mouse). The compound of the present invention was suspended in a medium, 20% hydroxypropyl-β-cyclodextrin solution, and orally administered using a sonde for oral administration. At the 24th hour from the OVA challenge, the abdominal cavity was washed with phosphate buffered saline containing 10 mmol/L EDTA (3 mL), and the peritoneal washing was recovered.

The total leukocytes in the recovered peritoneal washing were counted using an automatic cell counter F-800 (manufactured by Sysmex Corporation). For determination of the ratio of the leukocyte fraction in the peritoneal washing, a peritoneal washing cell smear sample was prepared using Cytospin-3 (manufactured by SHANDON), and after staining with Diff-Quick stain (manufactured by International Reagents Corp.), the ratio was calculated from the sample according to the standard morphological criteria under an optical microscope.

EXPERIMENTAL EXAMPLE 4

Effect on Antigen-Induced Allergic Biphasic Ear Edema Model

The effect of the compound of the present invention in vivo was evaluated using a mouse ovalbumin (OVA)-induced allergic biphasic ear edema model. The model was prepared according to the method of Sugawara et al. (Allergy & Clinical Immunology International, Supplement No 2, P785, 2000). Namely, male BALB/c mouse was actively sensitized by one time intraperitoneal administration of OVA (10 μg) adsorbed on aluminum hydroxide gel (Alum, 1 mg), and 14 days later, OVA (5 μg) was subcutaneously injected into both ears of the mouse to induce ear edema. The thickness of the ears was measured using a dial thickness gage immediately before subcutaneous injection and 1 and 24 hr after the subcutaneous injection of OVA. The compound of the present invention was suspended in a 0.5% hydroxypropylmethyl cellulose solution, which was a medium, and orally administered twice a day using a sonde for oral administration from 2 days before ear edema induction. As a result, no effect was observed 1 hr later (immediate response), and the compound showed effect 24 hr later (delayed response), as shown in FIG. 1.

EXPERIMENTAL EXAMPLE 5

Measurement of Blood Concentration

The compound of the present invention was administered orally and intravenously to female rat, and the plasma concentration of the compound was measured. That is, the test compound was weighed, dissolved or suspended in a medium, diluted to the objective concentration, and orally and intravenously administered. After the administration, the blood was drawn with time from the cervical vein with a heparin treated syringe. The blood was centrifuged, the plasma was separated, and the plasma was preserved at −20° C. until analysis. The concentration of the compound in plasma was measured using LC/MS. The results are shown in the following [Table 3].

TABLE 3

| Compound | $C_{max}$ (ng/mL) |
|---|---|
| Compound of Example 35 | 3122.7 |

INDUSTRIAL APPLICABILITY

The compound of the present invention has chemokine receptor antagonism and is useful as a therapeutic drug and/or a prophylactic drug for atherosclerosis, rheumatoid arthritis, osteoarthritis, psoriasis, asthma, allergic rhinitis, allergic conjunctivitis, allergic myelitis, atopic dermatitis, food allergy, ulcerative colitis, multiple sclerosis, chronic obstructive respiratory disease, myocarditis, rejection in organ transplantation, human immunodeficiency syndrome and the like, in which cells having a chemokine receptor play a key role in the onset, progression and maintenance of the disease state.

This application is based on patent application Nos. 2001-132853 and 2001-277139 filed in Japan, the contents of which are all hereby incorporated by reference.

The invention claimed is:
1. An optionally N-oxidized benzylpiperidine compound represented by the formula (1):

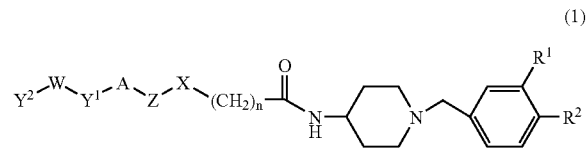

wherein
R$^1$ and R$^2$ are the same or different and each is hydrogen, halogen, cyano, nitro, amino, hydroxy, alkoxy or alkyl,
n is an integer of 1 to 5,
X is a bond, an oxygen atom, a sulfur atom, SO or SO$_2$,
Z is a bond,
Y$^1$ is a bond,
A is a 5-membered heteroaryl,
W is aryl, heteroaryl or thiazoline,
Y$^2$ is amino, alkylamino, arylamino, arylalkylamino, heteroarylalkylamino, acylamino, acylaminoalkyl, alkoxycarbonylamino, carboxymethylamino, aminoalkylamino, —NR$^4$CONR$^5$R$^6$, wherein R$^4$, R$^5$ and R$^6$ may be the same or different and each is hydrogen or alkyl, sulfonylamino, —CONR$^7$R$^8$, wherein R$^7$ and R$^8$ may be the same or different and each is hydrogen, alkyl, aryl, arylalkyl or heteroarylalkyl, provided that they are not both hydrogen at the same time, aminoalkyl, alkylaminoalkyl, arylaminoalkyl, heteroarylaminoalkyl, arylalkylaminoalkyl, heteroarylalkylaminoalkyl, cyclic amino, hydrazino, guanidino, amidino, hydroxyamidino, alkoxyamidino, aminomethyleneamino, iminomethylamino, imino or —SR$^{16}$, wherein R$^{16}$ is alkyl,
provided that the above-mentioned aryl, heteroaryl, alkylamino, arylamino, arylalkylamino, heteroarylalkylamino, acylamino, acylaminoalkyl, alkoxycarbonylamino, carboxymethylamino, aminoalkylamino, sulfonylamino, —CONR$^7$R$^8$, aminoalkyl, alkylaminoalkyl, arylaminoalkyl, heteroarylaminoalkyl, arylalkylaminoalkyl, heteroarylalkylaminoalkyl, cyclic amino, hydrazino, guanidino, amidino, aminomethyleneamino, iminomethylamino and imino optionally have substituents selected from halogen, haloalkyl, alkyl, alkoxy, aryl, hydroxy, mercapto, carboxy, nitro, amino and alkylamino, provided that when acylamino is aminoalkylcarbonylamino, 1 or 2 substituents are selected from hydroxy, alkyl, hydroxyalkyl, aryl, arylalkyl, heteroarylalkyl, side chain of amino acid and side chain of unnatural amino acid, when sulfonylamino is aminoalkylsulfonylamino, 1 or 2 substituents are selected from alkyl, aryl, side chain of amino acid and side chain of unnatural amino acid, in the case of aminoalkylamino, the substituents on the alkyl moiety are selected from alkyl, hydroxyalkyl and alkoxyalkyl, in the case of cyclic amino, the substituents are selected from amino, acylamino, hydroxy, alkoxy, alkyl, acyl, aryl and arylalkyl, in the case of hydrazino, guanidino, amidino, aminomethyleneamino or imino, the substituents are selected from alkyl and phenyl on the substitutable nitrogen atom, and nitrogen atom in amide, carbamate or sulfonamide contained in the above-mentioned acylamino, acylaminoalkyl, alkoxycarbonylamino and sulfonylamino may be substituted by alkyl, an optical isomer thereof or a pharmaceutically acceptable salt thereof.

2. The benzylpiperidine compound of claim 1, wherein, in the formula (1), $Y^2$ is amino, alkylamino, arylamino, arylalkylamino, heteroarylalkylamino, acylamino, alkoxycarbonylamino, —$NR^4CONR^5R^6$, wherein $R^4$, $R^5$ and $R^6$ may be the same or different and each is hydrogen or alkyl, sulfonylamino, aminoalkyl, alkylaminoalkyl, cyclic amino, hydrazino, guanidino, amidino, hydroxyamidino, alkoxyamidino, aminomethyleneamino, iminomethylamino or imino, an optical isomer thereof or a pharmaceutically acceptable salt thereof.

3. The benzylpiperidine compound of claim 1, wherein, in the formula (1), $R^1$ and $R^2$ are the same or different and each is hydrogen, halogen, nitro, cyano or alkyl, n is an integer of 1 to 4, an optical isomer thereof or a pharmaceutically acceptable salt thereof.

4. The benzylpiperidine compound of claim 1, wherein, in the formula (1), $R^1$ and $R^2$ are the same or different and each is halogen or nitro, n is an integer of 1 to 4, and $Y^2$ is amino, alkylamino, arylalkylamino, heteroarylalkylamino, acylamino, alkoxycarbonylamino, sulfonylamino, cyclic amino, hydrazino, guanidino, amidino, hydroxyamidino, alkoxyamidino, iminomethylamino or imino, an optical isomer thereof or a pharmaceutically acceptable salt thereof.

5. The benzylpiperidine compound of claim 1, wherein, in the formula (1), $R^1$ and $R^2$ are the same or different and each is halogen, n is an integer of 1 to 4, X is a bond, an oxygen atom or a sulfur atom, and $Y^2$ is amino, alkylamino, arylalkylamino, heteroarylalkylamino, acylamino, alkoxycarbonylamino, sulfonylamino, cyclic amino, hydrazino, guanidino, amidino, hydroxyamidino, alkoxyamidino or imino, an optical isomer thereof or a pharmaceutically acceptable salt thereof.

6. The benzylpiperidine compound of claim 1, which is selected from [4-(3-aminophenyl)thiazol-2-ylthio]-N-[1-(3,4-dichlorobenzyl)piperidin-4-yl]acetamide, N-[1-(3,4-dichlorobenzyl)-1-oxopiperidin-4-yl]-{4-[3-($N^2$-hydroxyamidino)phenyl]thiazol-2-ylthio}acetamide, N-[1-(3,4-dichlorobenzyl)piperidin-4-yl]-{4-[4-($N^2$-hydroxyamidino)phenyl]thiazol-2-ylthio}acetamide, {4-[3-(L-alanylamino)phenyl]thiazol-2-ylthio}-N-[1-(3,4-dichlorobenzyl)piperidin-4-yl]acetamide, N-[1-(3,4-dichlorobenzyl)piperidin-4-yl]-{4-[3-(4-imidazolecarboxamide)phenyl]thiazol-2-ylthio}acetamide, N-[1-(3,4-dichlorobenzyl)piperidin-4-yl]-{4-[3-(imidazol-2-yl-methylamino)phenyl]thiazol-2-ylthio}acetamide, N-[1-(3,4-dichlorobenzyl)piperidin-4-yl]-{4-[3-(imidazol-4-yl-methylamino)phenyl]thiazol-2-ylthio}acetamide,

[4-(3-aminophenyl)thiazol-2-ylthio]-N-[1-(3,4-dichlorobenzyl)-1-oxopiperidin-4-yl]acetamide, N-[1-(3,4-dichlorobenzyl)piperidin-4-yl]-{4-[3-($N^2$-hydroxyamidino)phenyl]thiazol-2-ylthio}acetamide, N-[1-(3 4-dichlorobenzyl)-1-oxopiperidin-4-yl]-{4-[4-($N^2$-hydroxyamidino)phenyl]thiazol-2-ylthio}acetamide, N-[1-(3,4-dichlorobenzyl)piperidin-4-yl]-{4-[3-(imidazol-4-ylacetamide)phenyl]thiazol-2-ylthio}acetamide, N-[1-(3,4-dichlorobenzyl)piperidin-4-yl]-{4-[3-(2-pyridylmethylamino)phenyl]thiazol-2-ylthio}acetamide, N-[1-(3,4-dichlorobenzyl)piperidin-4-yl]-[5-(2-guanidinothiazol-4-yl)-4-methylthiazol-2-ylthio]acetamide, N-[1-(3,4-dichlorobenzyl)piperidin-4-yl]-{4-[3-(pyridin-3-ylcarboxamide)phenyl]thiazol-2-ylthio}acetamide, and N-[1-(3,4-dichlorobenzyl)piperidin-4-yl]-{4-[3-(pyrrol-2-ylcarboxamide)phenyl]thiazol-2-ylthio}acetamide, or a pharmaceutically acceptable salt thereof.

7. A pharmaceutical composition comprising a benzylpiperidine compound of claim 1, an optical isomer thereof or a pharmaceutically acceptable salt thereof, and a pharmaceutically acceptable carrier.

8. The pharmaceutical composition of claim 7, for the treatment of rheumatoid arthritis, asthma, allergic rhinitis, allergic conjunctivitis, allergic myelitis, atopic dermatitis or ulcerative colitis.

9. The benzylpiperidine compound of claim 1, which is not N-oxidized, wherein, in the formula (1), $Y^2$ is amino, alkylamino, arylamino, arylalkylamino, heteroarylalkylamino, acylamino, acylaminoalkyl, alkoxycarbonylamino, —$NR^4CONR^5R^6$, wherein $R^4$, $R^5$ and $R^6$ may be the same or different and each is hydrogen or alkyl, sulfonylamino, —$CONR^7R^8$, wherein $R^7$ and $R^8$ may be the same or different and each is hydrogen, alkyl, aryl, arylalkyl, or heteroarylalkyl, provided that they are not both hydrogen at the same time, aminoalkyl, alkylaminoalkyl, arylaminoalkyl, heteroarylaminoalkyl, arylalkylaminoalkyl, heteroarylalkylaminoalkyl, cyclic amino, hydrazino, guanidino, amidino, hydroxyamidino, alkoxyamidino, aminomethyleneamino or imino, an optical isomer thereof or a pharmaceutically acceptable salt thereof.

10. The benzylpiperidine compound of claim 9, wherein, in the formula (1),
Y² is amino, alkylamino, arylamino, acylamino, alkoxycarbonylamino, —NR⁴CONR⁵R⁶, wherein R⁴, R⁵ and R⁶ may be the same or different and each is hydrogen or alkyl, sulfonylamino, aminoalkyl, alkylaminoalkyl, cyclic amino, hydrazino, guanidino, amidino, aminomethyleneamino or imino,
an optical isomer thereof or a pharmaceutically acceptable salt thereof.

11. The benzylpiperidine compound of claim 9, wherein, in the formula (1),
R¹ and R² are the same or different and each is hydrogen, halogen, nitro, cyano or alkyl,
n is an integer of 1 to 4,
an optical isomer thereof or a pharmaceutically acceptable salt thereof.

12. The benzylpiperidine compound of claim 9, wherein, in the formula (1),
R¹ and R² are the same or different and each is halogen or nitro,
n is an integer of 1 to 4, and
Y² is amino, alkylamino, arylalkylamino, heteroarylalkylamino, acylamino, alkoxycarbonylamino, sulfonylamino, cyclic amino, hydrazino, guanidino, amidino, hydroxyamidino, alkoxyamidino or imino,
an optical isomer thereof or a pharmaceutically acceptable salt thereof.

13. The benzylpiperidine compound of claim 9, wherein, in the formula (1),
R¹ and R² are the same or different and each is halogen,
n is an integer of 1 to 4,
X is a bond, an oxygen atom or a sulfur atom, and
Y² is amino, alkylamino, acylamino, alkoxycarbonylamino, sulfonylamino, cyclic amino, hydrazino, guanidino, amidino, hydroxyamidino, alkoxyamidino or imino,
an optical isomer thereof or a pharmaceutically acceptable salt thereof.

14. The benzylpiperidine compound of claim 9, which is selected from
[4-(4-aminophenyl)thiazol-2-ylthio]-N-[1-(3,4-dichlorobenzyl)piperidin-4-yl]acetamide,
[4-(4-acetylaminophenyl)thiazol-2-ylthio]-N-[1-(3,4-dichlorobenzyl)piperidin-4-yl]acetamide,
[4-(3-aminophenyl)thiazol-2-ylthio]-N-[1-(3,4-dichlorobenzyl)piperidin-4-yl]acetamide,
N-[1-(3,4-dichlorobenzyl)piperidin-4-yl]-{4-[3-(4-imidazolecarboxamide)phenyl]thiazol-2-ylthio}acetamide,
N-[1-(3,4-dichlorobenzyl)piperidin-4-yl]-{4-[3-(pyrrol-2-ylcarboxamide)phenyl]thiazol-2-ylthio}acetamide,
N-[1-(3,4-dichlorobenzyl)piperidin-4-yl]-{4-[3-(pyridin-2-ylcarboxamide)phenyl]thiazol-2-ylthio}acetamide,
N-[1-(3,4-dichlorobenzyl)piperidin-4-yl]-{4-[3-(pyridin-3-ylcarboxamide)phenyl]thiazol-2-ylthio }acetamide,
{4-[3-(L-prolylamino)phenyl]thiazol-2-ylthio}-N-[1-(3,4-dichlorobenzyl)piperidin-4-yl]acetamide,
[4-(2-aminopyridin-5-yl)thiazol-2-ylthio]-N-[1-(3,4-dichlorobenzyl)piperidin-4-yl]acetamide and
[4-(2-aminopyridin-4-yl)thiazol-2-ylthio]-N-[1-(3,4-dichlorobenzyl)piperidin-4-yl]acetamide,
or a pharmaceutically acceptable salt thereof.

15. A pharmaceutical composition comprising a benzylpiperidine compound of claim 9, an optical isomer thereof or a pharmaceutically acceptable salt thereof, and a pharmaceutically acceptable carrier.

16. The pharmaceutical composition of claim 15, for the treatment of rheumatoid arthritis, asthma, allergic rhinitis, allergic conjunctivitis, allergic myelitis, atopic dermatitis or ulcerative colitis.

17. The benzylpiperidine compound of claim 10, wherein, in the formula (1),
R¹ and R² are the same or different and each is halogen or nitro,
n is an integer of 1 to 4, and
Y² is amino, alkylamino, acylamino, alkoxycarbonylamino, cyclic amino, hydrazino, guanidino, amidino or imino,
an optical isomer thereof or a pharmaceutically acceptable salt thereof.

18. The benzylpiperidine compound of claim 10, wherein, in the formula (1),
R¹ and R² are the same or different and each is halogen,
n is an integer of 1 to 4,
X is a bond, an oxygen atom or a sulfur atom, and
Y² is amino, alkylamino, acylamino, alkoxycarbonylamino, cyclic amino, hydrazino, guanidino, amidino or imino,
an optical isomer thereof or a pharmaceutically acceptable salt thereof.

19. The benzylpiperidine compound of claim 10, which is selected from
[4-(4-aminophenyl)thiazol-2-ylthio]-N-[1-(3,4-dichlorobenzyl)piperidin-4-yl]acetamide and
[4-(4-acetylaminophenyl)thiazol-2-ylthio]-N-[1-(3,4-dichlorobenzyl)piperidin-4-yl]acetamide,
or a pharmaceutically acceptable salt thereof.

20. [4-(3-aminophenyl)thiazol-2-ylthio]-N-[1-(3,4-dichlorobenzyl)piperidin-4-yl]acetamide.

21. {4-[3-(L-alanylamino)phenyl]thiazol-2-ylthio}-N-[1-(3,4-dichlorobenzyl)piperidin-4-yl]acetamide.

* * * * *